(12) United States Patent  (10) Patent No.: US 7,728,146 B2
Thormann et al.  (45) Date of Patent: Jun. 1, 2010

(54) ENZYME INHIBITORS

(75) Inventors: Michael Thormann, Martinsried (DE);
Michael Almstetter, Martinsried (DE);
Andreas Treml, Martinsried (DE)

(73) Assignee: Probiodrug AG, Halle (Saale) (DE)

( * ) Notice: Subject to any disclaimer, the term of this patent is extended or adjusted under 35 U.S.C. 154(b) by 0 days.

(21) Appl. No.: 11/734,369

(22) Filed: Apr. 12, 2007

(65) Prior Publication Data

US 2007/0244177 A1  Oct. 18, 2007

Related U.S. Application Data

(60) Provisional application No. 60/791,302, filed on Apr. 12, 2006, provisional application No. 60/870,165, filed on Dec. 15, 2006.

(51) Int. Cl.
*A61K 31/4178* (2006.01)
*C07D 409/06* (2006.01)

(52) U.S. Cl. .................... 548/335.5; 514/396; 514/397; 514/399

(58) Field of Classification Search ............... 548/335.5
See application file for complete search history.

(56) References Cited

U.S. PATENT DOCUMENTS

| | | | |
|---|---|---|---|
| 6,011,155 A | 1/2000 | Villhauer | |
| 6,107,317 A | 8/2000 | Villhauer | |
| 6,110,949 A | 8/2000 | Villhauer | |
| 6,124,305 A | 9/2000 | Villhauer | |

FOREIGN PATENT DOCUMENTS

| | | |
|---|---|---|
| DE | 196164866 | 10/1997 |
| DE | 19828113 | 1/2000 |
| DE | 19828114 | 1/2000 |
| DE | 19834591 | 2/2000 |
| EP | 477778 A2 * | 4/1992 |
| EP | 1258476 | 11/2002 |
| WO | 9515309 | 6/1995 |
| WO | 9640143 | 12/1996 |
| WO | 9740832 | 11/1997 |
| WO | 9819998 | 5/1998 |
| WO | 9938501 | 8/1999 |
| WO | 9946272 | 9/1999 |
| WO | 9961431 | 12/1999 |
| WO | 9967228 | 12/1999 |
| WO | 9967229 | 12/1999 |
| WO | 0007617 | 2/2000 |
| WO | 0119866 | 3/2001 |
| WO | 0134594 | 5/2001 |
| WO | 0140180 | 6/2001 |
| WO | 0155105 | 8/2001 |
| WO | 0168603 | 9/2001 |
| WO | 0181304 | 11/2001 |
| WO | 0181337 | 11/2001 |
| WO | 0202560 | 1/2002 |
| WO | 0204610 | 1/2002 |
| WO | 0231134 | 4/2002 |
| WO | 0234242 | 5/2002 |
| WO | 0234900 | 5/2002 |
| WO | 0238541 | 5/2002 |
| WO | 02083128 | 10/2002 |
| WO | 03000180 | 1/2003 |
| WO | 03000181 | 1/2003 |
| WO | 03000250 | 1/2003 |
| WO | 03002530 | 1/2003 |
| WO | 03002531 | 1/2003 |
| WO | 03002553 | 1/2003 |
| WO | 03002593 | 1/2003 |
| WO | 03004496 | 1/2003 |
| WO | 03024942 | 3/2003 |
| WO | 03024965 | 3/2003 |
| WO | 03033524 | 4/2003 |
| WO | 03035057 | 5/2003 |
| WO | 03035067 | 5/2003 |
| WO | 03037327 | 5/2003 |
| WO | 03040174 | 5/2003 |
| WO | 03045977 | 6/2003 |
| WO | 03055881 | 7/2003 |
| WO | 03057144 | 7/2003 |
| WO | 2004004498 | 1/2004 |
| WO | 2004026822 | 1/2004 |
| WO | 2004018460 | 3/2004 |
| WO | 2004033455 | 4/2004 |

(Continued)

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
Golub et al., Science, vol. 286, Oct. 15, 1999, pp. 531-537.*
Xu, Jinyou et al, Discovery of potent, selective, and orally bioavailable pyridone-based dipeptidyl peptidase-4 inhibitors, Bioogranic & Medicinal Chemistry Letters 2006 vol. 16 pp. 1346-1349.

(Continued)

*Primary Examiner*—Laura L. Stockton
(74) *Attorney, Agent, or Firm*—Sonnenschein Nath & Rosenthal LLP

(57) ABSTRACT

There is disclosed herein compounds of formula (I),

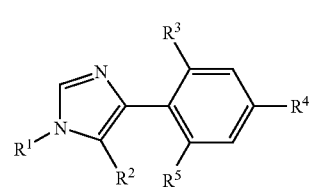

(I)

wherein:
$R^1$, $R^2$, $R^3$, $R^4$ and $R^5$ are defined throughout the description and the claims. The compounds of formula (I) are useful for the treatment of neurological diseases and neurodegenerative diseases, e.g. anxiety, depression, Alzheimer's disease etc.

65 Claims, 24 Drawing Sheets

FOREIGN PATENT DOCUMENTS

| | | |
|---|---|---|
| WO | 2004037169 | 5/2004 |
| WO | 2004043940 | 5/2004 |
| WO | 2004050022 | 6/2004 |
| WO | 2004052850 | 6/2004 |
| WO | 2004058266 | 7/2004 |
| WO | 2004064778 | 8/2004 |
| WO | 2004069162 | 8/2004 |
| WO | 2004071454 | 8/2004 |
| WO | 2004076433 | 9/2004 |
| WO | 2004076434 | 9/2004 |
| WO | 2004048352 | 10/2004 |
| WO | 2004087053 | 10/2004 |
| WO | 2004089362 | 10/2004 |
| WO | 2004098591 | 11/2004 |
| WO | 2004099185 | 11/2004 |
| WO | 2004103276 | 12/2004 |
| WO | 2004103993 | 12/2004 |
| WO | 2004108730 | 12/2004 |
| WO | 2004110436 | 12/2004 |
| WO | 2004111041 | 12/2004 |
| WO | 2004112701 | 12/2004 |
| WO | 2005000846 | 1/2005 |
| WO | 2005000848 | 1/2005 |
| WO | 2005011581 | 2/2005 |
| WO | 2005016911 | 2/2005 |
| WO | 2005023762 | 3/2005 |
| WO | 2005025554 | 3/2005 |
| WO | 2005026148 | 3/2005 |
| WO | 2005030751 | 4/2005 |
| WO | 2005037828 | 4/2005 |
| WO | 2005040095 | 5/2005 |
| WO | 2005044195 | 5/2005 |
| WO | 2005047297 | 5/2005 |
| WO | 2005051950 | 6/2005 |
| WO | 2005056003 | 6/2005 |
| WO | 2005056013 | 6/2005 |
| WO | 2005058849 | 6/2005 |
| WO | 2005075426 | 8/2005 |
| WO | 2005079795 | 9/2005 |
| WO | 2005082348 | 9/2005 |
| WO | 2005085246 | 9/2005 |
| WO | 2005087235 | 9/2005 |
| WO | 2005095339 | 10/2005 |
| WO | 2005095343 | 10/2005 |
| WO | 2005095381 | 10/2005 |
| WO | 2005108382 | 11/2005 |
| WO | 2005113510 | 12/2005 |
| WO | 2005116014 | 12/2005 |
| WO | 2005116029 | 12/2005 |
| WO | 2005118555 | 12/2005 |
| WO | 2005120494 | 12/2005 |
| WO | 2005121089 | 12/2005 |
| WO | 2005121131 | 12/2005 |
| WO | 2005123685 | 12/2005 |

OTHER PUBLICATIONS

Pederson, Raymond A. et al., Improved glucose tolerance in Zucker fatty rats by oral adminsitration of the dipeptidyl peptidase IV inhibitor isoleucine thiazolidide, Diabetes 1998 vol. 47 pp. 1253-1258.

Lankas, George R. et al, Dipeptidyl peptidase IV inhibition for the treatment of type 2 diabetes, Diabetes 2005 vol. 54 pp. 2988-2994.

Pauly, Robert P. et al, Improved glucose tolerance in rats treated with dipeptidyl peptidase IV (CD26) inhibitor Ile-thiazolidide, Metabolism 1999 vol. 48 pp. 385-389.

Bundgaard, Hans, Design of prodrugs, Elsevier 1985.

Sedo, Aleski et al., Dipeptidyl peptidase IV-like molecules: homologous proteins or homologous activities?, Biochimica et Biophysica Acta 2001 vol. 1550 pp. 107-116.

* cited by examiner

ENZYME INHIBITORS

CROSS-REFERENCE TO RELATED APPLICATIONS

The present application claims priority to U.S. Provisional Patent Applications Nos. 60/791,302, filed on Apr. 12, 2006 and 60/870,165, filed on Dec. 15, 2006, the entire contents both of which are incorporated herein by reference to the extent permitted by law.

FIELD OF THE INVENTION

The present invention relates to the area of dipeptidyl peptidase IV (DP IV) inhibition and, particularly, relates to novel specific DP IV-inhibitors, which are able to cross the blood-brain-barrier in mammals, pharmaceutical compositions containing said compounds, and the use of said compounds for specifically inhibiting DP IV with low or no activity against related enzymes (e.g. DP IV-like enzymes).

BACKGROUND ART

DP IV is a serine protease, which cleaves N-terminal dipeptides from a peptide chain containing, preferably, a proline residue in the penultimate position. Although the biological role of DP IV in mammalian systems has not been completely established, it is believed to play an important role in neuropeptide metabolism, T-cell activation, attachment of cancer cells to the endothelium and the entry of HIV into lymphoid cells.

Likewise, it was discovered that DP IV is responsible for inactivating glucagon-like peptide-1 (GLP-1) and glucose-dependent insulinotropic peptide also known as gastric-inhibitory peptide (GIP). Since GLP-1 is a major stimulator of pancreatic insulin secretion and has direct beneficial effects on glucose disposal, in WO 97/40832 and U.S. Pat. No. 6,303,661 inhibition of DP IV and DP IV-like enzyme activity was shown to represent an attractive approach e.g. for treating type 2 diabetes (also known as non-insulin-dependent diabetes mellitus or NIDDM).

It is known that DP IV inhibitors may be useful for the treatment of impaired glucose tolerance and diabetes mellitus (WO 99/61431; Pederson R A et al, *Diabetes* 1998 47(8): 1253-1258 and Pauly R P et al, *Metabolism* 1999 48(3):385-389). WO 99/61431 discloses DP IV inhibitors comprising an amino acid residue and a thiazolidine or pyrrolidine group, especially L-threo-isoleucyl thiazolidine, L-allo-isoleucyl thiazolidine, L-threo-isoleucyl pyrrolidine, L-allo-isoleucyl thiazolidine, L-allo-isoleucyl pyrrolidine, and salts thereof. WO 03/72556 discloses DP IV inhibitors comprising a glutaminyl residue and a thiazolidine or pyrrolidine group, especially glutaminyl thiazolidine and glutaminyl pyrrolidine, and salts thereof.

Further examples for low molecular weight DP IV inhibitors are agents such as tetrahydroisoquinolin-3-carboxamide derivatives, N-substituted 2-cyanopyroles and -pyrrolidines, N-(N'-substituted glycyl)-2-cyanopyrrolidines, N-(substituted glycyl)-thiazolidines, N-(substituted glycyl)-4-cyanothiazolidines, boronyl inhibitors and cyclopropyl-fused pyrrolidines. Inhibitors of DP IV are described in U.S. Pat. No. 6,011,155; U.S. Pat. No. 6,107,317; U.S. Pat. No. 6,110,949; U.S. Pat. No. 6,124,305; U.S. Pat. No. 6,172,081; WO 99/61431, WO 99/67278, WO 99/67279, DE 198 34 591, WO 97/40832, DE 196 16 486 C 2, WO 95/15309, WO 98/19998, WO 00/07617, WO 99/38501, WO 99/46272, WO 99/38501, WO 01/68603, WO 01/40180, WO 01/81337, WO 01/81304, WO 01/55105, WO 02/02560, WO 01/34594, WO 02/38541, WO 02/083128, WO 03/072556, WO 03/002593, WO 03/000250, WO 03/000180, WO 03/000181, EP 1 258 476, WO 03/002553, WO 03/002531, WO 03/002530, WO 03/004496, WO 03/004498, WO 03/024942, WO 03/024965, WO 03/033524, WO 03/035057, WO 03/035067, WO 03/037327, WO 03/040174, WO 03/045977, WO 03/055881, WO 03/057144, WO 03/057666, WO 03/068748, WO 03/068757, WO 03/082817, WO 03/101449, WO 03/101958, WO 03/104229, WO 03/74500, WO 04/007446, WO 04/007468, WO 04/018467, WO 04/018468, WO 04/018469, WO 04/026822, WO 04/032836, WO 04/033455, WO 04/037169, WO 04/041795, WO 04/043940, WO 04/048352, WO 04/050022, WO 04/052850, WO 04/058266, WO 04/064778, WO 04/069162, WO 04/071454, WO 04/076433, WO 04/076434, WO 04/087053, WO 04/089362, WO 04/099185, WO 04/103276, WO 04/103993, WO 04/108730, WO 04/110436, WO 04/111041, WO 04/112701, WO 05/000846, WO 05/000848, WO 05/011581, WO 05/016911, WO 05/023762, WO 05/025554, WO 05/026148, WO 05/030751, WO 05/033106, WO 05/037828, WO 05/040095, WO 05/044195, WO 05/047297, WO 05/051950, WO 05/056003, WO 05/056013, WO 05/058849, WO 05/075426, WO 05/082348, WO 05/085246, WO 05/087235, WO 05/095339, WO 05/095343, WO 05/095381, WO 05/108382, WO 05/113510, WO 05/116014, WO 05/116029, WO 05/118555, WO 05/120494, WO 05/121089, WO 05/121131, WO 05/123685 the teachings of which concerning the inhibitors, their production and their use are herein incorporated by reference in their entirety.

There is relatively little in the literature about the use of DP IV-inhibitors for the treatment of neurological diseases. WO 02/34242 and WO 02/34242 disclose the medical use of DP IV-inhibitors for maintenance or potentiation of endogenous neurological and neuropsychological effects of brain neuropeptide Y (NPY) systems via a potentiation of NPY Y1 receptor mediated effects within the central nervous system (CNS).

WO 01/34594 discloses DP IV-inhibitors comprising a proline mimetic, and a method of treating a patient having a disorder selected from the group consisting of strokes, tumors, ischemia, Parkinson's disease, memory loss, hearing loss, vision loss, migraines, brain injury, spinal cord injury, Alzheimer's disease, amyotrophic lateral, multiple sclerosis, diabetic neuropathy and prostate abnormalities.

WO 05/079795 relates to the use of a DP IV inhibitor for the prevention, delay of progression or the treatment of neurodegenerative disorders, cognitive disorders and for improving memory (both short term and long term) and learning ability.

Xu J et al, *Bioorg Med Chem Lett* 2006, Mar. 1;16(5): 1346-9 discloses anti-substituted beta-methylphenylalanine derived amides as potent DP IV-inhibitors with selectivity over both DPP8 and DPP9. These compounds are optimized for the treatment of metabolic disorders and thus are preferably not able to cross the blood brain barrier.

Lankas G R et al, *Diabetes* 2005 54(10):2988-2994, have tested selective inhibitors of DP IV, DPP8/9 and QPP in 2-week rat toxicity studies and in acute dog tolerability studies. In rats, the DPP8/9 inhibitor produced alopecia, thrombocytopenia, reticulocytopenia, enlarged spleen, multiorgan histopathological changes and mortality. In dogs, the DPP8/9 inhibitor produced gastrointestinal toxicity. The QPP inhibitor produced reticulocytopenia in rats only, and no toxicities were noted in either species for the selective DP IV inhibitor. The DPP8/9 inhibitor was also shown to attenuate T-cell activation in human in vitro models; a selective DP IV inhibitor was inactive in these assays. Moreover, it was found that DP IV inhibitors which were previously reported to be active in models of immune function are more potent inhibitors of DPP8/9. These results suggest that assessment of selectivity of potential clinical candidates may be important to an optimal safety profile for this class of agents.

Definitions:

The following definitions refer to the whole description and especially to the claims.

As used herein, the term "pharmaceutically acceptable" embraces both human and veterinary use: for example the term "pharmaceutically acceptable" embraces a veterinarily acceptable compound or a compound acceptable in human medicine and health care.

Stereoisomers:

All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. If the formation of an E configuration or, respectively, a Z configuration of a double bond in an "alkenyl group" is possible, both the E and Z configuration are comprised within the scope of the present invention.

It is to be understood that both individual isolated isomers (such as at least 75% pure, in particular at least 90% pure and especially at least 95% pure, for example at least 99% pure) and mixtures of isomers (for example a mixture of all possible isomers, or the two enantiomers of a diastereomer) are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts, whenever a compound is referred to in this context, a corresponding salt is also intended, provided such is possible or appropriate under the circumstances.

The pharmaceutically acceptable salt generally takes a form in which one or more basic moieties is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toulenesulfonic, cyclohexanesulfamic, salicylic, saccharinic or trifluoroacetic acid.

All pharmaceutically acceptable acid addition salt forms of the compounds of the present invention are intended to be embraced by the scope of this invention. Non-pharmaceutically acceptable salts forms of the compounds of the invention may be of use in the preparation of pharmaceutically acceptable salts.

Solvates:

Compounds of the invention may form solvates with water (i.e. hydrate) or common organic solvents which are embraced as an aspect of the invention. Pharmaceutically acceptable solvents (e.g. hydrates) are of particular interest.

Polymorph Crystal Forms:

Furthermore, compounds of the invention (including their salts and solvates) may exist as crystalline solids and all polymorphic forms thereof are included within the scope of the present invention.

Prodrugs:

The present invention further includes within its scope prodrugs of the compounds of this invention. In general, such prodrugs will be functional derivatives of the compounds which are readily convertible in vivo into the desired therapeutically active compound. Thus, in with respect to prodrugs, in the methods of treatment of the present invention, the term "administering" shall encompass the treatment of the various disorders described with prodrug versions of one or more of the claimed compounds of the invention, but which convert to one or more of the compounds of the invention in vivo after administration to the subject.

Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

DP IV-inhibitor

The term "DP IV-inhibitor" or "dipeptidyl peptidase IV inhibitor" is generally known to a person skilled in the art and means enzyme inhibitors, which inhibit the catalytic activity of DP IV.

DP IV-activity

"DP IV-activity" is defined as the catalytic activity of dipeptidyl peptidase IV (DP IV). These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

DP IV-like Enzymes

Among the rare group of proline-specific proteases, DP IV was originally believed to be the only membrane-bound enzyme specific for proline as the penultimate residue at the amino-terminus of the polypeptide chain. However, other molecules, even structurally non-homologous with the DP IV but bearing corresponding enzyme activity, have been identified recently. DP IV-like enzymes, which are identified so far, are e.g. fibroblast activation protein α, dipeptidyl peptidase IV β, dipeptidyl aminopeptidase-like protein, N-acetylated α-linked acidic dipeptidase, quiescent cell proline dipeptidase, dipeptidyl peptidase II, attractin and dipeptidyl peptidase IV related protein (DPP 8), and are described in the review article by Sedo & Malik (Sedo & Malik, Dipeptidyl peptidase IV-like molecules: homologous proteins or homologous activities? *Biochimica et Biophysica Acta* 2001 36506: 1-10).

Further DPIV-like enzymes are disclosed in WO 01/19866, WO 02/04610, WO 02/34900 and WO02/31134. WO 01/19866 discloses novel human dipeptidyl aminopeptidase (DPP8) with structural und functional similarities to DPIV and fibroblast activation protein (FAP). WO 02/04610 provides reagents, which regulate human dipeptidyl peptidase IV-like enzyme and reagents which bind to human dipeptidyl peptidase IV-like enzyme gene product. These reagents can play a role in preventing, ameliorating, or correcting dysfunctions or diseases including, but not limited to, tumors and peripheral and central nervous system disorders including pain and neurodegenerative disorders. The dipeptidyl peptidase IV-like enzyme of WO 02/04610 is well known in the art. In the Gene Bank data base, this enzyme is registered as KIAA1492 (registration in February 2001, submitted on Apr. 4, 2000, AB040925).

WO 02/34900 discloses a dipeptidyl peptidase 9 (DPP9) with significant homology with the amino acid sequences of DP IV and DPP8. WO 02/31134 discloses three DP IV-like enzymes, DPRP1, DPRP2 and DPRP3. Sequence analysis revealed, that DPRP1 is identical to DPP8, as disclosed in WO 01/19866, that DPRP2 is identical to DPP9 and that DPRP3 is identical to KIAA1492 as disclosed in WO 02/04610.

Subject

The term "subject" as used herein, refers to an animal, such as a mammal, in particular a human, who has been the object of treatment, observation or experiment.

Therapeutically Effective Amount

The term "therapeutically effective amount" as used herein, means that amount of a compound of the invention compound or pharmaceutical agent that is sufficient to elicit a biological or medicinal response in a tissue system, animal or human, being sought by a researcher, veterinarian, medical doctor or other clinician, which includes alleviation of the symptoms of the disease or disorder being treated.

Composition

As used herein, the term "composition" is intended to encompass a product comprising the claimed compounds in the therapeutically effective amounts, as well as any product which results, directly or indirectly, from combinations of the claimed compounds.

Co-Administration, Combination

"Co-administration" or "combination" includes administration of a formulation, which includes at least one DP IV-inhibitor of the present invention and at least one further drug agent (for example as listed in the section "Pharmaceutical combinations") or the essentially simultaneous administration of separate formulations of each agent. The DP IV-inhibitor and the other drug agent may be administered concomitantly or sequentially, as may be required by the appropriate treatment regime, via the same or different routes of administration.

Prevention

The term "prevention" means prophylactic administration of the combination to healthy patients to prevent the outbreak of the conditions mentioned herein. Moreover, the term "prevention" means prophylactic administration of such combination to patients being in a pre-stage of the conditions, to be treated.

Delay

The term "delay of progression" used herein means administration of the combination, such as a combined preparation or pharmaceutical composition, to patients being in a pre-stage of the condition to be treated in which patients a preform of the corresponding condition is diagnosed.

Treatment

By the term "treatment" is understood the management and care of a patient for the purpose of combating the disease, condition, or disorder.

Though the causes may differ, patients with neurodegenerative disorders are likely to show localized to generalized atrophy of brain cells leading to compromises in both mental and physical functions.

Dementia

The term "dementia" as used herein includes Alzheimer type dementia, Parkinson type dementia, Huntington type dementia, Pick's type dementia, Creutzfeldt-Jakob type dementia, senile dementia, pre-senile dementia, idiopathic-related dementia, trauma-related dementia, stroke-related dementia, cranial bleed-related dementia, vascular dementia, and includes acute, chronic or recurring forms.

Chemical Definitions

Throughout the description and the claims the expression "alkyl", unless specifically limited, denotes a $C_{1-12}$ alkyl group, such as a $C_{1-6}$ alkyl group (for example a $C_{1-4}$ alkyl group). Alkyl groups may be straight chain or branched. Suitable alkyl groups include, for example, methyl, ethyl, propyl (e.g. n-propyl and isopropyl), butyl (e.g. n-butyl, tert-butyl and sec-butyl), pentyl (e.g. n-pentyl, hexyl (e.g. n-hexyl heptyl (e.g. n-heptyl) and octyl (e.g. n-octyl).

Other suitable alkyl groups include 1-ethyl-propyl, 3-methyl-butyl and 2,2-dimethyl-propyl), and 3,3-dimethyl-butyl), nonyl (e.g. n-nonyl and 7-methyl-octyl) and decyl (e.g. n-decyl), in particular methyl and ethyl. Further suitable alkyl groups include isobutyl.

"Lower alkyl" refers to an alkyl group having 1-4 carbon atoms e.g. methyl or ethyl.

The expression "alk", for example in the expression "alkoxy", should be interpreted in accordance with the definition of "alkyl".

Exemplary alkoxy groups include methoxy, ethoxy, propoxy, butoxy, pentyloxy, hexyloxy, heptyloxy and octyloxy. Other examples include nonyloxy and decyloxy. Further examples include n-propoxy, n-butoxy, n-pentoxy, n-hexoxy, n-heptoxy and n-octoxy).

The expression "alk", in the expression "thioalkyl" should be interpreted in accordance with the definition of "alkyl". Exemplary thioalkyl groups include methylthio-.

The expression "alkan", for example in the expression "alkanoyl" should be interpreted in accordance with the definition of "alkyl". Exemplary alkanoyl (i.e. acyl groups) include ethanoyl (i.e. acetyl), propionyl and butyryl.

The expression "acyl", unless specifically limited, denotes a $C_{1-12}$acyl residue, such as a $C_{1-8}$acyl residue e.g. a $C_{1-6}$ acyl residue and in particular a $C_{1-4}$acyl residue. Examples of acyl include the alkanoyl groups mentioned previously.

The expression "alk" in the expressions "haloalkyl" and "haloalkoxy" should be interpreted in accordance with the definition of "alkyl". For instance, by the term "$C_{1-6}$haloalkyl" is meant a $C_{1-6}$alkyl group which is substituted by at least one halo atom (for example fluoro, chloro or bromo). $C_{1-6}$fluoroalkyl represents a $C_{1-6}$alkyl group (such as those specifically recited above) which is substituted by at least one fluoro atom, including for example, fluoromethyl, difluoromethyl and trifluoromethyl (in particular trifluoromethyl). The expressions $C_{1-6}$haloalkoxy and $C_{1-6}$fluoroalkoxy can be interpreted accordingly.

The expression "alkenyl", unless specifically limited, denotes a $C_{2-12}$alkenyl group, such as a $C_{2-6}$alkenyl group (for example a $C_{2-4}$alkenyl group), which contains at least one double bond at any desired location and which does not contain any triple bonds. Alkenyl groups may be straight chain or branched. Exemplary alkenyl groups include propenyl, butenyl. Other examples include ethenyl, pentenyl and hexenyl. Exemplary alkenyl groups including two double bonds include pentadienyl, e.g. (1E, 3E)-pentadienyl.

The expression "alkynyl", unless specifically limited, denotes a $C_{2-12}$ alkynyl group, such as a $C_{2-6}$alkynyl group (for example a $C_{2-4}$alkynyl group), which contains at least one triple bond at any desired location. Alkynyl groups may be straight chain or branched. Exemplary alkynyl groups include ethynyl, propynyl and butynyl. Further examples include ethynyl, pentynyl and hexynyl.

Generally, the term "alkynyl group" comprises also compounds having double bonds as well as triple bonds, i.e. "alkeninyl groups", for example having one double bond and additionally, one triple bond. As an example therefore, the group 4,7-dimethyl-oct-6-en-2-in-1-yl (i.e. —$CH_2$—C≡C—$CH(CH_3)$—$CH_2$—$CH$=$C(CH_3)_2$) may be given.

The expression "amino" means a primary, secondary or tertiary amine group. Suitably amino is represented by formula —$NR^aR^b$ wherein $R^a$ and $R^b$ are selected from hydrogen or alkyl (e.g. $C_{1-4}$alkyl) or $R^a$ and $R^b$ may be joined to form a 4-7 membered ring optionally containing a further N or O atom. Examples of amino include $NH_2$, NHMe, $NMe_2$, NHEt, $NEt_2$, NMeEt, azetidine, pyrrolidine, piperidine, morpholine, piperazine and N-methylpiperazine.

The expression "amine", unless qualified as "secondary amine" or "tertiary amine" means $NH_2$.

Exemplary cycloalkyl groups include cyclopropyl, cyclobutyl, cyclopentyl, cyclohexyl, cycloheptyl and cyclooctyl.

The expression "carbocycle", unless specifically limited, denotes any ring system in which all the ring atoms are carbon and which typically contain between three and twelve ring carbon atoms, suitably between three and ten carbon atoms and more suitably between three and eight carbon atoms. Carbocycle groups may be saturated or partially unsaturated, but do not include aromatic rings. Examples of carbocycle groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocycle group is a cycloalkyl group. A further example of a carbocycle group is a cycloalkenyl group. A further example of a carbocycle group is a cycloalkynyl group.

The term "cycloalkyl", unless specifically limited, denotes a $C_{3-12}$cycloalkyl group, such as a $C_{3-10}$cycloalkyl (for example a $C_{3-8}$ cycloalkyl group). Exemplary cycloalkyl groups include cyclopropyl, cyclobutyl, cyclopentyl, cyclohexyl, cycloheptyl and cyclooctyl. A most suitable number of ring carbon atoms is three to six. The term "cycloalkenyl", unless specifically limited, denotes a $C_{5-12}$cycloalkenyl group, for example a $C_{5-10}$cycloalkenyl group such as a $C_{5-8}$cycloalkenyl (for example a $C_{6-8}$ cycloalkenyl group or a $C_{5-6}$ cycloalkenyl group). A specific example is cyclohexenyl. Further specific examples include cyclopropenyl, cycloheptenyl and cyclooctenyl. A most suitable number of ring carbon atoms is five to six.

Other exemplary carbocycle groups include bridged ring systems (e.g. bicyclo[2.2.1]heptanyl bicyclo[2.2.1]heptenyl and adamantane, which are considered to be examples of cycloalkenyl and cycloalkyl groups respectively).

By the term "$C_{3-6}$cycloalkylimine" is meant $C_{3-6}$cycloalkyl group in which one of the ring carbon atoms is replaced by a nitrogen atom. Exemplary $C_{3-6}$cycloalkylimine groups include azetidine (also known as trimethylene imine, which may be 1-azetidine, 2-azetidine or 3-azetidine, in particular 3-azetidine), pyrrolidine (including pyrrolidin-1-yl, pyrrolidin-2-yl and pyrrolidin-3-yl) and piperidine (including piperidin-1-yl, piperidin-2-yl, piperidin-3-yl and piperidin-4-yl).

The expression "heterocyclic" or "heterocycle", unless specifically limited, denotes a carbocyclic residue (for example a cycloalkyl group, e.g. cyclopentyl or more particularly cyclohexyl), wherein one or more (e.g. 1, 2, 3 or 4, such as 1, 2 or 3, in particular 1 or 2, especially 1) ring atoms are replaced by heteroatoms selected from N, S or O. By the term "$C_{3-12}$heterocycle" is meant a $C_{3-12}$carbocyclyl group in which at least one of the ring carbon atoms is replaced by a heteroatom. A heterocyclic group could therefore be monocylic or could alternatively be bicyclic. More usually it will be monocyclic. Exemplary heterocyclic groups containing one hetero atom include: three membered rings (e.g. oxirane aziridine, thiirane); four membered rings (e.g. oxetane, azetidine, thietane); five membered rings (e.g. pyrrolidine and tetrahydrofuran, but also pyrroline and tetrahydrothiophene); and six membered rings (e.g. piperidine or tetrahydropyran). Exemplary heterocyclic groups containing two hetero atoms include five membered rings (e.g. pyrazoline, imidazoline, pyrazolidine, imidazolidine, dioxolane, thiazolidine, oxazolidine); and six membered rings (e.g. morpholine and piperazine but also dioxane). A further specific example of a heterocycle group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

An example of a bridged heterocyclic group is utropine.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings), but may also comprise partially or fully unsaturated rings. An example of a typical aryl group with one aromatic ring is phenyl. Examples of aromatic groups with two aromatic rings include naphthyl. Examples of naphthyl include naphth-1-yl- and naphth-2-yl-. Examples of aryl groups which contain partially or fully unsaturated rings include pentalene, indene and indane. Other aryl groups include tricyclic rings such as anthracene.

The expression "heteroaryl", unless specifically limited, denotes as an aryl residue, wherein one or more (e.g. 1, 2, 3, or 4, such as 1, 2 or 3) ring atoms are replaced by heteroatoms selected from N, S and O or else a 5-membered aromatic ring containing one or more (e.g. 1, 2, 3, or 4, such as 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole (e.g. pyrazol-3-yl), oxazole, isooxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: triazole e.g. 1,2,3-triazole and 1,2,4-triazole. Exemplary monocyclic heteroaryl groups having four heteroatoms include tetrazole.

Exemplary bicyclic heteroaryl groups include quinoline, benzothiophene, indazole, indole and purine. Exemplary bicyclic heteroaryl groups also include isoquinoline, quinolizine, benzodioxolane, benzodioxane, benzodioxepine (e.g. indol-6-yl), indoline, benzimidazole Further examples of bicyclic heteroaryl groups include (e.g. 1H-indol-6-yl), benzimidazole, chromene, benzodioxolane, benzodioxane (e.g. 2,3-dihydro-benzo[1,4]dioxin-6-yl) and benzodioxepine.

Exemplary tricyclic heteroaryl groups include carbazole and acridine groups.

The expression "-alkylaryl", unless specifically limited, denotes an aryl residue which is connected via an alkylene moiety such as a $C_{1-6}$alkylene moiety e.g. a $C_{1-4}$alkylene moiety. Examples of -alkylaryl include: -methylaryl and -ethylaryl (e.g. 1-arylethyl- or 2-arylethyl-); or phenylalkyl-, which may be optionally substituted. Specific examples of -alkylaryl functions include: phenylmethyl- (i.e. benzyl), phenylethyl- (e.g. 2-phenyleth-1-yl or 1-phenyl-eth-1-yl), p-tolyl-methyl-, (p-tolyl)-ethyl-, (m-tolyl)-methyl-, (m-tolyl)-ethyl-, (o-tolyl)-methyl-, (o-tolyl)-ethyl-, 2-(4-ethyl-phenyl)-eth-1-yl-, (2,3-dimethyl-phenyl)-methyl-, (2,4-dimethyl-phenyl)-methyl-, (2,5-dimethyl-phenyl)-methyl-, (2,6-dimethyl-phenyl)-methyl-, (3,4-dimethyl-phenyl)-methyl-, (3,5-dimethyl-phenyl)-methyl-, (2,4,6-trimethyl-phenyl)-methyl-, (2,3-dimethyl-phenyl)-ethyl-, (2,4-dimethyl-phenyl)-ethyl-, (2,5-dimethyl-phenyl)-ethyl-, (2,6-dimethyl-phenyl)-ethyl-, (3,4-dimethyl-phenyl)-ethyl-, (3,5-dimethyl-phenyl)-ethyl-, (2,4,6-trimethyl-phenyl)-ethyl-, (2-ethyl-phenyl)-methyl-, (3-ethyl-phenyl)-methyl-, (4-ethyl-phenyl)-methyl-, (2-ethyl-phenyl)-ethyl-, (3-ethyl-phenyl)-ethyl-, (4-ethyl-phenyl)-ethyl-, 2-fluoro-benzyl, (1-methyl-2-fluoro-phen-6-yl)-methyl-, (1-methyl-2-fluoro-phen-4-yl)-methyl-, (1-methyl-2-fluoro-phen-6-yl)-ethyl-, (1-methyl-2-fluoro-phen-4-yl)-ethyl-, 1H-indenyl-methyl-, 2H-indenyl-methyl-, 1H-indenyl-ethyl-, 2H-indenyl-ethyl-, indanyl-methyl-, indan-1-on-2-yl-methyl-, indan-1-on-2-yl-ethyl-, tetralinyl-methyl-, tetralinyl-ethyl-, fluorenyl-methyl-, fluorenyl-ethyl-, dihydronaphthalinyl-methyl-, dihydronaphthalinyl-ethyl-, or (4-cyclohexyl)-phenyl-methyl-, (4-cyclohexyl)-phenyl-ethyl-.

The expression "-alkylheteroaryl", unless specifically limited, denotes a heteroaryl residue which is connected via an alkylene moiety such as a $C_{1-6}$alkylene moiety e.g. a $C_{1-4}$alkylene moiety. Examples of -alkylheteroaryl include -methylheteroaryl and -ethylheteroaryl (e.g. 1-heteroarylethyl- and 2-heteroarylethyl-). Specific examples of -alkylheteroaryl groups include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl-, 4-methyl-pyridin-3-ethyl-.

The terms "halogen" and "halo" include fluorine, chlorine, bromine and iodine, especially fluorine, chlorine and bromine, in particular fluorine and chlorine (e.g. fluorine).

SUMMARY OF THE INVENTION

According to the invention there is provided a compound of formula (I)

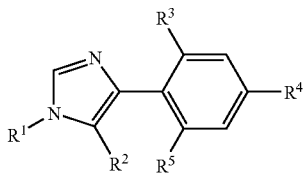

(I)

wherein
R¹ represents a group selected from the list consisting of:
$C_{1-12}$alkyl; —$C_{1-6}$alkylO$C_{1-6}$alkyl; $C_{2-12}$alkenyl; $C_{2-12}$alkynyl; $C_{1-12}$alkylamino; aryl, -aryl-aryl; —$C_{1-6}$alkylaryl; —$C_{1-6}$alkylaryl-aryl; —$C_{1-6}$alkylaryl-heteroaryl; —$C_{1-6}$alkylheteroaryl-aryl; —$C_{1-6}$alkylheteroaryl-heteroaryl; —$C_{1-6}$alkyl(aryl)$_2$; —$C_{1-6}$alkyl(heteroaryl)$_2$; —$C_{1-6}$alkyl(heteroaryl)(aryl); —$C_{1-6}$alkylOaryl; —$C_{1-6}$alkylNR⁹aryl; —$C_{2-6}$alkenylaryl; —$C_{2-6}$alkynylaryl; heteroaryl; —$C_{1-6}$alkylheteroaryl; —$C_{1-6}$alkyl(heteroaryl)$_2$; —$C_{1-6}$alkylOheteroaryl; —$C_{1-6}$alkylNR⁹heteroaryl; —$C_{2-6}$alkenylheteroaryl; —$C_{2-6}$alkynylheteroaryl; —$C_{3-12}$carbocycle; —$C_{1-6}$alkyl$C_{3-12}$carbocycle; —$C_{1-6}$alkylOC$_{3-12}$carbocycle; —$C_{1-6}$alkylNR⁹$C_{3-12}$carbocycle; —$C_{2-6}$alkenyl$C_{3-12}$carbocycle; —$C_{2-6}$alkynyl$C_{3-12}$carbocycle; —$C_{3-12}$heterocycle; —$C_{1-6}$alkyl$C_{3-12}$heterocycle; —$C_{2-6}$alkenyl$C_{3-12}$heterocycle; and —$C_{2-6}$alkynyl$C_{3-12}$heterocycle;
any of which alkyl, alkenyl or alkynyl groups may optionally be substituted by one or more halogen and/or hydroxyl groups; and
any of which carbocycle and heterocycle may optionally be substituted by one or more methyl groups
R² represents a group selected for the list consisting of —$C_{1-6}$alkylNR¹⁰R¹¹ and —$C_{3-6}$cycloalkylimine optionally N substituted by R¹²;
and R⁹, R¹⁰, R¹¹ and R¹² independently represents hydrogen or lower alkyl.
R³ represents H; halogen; $C_{1-4}$alkyl; $C_{1-4}$haloalkyl; $C_{1-4}$alkoxy or $C_{1-4}$haloalkoxy;
R⁴ represents H; halogen; $C_{1-4}$alkyl; $C_{1-4}$haloalkyl; $C_{1-4}$alkoxy or $C_{1-4}$haloalkoxy;
R⁵ represents H; halogen; $C_{1-4}$alkyl; $C_{1-4}$haloalkyl; $C_{1-4}$alkoxy or $C_{1-4}$haloalkoxy;
and wherein any of the aforesaid carbocycle and heterocycle groups may optionally be substituted by one or more groups (for example 1, 2, or 3, in particular one or two groups) selected from the list consisting of:
(i) $C_{1-6}$alkyl, $C_{1-6}$alkenyl, $C_{1-6}$alkynyl (e.g. $C_{1-6}$alkyl);
(ii) $C_{1-6}$haloalkyl (e.g. $C_{1-6}$fluoroalkyl, such as —$CF_3$);
(iii) halogen (e.g. fluoro, chloro and bromo);
(iv) oxo;
(v) —S—$C_{1-6}$alkyl (e.g. methylthio), —S(O)—$C_{1-6}$alkyl and —S(O)$_2$—$C_{1-6}$alkyl;
(vi) cyano;
(vii) nitro;
(viii) amino (e.g. —$NH_2$, —NH$C_{1-6}$alkyl (e.g. —NHMe), —N($C_{1-6}$alkyl)$_2$ (e.g. dimethylamino-));
(ix) —OR¹³; wherein R¹³ may represent hydrogen, $C_{1-6}$alkyl, $C_{1-6}$alkenyl, $C_{1-6}$alkynyl or $C_{1-6}$haloalkyl (e.g. hydrogen or $C_{1-6}$alkyl (e.g. Me));
(x) —C(O)OR¹³; wherein R¹³ is as defined above;
(xi) —S(O)$_2$—$C_{3-12}$cycloalkyl;
(xii) —S(O)$_2$—$C_{1-6}$alkyl;
(xiii) —S(O)$_2$-amino;
(xiv) —C(O)-amino;
(xv) $C_{1-6}$alkanoyl (e.g. COMe); and
(xvi) $C_{1-6}$alkoxy$C_{1-6}$alkanoyl;

and wherein any of the aforesaid aryl and heteroaryl groups may optionally be substituted by one or more groups (for example 1, 2, or 3, in particular one or two groups) selected from the list consisting of:
(i) $C_{1-6}$alkyl, $C_{1-6}$alkenyl, $C_{1-6}$alkynyl (e.g. $C_{1-6}$alkyl);
(ii) $C_{1-6}$haloalkyl (e.g. $C_{1-6}$fluoroalkyl, such as —$CF_3$);
(iii) halogen (e.g. fluoro, chloro and bromo);

(iv) oxo;
(v) —S—$C_{1-6}$alkyl (e.g. methylthio), —S(O)—$C_{1-6}$alkyl and —S(O)$_2$—$C_{1-6}$alkyl;
(vi) cyano;
(vii) nitro;
(viii) amino (e.g. —NH$_2$, —NHC$_{1-6}$alkyl (e.g. —NHMe), —N(C$_{1-6}$alkyl)$_2$ (e.g. dimethylamino-)),
(ix) —OR$^{13}$; wherein R$^{13}$ may represent hydrogen, $C_{1-6}$alkyl, $C_{1-6}$alkenyl, $C_{1-6}$alkynyl or $C_{1-6}$haloalkyl (e.g. hydrogen or $C_{1-6}$alkyl (e.g. Me));
(ix) —C(O)OR$^{13}$; wherein R$^{13}$ is as defined above;
(x) —S(O)$_2$—$C_{3-12}$cycloalkyl;
(xi) —S(O)$_2$—$C_{1-6}$alkyl;
(xii) —S(O)$_2$-amino;
(xiii) —C(O)-amino;
(xiv) $C_{1-6}$alkanoyl (e.g. COMe);
(xv) $C_{1-6}$alkoxy$C_{1-6}$alkanoyl;
(xvi) —$C_{2-6}$alkenyloxy-;
(xvii) $C_{2-6}$alkynyloxy-;
(xviii) $C_{1-6}$alkoxy$C_{1-6}$alkyl-;
(xix) —C(O)N(C$_{1-6}$alkyl)$_2$, —C(O)NH$_2$ and —C(O)NH(C$_{1-6}$alkyl); and
(xx) $C_{3-12}$cycloalkyl;
or a pharmaceutically acceptable salt, polymorph or solvate thereof, including all tautomers and stereoisomers thereof.

DETAILED DESCRIPTION OF THE INVENTION

Figure 1:
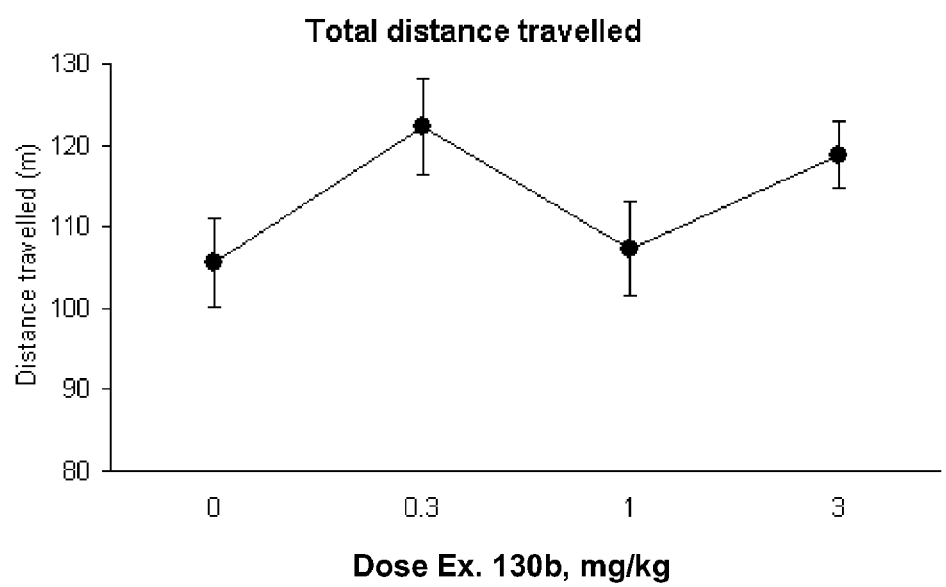
FIG. 1 Tetradic encounter test: Total distance travelled (upper panel) and distance travelled during first and during last 5 minutes of the test (lower panel) for animals treated with vehicle and with the different doses of Example 130b. Mean values±SEM.
Figure 1:
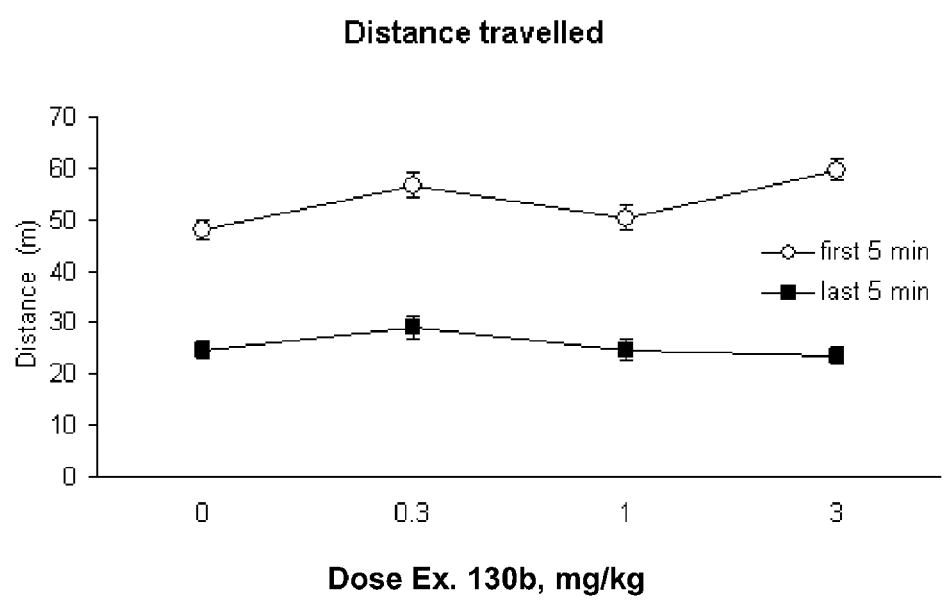
Figure 2:
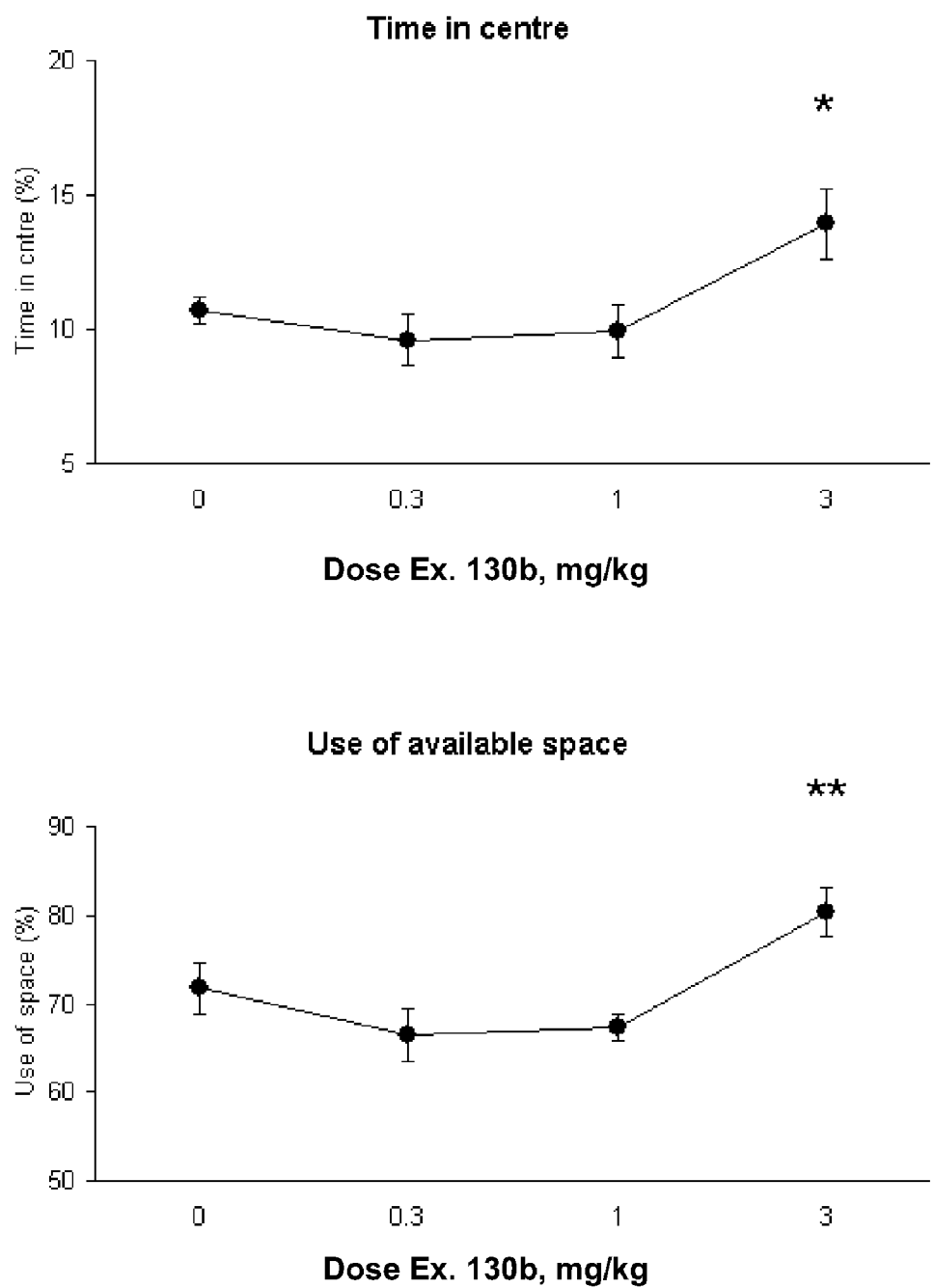
FIG. 2 Tetradic encounter test: Time spent in centre (upper panel) and use of available space (lower panel) for animals treated with vehicle and with the different doses of Example 130b. Mean values±SEM.
Figure 3:
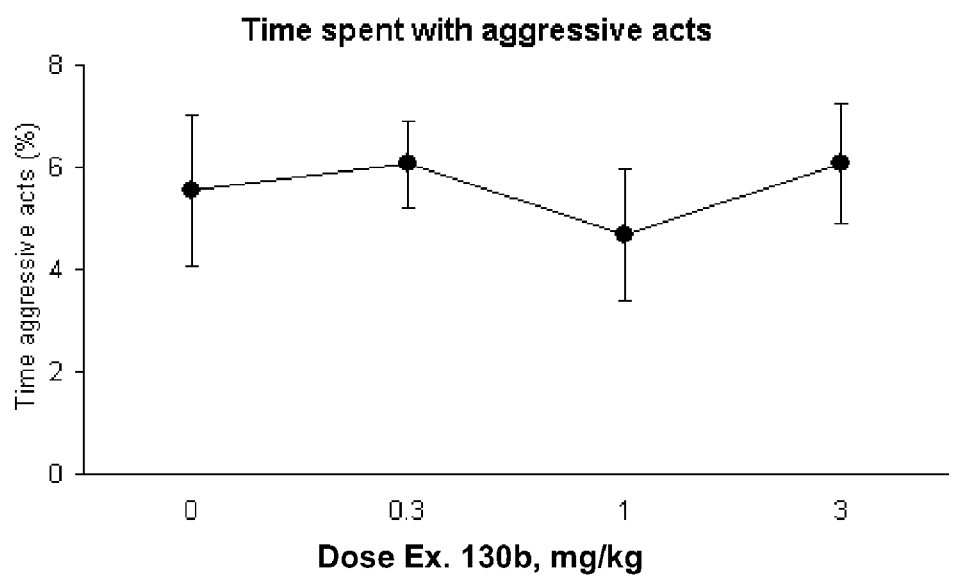
FIG. 3 Tetradic encounter test: Time spent with aggressive acts (upper panel) and time spent with defensive acts (lower panel) for animals treated with vehicle and with the different doses of Example 130b. Mean values±SEM.
Figure 3:
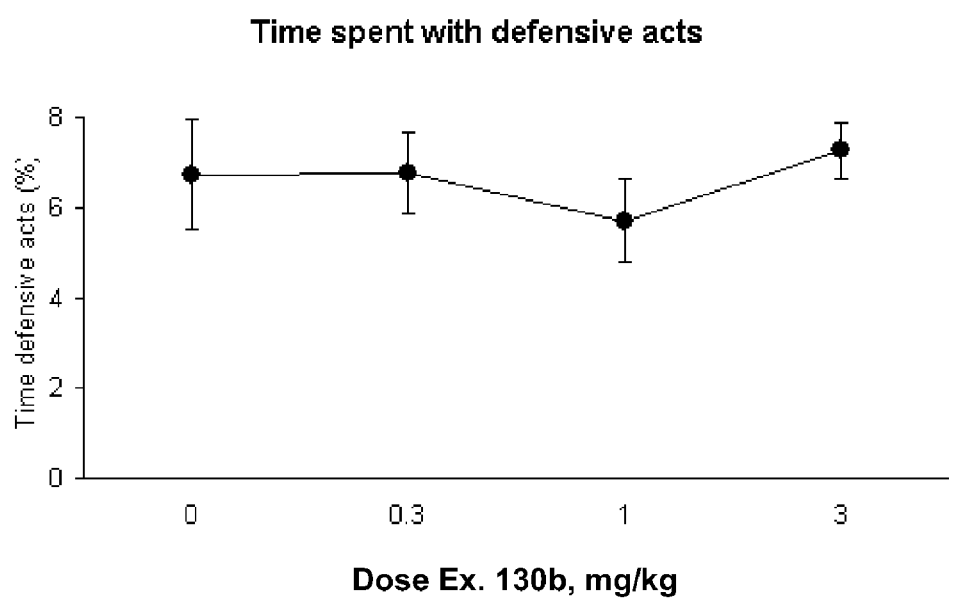
Figure 4:
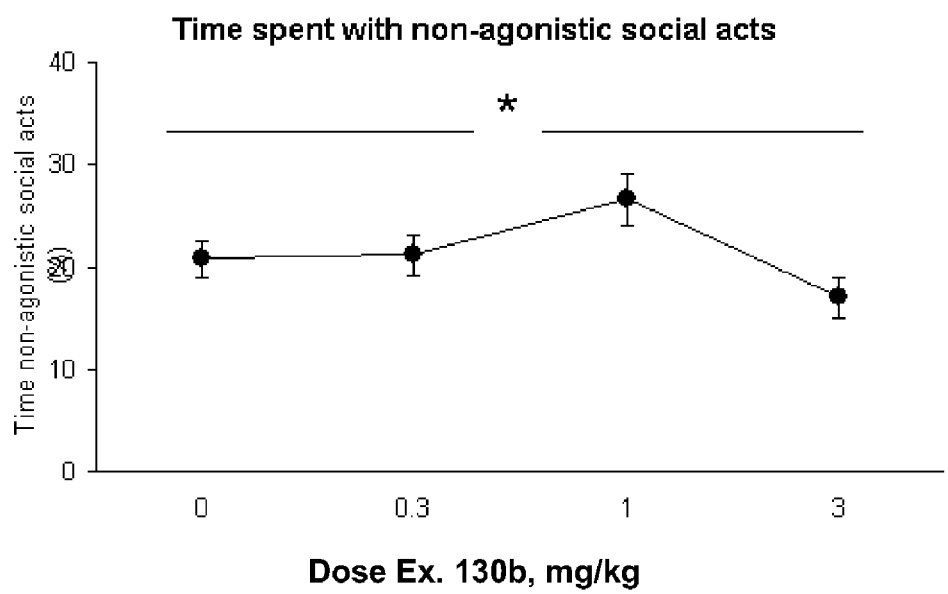
FIG. 4 Tetradic encounter test: Time spent with non-agonistic social acts (upper panel) and time mean distance to encounter mate (lower panel) for animals treated with vehicle and with the different doses of Example 130b. Mean values±SEM, Single comparison vs. vehicle: * $p<0.05$, ** $p<0.01$.
Figure 4:
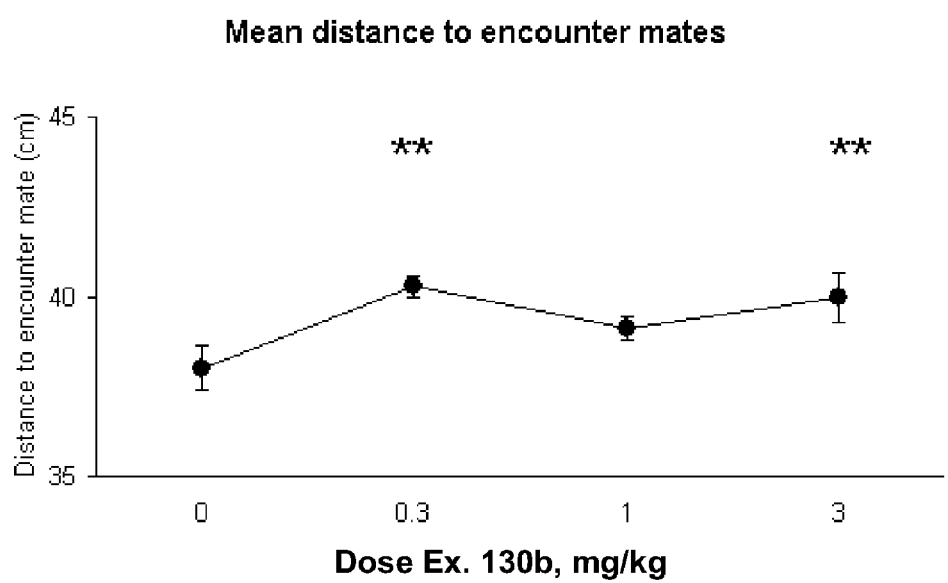

Typically carbocycle and heterocycle are not substituted or are substituted by at most one substituent (for example they are not substituted).

Typically aryl and heteroaryl are not substituted or are substituted by at most one substituent (for example they are substituted by one substituent).

Examples of substituted aryl groups include 4-fluoro-phenyl-, 3-fluoro-phenyl-, pentafluoro-phenyl-, 4-hydroxyphenyl-, 3-nitro-phenyl-, 4-(trifluoromethyl)-phenyl- and 4-anilinyl-, 2-chlorophenyl, 3-fluoro-5-trifluoromethylphenyl, 2-chloro-6-fluorophenyl, 4-bromophenyl, 3-fluorophenyl, 2-methylphenyl, 2,3-dichlorophenyl, 3-chlorophenyl, 2,4-difluorophenyl, 3,4-difluorophenyl, 4-fluorophenyl, 2,4-dimethoxyphenyl, 3,4-dimethoxyphenyl, 2-fluoro-5-bromophenyl, 2,4-dichlorophenyl, 4-methoxyphenyl, 2,6-difluorophenyl, 4-chlorophenyl, 4-methylphenyl, 2,5-difluorophenyl, 3-methoxyphenyl, 2,4-dimethylphenyl, 3,4-dichlorophenyl, 2-methoxyphenyl, 2-trifluoromethylphenyl, 3-trifluoromethylphenyl and 4-trifluoromethylphenyl.

Examples of substituted heteroaryl groups include N-methyl-2-pyrrolyl, 2-methyl-1-pyrrolyl and 3-methyl-2-pyrrolyl, 6F-(1H)-indol-3-yl-, 5-nitro-pyridin-2-yl, 5-methyl-furan-2-yl, 5-methyl-1H-pyrazol-4-yl, 5-methyl-pyrazin-2-yl.

Examples of substituted carbocycle groups include methylcyclohexyl. Generally carbocycle is not substituted.

Examples of substituted heterocycle groups include pyrrolidinone. Generally heterocycle is not substituted.

In one embodiment of the invention $R^1$ represents $C_{1-12}$alkyl (e.g. $C_{1-6}$alkyl). Particular $R^1$ $C_{1-12}$alkyl (e.g. $C_{1-6}$alkyl) groups of interest include ethyl and pentyl. Other $R^1$ $C_{1-12}$alkyl groups of interest include propyl, hexyl and nonyl for example ethyl-, n-propyl-, n-pentyl-, 3-methyl-butyl-, 2,2-dimethyl-propyl-, n-hexyl-, 3,3,-dimethyl-butyl- or 7-methyl-octyl-. When $R^1$ represents $C_{1-6}$ alkyl, further examples include methyl, n-propyl, isopropyl, butyl (e.g. n-butyl, iso-butyl, sec-butyl, tert-butyl), (e.g. n-pentyl), 2,2-dimethylpropyl and hexyl (e.g. n-hexyl).

Examples of substituted alkyl include ethan-2-ol-, propan-2-ol-, propan-3-ol-, pentan-5-ol- and hexan-6-ol-.

In another embodiment of the invention $R^1$ represents $C_{1-12}$alkenyl. Particular $R^1$ $C_{1-12}$alkenyl groups of interest include ethenyl and propenyl.

When $R^1$ represents $C_{1-12}$alkenyl, other examples include propen-2-yl, 2-methyl-propen-2-yl, buten-2-yl and buten-3-yl.

In another embodiment of the invention $R^1$ represents $C_{2-12}$alkynyl. Particular $R^1$ $C_{1-12}$alkynyl groups of interest include ethynyl and propynyl. When $R^1$ represents $C_{2-12}$alkynyl, other examples include propyn-2-yl, butyn-2-yl and butyn-3-yl.

In another embodiment of the invention $R^1$ represents aryl. A particular $R^1$ aryl groups of interest is phenyl which may optionally be substituted.

In another embodiment of the invention $R^1$ represents heteroaryl. Particular $R^1$ heteroaryl groups of interest include pyridinyl (e.g. 2-pyridinyl) which may optionally be substituted.

In another embodiment of the invention $R^1$ represents $C_{1-6}$alkylOC$_{1-6}$alkyl, for example $C_{1-6}$alkylOMe such as 2-(methoxy)-ethyl-. A further example in which alkyl is substituted is 1-(ethoxy)-ethan-2-ol-.

In another embodiment of the invention $R^1$ represents $C_{1-12}$alkylamino. Examples include 2-(ethylamine)-ethyl-, 2-(cyclohexylamine)-ethyl-, 2-(diisopropylamine)-ethyl- and 3-(cyclohexylamine)-propyl-.

In another embodiment of the invention $R^1$ represents -aryl-aryl, for example biphenyl.

In another embodiment of the invention $R^1$ represents —$C_{1-6}$alkylaryl (e.g. —$C_{1-4}$alkyl-aryl). Particular $C_{1-6}$alkylaryl groups of interest include methylaryl, ethylaryl, propylaryl and butylaryl especially methylaryl and ethylaryl. Most typically the aryl group is phenyl which may be optionally substituted. Typically the phenyl group is substituted by one or two substituents (in particular one substituent). For example substituents may be selected from $C_{1-6}$alkyl (e.g. methyl), halo (e.g. Br, Cl, F) $C_{1-6}$haloalkoxyl (e.g. trifluoromethoxy) and $C_{1-6}$alkoxy (e.g. methoxy). Other exemplary substituents include hydroxyl, and $C_{1-6}$haloalkyl (e.g. trifluoromethyl). Further exemplary substituents are selected from, ethyl, ethoxy, thiomethyl, thioethyl and trifluoromethyl.

One specific example of a $R^1$ $C_{1-6}$alkylaryl group is: benzyl-.

Further specific examples of -alkyl-aryl include 2-fluorobenzyl-, (3-fluoro-benzyl)-, (2-chloro-benzyl)-, (4-chlorobenzyl)-, (2-methyl-benzyl)-, (4-methyl-benzyl)-, (3-methoxy-benzyl)-, (2-ethoxy-benzyl)-, (3-trifluoromethylbenzyl)-, (2-trifluoromethyl-benzyl)-, (2,4-difluorobenzyl)-, (3,4-difluoro-benzyl)-, (2,5-difluoro-benzyl)-, (2,6-difluoro-benzyl)-, (2,3-dichloro-benzyl)-, (2,4-dichlorobenzyl)-, (3,4-dichloro-benzyl)- and (2-chloro-6-fluorobenzyl)-. Other examples include 2-phenyl-ethyl-, 3-phenylpropyl- and 4-phenyl-butyl-. Further specific examples of include: ((4-bromo-benzyl)-, (2-methoxy-benzyl)-, (4-methoxy-benzyl)-, (4-trifluoromethyl-benzyl)-, (2-trifluoromethoxy-benzyl)-, (4-trifluoromethoxy-benzyl)-, (5-bromo-2-fluoro-benzyl)-, (2-fluoro-3-trifluoromethylbenzyl)-, (3-fluoro-5-trifluoromethyl-benzyl)-, (2,4-dimethoxy-benzyl)-, (3,4-dimethoxy-benzyl)-, (4-hydroxyphenyl)-ethyl-, (1-phenyl)-ethan-2-ol-, 2-(2-fluoro-phenyl)-ethyl-, 2-(4-fluoro-phenyl)-ethyl-, 2-(2-chloro-phenyl)-ethyl-, 2-(3-chloro-phenyl)-ethyl-, 2-(4-chloro-phenyl)-ethyl-, 2-(4-bromo-phenyl)-ethyl-, 2-(4-methoxy-phenyl)-ethyl- and 2-(2,2-dichloro-phenyl)-ethyl-. Further examples include 2,6-dichloro-benzyl, 2-chloro-4-fluoro-benzyl, 4-fluoro-benzyl and 5-bromo-2-fluoro-benzyl.

In another embodiment of the invention $R^1$ represents $C_{1-6}$alkylaryl-aryl, for example (biphen-4-yl)-methyl-.

In another embodiment of the invention $R^1$ represents $C_{1-6}$alkyl(aryl)$_2$. Examples include 2,2-diphenyl-ethyl- and 3,3-diphenyl-propyl-.

In another embodiment of the invention $R^1$ represents $C_{1-6}$alkyl(heteroaryl)$_2$ e.g. ethyl(2,2-heteroaryl)$_2$. Examples include 2,2-dipyridinyl-ethyl-, 3,3-dipyridinyl-propyl- and 2,2-bifuranyl-ethyl.

In another embodiment of the invention $R^1$ represents $C_{2-6}$alkenylaryl. Examples include ethenylaryl e.g. ethenylphenyl which phenyl may optionally be substituted.

In another embodiment of the invention $R^1$ represents $C_{2-6}$alkynylaryl. Examples include ethynylaryl e.g. ethynylphenyl which phenyl may optionally be substituted.

In another embodiment of the invention $R^1$ represents $C_{1-6}$alkylaryl-heteroaryl, for example (2-pyridinyl)-4-phenyl-2-ethyl.

In another embodiment of the invention $R^1$ represents $C_{1-6}$alkylheteroaryl-aryl, for example 4-phenyl-2-pyridinyl-2-ethyl.

In another embodiment of the invention $R^1$ represents $C_{1-6}$alkylheteroaryl-heteroaryl, for example 4-(2-pyridinyl)-2-pyridinyl-2-ethyl.

In another embodiment of the invention $R^1$ represents $C_{1-6}$alkyl(heteroaryl)(aryl), for example 2-phenyl-2-pyridinyl-ethyl.

In another embodiment of the invention $R^1$ represents $C_{1-6}$alkylheteroaryl (e.g. —$C_{1-4}$alkyl-heteroaryl). Particular $C_{1-6}$alkylheteroaryl groups of interest include methylheteroaryl and ethylheteroaryl. Another $C_{1-6}$alkylheteroaryl groups of interest is propylheteroaryl. For example, $C_{1-6}$alkylheteroaryl groups of interest include $C_{1-6}$alkylbenzodioxolyl-, $C_{1-6}$alkylfuryl-$C_{1-6}$alkylthiophenyl-, $C_{1-6}$alkylpyridinyl-, $C_{1-6}$alkylpyrazinyl-, $C_{1-6}$alkylpyrimidinyl-, $C_{1-6}$alkylpyridazinyl-, $C_{1-6}$alkylisooxazolyl-, $C_{1-6}$alkylindolyl- and $C_{1-6}$alkylimidazolyl-, which heteroaryl groups may be optionally substituted. When $R^1$ represents $C_{1-6}$alkylheteroaryl, suitably the heteroaryl group is substituted by one or two substituents (in particular one substituent), for example selected from halo, $C_{1-6}$alkyl, $C_{1-6}$alkoxy, $C_{1-6}$thioalkyl, $C_{1-6}$haloalkyl and $C_{1-6}$haloalkoxy, particularly halo and $C_{1-6}$alkyl. When a heteroaryl group is substituted by $C_{1-6}$alkyl, suitably the $C_{1-6}$alkyl group is methyl or ethyl, particularly methyl. When a heteroaryl group is substituted by $C_{1-6}$alkoxy, suitably the $C_{1-6}$alkoxygroup is methoxy or ethoxy, particularly methoxy. When a heteroaryl group is substituted by $C_{1-6}$thioalkyl, suitably the $C_{1-6}$thioalkyl group is thiomethyl or thioethyl particularly thiomethyl. When a heteroaryl group is substituted by $C_{1-6}$haloalkyl, suitably the $C_{1-6}$haloalkyl group is a $C_{1-6}$fluoroalkyl group e.g. trifluoromethyl. When a heteroaryl group is substituted by $C_{1-6}$haloalkoxy, suitably the $C_{1-6}$haloalkoxygroup is a $C_{1-6}$fluoroalkoxy group e.g. trifluoromethoxy. When a heteroaryl group is substituted by halo, suitably the halo group is fluoro, chloro or bromo, particularly fluoro or chloro.

Specific examples of unsubstituted $R^1$ $C_{1-6}$alkylheteroaryl groups include: (thiophen-3-yl)-methyl-, (pyridin-2-yl)-methyl-, (pyridin-3-yl)-methyl-, (pyridin-4-yl)-methyl-. Other specific examples of $C_{1-6}$alkylheteroaryl include 3-(imidazol-1-yl)-propyl-2-(pyridin-2-yl)-ethyl-, 2-(pyridin-3-yl)-ethyl-, (benzo[1,3]dioxol-5-yl)-methyl-, 2-(1H-indol-3-yl)-ethyl. Specific examples of substituted $R^1$ $C_{1-6}$alkylheteroaryl groups include: (5-methyl-furan-2-yl)-methyl-, (1-methyl-1H-pyrazol-4-yl)-methyl-, 3-(5-methyl-1H-pyrazol-4-yl)-propyl-, (5-methyl-isoxazol-3-yl)-methyl-, (5-methyl-pyrazin-2-yl)-methyl-, 2-(6-fluoro-1H-indol-3-yl)-ethyl-2-(6-chloro-1H-indol-3-yl)-ethyl- and (6-methyl-1H-indol-3-yl)-ethyl. Further examples include (1-methyl-pyrrol-2-yl)-methyl-, (5-methyl-furan-2-yl)-methyl-, (benzo-[1,3]dioxol-4-yl)-methyl-, (2,3-dihydro-benzo[1,4]dioxin-4-yl)-methyl-, furan-2-yl-methyl-, furan-3-yl-methyl-, pyrrol-2-yl-methyl-, pyrrol-3-yl-methyl- and thiophen-2-yl-methyl-.

In another embodiment of the invention $R^1$ represents $C_{2-6}$alkenylheteroaryl, for example ethenylheteroaryl.

In another embodiment of the invention $R^1$ represents $C_{2-6}$alkynylheteroaryl, for example ethynylheteroaryl.

In another embodiment of the invention $R^1$ represents $C_{3-12}$carbocycle, for example cyclohexyl. When $R^1$ represents carbocycle, other examples include cyclopentyl, and cyclohexenyl (e.g. cyclohexen-2-yl, cyclohexen-3-yl). Examples of substituted carbocycle include methylcyclopentyl-, methylcyclohexyl- (e.g. 2-methyl-cyclohexyl-, 3-methyl-cyclohexyl, 4-methyl-cyclohexyl) and methylcyclohexenyl.

In another embodiment of the invention $R^1$ represents $C_{3-12}$heterocycle, for example piperidinyl.

In another embodiment of the invention $R^1$ represents $C_{1-6}$alkyl$C_{3-12}$carbocycle (e.g. —$C_{1-4}$alkyl$C_{3-12}$carbocycle). When $R^1$ represents $C_{1-6}$alkyl$C_{3-12}$carbocycle, suitably the $C_{3-12}$carbocycle group is unsubstituted or substituted by one or two substituents (in particular one substituent). Particular $C_{1-6}$alkyl$C_{3-12}$carbocycle groups of interest include methyl$C_{3-12}$carbocycle and ethyl$C_{3-12}$carbocycle (e.g. -methyl-cyclopentyl, -methyl-cyclohexyl), which carbocycles may be optionally substituted. Examples of substituted -alkyl-$C_{3-12}$carbocycle include methylcyclopentyl-methyl- and methylcyclohexyl-methyl-. Further particular $C_{1-6}$alkyl$C_{3-12}$carbocycle groups of interest include $C_{1-6}$alkyl$C_{3-12}$cycloalkyl, $C_{1-6}$alkyl$C_{3-12}$cycloalkenyl and $C_{1-6}$alkyl$C_{3-12}$cycloalkynyl, which cycloalkyl, cycloalkenyl and cycloalkynyl groups may be optionally substituted. An example of $C_{1-6}$alkyl$C_{3-12}$cycloalkenyl is -methyl-cyclohexenyl. Specific examples of unsubstituted $R^1$ $C_{1-6}$alkyl$C_{3-12}$carbocycle groups include (adamantan-1-yl)-methyl- and 2-(cyclohex-1-enyl)-ethyl-.

In another embodiment of the invention $R^1$ represents $C_{2-6}$alkenyl$C_{3-12}$carbocycle, for example ethenyl$C_{3-12}$carbocycle, $C_{2-6}$alkenylcyclohexyl or $C_{2-6}$alkenylcyclohexenyl.

In another embodiment of the invention $R^1$ represents $C_{2-6}$alkynyl$C_{3-12}$carbocycle, for example ethynyl$C_{3-12}$carbocycle, $C_{2-6}$alkynylcyclohexyl or $C_{2-6}$alkynylcyclohexenyl.

In another embodiment of the invention $R^1$ represents $C_{1-6}$alkyl$NR^9$aryl, for example ethyl$NR^9$aryl or $C_{1-6}$alkyl$NR^9$phenyl which phenyl may optionally be substituted. A specific example is 2-phenylamine-ethyl.

In another embodiment of the invention $R^1$ represents $C_{1-6}$alkyl$NR^9$heteroaryl, for example ethyl$NR^9$heteroaryl or $C_{1-6}$alkyl$NR^9$pyridinyl which pyridinyl may optionally be substituted. A specific example is 2-(nitropyridinylamine)-ethyl e.g. 2-(5-nitro-pyridin2-yl)-ethyl or 2-(pyridin-2-yl-amine)-ethyl-.

In another embodiment, $R^1$ represents $C_{1-6}$alkylO$C_{3-12}$carbocycle, for example ethylO$C_{3-12}$carbocycle or $C_{1-6}$alkylO$C_{3-8}$cycloalkyl.

In another embodiment, $R^1$ represents $C_{1-6}$alkyl$NR^9$$C_{3-12}$carbocycle, for example ethyl$NR^9$$C_{3-12}$carbocycle or $C_{1-6}$alkyl$NR^9$$C_{3-8}$cycloalkyl. A particular example is ethyl-NHcyclohexyl.

In another embodiment of the invention $R^1$ represents $C_{1-6}$alkylOaryl, for example $C_{1-6}$alkylOphenyl which phenyl may optionally be substituted or methyl-O-aryl. Specific examples include 2-phenoxyethyl.

In another embodiment of the invention $R^1$ represents $C_{1-6}$alkylOheteroaryl, for example $C_{1-6}$alkylOpyridinyl which pyridinyl may optionally be substituted or methyl-O-heteroaryl. Specific examples include 4-pyridinyloxyethyl.

In another embodiment of the invention $R^1$ represents $C_{1-6}$alkyl$C_{3-12}$heterocycle (e.g. $C_{1-4}$alkyl$C_{3-12}$heterocycle), which heterocycle may be optionally substituted. Particular $C_{1-6}$alkyl$C_{3-12}$heterocycle groups of interest include methyl$C_{3-12}$heterocycle, ethyl$C_{3-12}$heterocycle and propyl$C_{3-12}$heterocycle. Further specific $C_{1-6}$alkyl$C_{3-12}$heterocycle groups of interest include $C_{1-6}$alkyltetrahydrofuranyl (e.g. -methyl-tetrahydrofuranyl) and $C_{1-6}$alkylpyrrolidinyl (e.g. -methyl-pyrrolidinyl). Another example is $C_{1-6}$alkylpiperidinyl (e.g. -methyl-piperidinyl). Another example is $C_{1-6}$alkylmorpholinyl (e.g. -methyl-morpholinyl). When $R^1$ represents $C_{1-6}$alkyl$C_{3-12}$heterocycle, suitably the $C_{1-6}$alkyl$C_{3-12}$heterocycle group may be substituted by one or two substituents (in particular one substituent), for example selected from oxo and lower alkyl e.g. methyl. Specific examples of unsubstituted $C_{1-6}$alkyl$C_{3-12}$heterocycle include (tetrahydrofuran-2-yl)-methyl-, 2-(pyrrolidin-1-yl)-ethyl-, 2-(piperidin-1-yl)-ethyl- and 2-(morpholin-4-yl)-ethyl-. Specific examples of substituted $C_{1-6}$alkyl$C_{3-12}$heterocycle include 3-(2-oxo-pyrrolidin-1-yl)-propyl-.

In another embodiment of the invention $R^1$ represents $C_{2-6}$alkenyl$C_{3-12}$heterocycle, for example ethenyl$C_{3-12}$heterocycle.

In another embodiment of the invention $R^1$ represents $C_{2-6}$alkynyl$C_{3-12}$heterocycle, for example ethynyl$C_{3-12}$heterocycle.

When $R^1$ represents alkyl substituted by halogen (i.e. haloalkyl), examples include fluoromethyl, trifluoromethyl, fluoroethyl and fluoropropyl.

When $R^2$ represents —$C_{1-6}$alkyl-$NR^{10}R^{11}$, examples include amino-methyl-, 1-amino-ethyl-, 2-amino-ethyl-, 1-amino-propyl-, 2-amino-propyl- and 3-amino-propyl-.

When $R^2$ represents $C_{3-6}$cycloalkylimine optionally N-substituted by $R^{12}$, examples include azetidinyl (e.g. 3-azetidinyl) and pyrrolidinyl.

When $R^3$ represents Hal, examples include F, Cl and Br.
When $R^3$ represents $C_{1-4}$alkyl, examples include methyl, ethyl, n-propyl, iso-propyl and butyl.
When $R^3$ represents $C_{1-4}$haloalkyl, examples include fluoromethyl and trifluoromethyl.
When $R^3$ represents $C_{1-4}$alkoxy, examples include methoxy, ethoxy and propoxy.
When $R^3$ represents $C_{1-4}$haloalkoxy, examples include fluoromethoxy and trifluoromethoxy.
When $R^4$ represents Hal, examples include F, Cl and Br.
When $R^4$ represents $C_{1-4}$alkyl, examples include methyl, ethyl, n-propyl, iso-propyl and butyl.
When $R^4$ represents $C_{1-4}$haloalkyl, examples include fluoromethyl and trifluoromethyl.
When $R^4$ represents $C_{1-4}$alkoxy, examples include methoxy, ethoxy and propoxy.
When $R^4$ represents $C_{1-4}$haloalkoxy, examples include fluoromethoxy and trifluoromethoxy.
When $R^5$ represents Hal, examples include F, Cl and Br.
When $R^5$ represents $C_{1-4}$alkyl, examples include methyl, ethyl, n-propyl, iso-propyl and butyl.
When $R^5$ represents $C_{1-4}$haloalkyl, examples include fluoromethyl and trifluoromethyl.
When $R^5$ represents $C_{1-4}$alkoxy, examples include methoxy, ethoxy and propoxy.
When $R^5$ represents $C_{1-4}$haloalkoxy, examples include fluoromethoxy and trifluoromethoxy.

More Suitable Embodiments

In one aspect of the invention (hereafter "compounds of formula Ia"), suitable compounds are compounds of formula (I) wherein:
$R^1$ represents $C_{1-12}$alkyl; $C_{2-12}$alkenyl, wherein the double bond is not at the C-1 position;
  $C_{2-12}$alkynyl, wherein the triple bond is not at the C-1 position; $C_{3-12}$carbocycle; -which may optionally be substituted by one or more methyl groups; $C_{1-6}$alkyl-$C_{3-12}$carbocycle, in which the carbocycle ring may optionally be substituted by one or more methyl groups; $C_{1-6}$haloalkyl; —$C_{1-6}$alkyl-aryl;
  —$C_{1-6}$alkyl-$C_{3-12}$heterocycle in which the heterocycle ring may optionally be substituted by one or more methyl groups; or —$C_{1-6}$alkyl-heteroaryl;
$R^2$ represents —$C_{1-4}$alkyl-$NH_2$; azetidin-2-yl; azetidin-3-yl; pyrrolidin-2-yl or pyrrolidin-3-yl;
$R^3$ represents H; halogen (e.g. F, Cl, Br); $C_{1-4}$alkyl; $C_{1-4}$haloalkyl (e.g. $C_{1-4}$fluoroalkyl); $C_{1-4}$alkoxy or $C_{1-4}$haloalkoxy (e.g. $C_{1-4}$fluoroalkoxy);
$R^4$ represents H; halogen (e.g. F, Cl, Br); $C_{1-4}$alkyl; $C_{1-4}$haloalkyl (e.g. $C_{1-4}$fluoroalkyl); $C_{1-4}$alkoxy or $C_{1-4}$haloalkoxy (e.g. $C_{1-4}$fluoroalkoxy);
$R^5$ represents H; halogen (e.g. F, Cl, Br); $C_{1-4}$alkyl; $C_{1-4}$haloalkyl (e.g. $C_{1-4}$fluoroalkyl); $C_{1-4}$alkoxy or $C_{1-4}$haloalkoxy (e.g. $C_{1-4}$fluoroalkoxy);

wherein any of the forementioned aryl and heteroaryl groups may optionally be substituted by one or more (e.g. 1, 2 or 3, suitably 1 or 2) substituent groups selected from $C_{1-12}$alkyl, $C_{2-12}$alkenyl, $C_{2-12}$alkynyl, $C_{1-6}$haloalkyl (e.g. $C_{1-6}$fluoroalkyl), -thio$C_{1-6}$alkyl (e.g. -thiomethyl), —$SO_2C_{1-6}$alkyl (e.g. $SO_2Me$), $C_{1-6}$alkoxy- (e.g. OMe), $C_{3-12}$cycloalkyl, —$SO_2C_{3-12}$cycloalkyl, $C_{2-6}$alkenyloxy-, $C_{2-6}$alkynyloxy-, —C(O)—$C_{1-6}$alkyl (e.g. COMe), $C_{1-6}$alkoxy $C_{1-6}$alkyl-, nitro, halogen (e.g. fluoro, chloro and bromo), cyano, hydroxyl, oxo, —C(O)OH, —C(O)O$C_{1-6}$alkyl (e.g. —C(O)OMe), —$NH_2$, —NH$C_{1-6}$alkyl (e.g. —NHMe), —N($C_{1-6}$alkyl)$_2$ (e.g. —$NMe_2$), —C(O)N($C_{1-6}$alkyl)$_2$, —C(O)$NH_2$ and —C(O)NH($C_{1-6}$alkyl). More typically, substituents will be selected from $C_{1-12}$alkyl (e.g. Me), $C_{1-6}$fluoroalkyl (e.g. $CF_3$), $C_{1-6}$alkoxy (e.g. OMe), halogen (e.g. F, Cl, Br) and hydroxy;
or a pharmaceutically acceptable salt, polymorph or solvate thereof, including all tautomers and stereoisomers thereof.

Examples of substituted aryl groups include fluorophenyl- (e.g. 4-fluoro-phenyl- or 3-fluoro-phenyl-), pentafluoro-phenyl-, 4-hydroxyphenyl-, 3-nitro-phenyl-, 4-(trifluoromethyl)-phenyl- and 4-anilinyl-groups. Exemplary substituted monocyclic heteroaryl groups include methylfuranyl-.

Exemplary substituted bicyclic heteroaryl groups include chromen-4-one, chromen-2-one and methylbenzothiophenyl.

When $R^1$ represents —$C_{1-6}$alkyl-aryl, aryl is suitably optionally substituted phenyl. When $R^1$ represents —$C_{1-6}$alkyl-aryl, alkyl is suitably —$CH_2$. More suitably, $R^1$ represents -$CH_2$-phenyl wherein phenyl is optionally substituted by one or more e.g. one or two substituents. Suitable optional substituents of aryl are selected from F, Cl, Br, methyl, methoxy, ethoxy, trifluoromethyl and trifluoromethoxy. Examples include 4-fluoro-benzyl, 3-methoxy-benzyl, benzyl, 3,4-difluoro-benzyl, 2-ethoxy-benzyl, 2-trifluoromethoxy-benzyl, 2-fluoro-benzyl, 2-chloro-benzyl, 3-trifluoromethyl-benzyl, 2,4-difluoro-benzyl, 3-fluoro-benzyl and 2-methyl-benzyl.

When $R^1$ represents —$C_{1-6}$alkyl-heteroaryl, heteroaryl is suitably monocyclic. When $R^1$ represents —$C_{1-6}$alkyl-heteroaryl, alkyl is suitably —$CH_2$. Heteroaryl is suitably an optionally substituted five or six-membered ring containing one atom selected from N, S and O and is optionally substituted. Most suitably, heteroaryl is unsubstituted or is substituted by methyl.

Most suitably $R^1$ represents $C_{1-12}$alkyl, —$C_{1-6}$alkyl-aryl or —$C_{1-6}$alkyl-heteroaryl, particularly —$C_{1-6}$alkyl-aryl or —$C_{1-6}$alkyl-heteroaryl, wherein any of aryl and heteroaryl are optionally substituted.

When $R^2$ represents —$C_{1-4}$alkyl-$NH_2$, $R^2$ suitably represents amino-methyl-, 1-amino-ethyl-, 2-amino-ethyl or 3-amino propyl.

Most suitably, $R^2$ represents amino-methyl-, 1-amino-ethyl-, 2-amino-ethyl-, 3-amino-propyl- or azetidin-3-yl, especially amino-methyl-.

When $R^3$ represents $C_{1-4}$alkyl, $R^3$ suitably represents methyl.

When $R^3$ represents alkoxy, $R^3$ suitably represents methoxy.

Most suitably $R^3$ represents halogen or methyl, particularly halogen. More suitably, $R^3$ represents Cl or F.

Most suitably $R^3$ represents Cl.

When $R^4$ represents $C_{1-4}$alkyl, $R^4$ suitably represents methyl.

When $R^4$ represents alkoxy, $R^4$ suitably represents methoxy.

Most suitably $R^4$ represents halogen, methyl or methoxy, particularly halogen. More suitably, $R^4$ represents Cl or F. Most suitably $R^4$ represents Cl.

When $R^5$ represents $C_{1-4}$alkyl, $R^5$ suitably represents methyl.

When $R^5$ represents alkoxy, $R^5$ suitably represents methoxy.

When $R^5$ represents Hal, $R^5$ suitably represents Cl or F. More suitably $R^5$ represents Cl.

Most suitably $R^5$ represents H.

Further Suitable Embodiments

In another aspect of the invention (hereafter "compounds of formula Ib"), suitable compounds are compounds of formula (I) wherein:

$R^1$ represents a group selected from the list consisting of:
  $C_{1-12}$alkyl; —$C_{1-6}$alkylO$C_{1-6}$alkyl; —$C_{2-12}$alkenyl; —$C_{2-12}$alkynyl; —$C_{1-12}$alkylamino; aryl; aryl-aryl; —$C_{1-6}$alkylaryl; —$C_{1-6}$alkylaryl-aryl; —$C_{1-6}$alkylaryl-heteroaryl; —$C_{1-6}$alkylheteroaryl-aryl; —$C_{1-6}$alkylheteroaryl-heteroaryl; —$C_{1-6}$alkyl(aryl)$_2$; —$C_{1-6}$alkyl(heteroaryl)$_2$; —$C_{1-6}$alkyl(heteroaryl)(aryl); —$C_{1-6}$alkylOaryl; —$C_{1-6}$alkylNR$^9$aryl; —$C_{2-6}$alkenylaryl; —$C_{2-6}$alkynylaryl; heteroaryl; —$C_{1-6}$alkylheteroaryl; —$C_{1-6}$alkyl(heteroaryl)$_2$; —$C_{1-6}$alkylOheteroaryl; —$C_{1-6}$alkylNR$^9$heteroaryl; —$C_{2-6}$alkenylheteroaryl; —$C_{2-6}$alkynylheteroaryl; $C_{3-12}$carbocycle; —$C_{1-6}$alkyl$C_{3-12}$carbocycle; —$C_{1-6}$alkylO$C_{3-12}$carbocycle; —$C_{1-6}$alkylNR$^9$$C_{3-12}$carbocycle; —$C_{2-6}$alkenyl$C_{3-12}$carbocycle; —$C_{2-6}$alkynyl$C_{3-12}$carbocycle; —$C_{3-12}$heterocycle; —$C_{1-6}$alkyl$C_{3-12}$heterocycle; —$C_{2-6}$alkenyl$C_{3-12}$heterocycle; and —$C_{2-6}$alkynyl$C_{3-12}$heterocycle;

any of which alkyl, alkenyl or alkynyl groups may optionally be substituted by one or more halogen and/or hydroxyl groups;

$R^2$ represents a group selected from the list consisting of:
  $C_{1-6}$alkylNR$^{10}$R$^{11}$ and $C_{3-6}$cycloalkylimine optionally N substituted by R$^{12}$;
  and R$^9$, R$^{10}$, R$^{11}$ and R$^{12}$ independently represents hydrogen or $C_{1-4}$alkyl.

$R^3$ represents Cl;
$R^4$ represents Cl and
$R^5$ represents H;

wherein any of the aforementioned aryl, heteroaryl, carbocycle and heterocycle groups may optionally be substituted by one or more (for example 1, 2, or 3, in particular one or two) groups selected from the list consisting of:
  (i) $C_{1-6}$alkyl, $C_{1-6}$alkenyl, $C_{1-6}$alkynyl (e.g. $C_{1-6}$alkyl);
  (ii) $C_{1-6}$haloalkyl (e.g. $C_{1-6}$fluoroalkyl, such as —CF$_3$);
  (iii) halogen (e.g. fluoro, chloro and bromo);
  (iv) oxo
  (v) —S—$C_{1-6}$alkyl (e.g. methylthio), —S(O)—$C_{1-6}$alkyl and —S(O)$_2$—$C_{1-6}$alkyl;
  (vi) cyano;
  (vii) nitro;
  (viii) amino (e.g. —NH$_2$)
  (ix) —OR$^{13}$; wherein R$^{13}$ may represent hydrogen, $C_{1-6}$alkyl, $C_{1-6}$alkenyl, $C_{1-6}$alkynyl or $C_{1-6}$haloalkyl (e.g. hydrogen or $C_{1-6}$alkyl (e.g. Me));
  (ix) —C(O)OR$^{13}$; wherein R$^{13}$ is as defined above;
  (x) —S(O)$_2$—$C_{3-12}$cycloalkyl;
  (xi) —S(O)$_2$—$C_{1-6}$alkyl;
  (xii) —S(O)$_2$-amino;
  (xiii) —C(O)-amino;
  (xiv) $C_{1-6}$alkanoyl (e.g. COMe);
  (xv) $C_{1-6}$alkoxy$C_{1-6}$alkanoyl;

or a pharmaceutically acceptable salt, polymorph or solvate thereof, including all tautomers and stereoisomers thereof.

When aryl and heteroaryl are substituted, more suitable substituent groups are selected from $C_{1-6}$alkyl, $C_{1-6}$fluoroalkyl, halogen, nitro, amino, hydroxyl and $C_{1-6}$alkoxy.

When carbocycle and heterocycle are substituted, more suitable substituent groups are selected from $C_{1-6}$alkyl, $C_{1-6}$fluoroalkyl, halogen, nitro, amino, hydroxyl, $C_{1-6}$alkoxy and oxo. In one embodiment, carbocycle and heterocycle are unsubstituted. In another embodiment, carbocycle and heterocycle are substituted by one or more methyl groups.

Suitably $R^1$ represents a group selected from —$C_{1-12}$alkyl, —$C_{1-6}$alkylO$C_{1-6}$alkyl, $C_{2-12}$alkenyl or $C_{2-12}$alkynyl, any of which alkyl, alkenyl or alkynyl groups may optionally be substituted by one or more halogen (e.g. fluorine) groups or a hydroxyl group; —$C_{1-12}$alkylamino, aryl, -aryl-aryl, —$C_{1-6}$alkylaryl, —$C_{1-6}$alkylaryl-aryl, —$C_{1-6}$alkylaryl-heteroaryl, —$C_{1-6}$alkylheteroaryl-aryl, —$C_{1-6}$alkylheteroaryl-heteroaryl, —$C_{1-6}$alkyl(aryl)$_2$, —$C_{1-6}$alkyl(heteroaryl)$_2$, —$C_{1-6}$alkyl(heteroaryl)(aryl), —$C_{1-6}$alkylOaryl, —$C_{1-6}$alkylNR$^9$aryl, —$C_{2-6}$alkenylaryl, —$C_{2-6}$alkynylaryl, heteroaryl, —$C_{1-6}$alkylheteroaryl, —$C_{1-6}$alkyl(heteroaryl)$_2$, —$C_{1-6}$alkylOheteroaryl, —$C_{1-6}$alkylNR$^9$heteroaryl, —$C_{2-6}$alkenylheteroaryl, —$C_{2-6}$alkynylheteroaryl, —$C_{3-12}$carbocycle, —$C_{1-6}$alkyl$C_{3-12}$carbocycle, —$C_{1-6}$alkylO$C_{3-12}$carbocycle, —$C_{1-6}$alkylNR$^9$$C_{3-12}$carbocycle, —$C_{2-6}$alkenyl$C_{3-12}$carbocycle, —$C_{2-6}$alkynyl$C_{3-12}$carbocycle, —$C_{3-12}$heterocycle, —$C_{1-6}$alkyl$C_{3-12}$heterocycle, —$C_{2-6}$alkenyl$C_{3-12}$heterocycle, and —$C_{2-6}$alkynyl$C_{3-12}$heterocycle; wherein any of the aforesaid aryl, heteroaryl, carbocycle and heterocyle groups are optionally substituted.

Most suitably $R^1$ represents a group selected from $C_{1-12}$alkyl optionally substituted by one or more halogen groups or by a hydroxyl group, —$C_{1-6}$alkyl (optionally substituted by hydroxy)-O$C_{1-6}$alkyl, —$C_{1-12}$alkylamino, aryl, —$C_{1-6}$alkylaryl, —$C_{1-6}$alkylaryl-aryl, —$C_{1-6}$alkyl(aryl)$_2$, —$C_{1-6}$alkylOaryl, —$C_{1-6}$alkylNR$^9$aryl, —$C_{1-6}$alkylNR$^9$heteroaryl, -heteroaryl, —$C_{1-6}$alkylheteroaryl, —$C_{3-12}$carbocycle, —$C_{1-6}$alkyl$C_{3-12}$carbocycle, —$C_{1-6}$alkylO$C_{3-12}$carbocycle, —$C_{1-6}$alkylNR$^9$$C_{3-12}$carbocycle, —$C_{3-12}$heterocycle and —$C_{1-6}$alkyl$C_{3-12}$heterocycle; wherein any of the aforesaid aryl, heteroaryl, carbocycle and heterocyle groups are optionally substituted.

Preferably $R^1$ represents a group selected from $C_{1-12}$alkyl optionally substituted by hydroxy; —$C_{1-6}$alkylaryl (e.g. $C_{1-2}$alkylaryl); —$C_{1-6}$alkylheteroaryl (e.g. $C_{1-2}$alkylheteroaryl); —$C_{1-6}$alkylcarbocycle (e.g. $C_{1-2}$alkylcarbocycle), —$C_{1-12}$alkylamino, —$C_{1-6}$alkyl(aryl)$_2$ (e.g. $C_{1-3}$alkyl(aryl)$_2$), —$C_{1-6}$alkylNR$^9$heteroaryl, —$C_{1-6}$alkylNR$^9$$C_{3-12}$carbocycle, and —$C_{1-6}$alkylheterocycle (e.g. $C_{1-2}$alkylheterocycle). More preferably aryl represents optionally substituted phenyl; heteroaryl represents optionally substituted pyridinyl, furanyl, pyrazolyl, pyrazinyl, indolyl or imidazolyl; carbocycle represents cycloalkenyl especially cyclohexenyl or cycloalkyl especially cyclohexyl; and heterocycle represents tetrahydrofuran or morpholinyl. Preferred substituents for aryl and heteroaryl are one or two groups selected from nitro, hydroxyl, $C_{1-6}$alkyl (e.g. methyl), halo (e.g. Br, Cl, F), nitro, $C_{1-6}$haloalkyl (e.g. trifluoromethyl), $C_{1-6}$haloalkoxy (e.g. trifluoromethoxy) and $C_{1-6}$alkoxy (e.g. methoxy). Yet more preferably $R^1$ represents a group selected from $C_{1-12}$alkyl optionally substituted by hydroxy; —$C_{1-6}$alkylaryl (e.g. $C_{1-2}$alkylaryl); and $C_{1-6}$alkylheteroaryl (e.g. $C_{1-2}$alkylheteroaryl) especially in which aryl represents phenyl optionally substituted by substituents (e.g. one or two substituents) selected from $C_{1-6}$alkyl (e.g. methyl), halo (e.g. Br, Cl, F), nitro, $C_{1-6}$haloalkyl (e.g. trifluoromethyl) and $C_{1-6}$alkoxy (e.g. methoxy) and heteroaryl represents pyridinyl, furanyl, pyrazolyl, pyrazinyl, indolyl or imidazolyl optionally substituted by substituents (e.g. one or two substituents) selected from $C_{1-6}$alkyl (e.g. methyl) or halo (e.g. Br, Cl, F).

Suitably $R^9$ represents hydrogen, methyl or ethyl, more suitably hydrogen or methyl, most suitably hydrogen.

Suitably $R^{10}$ represents hydrogen, methyl or ethyl, more suitably hydrogen or methyl, most suitably hydrogen.

Suitably $R^{11}$ represents hydrogen, methyl or ethyl, more suitably hydrogen or methyl, most suitably hydrogen.

Suitably $R^{12}$ represents hydrogen, methyl or ethyl, more suitably hydrogen or methyl, most suitably hydrogen.

In one embodiment of the invention $R^2$ represents $C_{1-6}$alkyl$NR^{10}R^{11}$. Specific examples include methylamine, ethylamine (e.g. 1-ethylamine and 2-ethylamine) and propylamine (e.g.2-(1-methyl)-ethylamine and 3-propylamine, in particular 3-propylamine). When $R^2$ represents $C_{1-6}$alkyl$NR^{10}R^{11}$, suitably $R^2$ is methylamine, ethylamine or propylamine. One $R^2$ group of interest is methylamine. Another $R^2$ group of interest is 1-ethylamine. A further $R^2$ group of interest is 2-ethylamine. An additional $R^2$ group of interest is 3-propylamine.

In another embodiment of the invention $R^2$ represents $C_{3-6}$cycloalkylimine optionally N substituted by $R^{11}$ and suitably represents $C_{4-6}$cycloalkylimine, in particular azetidine (for example 1-azetidine, 2-azetidine or 3-azetidine, especially 3-azetidine).

Most suitably, $R^2$ represents a group selected from:

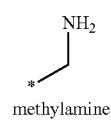

(a) methylamine

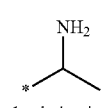

(b) 1-ethylamine

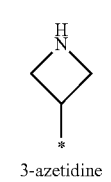

(c) 3-azetidine

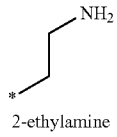

(d) 2-ethylamine

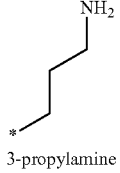

(e) 3-propylamine

The $R^2$ group of most particular interest is methylamine.

Particular compounds of interest are those recited in the Examples.

Special Advantages of the Compounds of the Present Invention

The compounds of the present invention may have an improved ability to cross the blood-brain-barrier in mammals, preferably in humans, and may thus be especially suitable for the treatment of neurological disorders and/or CNS diseases. The ability of the compounds of the present invention to cross the blood-brain-barrier is demonstrated in the Biological Example 7.

Further, the compounds of the present invention may be highly specific against DP IV, i.e. may have less or no effectivity against DP IV-like enzymes, e.g. DP9, compared to conventional DP IV inhibitors. The high specificity of the compounds of the present invention is demonstrated in the Biological Example 1.

The compounds of the present invention may be less cytotoxic than conventional DP IV inhibitors. The low cytotoxicity of the compounds of the present invention is demonstrated in the Biological Example 2.

The compounds of the present invention are well transported through Caco-2 monolayers. The transportability of the compounds of the present invention through Caco-2 monolayers is demonstrated in the Biological Example 3.

The compounds of the present invention may be suitable for the treatment of anxiety. The suitability of the compounds of the present invention for the treatment of anxiety is demonstrated in the Biological Example 4.

The compounds of the present invention may be suitable for the improvement of the social behaviour and treatment of schizophrenia. The suitability of the compounds of the present invention for the improvement of the social behaviour and treatment of schizophrenia may be demonstrated in the Tetradic Encounter Test, as shown in the Biological Example 5.

The compounds of the present invention have a high bioavailability in vivo. The bioavailability of the compounds of the present invention is demonstrated in the Biological Example 6.

Pharmaceutical Combinations

In a preferred embodiment, the present invention provides a composition, preferably a pharmaceutical composition, comprising at least one DP IV inhibitor optionally in combination with at least one other agent e.g. selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most preferably, said DP IV inhibitor is a compound of formula (I) of the present invention.

More specifically, the aforementioned other agent is selected from the group consisting PEP-inhibitors, LiCl, inhibitors of glutaminyl cyclase (QC), other inhibitors of DP IV or DP IV-like enzymes; acetylcholinesterase (AChE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), IR 208, NBI 5788/ MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Especially for the treatment of neurodegenerative diseases, the further drug agent may be selected from the group consisting of glutaminyl cyclase (QC) inhibitors, prolyl endopeptidase (PEP) inhibitors, LiCl, inhibitors of dipeptidyl aminopeptidases, other inhibitors of DP IV or DP IV-like enzymes, ACE inhibitors, PIMT enhancers, inhibitors of beta secretases, inhibitors of gamma secretases, inhibitors of neutral endopeptidase, inhibitors of PDE-4, TNFalpha inhibitors, amyloid protein or amyloid peptide deposition inhibitors, sigma-1 receptor inhibitors and histamine H3 antagonists.

Furthermore, the other agent may be, for example, an anti-anxiety drug or antidepressant selected from the group consisting of
(a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene,
(b) Selective serotonin re-uptake inhibitors (SSRI's), e.g. citalopram, fluoxetine, fluvoxamine, escitalopram, sertraline, paroxetine,
(c) Tricyclic antidepressants, e.g. amitryptiline, clomipramine, desipramine, doxepin, imipramine
(d) Monoamine oxidase (MAO) inhibitors,
(e) Azapirones, e.g. buspirone, tandopsirone,
(f) Serotonin-norepinephrine reuptake inhibitors (SNRI's), e.g. venlafaxine, duloxetine,
(g) Mirtazapine,
(h) Norepinephrine reuptake inhibitors (NRI's), e.g. reboxetine,
(i) Bupropione,
(j) Nefazodone,
(k) beta-blockers,
(l) NPY-receptor ligands: NPY agonists or antagonists.

In a further embodiment, the other agent may be, for example, an anti-multiple sclerosis drug selected from the group consisting of
a) dihydroorotate dehydrogenase inhibitors, e.g. SC-12267, teriflunomide, MNA-715, HMR-1279 (syn. to HMR-1715, MNA-279),
b) autoimmune suppressant, e.g. laquinimod,
c) paclitaxel,
d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
e) peptide nucleic acid (PNA) preparations, e.g. reticulose,
f) interferon alpha, e.g. Alfaferone, human alpha interferon (syn. to Omniferon, Alpha Leukoferon),
g) interferon beta, e.g. Frone, interferon beta-1a like Avonex, Betron (Rebif), interferon beta analogs, interferon beta-transferrin fusion protein, recombinant interferon beta-1b like Betaseron,
h) interferon tau,
i) peptides, e.g. AT-008, AnergiX.MS, Immunokine (alpha-Immunokine-NNSO3), cyclic peptides like ZD-7349,
j) therapeutic enzymes, e.g. soluble CD8 (sCD8),
k) multiple sclerosis-specific autoantigen-encoding plasmid and cytokine-encoding plasmid, e.g. BHT-3009;
l) inhibitor of TNF-alpha, e.g. BLX-1002, thalidomide, SH-636,
m) TNF antagonists, e.g. solimastat, lenercept (syn. to RO-45-2081, Tenefuse), onercept (sTNFR1), CC-1069,
n) TNF alpha, e.g. etanercept (syn. to Enbrel, TNR-001)
o) CD28 antagonists, e.g. abatacept,
p) Lck tyrosine kinase inhibitors,
q) cathepsin K inhibitors,
r) analogs of the neuron-targeting membrane transporter protein taurine and the plant-derived calpain inhibitor leupeptin, e.g. Neurodur,
s) chemokine receptor-1 (CCR1) antagonist, e.g. BX-471,
t) CCR2 antagonists,
u) AMPA receptor antagonists, e.g. ER-167288-01 and ER-099487, E-2007, talampanel,
v) potassium channel blockers, e.g. fampridine,
w) tosyl-proline-phenylalanine small-molecule antagonists of the VLA-4/VCAM interaction, e.g. TBC-3342,
x) cell adhesion molecule inhibitors, e.g. TBC-772,
y) antisense oligonucleotides, e.g. EN-101,
z) antagonists of free immunoglobulin light chain (IgLC) binding to mast cell receptors, e.g. F-991,
aa) apoptosis inducing antigenes, e.g. Apogen MS,
bb) alpha-2 adrenoceptor agonist, e.g. tizanidine (syn. to Zanaflex, Ternelin, Sirdalvo, Sirdalud, Mionidine),
cc) copolymer of L-tyrosine, L-lysine, L-glutamic acid and L-alanine, e.g. glatiramer acetate (syn. to Copaxone, COP-1, copolymer-1),
dd) topoisomerase II modulators, e.g. mitoxantrone hydrochloride,
ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SRI-62-834 (syn. to CRC-8605, NSC-614383),
ii) immunomodulators, e.g. SAIK-MS, PNU-156804, alpha-fetoprotein peptide (AFP), IPDS,
jj) retinoid receptor agonists, e.g. adapalene (syn. to Differin, CD-271),
kk) TGF-beta, e.g. GDF-1 (growth and differentiation factor 1),
ll) TGF-beta-2, e.g. BetaKine,
mm) MMP inhibitors, e.g. glycomed,
nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34, TO-200),
mm) alpha-4/beta-1 integrin antagonists, e.g. ISIS-104278,
nn) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S— inhibitors,
ww) bropirimine analogs, e.g. PNU-56169, PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

In another preferred embodiment, the present invention provides a composition, preferably a pharmaceutical composition, comprising at least one compound of formula 1, optionally in combination with at least one anti-multiple sclerosis drug selected from the groups mentioned above.

Examples of suitable PIMT enhancers are 10-aminoaliphatyl-dibenz[b, f]oxepines described in WO 98/15647 and WO 03/057204, respectively. Further useful according to the present invention are modulators of PIMT activity described in WO 2004/039773.

Examples of suitable PIMT enhancers are 10-aminoaliphatyl-dibenz[b, f]oxepines of the general formula:

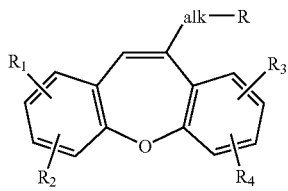

as described in WO 98/15647 and WO 03/057204, wherein alk is a divalent aliphatic radical, R is an amino group that is unsubstituted or mono- or di-substituted by monovalent aliphatic and/or araliphatic radicals or disubstituted by divalent aliphatic radicals, and $R_1$, $R_2$, $R_3$ and $R_4$ are each, independently of the others, hydrogen, lower alkyl, lower alkoxy, halogen or trifluoromethyl.

WO 98/15647 discloses the compounds above for use in methods for modulating the activity of PIMT in order to specifically enhance or prevent apoptotic processes in a cell.

WO 03/057204 discloses the compounds above for use in methods for preventing or alleviating an autoimmune response in a mammal, which may act through the activity of PIMT.

Other modulators of PIMT activity are compounds of the general formulae I-IV:

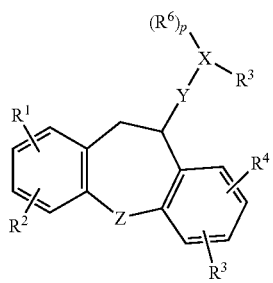
(I)

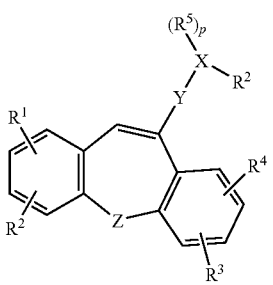
(II)

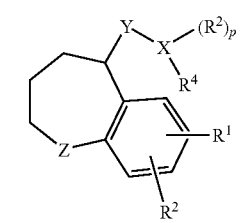
(III)

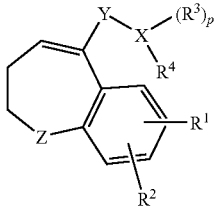
(IV)

wherein the definition of the substituents $R^1$-$R^5$, $(R^3)p$, $(R^6)p$, X, Y and Z is described in WO 2004/039773.

WO 2004/039773 discloses the compounds above for use in methods for preventing or alleviating diabetes, autoimmune diseases and neurodegenerative diseases which may act through the activity of PIMT and/or glyceraldehyde-3-phosphate dehydrogenase.

WO 98/15647, WO 03/057204 and WO 2004/039773 are incorporated herein in their entirety and are part of this invention with regard to the synthesis and use of the compounds described therein in pharmaceutical combinations comprising a compound of the present invention.

Inhibitors of beta secretase and compositions containing such inhibitors are described, e.g. in WO03/059346, WO2006/099352, WO2006/078576, WO2006/060109, WO2006/057983, WO2006/057945, WO2006/055434, WO2006/044497, WO2006/034296, WO2006/034277, WO2006/029850, WO2006/026204, WO2006/014944, WO2006/014762, WO2006/002004, U.S. Pat. No. 7,109,217, WO2005/113484, WO2005/103043, WO2005/103020, WO2005/065195, WO2005/051914, WO2005/044830, WO2005/032471, WO2005/018545, WO2005/004803, WO2005/004802, WO2004/062625, WO2004/043916, WO2004/013098, WO03/099202, WO03/043987, WO03/039454, U.S. Pat. No. 6,562,783, WO02/098849 and WO02/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.) and DNP-004089 (De Novo Pharmaceuticals Ltd.).

Inhibitors of gamma secretase and compositions containing such inhibitors are described, e.g. in WO2005/008250, WO2006/004880, U.S. Pat. No. 7,122,675, U.S. Pat. No. 7,030,239, U.S. Pat. No. 6,992,081, U.S. Pat. No. 6,982,264, WO2005/097768, WO2005/028440, WO2004/101562, U.S. Pat. No. 6,756,511, U.S. Pat. No. 6,683,091, WO03/066592, WO03/014075, WO03/013527, WO02/36555, WO01/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO2005/040126, WO2005/030731, WO2005/014553, U.S. Pat. No. 6,890,956, EP 1334085, EP 1263774, WO2004/101538, WO2004/00958, WO2004/0899 11, WO2004/073630, WO2004/069826, WO2004/039370, WO2004/031139, WO2004/031137, U.S. Pat. No. 6,713,276, U.S. Pat. No. 6,686,449, WO03/091278, U.S. Pat. No. 6,649,196, U.S. Pat. No. 6,448,229, WO01/77144 and WO01/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); and NGX-555 (TorreyPines Therapeutics Inc.).

Suitable inhibitors of beta and/or gamma secretases and compositions containing such inhibitors are described, e.g. in GB 2 385 124, GB 2 389 113, US 2002-115616, WO 01/87293, WO 03/057165, WO 2004/052348 and WO 2004/062652. These references are incorporated herein in their entirety and are part of this invention with regard to the synthesis, manufacture and use of the compounds and compositions described therein in pharmaceutical combinations comprising a compound of the present invention.

A potent selective and cell permeable gamma secretase inhibitor is (5S)-(t-Butoxycarbonylamino)-6-phenyl-(4R) hydroxy-(2R)benzylhexanoyl)-L-leu-L-phe-amide with the formula:

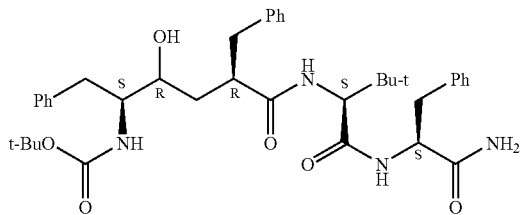

A potent beta secretase inhibitor is PNU-33312 of the formula:

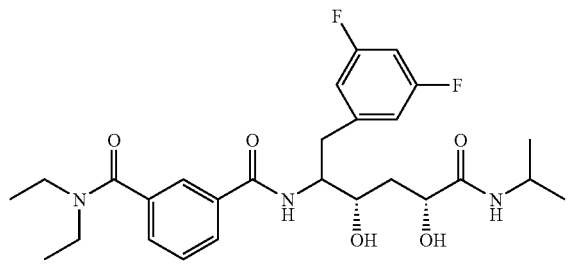

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, Cl-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.).

Suitable PDE-4 inhibitors are, e.g. shown in the table below:

| Company | Drug Code | Structure |
|---|---|---|
| Celgene Corp | CC-002 | |
| Celltech Group plc/ Merck Frosst | L-826141 | The correct structure would show N+–O- 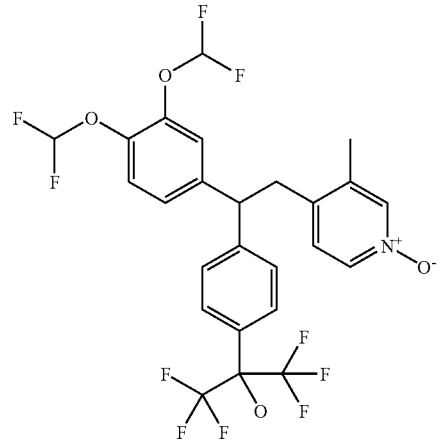 |

| Company | Drug Code | Structure |
|---|---|---|
| Celltech Group plc | Sch-351591 (D-4396) | The correct structure would show N+–O- 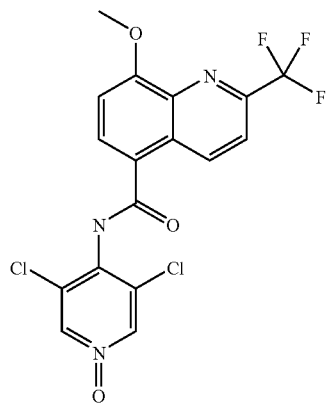 |
| Dainippon Pharmaceutical Co Ltd | OS-0217 | 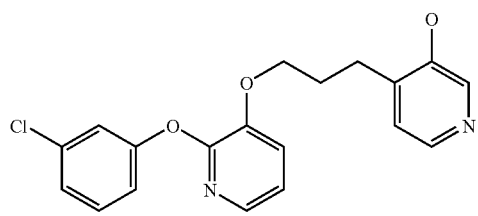 |
| IBFB Pharma GmbH | IBFB-130011<br>IBFB-150007<br>IBFB-130020<br>IBFB-140301 | |
| ICOS Corp | IC-485 | 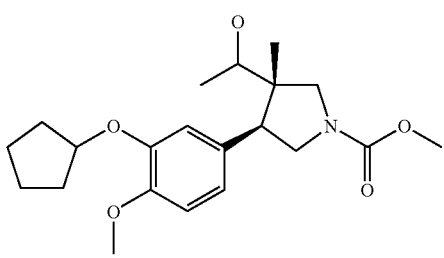 |
| Kings College London | VMX-554,<br>VMX-565 | |
| Memory Pharmaceuticals Corp | MEM-1414<br>MEM-1018<br>MEM-1091<br>MEM-1145 | |
| Pfizer Inc | CI-1044 | 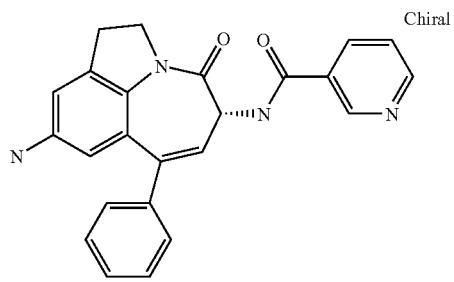 |

| Company | Drug Code | Structure |
|---|---|---|
| Pfizer Inc. | BHN | 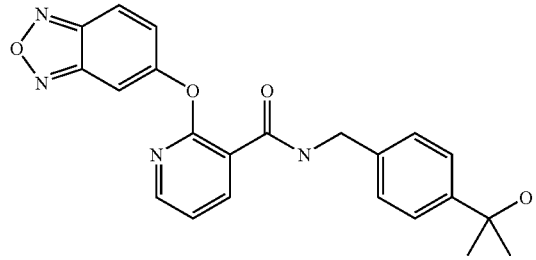 |
| Schering AG | ZK-117137 | 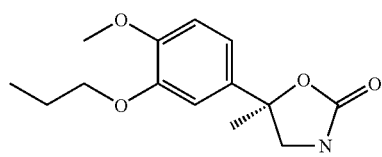 |
| SmithKline Beecham Pharmaceuticals | SB-207499 and analogues | 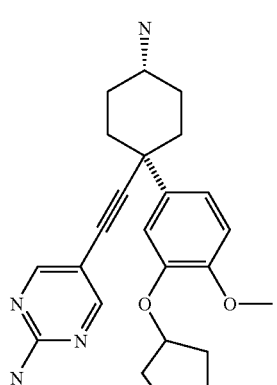 |

A more suitable PDE-4-inhibitor is rolipram.

MAO inhibitors and compositions containing such inhibitors are described, e.g. in WO2006/091988, WO2005/007614, WO2004/089351, WO01/26656, WO01/12176, WO99/57120, WO99/57119, WO99/13878, WO98/40102, WO98/01157, WO96/20946, WO94/07890 and WO92/21333.

Suitable MAO-inhibitors for the purpose of the present invention are for example Linezolid (Pharmacia Corp.); RWJ-416457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer) and NW-1048 (Newron Pharmaceuticals SpA.).

A suitable MAO-inhibitor is the compound ladostigil of the formula

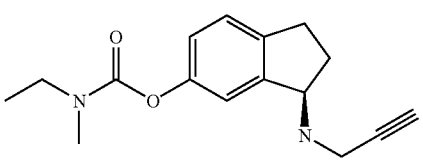

Suitable histamine H3 antagonists are, e.g. shown in the table below:

| Company | Drug | Structure |
|---|---|---|
| Abbott Laboratories | A-331440 | |
| Abbott Laboratories | A-349821 | |
| Aventis Pharma AG | 3874-H1 | 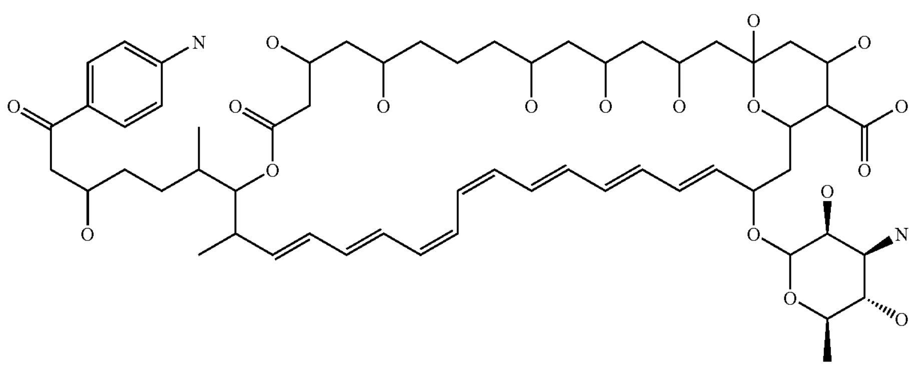 |
| Berlin Free University | UCL-2173 | 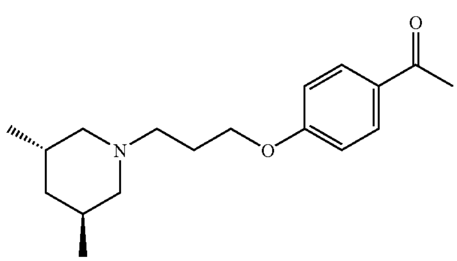 |
| BioProjet, Societe Civile de Recherche | | 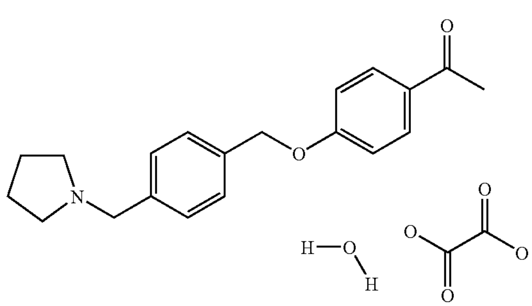 |

-continued

| Company | Drug | Structure |
|---|---|---|
| BioProjet, Societe Civile de Recherche | UCL-1470 | 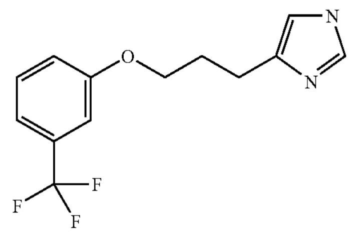 |
| Daewoong Pharmaceutical Co Ltd | DWP-302 | |
| Glaxo-SmithKline | GSK-189254A GSK-207040A | |
| Gliatech Inc | cipralisant | |
| Gliatech Inc | GT-2203 | |
| Hokkaido university | 1S,2S)-2-(2-Amino-ethyl)-1-(1H-imidazol-4-yl)cyclo-propane | 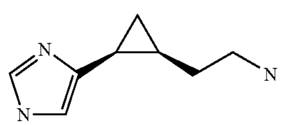 |
| Johnson & Johnson | JNJ-5207852 | |
| Novo Nordisk A/S | NNC-0038-0000-1049 | 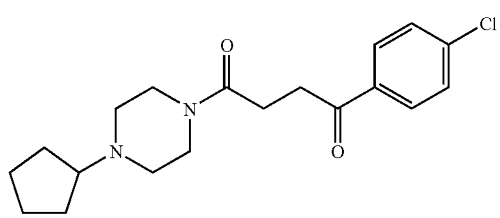 |
| Schering-Plough Research Institute | dual H1/H3 antagonists | 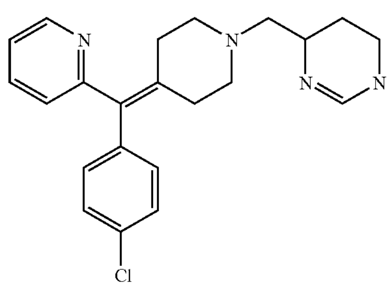 |

| Company | Drug | Structure |
|---|---|---|
| Schering-Plough Research Institute | Sch-79687 | 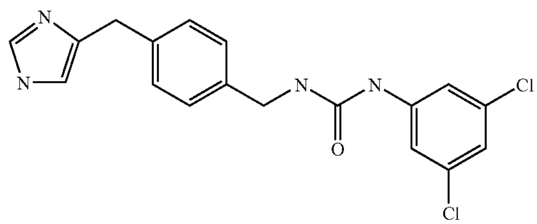 |

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 95/15310, WO 93/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5506256, JP 06192298, EP 0618193, JP 03255080, EP 0468469, U.S. Pat. No. 5,118,811, JP 05025125, WO 93/13065, JP 05201970, WO 94/12474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 95/01352, JP 01250370, JP 02207070, U.S. Pat. No. 5,221,752, EP 0468339, JP 04211648, WO 99/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Suitable inhibitors of prolyl endopeptidase (PEP) are, e.g. chemical derivatives of proline or small peptides containing terminal prolines. Benzyloxycarbonyl-prolyl-prolinal has been shown to be a specific transition state inhibitor of the enzyme (Wilk, S. and Orloeski, M., J. Neurochem., 41, 69 (1983), Friedman, et al., Neurochem., 42, 237 (1984)). N-terminal substitutions of L-proline or L-prolylpyrrolidine (Atack, et al., Eur. J. of Pharm., 205, 157-163 (1991), JP 03 56,460, EP 384,341), as well as variations of N-benzyloxycarbonyl (Z) dipeptides containing prolinal at the carboxy terminus have been synthesized as prolyl endopeptidase inhibitors (Nishikata, et al., Chem. Pharm. Bull. 34(7), 2931-2936 (1986), Baker, A. et al., Bioorganic & Medicinal Chem. Letts., 1(11), 585-590 (1991)). Thioproline, thiazolidine, and oxopyrrolidine substitutions of the core structure have been reported to inhibit prolyl endopeptidase (Tsuru, et al., J. Biochem., 94, 1179 (1988), Tsuru, et al., J. Biochem., 104, 580-586 (1988), Saito et al., J. Enz. Inhib. 5, 51-75 (1991), Uchida, I., et al. PCT Int. Appl. WO 90 12,005, JP 03 56,461, JP 03 56,462). Similarly, various modifications of the carboxy terminal proline have been made, including various fluorinated ketone derivatives (Henning, EP 4,912,127). General syntheses of fluorinated ketone derivatives has been described (Angelastro, M. R., et al., Tetrahedron Letters 33(23), 3265-3268 (1992)). Other compounds such as chloromethyl ketone derivatives of acyl-proline or acylpeptide-proline (Z-Gly-Pro-CH$_2$Cl) have been demonstrated to inhibit the enzyme by alkylating the enzyme's active site (Yoshimoto, T., et al., Biochemistry 16, 2942 (1977)).

EP-A-0 286 928 discloses 2-acylpyrrolidine derivatives useful as propyl endopeptidase inhibitors.

Further suitable prolyl endopeptidase inhibitors according to the present invention are, e.g. Fmoc-Ala-Pyrr-CN and those listed below:

Z-321
Zeria Pharmaceutical Co Ltd

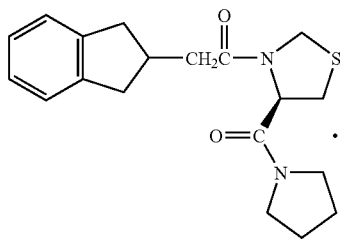

(4R)-3-(indan-2-ylacetyl)-4-(1-pyrrolidinyl-carbonyl)-1,3-thiazolidin

ONO-1603
Ono Pharmaceutical Co Ltd

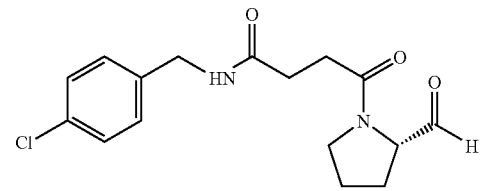

(S)-1-[N-(4-chlorobenzyl)-succinamoyl]pyrrolidin-2-carbaldehyd

-continued

| JTP-4819<br>Japan Tobacco Inc | S-17092<br>Servier |
|---|---|
| 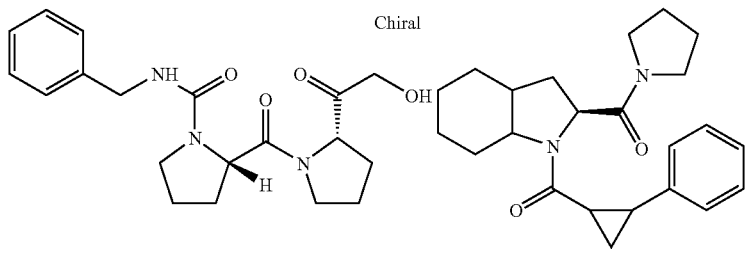 | |
| (S)-2-{[(S).(hydroxyacatyl)-1-pyr-rolidinyl]carbonyl}-N-(phenyl-methyl)-1-pyrrolidin-car-boxamid | (2S,3aS,7aS)-1{[(R,R)-2-phenyl-cyclopropyl]carbonyl}-2-[(thia-zolidin-3-yl)carbonyl]octa-hydro-1H-indol |

Further suitable prolyl endopeptidase inhibitors according to the present invention are disclosed in JP 01042465, JP 03031298, JP 04208299, WO 0071144, U.S. Pat. No. 5847155; JP 09040693, JP 10077300, JP 05331072, JP 05015314, WO 9515310, WO 9300361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 9313065, JP 05201970, WO 9412474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 9118877, JP 04009367, JP 04235162, U.S. Pat. No. 5,407,950, WO 9501352, JP 01250370, JP 02207070, U.S. Pat. No. 5,221,752, EP 0468339, JP 04211648 and WO 9946272, the teachings of which are herein incorporated by reference in their entirety, especially concerning these inhibitors, their definition, uses and their production.

Most preferred is the PEP-inhibitor of the formula:

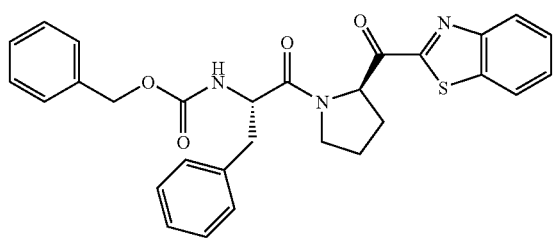

This compound is disclosed in US2005/0171112, the disclosure of which is herein incorporated by reference.

Other suitable compounds that can be used according to the present invention in combination with QC-inhibitors are NPY, a NPY mimetic or a NPY agonist or antagonist or a ligand of the NPY receptors.

Preferred according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 00/68197.

NPY receptor antagonists which may be mentioned include those disclosed in European patent applications EP 0 614 911, EP 0 747 357, EP 0 747 356 and EP 0 747 378; international patent applications WO 9417035, WO 9719911, WO 9719913, WO 9612489, WO 9719914, WO 9622305, WO 9640660, WO 9612490, WO 9709308, WO 9720820, WO 9720821, WO 9720822, WO 9720823, WO 9719682, WO 9725041, WO 9734843, WO 9746250, WO 9803492, WO 9803493, WO 9803494 and WO 9807420; WO 0030674, U.S. Pat. Nos. 5,552,411, 5,663,192 and 5,567,714; 6,114,336, Japanese patent application JP 09157253; international patent applications WO 9400486, WO 9312139, WO 9500161 and WO 9915498; U.S. Pat. No. 5,328,899; German patent application DE 393 97 97; European patent applications EP 355 794 and EP 355 793; and Japanese patent applications JP 06116284 and JP 07267988, the disclosures in all of which documents are hereby incorporated by reference. Preferred NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 9417035, WO 9719911, WO 9719913, WO 9612489, WO 9719914, WO 9622305, WO 9640660, WO 9612490, WO 9709308, WO 9720820, WO 9720821, WO 9720822, WO 9720823, WO 9719682, WO 9725041, WO 9734843, WO 9746250, WO 9803492, WO 9803493, WO 9803494, WO 9807420 and WO 9915498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds which may be mentioned include those disclosed in international patent applications WO 9417035, WO 9719911, WO 9719913, WO 9719914 or, preferably, WO 9915498. Preferred amino acid-based NPY antagonists include those that are specifically disclosed in these patent documents, for example BIBP3226 and, especially, (R)-N2-(diphenylacetyl)-(R)—N-[1-(4-hydroxy-phenyl)ethyl]arginine amide (Example 4 of international patent application WO 9915498).

M1 receptor agonists and compositions containing such inhibitors are described, e.g. in WO2004/087158, WO91/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth) and Cl-101/(PD-151832) (Pfizer Inc.).

Acetylcholinesterase inhibitors and compositions containing such inhibitors are described, e.g. in WO2006/071274, WO2006/070394, WO2006/040688, WO2005/092009, WO2005/079789, WO2005/039580, WO2005/027975, WO2004/084884, WO2004/037234, WO2004/032929, WO03/101458, WO03/091220, WO03/082820, WO03/020289, WO02/32412, WO01/85145, WO01/78728, WO01/66096, WO00/02549, WO01/00215, WO00/15205, WO00/23057, WO00/33840, WO00/30446, WO00/23057, WO00/15205, WO00/09483, WO00/07600, WO00/02549, WO99/47131, WO99/07359, WO98/30243, WO97/38993, WO97/13754, WO94/29255, WO94/20476, WO94/19356, WO93/03034 and WO92/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.) and INM-176 (Whanln).

NMDA receptor antagonists and compositions containing such inhibitors are described, e.g. in WO2006/094674, WO2006/058236, WO2006/058059, WO2006/010965, WO2005/000216, WO2005/102390, WO2005/079779, WO2005/079756, WO2005/072705, WO2005/070429, WO2005/055996, WO2005/035522, WO2005/009421, WO2005/000216, WO2004/092189, WO2004/039371, WO2004/028522, WO2004/009062, WO03/010159, WO02/072542, WO02/34718, WO01/98262, WO01/94321, WO01/92204, WO01/81295, WO01/32640, WO01/10833, WO01/10831, WO00/56711, WO00/29023, WO00/00197, WO99/53922, WO99/48891, WO99/45963, WO99/01416, WO99/07413, WO99/01416, WO98/50075, WO98/50044, WO98/10757, WO98/05337, WO97/32873, WO97/23216, WO97/23215, WO97/23214, WO96/14318, WO96/08485, WO95/31986, WO95/26352, WO95/26350, WO95/26349, WO95/26342, WO95/12594, WO95/02602, WO95/02601, WO94/20109, WO94/13641, WO94/09016 and WO93/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); EpiCept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, Cl-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-Cl-kynurenine (4-Cl—KYN)), 7-chloro-kynurenic acid (7-Cl—KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR—R-15896) (AstraZeneca); EVT-102, Ro-25-6981 and Ro-63-1908 (Hoffmann-La Roche AG/Evotec).

DP IV-inhibitors and compositions containing such inhibitors are described, e.g. in U.S. Pat. No. 6,011,155; U.S. Pat. No. 6,107,317; U.S. Pat. No. 6,110,949; U.S. Pat. No. 6,124,305; U.S. Pat. No. 6,172,081; WO99/61431, WO99/67278, WO99/67279, DE19834591, WO97/40832, WO95/15309, WO98/19998, WO00/07617, WO99/38501, WO99/46272, WO99/38501, WO01/68603, WO01/40180, WO01/81337, WO01/81304, WO01/55105, WO02/02560, WO01/34594, WO02/38541, WO02/083128, WO03/072556, WO03/002593, WO03/000250, WO03/000180, WO03/000181, EP1258476, WO03/002553, WO03/002531, WO03/002530, WO03/004496, WO03/004498, WO03/024942, WO03/024965, WO03/033524, WO03/035057, WO03/035067, WO03/037327, WO03/040174, WO03/045977, WO03/055881, WO03/057144, WO03/057666, WO03/068748, WO03/068757, WO03/082817, WO03/101449, WO03/101958, WO03/104229, WO03/74500, WO2004/007446, WO2004/007468, WO2004/018467, WO2004/018468, WO2004/018469, WO2004/026822, WO2004/032836, WO2004/033455, WO2004/037169, WO2004/041795, WO2004/043940, WO2004/048352, WO2004/050022, WO2004/052850, WO2004/058266, WO2004/064778, WO2004/069162, WO2004/071454, WO2004/076433, WO2004/076434, WO2004/087053, WO2004/089362, WO2004/099185, WO2004/103276, WO2004/103993, WO2004/108730, WO2004/110436, WO2004/111041, WO2004/112701, WO2005/000846, WO2005/000848, WO2005/011581, WO2005/016911, WO2005/023762, WO2005/025554, WO2005/026148, WO2005/030751, WO2005/033106, WO2005/037828, WO2005/040095, WO2005/044195, WO2005/047297, WO2005/051950, WO2005/056003, WO2005/056013, WO2005/058849, WO2005/075426, WO2005/082348, WO2005/085246, WO2005/087235, WO2005/095339, WO2005/095343, WO2005/095381, WO2005/108382, WO2005/113510, WO2005/116014, WO2005/116029, WO2005/118555, WO2005/120494, WO2005/121089, WO2005/121131, WO2005/123685, WO2006/995613; WO2006/009886; WO2006/013104; WO2006/017292; WO2006/019965; WO2006/020017; WO2006/023750; WO2006/039325; WO2006/041976; WO2006/047248; WO2006/058064; WO2006/058628; WO2006/066747; WO2006/066770 and WO2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98; BI-A, BI-B (Boehringer Ingelheim Corp.); SK-0403 (Sanwa Kagaku Kenkyusho Co. Ltd.); and NNC-72-2138 (Novo NordiskA/S).

Other preferred DP IV-inhibitors are
(i) dipeptide-like compounds, disclosed in WO 99/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;
(ii) peptide structures, disclosed in WO 03/002593, e.g. tripeptides;
(iii) peptidylketones, disclosed in WO 03/033524;
(vi) substituted aminoketones, disclosed in WO 03/040174;
(v) topically active DP IV-inhibitors, disclosed in WO 01/14318;
(vi) prodrugs of DP IV-inhibitors, disclosed in WO 99/67278 and WO 99/67279; and
(v) glutaminyl based DP IV-inhibitors, disclosed in WO 03/072556 and WO 2004/099134.

Inhibitors of QC are described in WO 2004/098625, WO 2004/098591, WO 2005/039548 and WO 2005/075436.

For the avoidance of doubt, the examples disclosed in each of the above mentioned publications are specifically incorporated herein by reference in their entirety, as individually disclosed compounds, especially concerning their structure, their definition, uses and their production.

In a further preferred embodiment, the present invention provides a composition, preferably a pharmaceutical composition, comprising at least one compound of the invention, optionally in combination with at least one anti-diabetic drug selected from the group consisting of
(a) other DP IV inhibitors
(b) insulin sensitizers selected from the group consisting of
  (i) PPAR agonists,
  (ii) biguanides, e.g. metformin, and
  (iii) protein tyrosin phosphatase-1B (PTP-1B) inhibitors;
(c) insulin and insulin mimetics;
(d) sulfonylureas and other insulin secretagogues;
(e) α-glucosidase inhibitors;
(f) glucagon receptor agonists;
(g) GLP-1; GLP-1 mimetics, e.g. NN-2211 (liraglutide from Novo Nordisk), and GLP-1 receptor agonists;
(h) GLP-2; GLP-2 mimetics, e.g. ALX-0600 (teduglutide from NPS Allelix Corp.) and GLP-2 receptor agonists;
(i) exendin-4 and exendin-4 mimetics, e.g. exenatide (AC-2993, synthetic exendin-4 from Amylin/Eli Lilly);
(j) GIP, GIP mimetics, and GIP receptor agonists;
(k) PACAP, PACAP mimetics, and PACAP receptor 3 agonists;
(l) choleserol lowering agents selected from the group consisting of
  (i) HMG-CoA reductase inhibitors,
  (ii) sequestrants,
  (iii) nicotinyl alkohol, nicotinic acid and salts thereof,
  (iv) PPARα agonists,
  (v) PPARα/γ dual agonists,
  (vi) inhibitors of cholesterol absorption,
  (vii) acyl CoA:cholesterol acyltransferase inhibitors, and
  (viii) antioxidants;
(m) PPARδ agonists;
(n) antiobesity compounds;
(o) an ileal bile acid transporter inhibitor; and
(p) anti-inflammatory agents.

Furthermore, the compositions or pharmaceutical compositions according to any one of the embodiments described above optionally comprise additionally at least one carrier or excipient.

Further, the present invention provides pharmaceutical compositions e.g. for parenteral, enteral or oral administration, comprising at least one DP IV inhibitor of formula (I) optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one DP IV inhibitor of formula (I) and at least one of the other agents or the sequential administration thereof.

Co-administration includes administration of a formulation, which comprises at least one DP IV inhibitor of formula (I) and at least one of the other agents or the essentially simultaneous administration of separate formulations of each agent.

Furthermore, the compositions or pharmaceutical compositions according to any one of the embodiments described above comprise additionally at least one carrier or excipient.

Galenic Preparations and Formulations

Compounds of the present invention will typically be presented as pharmaceutical compositions which comprise a compound of the invention together with one or more pharmaceutically acceptable diluents or carriers.

Suitably these pharmaceutical compositions are in unit dosage forms from such as tablets, pills, capsules, powders, granules, sterile parenteral solutions or suspensions, metered aerosol or liquid sprays, drops, ampoules, autoinjector devices or suppositories. The composition may be formulated for administration to a patient by any conventional route, including, but not limited to, intravenous, oral, subcutaneous, intramuscular, intradermal, parenteral, intranasal, sublingual or rectal administration, or for administration by inhalation or insufflation.

Compounding techniques: To prepare the pharmaceutical compositions of this invention, one or more compounds of the present invention, especially the DP IV inhibitors according to formula 1, as well as optionally, other agents as described for the "pharmaceutical combinations", and their corresponding pharmaceutically acceptable acid addition salt forms, as the active ingredients, are intimately admixed with a pharmaceutical carrier according to conventional pharmaceutical compounding techniques, which carrier may take a wide variety of forms depending of the form of preparation desired for administration. Compounds of the present invention may also be coupled with soluble polymers as targetable drug carriers.

Homogeneous preparation: For preparing solid compositions such as tablets, the principal active ingredient is ideally mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is ideally dispersed evenly throughout the composition so that the composition may be readily subdivided into equally effective dosage forms such as tablets, pills and capsules. This solid preformulation composition may then be subdivided into unit dosage forms of the type described above containing from about 0.1 to about 1000 mg, preferably from about 5 to about 500 mg of the active ingredient of the present invention.

Concentration and content of active agent: The pharmaceutical compositions herein will contain, per dosage unit, e.g., tablet, capsule, powder, injection, suppository, teaspoonful and the like, of from about 0.01 mg to about 1000 mg (preferably about 5 to about 500 mg) and may be given at a dosage of from about 0.1 to about 300 mg/kg bodyweight per day (preferably 1 to 50 mg/kg per day).

Oral dosage forms: In preparing the compositions in oral dosage form, any of the usual pharmaceutical media may be employed. Compositions suitable for oral administration include solid forms, such as pills, tablets, caplets, capsules (each including immediate release, timed release and sustained release formulations), granules, and powders. For solid oral preparations such as, for example, powders, capsules, gelcaps and tablets, suitable carriers and additives may advantageously include starches, sugars, diluents, granulating agents, lubricants, binders, disintegrating agents and the like. More preferably, for oral administration in the form of a tablet or capsule, the active drug component can be combined with an oral, non-toxic pharmaceutically acceptable inert carrier such as ethanol, glycerol, water and the like.

Coating of tablets, pills and capsules: Because of their ease in administration, tablets, pills and capsules represent the most advantageous oral dosage unit form, in which case solid pharmaceutical carriers are employed. If desired, the tablets, pills or capsules of the novel composition can be advantageously sugar coated or enteric coated by standard techniques or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be advantageously incorporated for administration orally or by injection include aqueous solutions, suitably flavoured syrups, elixirs, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. The liquid forms are suitable in flavored suspending or dispersing agents such as the synthetic and natural gums, for example, tragacanth, acacia, methyl-cellulose and the like. Isotonic preparations which generally contain suitable preservatives are employed when intravenous administration is desired.

For liquid oral preparations, such as for example, suspensions, elixirs and solutions, suitable carriers and additives may advantageously include water, glycols, oils, alcohols, flavoring agents, preservatives, coloring agents and the like.

Forms useful for parenteral administration include sterile solutions, emulsions and suspensions. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. For parenteral administration, sterile suspensions and solutions are desired. The pharmaceutical compositions herein will contain, per dosage unit, e.g. solution, suspension, emulsion, injection, teaspoonful and the like, an amount of the active ingredient necessary to deliver an effective dose as described above.

Depot formulations for intramuscular injection: Alternatively, the composition may be presented in a form suitable for once-weekly or once-monthly administration; for example, an insoluble salt of the active compound, such as the decanoate salt, may be adapted to provide a depot preparation for intramuscular injection.

Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen and dosage strength will need to be accordingly modified to obtain the desired therapeutic effects.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines using processes well described in the art.

Compounds of this invention may be administered in any of the foregoing compositions and according to dosage regimens established in the art whenever treatment of the addressed disorders is required.

Dosage regimen and strength:

Advantageously, compounds of the present invention may be administered in a single daily dose, or the total daily dosage may be administered in divided doses of two, three or four times daily.

The daily dosage of the products may be varied over a wide range from 0.01 to 1.000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, bioavailability due to the mode of administration, and the advancement of disease condition. In addition, factors associated with the particular patient being treated, including patient age, weight, diet and time of administration, should generally be considered in adjusting dosages.

The dosages, however, may be varied depending upon the requirement of the patients, the severity of the condition being treated and the compound being employed. The use of either daily administration or post-periodic dosing may be employed. Typically the dosage will be regulated by the physician based on the characteristics of the patient, his/her condition and the therapeutic effect desired.

The compounds or compositions of the present invention may be taken before a meal, while taking a meal or after a meal. When taken before a meal the compounds or composition of the present invention an be taken 1 hour, preferably 30 or even 15 or 5 minutes before eating. When taken while eating, the compounds or compositions of the present invention can be mixed into the meal or taken in a separate dosage form as described above. When taken after a meal, the compounds or compositions of the present invention can be taken 5, 15 or 30 minutes or even 1 hour after finishing a meal.

The inhibitors according to the present invention will typically possess a $K_i$-value of 100 nM or less, for example 10 nM or less, especially 5 nM or less. Compounds of the invention of particular interest possess a $K_i$-value of 1 nM or less, for example 100 pM or less (such as 10 pM).

Suitably the compounds of the invention molecular weights of 1000 Da or less, for example 800 Da or less, in particular 500 Da or less (such as 400 Da or less) e.g. 350 Da or less or 300 Da or less.

Suitably the compounds of the invention are reversible non-covalent inhibitors. Certain compounds of the present invention typically show a selectivity for DP IV over DPII (i.e. as defined by the ratio of $K_i$-values) which is at least 10 fold, such as at least 100 fold, especially at least 1,000 fold. Compounds of the present invention which are of particular interest for their selectivity over DPII will typically have a selectivity of at least 10,000 fold, such as at least 20,000, especially at least 30,000 fold (for example at least 40,000 fold or 50,000 fold).

Certain compounds of the present invention typically show a selectivity for DP IV over DP9 (i.e. as defined by the ratio of $K_i$-values) which is at least 10 fold, such as at least 100 fold, especially at least 1,000 fold. Compounds of the present invention which are of particular interest for their selectivity over DP9 will typically have a selectivity of at least 10,000 fold, such as at least 20,000, especially at least 30,000 fold (for example at least 40,000 fold or 50,000 fold).

Preferred compounds of the present invention are not cytotoxic or may have less cytotoxicity than prior art compounds.

Where the compounds of the invention are to be used to treat disorders involving the central nervous system, the compounds will suitably be sufficiently neutral and non-polar such that they can cross the blood-brain barrier via passive diffusion. In many cases, compounds that cannot cross by passive diffusion instead cross by active transport. Of course, administration approaches also can be employed when treating the central nervous system to avoid adverse interference from the blood-brain barrier.

The present invention provides specific DP IV-inhibitors which are expected to have efficacy for the prophylaxis and treatment of neurological diseases, especially of the central nervous system (CNS), compared with DP IV-inhibitors of the prior art.

The compounds of the present invention are believed to be especially useful for the prevention or treatment of a disease selected from anxiety and depression. For all of the current available anti-anxiety and anti-depressive drugs, important class specific disadvantages and side effects have been observed, which are, for instance sedative effects, withdrawal effects and risk for substance abuse in case of benzodiazepines, and slow onset of effect, nausea, restlessness, dizziness, weight loss and insomnia for the other classes. Consequently new treatment concepts with lower side effects and an acute action are needed for treatment of anxiety and panic attacks.

It is thus a further object of the present invention to provide DP IV-inhibitors, which are safe and have fewer (or none) of the unwanted side effects seen for current available anti-anxiety and anti-depressive drugs.

An important problem of current anti-anxiety or anti-depressive medications is the time until onset of action and the speed of action. The sedative drugs work fast—in hours or days—whereas the onset of action of antidepressants and 5-HT1A acting drugs is delayed—and usually takes weeks or even months. Another clinically important problem with current treatments is that the antidepressants and selective serotonin reuptake inhibitors (SSRIs) as well as 5-HT1A agonist drugs may actually worsen anxiety at the start of therapy.

Consequently, it is therefore a further object of the present invention to provide DP IV-inhibitors, which have a fast onset of action (for example which show an acute effect after administration of a single dose). Moreover, DP IV-inhibitors of the present invention are preferred, which are effective after acute and chronic dosing.

Medical Use/methods of Treatment

The present invention provides the use of a compound of the invention as a medicament.

Also provided is the use of a compound of the invention in the manufacture of a medicament for the prevention, delay or treatment of a disease listed in section "Diseases" below.

Further, there is provided a method of prevention, delay or treatment of diseases selected from the group consisting of the diseases listed in section "diseases" below, comprising the step of administering a safe and therapeutically effective amount of a compound of the invention to a subject in need thereof.

Diseases

The following diseases in mammals, in particular humans, are expected to be treated by the compounds of the present invention:

Neuronal disorders as well as psychosomatic, neuropsychiatric and depressive illnesses, such as anxiety, depression, sleep disorders, chronic fatigue, schizophrenia, epilepsy, nutritional disorders, spasm and chronic pain.

The indications above refer each to both acute and chronic form of the disease. It may be expected that the compounds of the invention are highly effective in the treatment of the acute form of the diseases above.

Metabolic diseases like impaired glucose tolerance, glucosuria, hyperlipidemia, metabolic acidosis, diabetes mellitus, non-insulin dependent diabetes mellitus, diabetic neuropathy and nephropathy and of sequelae caused by diabetes mellitus; high blood pressure and disturbance of signal action at the cells of the islets of Langerhans and insulin sensitivity in the peripheral tissue in the postprandial phase, metabolism-related hypertension and cardiovascular sequelae caused by hypertension in mammals.

Conditions, characteristic for the prediabetic state: pathological states, selected from the group consisting of impaired glucose tolerance (IGT), impaired fasting glucose (IFG) and impaired glucose metabolism (IGM);

Cancer: The present invention can be used for treatment and/or prophylaxis of cancer and tumors and the prophylaxis and inhibition of metastasis and tumor colonization including, but not limited to, adenocarcinomas, melanomas, lymphomas, sarcomas, leukemias, and different organ tumors like lung, breast, ovarian, head and/or neck, prostate, cervical, endometrial, colorectal, gastric, liver, fallopian tubes, esophagus, small intestine, pancreas, kidney, adrenal, vaginal, vulvar, brain and testicular tumors.

Dermal diseases like skin diseases and diseases of the mucosae, for example psoriasis, neurodermitis, acne;

Immune and autoimmune disorders, multiple sclerosis, and inflammatory conditions, arthritis, obesity, allograft transplantation.

Neurodegenerative disorders, cognitive disorders and for improving memory (both short term and long term) and learning ability.

Suitably, the neurodegenerative disorder is selected from conditions and diseases like dementia (e.g. senile dementia, pre-senile dementia (also known as mild cognitive impairment), Alzheimer related dementia (Alzheimer type dementia)), Huntington's chorea, tardive dyskinesia, hyperkinesias, mania, Morbus Parkinson, steel-Richard syndrome, Down's syndrome, myasthenia gravis, nerve and brain trauma, vascular amyloidosis, cerebral haemorrhage with amyloidosis, brain inflammation, Friedrich's ataxia, acute confusion disorders and especially those in which apoptotic necrocytosis plays a part, such as amyotrophic lateral sclerosis, glaucoma and especially Alzheimer's disease.

In particular, the neurodegenerative disorder is selected from Alzheimer's disease and dementia, preferably senile dementia, mild cognitive impairment or Alzheimer type dementia (for example the neurodegenerative disorder is Alzheimer's disease).

Suitably, the cognitive disorder is selected from conditions and diseases like cognitive deficits associated with schizophrenia, age-induced memory impairment, cognitive deficits associated with psychosis, cognitive impairment associated with diabetes, cognitive deficits associated with post-stroke, memory defects associated with hypoxia, cognitive and attention deficits associated with senile dementia, attention-deficit disorders, memory problems associated with mild cognitive impairment, impaired cognitive function associated with dementias, impaired cognitive function associated with Alzheimer's disease, impaired cognitive function associated with Parkinson's disease, impaired cognitive function associated with vascular dementia, cognitive problems associated with brain tumors, Pick's disease, cognitive deficits due to autism, cognitive deficits post electroconvulsive therapy, cognitive deficits associated with traumatic brain injury, amnesic disorders, delirium, dementias. Cognitive disorder also include, but are not limited to, disorders of learning acquisition (learning disorders), memory consolidation, retrieval memory and retention disorders.

In particular, the cognitive disorder is selected from cognitive impairment associated with diabetes, impaired cognitive function associated with Alzheimer's disease, impaired cognitive function associated with Parkinson's disease, cognitive deficits associated with post-stroke, cognitive and attention deficits associated with senile dementia, memory problems associated with mild cognitive impairment (for example, cognitive impairment associated with diabetes and impaired cognitive function associated with Alzheimer's disease, cognitive deficits associated with post-stroke).

Further, the compounds of the present invention are useful for the prophylaxis or treatment of psychosomatic, neuropsychiatric and depressive illness, and neurodegenerative diseases such as anxiety, depression, sleep disorders, chronic fatigue, schizophrenia, epilepsy, nutritional disorders, spasm, and chronic pain, and a simple method for the treatment of those disorders.

The DP IV-inhibitors of the present invention are of particular interest for the prophylaxis or the treatment of neurological diseases, especially for the treatment of a disease selected from anxiety, depression and schizophrenia.

Classification of Anxiety Disorders

Anxiety is a vital reaction and experience, which similar to pain, constitutes a biological alarm system to protect a living organism from threats coming from the environment, or alternatively, being represented internally. Pathological anxiety, however, is an escalating reaction of the body becoming independent, negatively influencing the decision making process and the development of strategies to accomplish survival. This state differs from normal anxiety through its intensity, duration and inadequate timing to the triggering event and may need treatment, if this anxiety causes a significant disability, which cannot be explained by external cause and which cannot be solved by the patient.

Anxiety can be distinguished into the following primary forms: Generalized anxiety disorder, GAD, is an exaggerated and unrealistic anxiety relating to general or special circumstances without external cause; Panic disorder, PD, specifies fear triggered by no obvious cause and occurs in attacks; Phobia is the fear of certain objects or situations, Social anxiety disorder, SAD, plays a specific role in this later form.

Secondary anxiety forms can be caused by a series of psychotic or physical disorders like depression, schizophrenia, obsessive-compulsive disorder (OCD), cardiovascular and metabolic diseases, epilepsy as well as posttraumatic stress disorder (PTSD)

So far the reasons for pathological anxiety are not fully understood. Besides the individual digestion of events and experiences, a genetical predisposition as well as congenital and acquired changes in the brain are being discussed. A major role is attributed to the hypothalamic-pituitary-adrenal axis. Besides the Corticotropin-Releasing-Hormone (CRH), Neurotransmitters, like gamma-aminobutyric acid (GABA), Serotonin and Noradrenalin, play an important role.

Currently, there are a number of drugs available for anxiety and depression treatment. Essentially these drugs belong to the classes of benzodiazepines, tricyclic antidepressives, selective serotonin-reuptake inhibitors, serotonin-norepinephrine-reuptake inhibitors, MAO inhibitors and serotonin-1A receptor agonists. For all of them, important class specific disadvantages and side effects have been observed, which are, for instance sedative effects, withdrawal effects and risk for substance abuse in case of benzodiazepines, and slow onset of effect, nausea, restlessness, dizziness, weight loss and insomnia for the other classes. Consequently new treatment concepts with lower side effects and an acute action are needed for treatment of anxiety and panic attacks.

Processes

A process for preparation of a compound of formula (I)

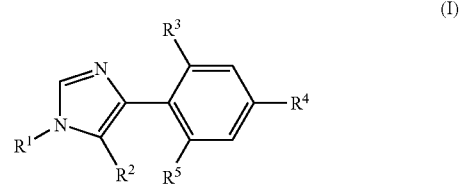

wherein $R^1$, $R^2$, $R^3$, $R^4$ and $R^5$ are as defined above, or a protected derivative thereof, comprises reaction of a compound of formula (II)

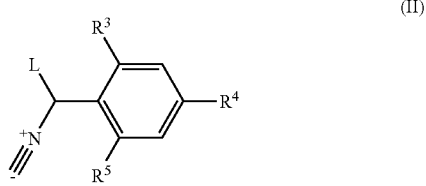

(II)

or a protected version thereof, wherein L represents an anion-stabilising leaving group; with a compound of formula (III)

(III)

or a protected derivative thereof.

Suitably the primary or secondary amine group of $R^2$ is protected e.g. by Boc. This protecting group can be removed at the end of the process e.g. by treatment with HCl.

The reaction is typically carried out in a polar, protic organic solvent such as an alcohol (e.g. methanol) and may be carried out at elevated temperature.

Exemplary anion stabilising leaving groups L include sulfonic acid derivatives such as $-SO_2X$ where X represents aryl or alkyl or -alkylaryl e.g. tosyl, mesyl, especially tosyl.

Compounds (II) and (III) may be prepared by standard methods.

Novel intermediate compounds are provided as an aspect of the invention.

General Synthesis Scheme

Thus, compounds of the invention may generally be prepared by the following route:

Scheme 1

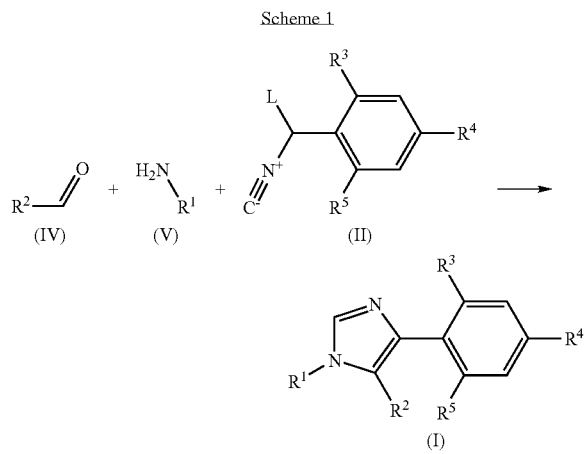

Generally, an $R^2$ containing compound of formula (IV), or a protected derivative thereof, is mixed with the $R^1$ containing compound of formula (V), or a protected derivative thereof, in a suitable solvent (such as dry methanol). Suitably the amine function of the compound of formula (IV) will be protected, for example by a Boc protecting group. After a short period of time (for example around 30 minutes), the compound of formula (II), wherein L indicates a leaving group, may be added. Reaction is suitably facilitated at elevated temperature (for example around 45° C.) for a sufficient period of time (for example around 24 hours). Subsequently, protecting groups are then removed, for example a Boc-protecting group can be removed by treatment with an acid, such as HCl, in a suitable solvent, such as a mixture of dioxan and water. The leaving group L can be any suitable leaving group known in organic chemistry. Suitably, L is: a halogen atom, (such as a bromine atom); arylsulfonyl optionally substituted by alkyl (such as toluenesulfonyl); or optionally halogenated alkylsulfonyl (such as mesyl or $CF_3-SO_2-$). $R^5$ can, for example, represent H. $R^3$ and $R^4$ can, for example, represent Cl.

Parallel Synthesis

The following compounds were synthesized according to (or by an analogous process to) the general synthesis Scheme 2 and their identity confirmed by mass spectrometry.

Scheme 2

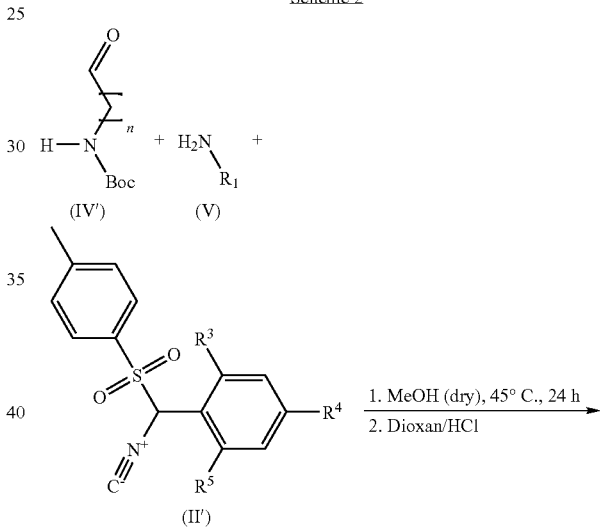

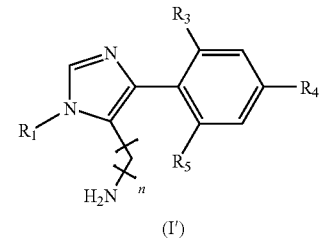

Briefly:

200 μl of a 0.2 M solution of amine in dry methanol was dispensed on 96-well plates. 200 μl of a 0.2M solution of aldehydes were added. The well plates were stacked for 30 minutes at room temperature. Subsequently 50 μl of a 0.2 M solution of isocyanides in dry methanol were dispensed. The well plates were sealed and stacked for 24 hours at 40° C. After finishing the solvent was evaporated.

In a next step the Boc-protecting group was cleaved away with an addition of 200 μl of a 4 M solution of HCl in 1,4 Dioxan, 20 μl $H_2O$, and shaking for 3 hours at room temperature. Afterwards the solvent was evaporated.

The following examples were prepared according to synthesis scheme 1.

Compounds were immediately tested regarding their activity as DP IV inhibitors. $IC_{50}$ values were found to be in the range of 1 to 50 μM when tested directly following synthesis (i.e. without purification). All compounds were detected via HPLC-MS either as mass plus proton ([M+H]) or mass plus sodium ([M+Na]) or both when calculated (Calc.) and experimentally determined (Det.) masses did not differ by more than 0.1 Dalton.

Examples of a compound of formula (Ia) are shown in the following table:

| Ex. No. | IUPAC-Name | Structure | IC50 DP4 uM | calc. m + h | found m + h | calc. m + Na | found m + Na |
|---|---|---|---|---|---|---|---|
| 1a | C-[5-(2-Chloro-4-fluoro-phenyl)-3-thiophen-2-yl-methyl-3H-imidazol-4-yl]-methyl-amine | 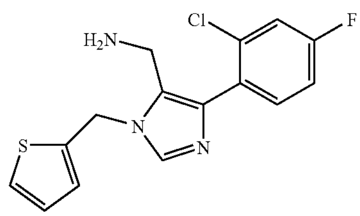 | 11.8 | 322.08 | 322.08 | 344.06 | |
| 2a | C-[5-(2-Chloro-4-fluoro-phenyl)-3-furan-2-yl-methyl-3H-imidazol-4-yl]-methyl-amine | 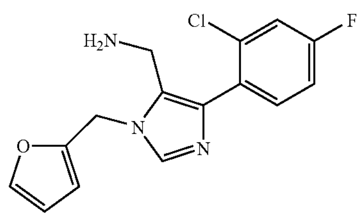 | 16.3 | 306.1 | 306.1 | 328.08 | |
| 3a | C-[3-(2-Chloro-benzyl)-5-(2-chloro-4-fluoro-phenyl)-3H-imidazol-4-yl]-methyl-amine | 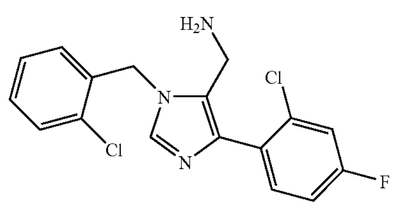 | 18.1 | 350.08 | 350.09 | 372.06 | |
| 4a | C-[5-(2-Chloro-4-fluoro-phenyl)-3-(5-methyl-furan-2-yl-methyl)-3H-imidazol-4-yl]-methyl-amine | 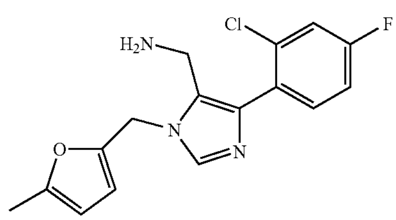 | 34.3 | 320.12 | 320.04 | 342.1 | |
| 5a | C-[5-(2-Chloro-4-fluoro-phenyl)-3-(4-fluoro-benzyl)-3H-imidazol-4-yl]-methyl-amine | 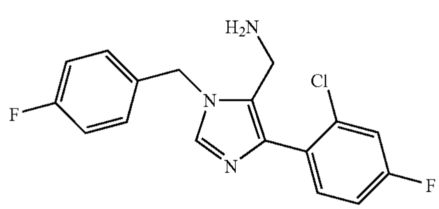 | 10.9 | 334.11 | 334.11 | 356.09 | |
| 6a | C-[5-(2-Chloro-4-fluoro-phenyl)-3-(3-trifluoromethyl-benzyl)-3H-imidazol-4-yl]-methyl-amine | 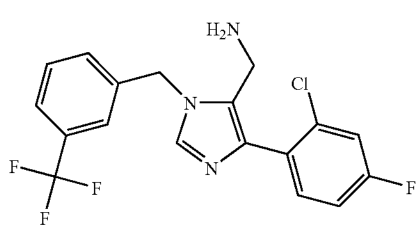 | 17.2 | 384.11 | 384.13 | 406.09 | |

-continued

| Ex. No. | IUPAC-Name | Structure | IC50 DP4 uM | calc. m + h | found m + h | calc. m + Na | found m + Na |
|---|---|---|---|---|---|---|---|
| 7a | C-[5-(2-Chloro-4-fluoro-phenyl)-3-(2,4-difluoro-benzyl)-3H-imidazol-4-yl]-methyl-amine | 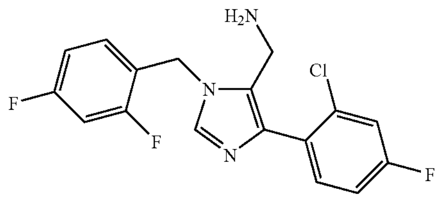 | 27.1 | 352.1 | 352.09 | 374.08 | |
| 8a | C-[5-(2-Chloro-4-fluoro-phenyl)-3-propyl-3H-imidazol-4-yl]-methyl-amine | 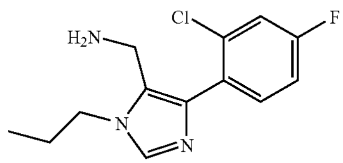 | 48.7 | 268.12 | 268.18 | 290.11 | |
| 9a | C-[5-(2-Chloro-4-fluoro-phenyl)-3-(3-methoxy-benzyl)-3H-imidazol-4-yl]-methyl-amine | 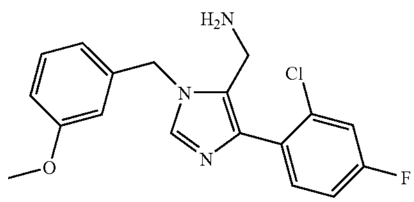 | 16.3 | 346.14 | 346.14 | 368.12 | |
| 10a | C-[5-(2-Chloro-4-fluoro-phenyl)-3-(3-fluoro-benzyl)-3H-imidazol-4-yl]-methyl-amine | 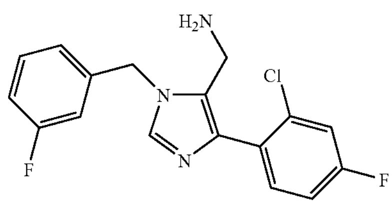 | 14.5 | 334.11 | 334.11 | 356.09 | 356.17 |
| 11a | C-[5-(2-Chloro-4-fluoro-phenyl)-3-thiophen-3-yl-methyl-3H-imidazol-4-yl]-methyl-amine | 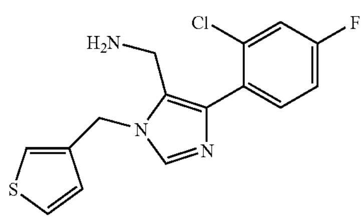 | 4.6 | 322.08 | 322.08 | 344.06 | 344.14 |
| 12a | C-[3-(5-Bromo-2-fluoro-benzyl)-5-(2-chloro-4-fluoro-phenyl)-3H-imidazol-4-yl]-methyl-amine | 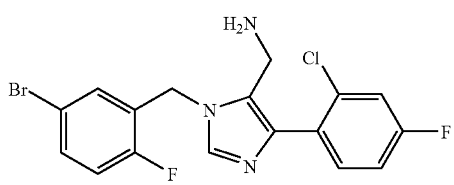 | 32.5 | 412.02 | 412.02 | 434 | |
| 13a | C-[3-(2-Chloro-6-fluoro-benzyl)-5-(2-chloro-4-fluoro-phenyl)-3H-imidazol-4-yl]-methyl-amine | 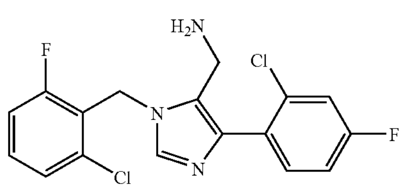 | 36.1 | 368.07 | 368.08 | 390.05 | |

-continued

| Ex. No. | IUPAC-Name | Structure | IC50 DP4 uM | calc. m + h | found m + h | calc. m + Na | found m + Na |
|---|---|---|---|---|---|---|---|
| 14a | C-[5-(2-Chloro-4-fluoro-phenyl)-3-(2-methyl-benzyl)-3H-imidazol-4-yl]-methyl-amine | 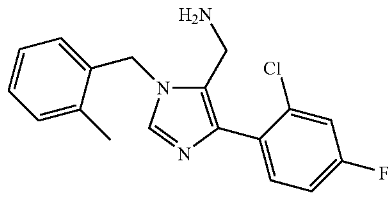 | 19.9 | 330.14 | 330.14 | 352.12 | |
| 15 | C-[3-Benzyl-5-(2-chloro-4-fluoro-phenyl)-3H-imidazol-4-yl]-methyl-amine | 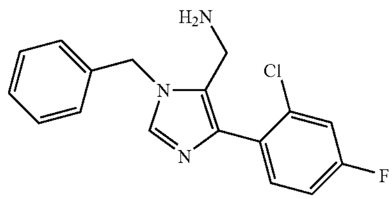 | 10.9 | 316.12 | 316.03 | 338.1 | |
| 16a | C-[3-Benzo[1,3]dioxol-5-yl-methyl-5-(2-chloro-4-fluoro-phenyl)-3H-imidazol-4-yl]-methyl-amine | 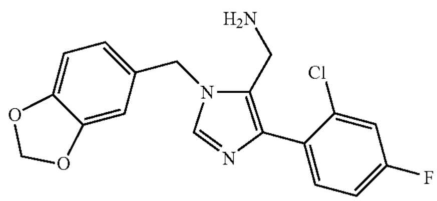 | 28 | 360.11 | 360.12 | 382.09 | |
| 17a | C-[5-(2-Chloro-4-fluoro-phenyl)-3-(3,4-difluoro-benzyl)-3H-imidazol-4-yl]-methyl-amine | 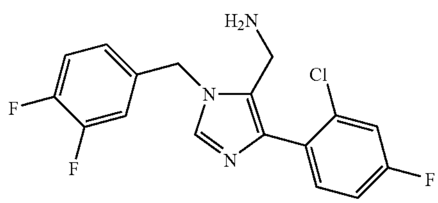 | 19 | 352.1 | 352.11 | 374.08 | |
| 18a | C-[5-(2-Chloro-4-fluoro-phenyl)-3-(2-ethoxy-benzyl)-3H-imidazol-4-yl]-methyl-amine | 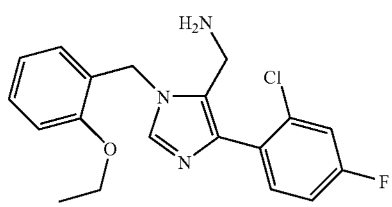 | 6.4 | 360.16 | 360.15 | 382.14 | 382.24 |
| 19a | C-[5-(2-Chloro-4-fluoro-phenyl)-3-(2-trifluoromethyl-benzyl)-3H-imidazol-4-yl]-methyl-amine | 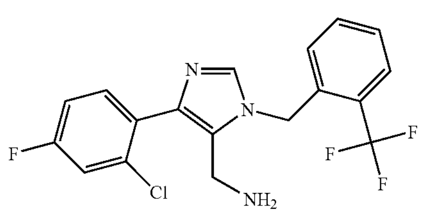 | 35.2 | 384.11 | 384.11 | 406.09 | |
| 20a | C-[5-(2-Chloro-4-fluoro-phenyl)-3-(2,3-dichloro-benzyl)-3H-imidazol-4-yl]-methylamine | 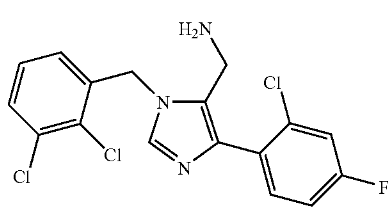 | 34.3 | 384.04 | 384.05 | 406.02 | |

-continued

| Ex. No. | IUPAC-Name | Structure | IC50 DP4 uM | calc. m + h | found m + h | calc. m + Na | found m + Na |
|---|---|---|---|---|---|---|---|
| 21a | C-[5-(2-Chloro-4-fluoro-phenyl)-3-(2,2-di-methyl-propyl)-3H-imid-azol-4-yl]-methyl-amine | 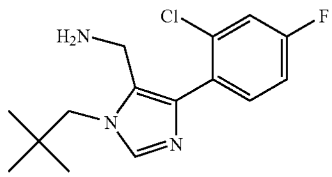 | 35.2 | 296.16 | 296.15 | 318.15 | |
| 22a | C-[3-(4-Chloro-benzyl)-5-(2-chloro-4-fluoro-phenyl)-3H-imid-azol-4-yl]-methyl-amine | 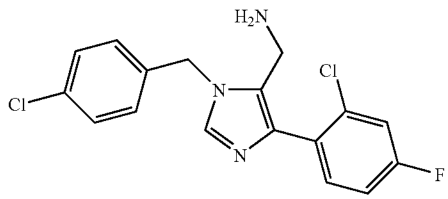 | 37.9 | 350.08 | 350.09 | 372.06 | |
| 23a | C-[5-(2-Chloro-4-fluoro-phenyl)-3-(2-tri-fluoromethoxy-benzyl)-3H-imid-azl-4-yl]-methyl-amine | 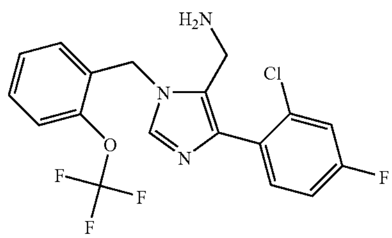 | 5.5 | 400.1 | 400.11 | 422.08 | 422.16 |
| 24a | C-[5-(2-Chloro-4-fluoro-phenyl)-3-(4-methyl-benzyl)-3H-imid-dazol-4-yl]-methyl-amine | 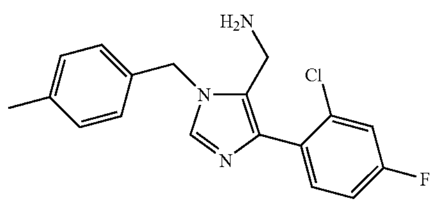 | 43.3 | 330.14 | 330.14 | 352.12 | |
| 25a | C-[5-(2-Chloro-4-fluoro-phenyl)-3-(3,4-di-chloro-benzyl)-3H-imid-azol-4-yl]-methyl-amine | 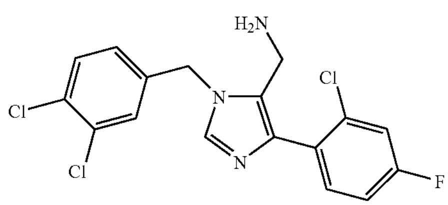 | 33.4 | 384.04 | 384.05 | 406.02 | |
| 26a | C-[5-(2-Chloro-4-fluoro-phenyl)-3-(2,6-di-chloro-benzyl)-3H-imid-azol-4-yl]-methyl-amine | 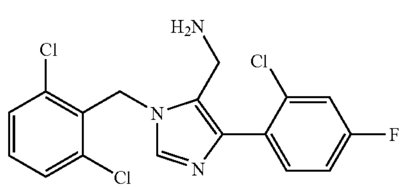 | 39.7 | 384.04 | 384.05 | 406.02 | |
| 27a | C-[5-(2-Chloro-4-fluoro-phenyl)-3-(2,5-difluoro-benzyl)-3H-imid-azol-4-yl]-methyl-amine | 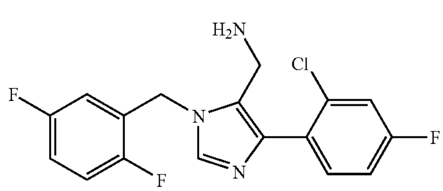 | 22.6 | 352.1 | 352.12 | 374.08 | |

-continued

| Ex. No. | IUPAC-Name | Structure | IC50 DP4 uM | calc. m + h | found m + h | calc. m + Na | found m + Na |
|---|---|---|---|---|---|---|---|
| 28a | C-[5-(2-Chloro-4-fluoro-phenyl)-3-(2-fluoro-benzyl)-3H-imid-azol-4-yl]-methyl-amine | 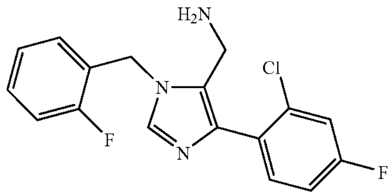 | 19 | 334.11 | 334.11 | 356.09 | |
| 29a | C-[3-(2-Chloro-4-fluoro-benzyl)-5-(2-chloro-4-fluoro-phenyl)-3H-imid-azol-4-yl]-methyl-amine | 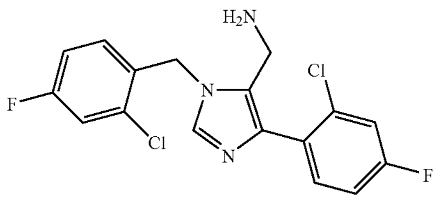 | 31.6 | 368.07 | 368.08 | 390.05 | |
| 30a | C-[5-(2-Chloro-4-fluoro-phenyl)-3-pyridin-2-yl-methyl-3H-imid-azol-4-yl]-methyl-amine | 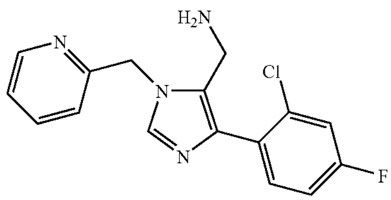 | 25.3 | 317.12 | 317.13 | 339.1 | |
| 31a | C-[5-(2-Chloro-4-fluoro-phenyl)-3-pyridin-3-ylmethyl-3H-imid-azol-4-yl]-methyl-amine | 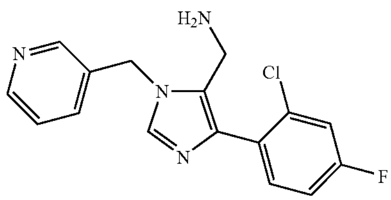 | 5.5 | 317.12 | 317.12 | 339.1 | |
| 32a | C-[5-(2,4-Dichloro-phenyl)-3-thiophen-2-yl-methyl-3H-imid-azol-4-yl]-methyl-amine | 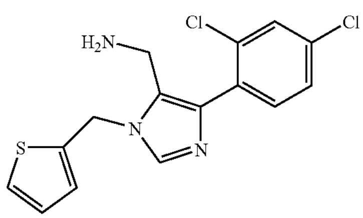 | 0.1 | 338.05 | 338.05 | 360.03 | |
| 33a | C-[5-(2,4-Dichloro-phenyl)-3-furan-2-yl-methyl-3H-imid-azol-4-yl]-methyl-amine | 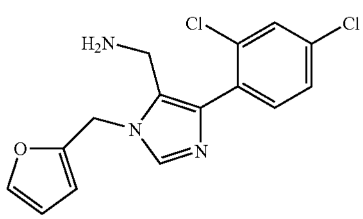 | 0.1 | 322.07 | 322.08 | 344.05 | |
| 34a | C-[3-(2-Chloro-benzyl)-5-(2,4-dichloro-phenyl)-3H-imid-azol-4-yl]-methyl-amine | 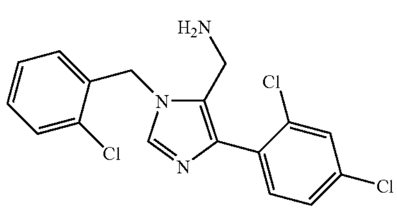 | 1 | 366.05 | 366.06 | 388.03 | |

-continued

| Ex. No. | IUPAC-Name | Structure | IC50 DP4 uM | calc. m + h | found m + h | calc. m + Na | found m + Na |
|---|---|---|---|---|---|---|---|
| 35a | C-[5-(2,4-Dichloro-phenyl)-3-(5-methyl-furan-2-yl-methyl)-3H-imid-azol-4-yl]-methyl-amine | 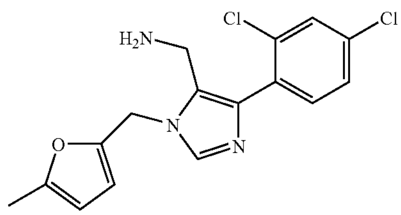 | 0.1 | 336.09 | 336.09 | 358.07 | |
| 36a | C-[5-(2,4-Dichloro-phenyl)-3-(4-fluoro-benzyl)-3H-imid-azol-4-yl]-methyl-amine | 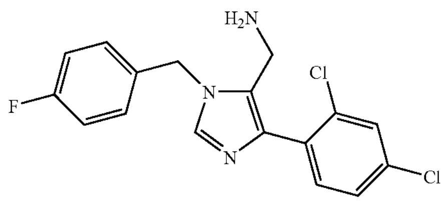 | 0.1 | 350.08 | 350.09 | 372.06 | |
| 37a | C-[5-(2,4-Dichloro-phenyl)-3-(2,6-difluoro-benzyl)-3H-imid-azol-4-yl]-methyl-amine | 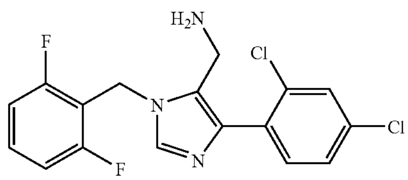 | 4.6 | 368.07 | 368.08 | 390.05 | |
| 38a | C-[5-(2,4-Dichloro-phenyl)-3-(3-tri-fluoromethyl-benzyl)-3H-imid-azol-4-yl]-methyl-amine | 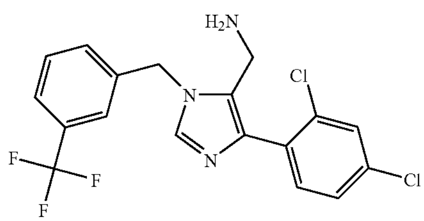 | 1 | 400.08 | 400.1 | 422.06 | |
| 39a | C-[5-(2,4-Dichloro-phenyl)-3-(2,4-difluoro-benzyl)-3H-imid-azol-4-yl]-methyl-amine | 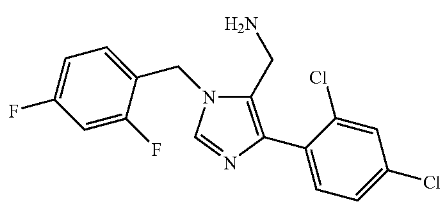 | 1 | 368.07 | 368.08 | 390.05 | |
| 40a | C-[5-(2,4-Dichloro-phenyl)-3-pro-pyl-3H-imid-azol-4-yl]-methyl-amine | 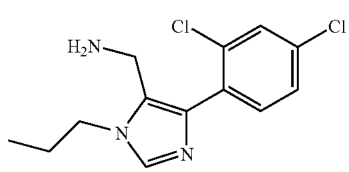 | 3.7 | 284.1 | 284.09 | 306.08 | |
| 41a | C-[5-(2,4-Dichloro-phenyl)-3-(3-methoxy-benzyl)-3H-imid-azol-4-yl]-methyl-amine | 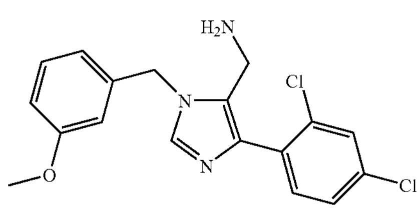 | 0.1 | 362.11 | 362.11 | 384.09 | |

-continued

| Ex. No. | IUPAC-Name | Structure | IC50 DP4 uM | calc. m + h | found m + h | calc. m + Na | found m + Na |
|---|---|---|---|---|---|---|---|
| 42a | C-[5-(2,4-Dichloro-phenyl)-3-(3-fluoro-benzyl)-3H-imid-azol-4-yl]-methyl-amine | 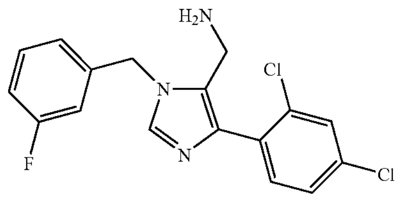 | 1 | 350.08 | 350.09 | 372.06 | |
| 43a | C-[5-(2,4-Dichloro-phenyl)-3-thio-phen-3-yl-methyl-3H-imid-azol-4-yl]-methyl-amine | 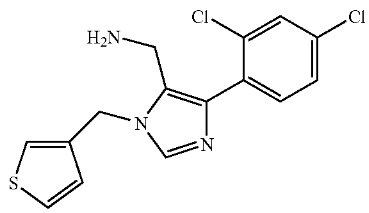 | 0.1 | 338.05 | 338.06 | 360.03 | |
| 44a | C-[3-(5-Bromo-2-fluoro-benzyl)-5-(2,4-dichloro-phenyl)-3H-imid-azol-4-yl]-methyl-amine | 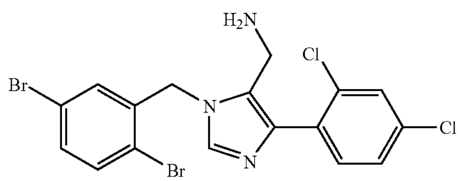 | 30.7 | 427.99 | 428.00 | 449.97 | 450.02 |
| 45a | C-[3-(2-Chloro-6-fluoro-benzyl)-5-(2,4-dichloro-phenyl)-3H-imid-azol-4-yl]-methyl-amine | 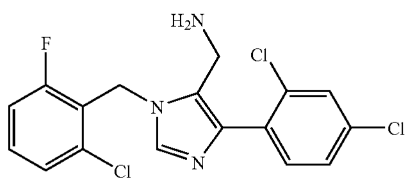 | 1.9 | 384.04 | 384.05 | 406.02 | |
| 46a | C-[5-(2,4-Dichloro-phenyl)-3-(2-methyl-benzyl)-3H-imid-azol-4-yl]-methyl-amine | 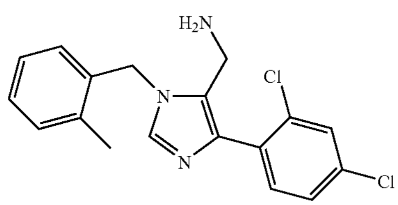 | 1 | 346.11 | 346.12 | 368.09 | |
| 47a | C-[3-Ben-zyl-5-(2,4-dichloro-phenyl)-3H-imid-azol-4-yl]-methyl-amine | 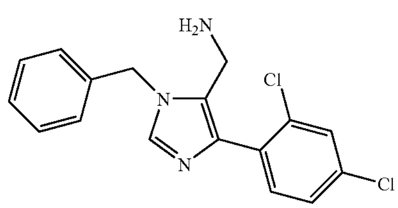 | 0.1 | 332.09 | 332.1 | 354.08 | |
| 48a | C-[3-Ben-zo[1,3]di-oxol-5-yl-methyl-5-(2,4-dichloro-phenyl)-3H-imid-azol-4-yl]-methyl-amine | 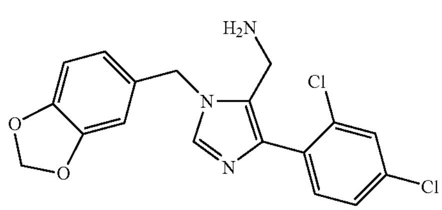 | 0.1 | 376.08 | 376.09 | 398.06 | |

-continued

| Ex. No. | IUPAC-Name | Structure | IC50 DP4 uM | calc. m + h | found m + h | calc. m + Na | found m + Na |
|---|---|---|---|---|---|---|---|
| 49a | C-[5-(2,4-Dichloro-phenyl)-3-(3,4-difluoro-benzyl)-3H-imidazol-4-yl]-methyl-amine | 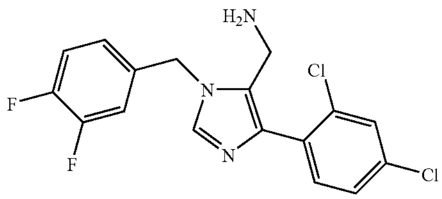 | 0.1 | 368.07 | 368.08 | 390.05 | |
| 50a | C-[5-(2,4-Dichloro-phenyl)-3-(2-ethoxy-benzyl)-3H-imidazol-4-yl]-methyl-amine | 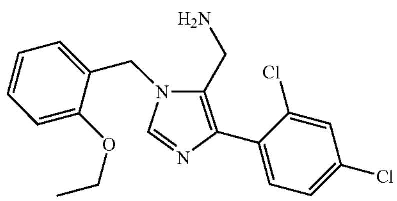 | 0.1 | 376.13 | 376.13 | 398.11 | |
| 51a | C-[5-(2,4-Dichloro-phenyl)-3-(2-tri-fluoromethyl-benzyl)-3H-imidazol-4-yl]-methyl-amine | 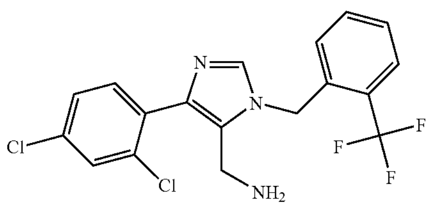 | 3.7 | 400.08 | 400.1 | 422.06 | |
| 52a | C-[3-(2,3-Dichloro-benzyl)-5-(2,4-dichloro-phenyl)-3H-imidazol-4-yl]-methyl-amine | 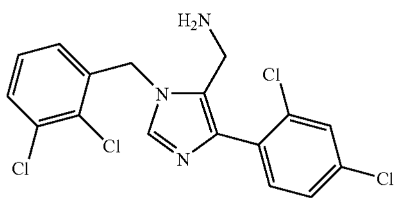 | 2.8 | 400.01 | 400.02 | 421.99 | |
| 53a | C-[5-(2,4-Dichloro-phenyl)-3-(2,2-dimethyl-propyl)-3H-imidazol-4-yl]-methyl-amine | 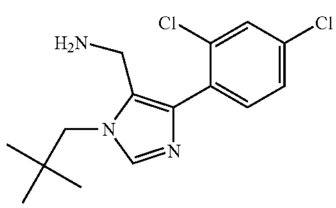 | 1 | 312.13 | 312.13 | 334.12 | |
| 54a | C-[3-(4-Chloro-benzyl)-5-(2,4-dichloro-phenyl)-3H-imidazol-4-yl]-methyl-amine | 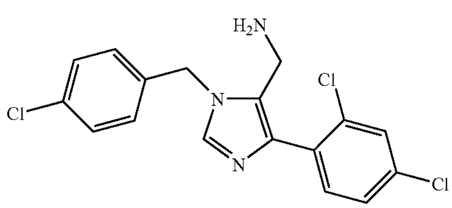 | 1.9 | 366.05 | 366.06 | 388.03 | |
| 55a | C-[5-(2,4-Dichloro-phenyl)-3-(2-tri-fluorometh-oxy-benzyl)-3H-imidazol-4-yl]-methyl-amine | 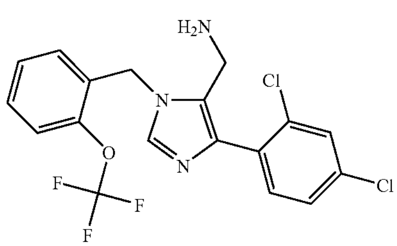 | 0.1 | 416.07 | 416.09 | 438.05 | |

-continued

| Ex. No. | IUPAC-Name | Structure | IC50 DP4 uM | calc. m + h | found m + h | calc. m + Na | found m + Na |
|---|---|---|---|---|---|---|---|
| 56a | C-[5-(2,4-Dichloro-phenyl)-3-(4-methyl-benzyl)-3H-imid-azol-4-yl]-methyl-amine | 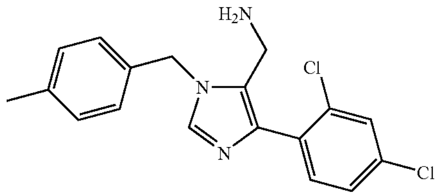 | 2.8 | 346.11 | 346.12 | 368.09 | |
| 57a | C-[3-(2,4-Dichloro-benzyl)-5-(2,4-dichloro-phenyl)-3H-imid-azol-4-yl]-methyl-amine | 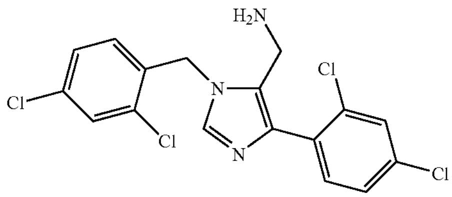 | 9.1 | 400.01 | 400.05 | 421.99 | |
| 58a | C-[3-(3,4-Dichloro-benzyl)-5-(2,4-dichloro-phenyl)-3H-imid-azol-4-yl]-methyl-amine | 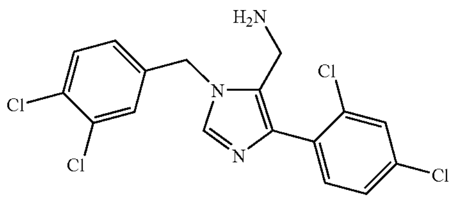 | 1.9 | 400.01 | 400.01 | 421.99 | |
| 59a | C-[5-(2,4-Dichloro-phenyl)-3-eth-yl-3H-imid-azol-4-yl]-methyl-amine | 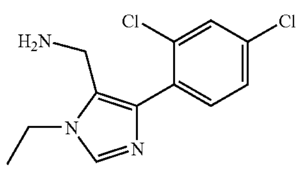 | 25.3 | 270.08 | 270.07 | 292.06 | |
| 60a | C-[3-(2,6-Dichloro-benzyl)-5-(2,4-dichloro-phenyl)-3H-imid-azol-4-yl]-methyl-amine | 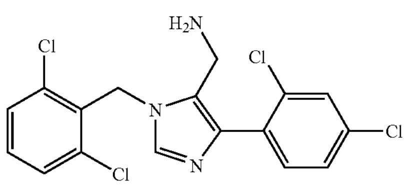 | 2.8 | 400.01 | 400.02 | 421.99 | 422 |
| 61a | C-[5-(2,4-Dichloro-phenyl)-3-(2,5-difluoro-benzyl)-3H-imid-azol-4-yl]-methyl-amine | 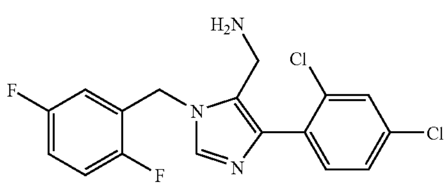 | 1.9 | 368.07 | 368.08 | 390.05 | |
| 62a | C-[5-(2,4-Dichloro-phenyl)-3-(2-fluoro-benzyl)-3H-imid-azol-4-yl]-methyl-amine | 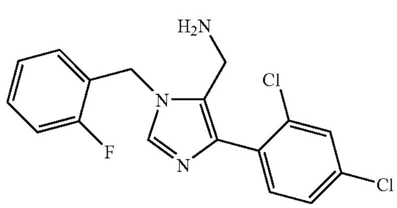 | 0.1 | 350.08 | 350.09 | 372.06 | |
| 63a | C-[3-(2-Chloro-4-fluoro-benzyl)-5-(2,4-di-chloro-phenyl)-3H-imid-azol-4-yl]-methyl-amine | 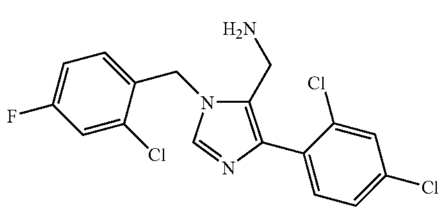 | 1.9 | 384.04 | 384.05 | 406.02 | |

| Ex. No. | IUPAC-Name | Structure | IC50 DP4 uM | calc. m + h | found m + h | calc. m + Na | found m + Na |
|---|---|---|---|---|---|---|---|
| 64a | C-[5-(2,4-Dichloro-phenyl)-3-(1-methyl-1H-pyrrol-2-yl-methyl)-3H-imid-azol-4-yl]-methyl-amine | 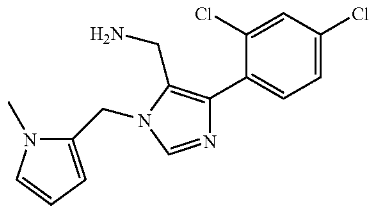 | 27.1 | 335.11 | 335.11 | 357.09 | |
| 65a | C-[5-(2,4-Dichloro-phenyl)-3-pyri-din-2-yl-methyl-3H-imid-azol-4-yl]-methyl-amine | 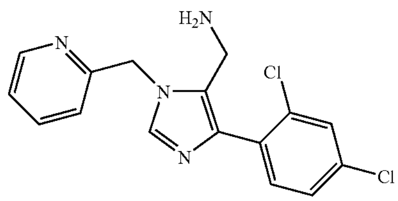 | 1.9 | 333.09 | 333.09 | 355.07 | |
| 66a | C-[5-(2,4-Dichloro-phenyl)-3-pyri-din-3-yl-methyl-3H-imid-azol-4-yl]-methyl-amine | 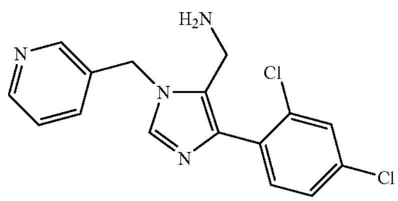 | 0.1 | 333.09 | 333.1 | 355.07 | |
| 67a | C-[5-(2,4-Dimethyl-phenyl)-3-thio-phen-3-yl-methyl-3H-imid-azol-4-yl]-methyl-amine | 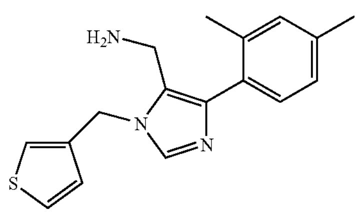 | 42.4 | 298.17 | 298.13 | 320.15 | |
| 68a | C-[3-(5-Bro-mo-2-fluoro-benzyl)-5-(2,4-dimethyl-phenyl)-3H-imid-azol-4-yl]-methyl-amine | 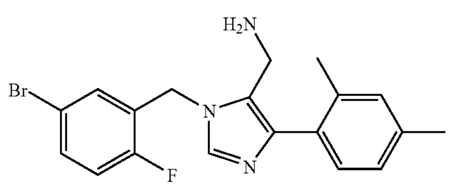 | 37.9 | 388.11 | 388.13 | 410.09 | |
| 69a | C-[3-Benzyl-5-(2,4-di-methyl-phenyl)-3H-imid-azol-4-yl]-methyl-amine | 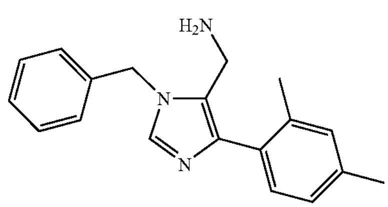 | 40.6 | 292.22 | 292.21 | 314.2 | |
| 70a | C-[5-(2,4-Dimethyl-phenyl)-3-(2-ethoxy-benzyl)-3H-imid-azol-4-yl]-methyl-amine | 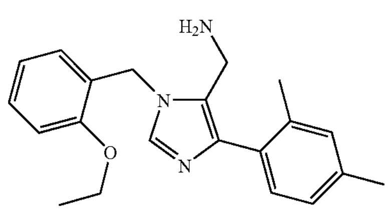 | 16.3 | 336.25 | 336.24 | 358.23 | |

-continued

| Ex. No. | IUPAC-Name | Structure | IC50 DP4 uM | calc. m + h | found m + h | calc. m + Na | found m + Na |
|---|---|---|---|---|---|---|---|
| 71a | C-[3-(5-Bromo-2-fluoro-benzyl)-5-(4-methoxy-2-methyl-phenyl)-3H-imidazol-4-yl]-methyl-amine | 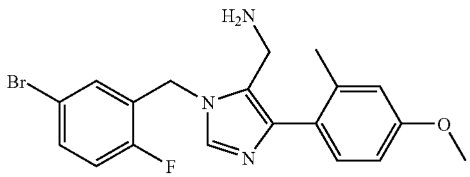 | 30.7 | 404.11 | 404.12 | 426.09 | |
| 72a | C-[5-(2,4-Difluoro-phenyl)-3-furan-2-yl-methyl-3H-imidazol-4-yl]-methyl-amine | 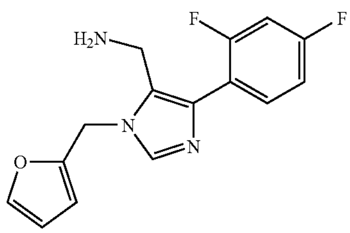 | 11.8 | 290.13 | 290.13 | 312.11 | |
| 73a | C-[3-(2-Chloro-benzyl)-5-(2,4-difluoro-phenyl)-3H-imidazol-4-yl]-methyl-amine | 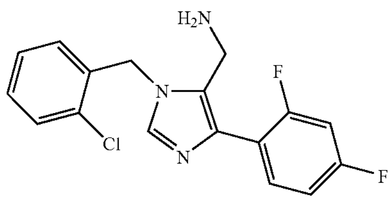 | 27.1 | 334.11 | 334.12 | 356.09 | |
| 74a | C-[5-(2,4-Difluoro-phenyl)-3-(4-fluoro-benzyl)-3H-imidazol-4-yl]-methyl-amine | 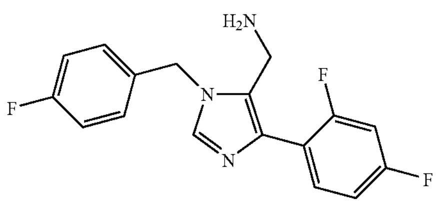 | 44.2 | 318.14 | 318.15 | 340.12 | |
| 75a | C-[5-(2,4-Difluoro-phenyl)-3-(3-trifluoromethyl-benzyl)-3H-imidazol-4-yl]-methyl-amine | 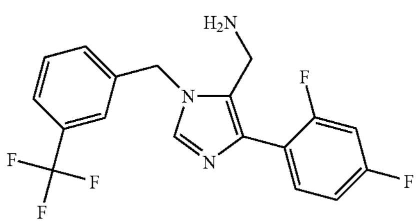 | 28.9 | 368.14 | 368.15 | 390.12 | 390.17 |
| 76a | C-[3-(2,4-Difluoro-benzyl)-5-(2,4-difluoro-phenyl)-3H-imidazol-4-yl]-methyl-amine | 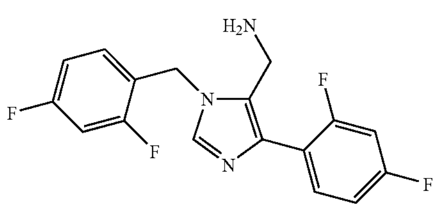 | 40.6 | 336.13 | 336.14 | 358.11 | |
| 77a | C-[5-(2,4-Difluoro-phenyl)-3-(3-methoxy-benzyl)-3H-imidazol-4-yl]-methyl-amine | 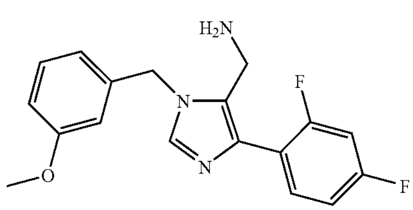 | 24.4 | 330.17 | 330.17 | 352.15 | |

-continued

| Ex. No. | IUPAC-Name | Structure | IC50 DP4 uM | calc. m + h | found m + h | calc. m + Na | found m + Na |
|---|---|---|---|---|---|---|---|
| 78a | C-[5-(2,4-Difluoro-phenyl)-3-(3-fluoro-benzyl)-3H-imid-azol-4-yl]-methyl-amine | 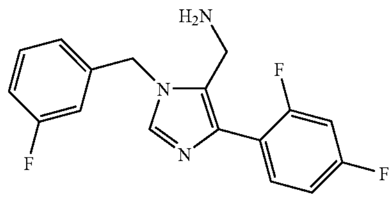 | 46 | 318.14 | 318.15 | 340.12 | |
| 79a | C-[3-(5-Bro-mo-2-fluoro-benzyl)-5-(2,4-difluoro-phenyl)-3H-imid-azol-4-yl]-methyl-amine | 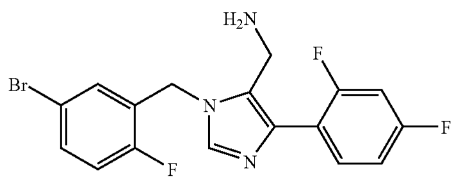 | 32.5 | 396.05 | 396.05 | 418.03 | |
| 80a | C-[3-Benzyl-5-(2,4-di-fluoro-phenyl)-3H-imid-azol-4-yl]-methyl-amine | 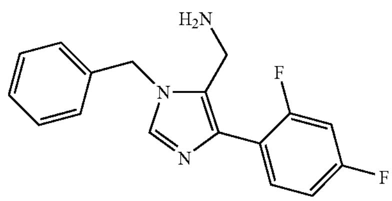 | 19.9 | 300.15 | 300.17 | 322.13 | |
| 81a | C-[3-Ben-zo[1,3]di-oxol-5-yl-methyl-5-(2,4-difluoro-phenyl)-3H-imid-azol-4-yl]-methyl-amine | 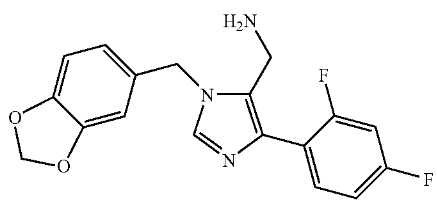 | 46.9 | 344.14 | 344.15 | 366.12 | 366.18 |
| 82a | C-[5-(2,4-Difluoro-phenyl)-3-(2-ethoxy-benzyl)-3H-imid-azol-4-yl]-methyl-amine | 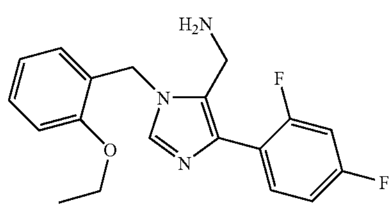 | 14.5 | 344.19 | 344.19 | 366.17 | 366.15 |
| 83a | C-[5-(2,4-Difluoro-phenyl)-3-(2,2-dimethyl-propyl)-3H-imid-azol-4-yl]-methyl-amine | 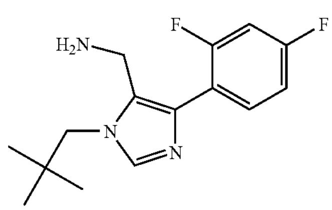 | 27.1 | 280.19 | 280.19 | 302.18 | 302.19 |
| 84a | C-[5-(2,4-Difluoro-phenyl)-3-(2-tri-fluoromethoxy-benzyl)-3H-imid-azol-4-yl]-methyl-amine | 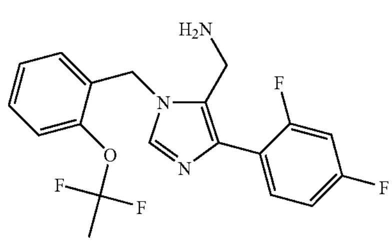 | 9.1 | 384.13 | 384.15 | 406.11 | |

-continued

| Ex. No. | IUPAC-Name | Structure | IC50 DP4 uM | calc. m + h | found m + h | calc. m + Na | found m + Na |
| --- | --- | --- | --- | --- | --- | --- | --- |
| 85a | C-[3-(2,5-Difluoro-benzyl)-5-(2,4-difluoro-phenyl)-3H-imidazol-4-yl]-methyl-amine | 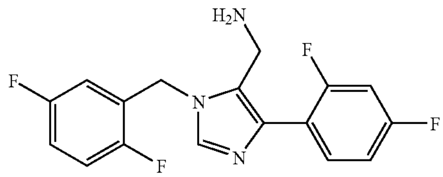 | 36.1 | 336.13 | 336.13 | 358.11 | |
| 86a | C-[5-(2,4-Difluoro-phenyl)-3-(2-fluoro-benzyl)-3H-imidazol-4-yl]-methyl-amine | 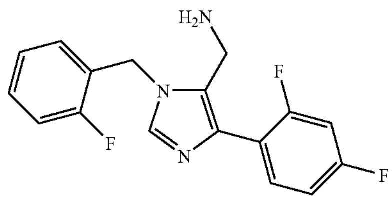 | 32.5 | 318.14 | 318.14 | 340.12 | |
| 87a | C-[3-(2-Chloro-4-fluoro-benzyl)-5-(2,4-difluoro-phenyl)-3H-imidazol-4-yl]-methyl-amine | 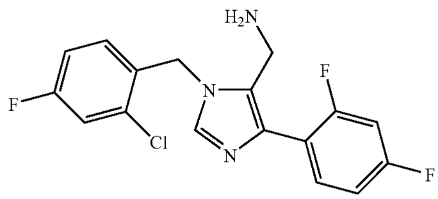 | 25.3 | 352.1 | 352.1 | 374.08 | |
| 88a | C-[5-(2,4-Difluoro-phenyl)-3-pyridin-2-yl-methyl-3H-imidazol-4-yl]-methyl-amine | 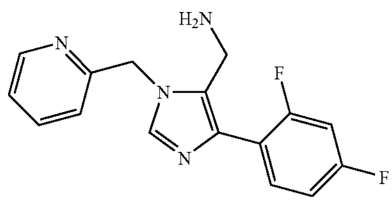 | 29.8 | 301.15 | 301.14 | 323.13 | |
| 89a | C-[5-(2,4-Difluoro-phenyl)-3-pyridin-3-yl-methyl-3H-imidazol-4-yl]-methyl-amine | 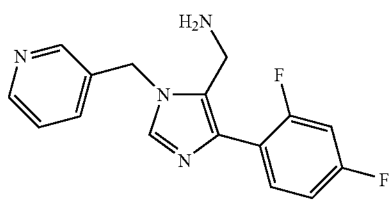 | 22.6 | 301.15 | 301.14 | 323.13 | |

Examples of a compound of formula (Ib) are shown in the following table:

| Ex. No. | IUPAC Name | Calc. [M + H] | Det. [M + H] | Calc. [M + Na] | Det. [M + Na] | $IC_{50}$ [uM] |
| --- | --- | --- | --- | --- | --- | --- |
| 1b | C-{5-(2,4-Dichloro-phenyl)-3-[2-(1H-indol-3-yl)-ethyl]-3H-imidazol-4-yl}-methylamine | 385.12 | 385.1 | 407.11 | — | 3.7 |
| 2b | 1-[5-(2,4-Dichloro-phenyl)-3-phenethyl-3H-imidazol-4-yl]-ethylamine | 360.13 | 360.11 | 382.11 | 382.08 | 32.5 |
| 3b | C-[5-(2,4-Dichloro-phenyl)-3-(3-fluoro-5-trifluoromethyl-benzyl)-3H-imidazol-4-yl]-methylamine | 418.06 | 418.15 | 440.05 | — | 2.8 |
| 4b | {2-[5-Aminomethyl-4-(2,4-dichloro-phenyl)-imidazol-1-yl]-ethyl}-cyclohexyl-amine | 367.19 | 367.16 | 389.17 | — | 10 |

-continued

| Ex. No. | IUPAC Name | Calc. [M + H] | Det. [M + H] | Calc. [M + Na] | Det. [M + Na] | IC$_{50}$ [uM] |
|---|---|---|---|---|---|---|
| 5b | C-[5-(2,4-Dichloro-phenyl)-3-(3,4-dimethoxy-benzyl)-3H-imidazol-4-yl]-methylamine | 392.12 | 392.19 | 414.1 | — | 19.9 |
| 6b | {2-[5-Aminomethyl-4-(2,4-dichloro-phenyl)-imidazol-1-yl]-ethyl}-diisopropyl-amine | 369.21 | 369.25 | 391.19 | — | 10.9 |
| 7b | C-[5-(2,4-Dichloro-phenyl)-3-(3-methyl-butyl)-3H-imidazol-4-yl]-methylamine | 312.13 | 312.17 | 334.12 | — | 8.2 |
| 8b | C-[5-(2,4-Dichloro-phenyl)-3-(2,4-dimethoxy-benzyl)-3H-imidazol-4-yl]-methylamine | 392.12 | 392.2 | 414.1 | — | 12.7 |
| 9b | C-[5-(2,4-Dichloro-phenyl)-3-(2-pyridin-3-yl-ethyl)-3H-imidazol-4-yl]-methylamine | 347.11 | 347.16 | 369.09 | — | 7.3 |
| 10b | C-[5-(2,4-Dichloro-phenyl)-3-(2-morpholin-4-yl-ethyl)-3H-imidazol-4-yl]-methylamine | 355.14 | 355.2 | 377.12 | — | 12.7 |
| 11b | C-[5-(2,4-Dichloro-phenyl)-3-(2,2-dimethyl-propyl)-3H-imidazol-4-yl]-methylamine | 312.13 | 312.1 | 334.12 | — | 6.4 |
| 12b | C-[5-(2,4-Dichloro-phenyl)-3-pentyl-3H-imidazol-4-yl]-methylamine | 312.13 | 312.18 | 334.12 | — | 6.4 |
| 13b | C-[5-(2,4-Dichloro-phenyl)-3-(5-methyl-isoxazol-3-ylmethyl)-3H-imidazol-4-yl]-methylamine | 337.08 | 337.08 | 359.06 | — | 20.8 |
| 14b | C-[3-Adamantan-1-ylmethyl-5-(2,4-dichloro-phenyl)-3H-imidazol-4-yl]-methylamine | 390.19 | 390.25 | 412.17 | — | 19 |
| 15b | 1-[5-(2,4-Dichloro-phenyl)-3-(2-methyl-benzyl)-3H-imidazol-4-yl]-ethylamine | 360.13 | 360.11 | 382.11 | — | 19 |
| 16b | 6-[5-Aminomethyl-4-(2,4-dichloro-phenyl)-imidazol-1-yl]-hexan-1-ol | 342.15 | 342.22 | 364.13 | — | 12.7 |
| 17b | C-[5-(2,4-Dichloro-phenyl)-3-(tetrahydro-furan-2-ylmethyl)-3H-imidazol-4-yl]-methylamine | 326.11 | 326.1 | 348.09 | — | 1.9 |
| 18b | 2-{2-[5-Aminomethyl-4-(2,4-dichloro-phenyl)-imidazol-1-yl]-ethoxy}-ethanol | 330.1 | 330.16 | 352.09 | — | 20.8 |
| 19b | {3-[5-Aminomethyl-4-(2,4-dichloro-phenyl)-imidazol-1-yl]-propyl}-cyclohexyl-amine | 381.2 | 381.27 | 403.19 | — | 45.1 |
| 20b | {2-[5-Aminomethyl-4-(2,4-dichloro-phenyl)-imidazol-1-yl]-ethyl}-(5-nitro-pyridin-2-yl)-amine | 407.1 | 407.18 | 429.08 | — | 8.2 |
| 21b | C-[3-[2-(2-Chloro-phenyl)-ethyl]-5-(2,4-dichloro-phenyl)-3H-imidazol-4-yl]-methylamine | 380.07 | 380.06 | 402.05 | — | 1.9 |
| 22b | 1-{3-[5-(1-Amino-ethyl)-4-(2,4-dichloro-phenyl)-imidazol-1-yl]-propyl}-pyrrolidin-2-one | 381.16 | 381.14 | 403.14 | — | 30.7 |
| 23b | C-[5-(2,4-Dichloro-phenyl)-3-(3,3-dimethyl-butyl)-3H-imidazol-4-yl]-methylamine | 326.15 | 326.2 | 348.14 | — | 8.2 |
| 24b | C-[3-Benzyl-5-(2,4-dichloro-phenyl)-3H-imidazol-4-yl]-methylamine | 332.09 | 332.15 | 354.08 | — | 0.9 |
| 25b | C-[3-(4-Bromo-benzyl)-5-(2,4-dichloro-phenyl)-3H-imidazol-4-yl]-methylamine | 410 | 410.08 | 431.98 | — | 6.4 |
| 26b | C-[5-(2,4-Dichloro-phenyl)-3-(2-pyrrolidin-1-yl-ethyl)-3H-imidazol-4-yl]-methylamine | 339.15 | 339.09 | 361.13 | — | 40.6 |
| 27b | C-[5-(2,4-Dichloro-phenyl)-3-(5-methyl-pyrazin-2-ylmethyl)-3H-imidazol-4-yl]-methylamine | 348.1 | 348.1 | 370.08 | — | 19.9 |
| 28b | C-[5-(2,4-Dichloro-phenyl)-3-(3-fluoro-benzyl)-3H-imidazol-4-yl]-methylamine | 350.08 | 350.08 | 372.06 | 372.05 | 1.9 |
| 29b | 1-{3-[5-Aminomethyl-4-(2,4-dichloro-phenyl)-imidazol-1-yl]-propyl}-pyrrolidin-2-one | 367.14 | 367.2 | 389.12 | — | 22.6 |
| 30b | 3-[3-(5-Bromo-2-fluoro-benzyl)-5-(2,4-dichloro-phenyl)-3H-imidazol-4-yl]-propylamine | 456.03 | 456.1 | 478.01 | — | 17.2 |
| 31b | C-[5-(2,4-Dichloro-phenyl)-3-(2,2-diphenyl-ethyl)-3H-imidazol-4-yl]-methylamine | 422.15 | 422.22 | 444.13 | — | 45.1 |

-continued

| Ex. No. | IUPAC Name | Calc. [M + H] | Det. [M + H] | Calc. [M + Na] | Det. [M + Na] | IC$_{50}$ [uM] |
|---|---|---|---|---|---|---|
| 32b | C-{5-(2,4-Dichloro-phenyl)-3-[2-(2,4-dichloro-phenyl)-ethyl]-3H-imidazol-4-yl}-methylamine | 414.03 | 414.01 | 436.01 | — | 15.4 |
| 33b | C-[5-(2,4-Dichloro-phenyl)-3-(2-methyl-benzyl)-3H-imidazol-4-yl]-methylamine | 346.11 | 346.17 | 368.09 | — | 4.6 |
| 34b | 6-[5-(1-Amino-ethyl)-4-(2,4-dichloro-phenyl)-imidazol-1-yl]-hexan-1-ol | 356.17 | 356.14 | 378.15 | — | 38.8 |
| 35b | C-[5-(2,4-Dichloro-phenyl)-3-(4-methoxy-benzyl)-3H-imidazol-4-yl]-methylamine | 362.11 | 362.17 | 384.09 | — | 11.8 |
| 36b | 1-[5-(2,4-Dichloro-phenyl)-3-(2,5-difluoro-benzyl)-3H-imidazol-4-yl]-ethylamine | 382.09 | 382.08 | 404.07 | — | 25.3 |
| 37b | 2-[3-[2-(3-Chloro-phenyl)-ethyl]-5-(2,4-dichloro-phenyl)-3H-imidazol-4-yl]-ethylamine | 394.09 | 394.12 | 416.07 | 416.14 | 48.7 |
| 38b | 5-[5-Aminomethyl-4-(2,4-dichloro-phenyl)-imidazol-1-yl]-pentan-1-ol | 328.13 | 328.12 | 350.11 | — | 1.9 |
| 39b | C-[5-(2,4-Dichloro-phenyl)-3-pyridin-2-ylmethyl-3H-imidazol-4-yl]-methylamine | 333.09 | 333.15 | 355.07 | — | 4.6 |
| 40b | C-[5-(2,4-Dichloro-phenyl)-3-(2,6-difluoro-benzyl)-3H-imidazol-4-yl]-methylamine | 368.07 | 368.06 | 390.05 | — | 10.9 |
| 41b | {2-[5-Aminomethyl-4-(2,4-dichloro-phenyl)-imidazol-1-yl]-ethyl}-phenyl-amine | 361.13 | 361.12 | 383.11 | — | 32.5 |
| 42b | C-[5-(2,4-Dichloro-phenyl)-3-(4-phenyl-butyl)-3H-imidazol-4-yl]-methylamine | 374.15 | 374.21 | 396.13 | — | 7.3 |
| 43b | 1-[5-(2,4-Dichloro-phenyl)-3-(4-methoxy-benzyl)-3H-imidazol-4-yl]-ethylamine | 376.13 | 376.11 | 398.11 | — | 27.1 |
| 44b | 1-[5-(2,4-Dichloro-phenyl)-3-(3-methyl-butyl)-3H-imidazol-4-yl]-ethylamine | 326.15 | 326.13 | 348.14 | — | 40.6 |
| 45b | C-{5-(2,4-Dichloro-phenyl)-3-[2-(4-methoxy-phenyl)-ethyl]-3H-imidazol-4-yl}-methylamine | 376.13 | 376.19 | 398.11 | — | 27.1 |
| 46b | C-[3-(2,3-Dichloro-benzyl)-5-(2,4-dichloro-phenyl)-3H-imidazol-4-yl]-methylamine | 400.01 | 400.01 | 421.99 | 422.02 | 2.8 |
| 47b | 3-[5-Aminomethyl-4-(2,4-dichloro-phenyl)-imidazol-1-yl]-propan-1-ol | 300.09 | 300.11 | 322.07 | — | 10.9 |
| 48b | C-[5-(2,4-Dichloro-phenyl)-3-(5-methyl-furan-2-ylmethyl)-3H-imidazol-4-yl]-methylamine | 336.09 | 336.16 | 358.07 | — | 5.5 |
| 49b | C-[3-[2-(4-Bromo-phenyl)-ethyl]-5-(2,4-dichloro-phenyl)-3H-imidazol-4-yl]-methylamine | 424.02 | 424.1 | 446 | — | 9.1 |
| 50b | C-[5-(2,4-Dichloro-phenyl)-3-(2-fluoro-3-trifluoromethyl-benzyl)-3H-imidazol-4-yl]-methylamine | 418.06 | 418.15 | 440.05 | — | 15.4 |
| 51b | 1-[5-(2,4-Dichloro-phenyl)-3-(7-methyl-octyl)-3H-imidazol-4-yl]-ethylamine | 382.23 | 382.19 | 404.21 | — | 37.9 |
| 52b | C-[3-[2-(3-Chloro-phenyl)-ethyl]-5-(2,4-dichloro-phenyl)-3H-imidazol-4-yl]-methylamine | 380.07 | 380.14 | 402.05 | — | 5.5 |
| 53b | C-[5-(2,4-Dichloro-phenyl)-3-(3,3-diphenyl-propyl)-3H-imidazol-4-yl]-methylamine | 436.17 | 436.24 | 458.15 | — | 18.1 |
| 54b | C-[5-(2,4-Dichloro-phenyl)-3-(2,4-difluoro-benzyl)-3H-imidazol-4-yl]-methylamine | 368.07 | 368.14 | 390.05 | — | 4.6 |
| 55b | C-{5-(2,4-Dichloro-phenyl)-3-[2-(4-fluoro-phenyl)-ethyl]-3H-imidazol-4-yl}-methylamine | 364.1 | 364.17 | 386.08 | — | 3.7 |
| 56b | 2-[5-Aminomethyl-4-(2,4-dichloro-phenyl)-imidazol-1-yl]-ethanol | 286.07 | 286.08 | 308.05 | — | 19.9 |
| 57b | C-[5-(2,4-Dichloro-phenyl)-3-phenethyl-3H-imidazol-4-yl]-methylamine | 346.11 | 346.08 | 368.09 | — | 9.1 |
| 58b | C-[5-(2,4-Dichloro-phenyl)-3-(2-piperidin-1-yl-ethyl)-3H-imidazol-4-yl]-methylamine | 353.17 | 353.22 | 375.15 | — | 42.4 |

-continued

| Ex. No. | IUPAC Name | Calc. [M + H] | Det. [M + H] | Calc. [M + Na] | Det. [M + Na] | IC$_{50}$ [uM] |
|---|---|---|---|---|---|---|
| 59b | C-[5-(2,4-Dichloro-phenyl)-3-(3-methoxy-benzyl)-3H-imidazol-4-yl]-methylamine | 362.11 | 362.17 | 384.09 | — | 3.7 |
| 60b | C-[5-(2,4-Dichloro-phenyl)-3-(2-methoxy-ethyl)-3H-imidazol-4-yl]-methylamine | 300.09 | 300.16 | 322.07 | — | 20.8 |
| 61b | 1-[5-(2,4-Dichloro-phenyl)-3-hexyl-3H-imidazol-4-yl]-ethylamine | 340.17 | 340.14 | 362.16 | — | 40.6 |
| 62b | (S)-1-[5-(2,4-Dichloro-phenyl)-3-(2,4-dimethoxy-benzyl)-3H-imidazol-4-yl]-ethylamine | 406.14 | 406.11 | 428.12 | — | 10 |
| 63b | 1-[3-[2-(2-Chloro-phenyl)-ethyl]-5-(2,4-dichloro-phenyl)-3H-imidazol-4-yl]-ethylamine | 394.09 | 394.07 | 416.07 | 416.09 | 19 |
| 64b | 1-[3-[2-(3-Chloro-phenyl)-ethyl]-5-(2,4-dichloro-phenyl)-3H-imidazol-4-yl]-ethylamine | 394.09 | 394.07 | 416.07 | 416.09 | 28.9 |
| 65b | C-[3-(2-Cyclohex-1-enyl-ethyl)-5-(2,4-dichloro-phenyl)-3H-imidazol-4-yl]-methylamine | 350.15 | 350.21 | 372.13 | — | 2.8 |
| 66b | C-[5-(2,4-Dichloro-phenyl)-3-(4-methyl-benzyl)-3H-imidazol-4-yl]-methylamine | 346.11 | 346.17 | 368.09 | — | 11.8 |
| 67b | 1-[3-(2-Chloro-benzyl)-5-(2,4-dichloro-phenyl)-3H-imidazol-4-yl]-ethylamine | 380.07 | 380.06 | 402.05 | 402.07 | 28.9 |
| 68b | 1-[5-(2,4-Dichloro-phenyl)-3-(3,4-difluoro-benzyl)-3H-imidazol-4-yl]-ethylamine | 382.09 | 382.08 | 404.07 | — | 26.2 |
| 69b | {2-[5-Aminomethyl-4-(2,4-dichloro-phenyl)-imidazol-1-yl]-ethyl}-ethyl-amine | 313.13 | 313.12 | 335.11 | — | 19 |
| 70b | 1-[5-(2,4-Dichloro-phenyl)-3-(3-phenyl-propyl)-3H-imidazol-4-yl]-ethylamine | 374.15 | 374.13 | 396.13 | 396.14 | 41.5 |
| 71b | 1-[3-(2-Cyclohex-1-enyl-ethyl)-5-(2,4-dichloro-phenyl)-3H-imidazol-4-yl]-ethylamine | 364.17 | 364.14 | 386.15 | — | 35.2 |
| 72b | 1-[5-Aminomethyl-4-(2,4-dichloro-phenyl)-imidazol-1-yl]-propan-2-ol | 300.09 | 300.07 | 322.07 | — | 20.8 |
| 73b | 1-[5-(2,4-Dichloro-phenyl)-3-(2-pyridin-2-yl-ethyl)-3H-imidazol-4-yl]-ethylamine | 361.13 | 361.11 | 383.11 | — | 38.8 |
| 74b | {2-[5-(3-Amino-propyl)-4-(2,4-dichloro-phenyl)-imidazol-1-yl]-ethyl}-(5-nitro-pyridin-2-yl)-amine | 435.14 | 435.21 | 457.12 | — | 12.7 |
| 75b | C-[3-Biphenyl-4-ylmethyl-5-(2,4-dichloro-phenyl)-3H-imidazol-4-yl]-methylamine | 408.13 | 408.2 | 430.11 | — | 23.5 |
| 76b | 1-[5-(2,4-Dichloro-phenyl)-3-(3-methoxy-benzyl)-3H-imidazol-4-yl]-ethylamine | 376.13 | 376.12 | 398.11 | — | 10 |
| 77b | C-[3-(3,4-Dichloro-benzyl)-5-(2,4-dichloro-phenyl)-3H-imidazol-4-yl]-methylamine | 400.01 | 400.09 | 421.99 | — | 7.3 |
| 78b | 1-[5-(2,4-Dichloro-phenyl)-3-pyridin-3-ylmethyl-3H-imidazol-4-yl]-ethylamine | 347.11 | 347.1 | 369.09 | — | 28 |
| 79b | {2-[5-(2-Amino-ethyl)-4-(2,4-dichloro-phenyl)-imidazol-1-yl]-ethyl}-(5-nitro-pyridin-2-yl)-amine | 421.12 | 421.18 | 443.1 | — | 16.3 |
| 80b | 1-[5-(2,4-Dichloro-phenyl)-3-(2-methoxy-benzyl)-3H-imidazol-4-yl]-ethylamine | 376.13 | 376.12 | 398.11 | — | 2.8 |
| 81b | C-[3-(2-Chloro-benzyl)-5-(2,4-dichloro-phenyl)-3H-imidazol-4-yl]-methylamine | 366.05 | 366.05 | 388.03 | — | 1 |
| 82b | C-[3-(4-Chloro-benzyl)-5-(2,4-dichloro-phenyl)-3H-imidazol-4-yl]-methylamine | 366.05 | 366.12 | 388.03 | — | 15.4 |
| 83b | C-{5-(2,4-Dichloro-phenyl)-3-[2-(2-fluoro-phenyl)-ethyl]-3H-imidazol-4-yl}-methylamine | 364.1 | 364.17 | 386.08 | — | 5.5 |
| 84b | C-[5-(2,4-Dichloro-phenyl)-3-hexyl-3H-imidazol-4-yl]-methylamine | 326.15 | 326.13 | 348.14 | — | 1 |
| 85b | C-[5-(2,4-Dichloro-phenyl)-3-(2-pyridin-2-yl-ethyl)-3H-imidazol-4-yl]-methylamine | 347.11 | 347.17 | 369.09 | — | 24.4 |
| 86b | C-[5-(2,4-Dichloro-phenyl)-3-propyl-3H-imidazol-4-yl]-methylamine | 284.1 | 284.15 | 306.08 | — | 17.2 |

-continued

| Ex. No. | IUPAC Name | Calc. [M + H] | Det. [M + H] | Calc. [M + Na] | Det. [M + Na] | IC$_{50}$ [uM] |
|---|---|---|---|---|---|---|
| 87b | C-{5-(2,4-Dichloro-phenyl)-3-[3-(5-methyl-1H-pyrazol-4-yl)-propyl]-3H-imidazol-4-yl}-methylamine | 364.14 | 364.2 | 386.12 | — | 8.2 |
| 88b | (S)-1-[5-(2,4-Dichloro-phenyl)-3-(3,3-diphenyl-propyl)-3H-imidazol-4-yl]-ethylamine | 450.19 | 450.15 | 472.17 | — | 28 |
| 89b | C-[5-(2,4-Dichloro-phenyl)-3-(3-trifluoromethyl-benzyl)-3H-imidazol-4-yl]-methylamine | 400.08 | 400.15 | 422.06 | — | 1.9 |
| 90b | 3-[3-[2-(2-Chloro-phenyl)-ethyl]-5-(2,4-dichloro-phenyl)-3H-imidazol-4-yl]-propylamine | 408.11 | 408.17 | 430.09 | — | 14.5 |
| 91b | C-[5-(2,4-Dichloro-phenyl)-3-(3-phenyl-propyl)-3H-imidazol-4-yl]-methylamine | 360.13 | 360.21 | 382.11 | — | 12.7 |
| 92b | C-[5-(2,4-Dichloro-phenyl)-3-(3,4-difluoro-benzyl)-3H-imidazol-4-yl]-methylamine | 368.07 | 368.14 | 390.05 | — | 1 |
| 93b | C-[3-(2,4-Dichloro-benzyl)-5-(2,4-dichloro-phenyl)-3H-imidazol-4-yl]-methylamine | 400.01 | 400.08 | 421.99 | — | 35.2 |
| 94b | C-[5-(2,4-Dichloro-phenyl)-3-pyridin-4-ylmethyl-3H-imidazol-4-yl]-methylamine | 333.09 | 333.09 | 355.07 | — | 8.2 |
| 95b | 1-[5-(2,4-Dichloro-phenyl)-3-(3,4-dimethoxy-benzyl)-3H-imidazol-4-yl]-ethylamine | 406.14 | 406.13 | 428.12 | — | 19.9 |
| 96b | 1-[5-(2,4-Dichloro-phenyl)-3-pyridin-2-ylmethyl-3H-imidazol-4-yl]-ethylamine | 347.11 | 347.1 | 369.09 | — | 14.5 |
| 97b | C-[5-(2,4-Dichloro-phenyl)-3-(4-trifluoromethoxy-benzyl)-3H-imidazol-4-yl]-methylamine | 416.07 | 416.07 | 438.05 | — | 2.8 |
| 98b | C-[5-(2,4-Dichloro-phenyl)-3-(4-trifluoromethyl-benzyl)-3H-imidazol-4-yl]-methylamine | 400.08 | 400.16 | 422.06 | — | 27.1 |
| 99b | C-[5-(2,4-Dichloro-phenyl)-3-(7-methyl-octyl)-3H-imidazol-4-yl]-methylamine | 368.21 | 368.26 | 390.19 | — | 4.6 |
| 100b | C-[5-(2,4-Dichloro-phenyl)-3-(2-phenoxy-ethyl)-3H-imidazol-4-yl]-methylamine | 362.11 | 362.17 | 384.09 | — | 34.3 |
| 101b | (S)-1-[3-[2-(6-Chloro-1H-indol-3-yl)-ethyl]-5-(2,4-dichloro-phenyl)-3H-imidazol-4-yl]-ethylamine | 433.1 | 433.08 | 455.08 | — | 47.8 |
| 102b | C-[3-[2-(4-Chloro-phenyl)-ethyl]-5-(2,4-dichloro-phenyl)-3H-imidazol-4-yl]-methylamine | 380.07 | 380.14 | 402.05 | — | 19 |
| 103b | (S)-1-{5-(2,4-Dichloro-phenyl)-3-[2-(1H-indol-3-yl)-ethyl]-3H-imidazol-4-yl}-ethylamine | 399.14 | 399.11 | 421.13 | 421.15 | 44.2 |
| 104b | C-[5-(2,4-Dichloro-phenyl)-3-(3-imidazol-1-yl-propyl)-3H-imidazol-4-yl]-methylamine | 350.12 | 350.18 | 372.1 | — | 5.5 |
| 105b | 3-[3-[2-(6-Chloro-1H-indol-3-yl)-ethyl]-5-(2,4-dichloro-phenyl)-3H-imidazol-4-yl]-propylamine | 447.12 | — | 469.1 | 469.18 | 37.9 |
| 106b | 1-[5-(2,4-Dichloro-phenyl)-3-(4-phenyl-butyl)-3H-imidazol-4-yl]-ethylamine | 388.17 | 388.14 | 410.15 | — | 28 |
| 107b | 3-[3-[2-(3-Chloro-phenyl)-ethyl]-5-(2,4-dichloro-phenyl)-3H-imidazol-4-yl]-propylamine | 408.11 | 408.17 | 430.09 | 430.19 | 42.4 |
| 108b | C-[5-(2,4-Dichloro-phenyl)-3-(2-trifluoromethyl-benzyl)-3H-imidazol-4-yl]-methylamine | 400.08 | 400.16 | 422.06 | — | 5.5 |
| 109b | 1-[3-Benzyl-5-(2,4-dichloro-phenyl)-3H-imidazol-4-yl]-ethylamine | 346.11 | 346.11 | 368.09 | 368.11 | 7.3 |
| 110b | (S)-1-{5-(2,4-Dichloro-phenyl)-3-[2-(6-fluoro-1H-indol-3-yl)-ethyl]-3H-imidazol-4-yl}-ethylamine | 417.13 | 417.11 | 439.11 | 439.14 | 42.4 |
| 111b | {2-[5-((S)-1-Amino-ethyl)-4-(2,4-dichloro-phenyl)-imidazol-1-yl]-ethyl}-(5-nitro-pyridin-2-yl)-amine | 421.12 | 421.1 | 443.1 | 443.11 | 21.7 |
| 112b | C-[5-(2,4-Dichloro-phenyl)-3-(2-fluoro-benzyl)-3H-imidazol-4-yl]-methylamine | 350.08 | 350.15 | 372.06 | — | 3.7 |
| 113b | 4-{2-[5-Aminomethyl-4-(2,4-dichloro-phenyl)-imidazol-1-yl]-ethyl}-phenol | 362.11 | 362.18 | 384.09 | — | 21.7 |

-continued

| Ex. No. | IUPAC Name | Calc. [M + H] | Det. [M + H] | Calc. [M + Na] | Det. [M + Na] | IC$_{50}$ [uM] |
|---|---|---|---|---|---|---|
| 114b | C-{5-(2,4-Dichloro-phenyl)-3-[2-(6-fluoro-1H-indol-3-yl)-ethyl]-3H-imidazol-4-yl}-methylamine | 403.11 | — | 425.09 | 425.12 | 3.7 |
| 115b | 1-[5-(2,4-Dichloro-phenyl)-3-pentyl-3H-imidazol-4-yl]-ethylamine | 326.15 | 326.13 | 348.14 | — | 29.8 |
| 116b | 1-[5-(2,4-Dichloro-phenyl)-3-(4-methyl-benzyl)-3H-imidazol-4-yl]-ethylamine | 360.13 | 360.12 | 382.11 | 382.12 | 23.5 |
| 117b | 5-Azetidin-3-yl-1-[2-(2-chloro-phenyl)-ethyl]-4-(2,4-dichloro-phenyl)-1H-imidazole | 406.09 | 406.08 | 428.07 | 428.08 | 39.7 |
| 118b | 1-[5-(2,4-Dichloro-phenyl)-3-(2-morpholin-4-yl-ethyl)-3H-imidazol-4-yl]-ethylamine | 369.16 | 369.16 | 391.14 | 391.23 | 49.6 |
| 119b | C-[5-(2,4-Dichloro-phenyl)-3-(2,5-difluoro-benzyl)-3H-imidazol-4-yl]-methylamine | 368.07 | 368.14 | 390.05 | — | 2.8 |
| 120b | C-[5-(2,4-Dichloro-phenyl)-3-(2-methoxy-benzyl)-3H-imidazol-4-yl]-methylamine | 362.11 | 362.17 | 384.09 | — | 1.9 |
| 121b | C-[5-(2,4-Dichloro-phenyl)-3-pyridin-3-ylmethyl-3H-imidazol-4-yl]-methylamine | 333.09 | 333.15 | 355.07 | — | 4.6 |
| 122b | C-[5-(2,4-Dichloro-phenyl)-3-ethyl-3H-imidazol-4-yl]-methylamine | 270.08 | 270.12 | 292.06 | — | 46 |
| 123b | C-[3-(2-Chloro-6-fluoro-benzyl)-5-(2,4-dichloro-phenyl)-3H-imidazol-4-yl]-methylamine | 384.04 | 384.12 | 406.02 | — | 1.9 |
| 124b | C-[3-(5-Bromo-2-fluoro-benzyl)-5-(2,4-dichloro-phenyl)-3H-imidazol-4-yl]-methylamine | 427.99 | — | 449.97 | 449.99 | 34.3 |

Preparative Synthesis

The following compounds of the invention were prepared by preparative synthesis following essentially the route used for the parallel synthesis.

| Ex. No. | IUPAC Name |
|---|---|
| 11a | C-[5-(2-Chloro-4-fluoro-phenyl)-3-thiophen-3-ylmethyl-3H-imidazol-4-yl]-methylamine |
| 18a | C-[5-(2-Chloro-4-fluoro-phenyl)-3-(2-ethoxy-benzyl)-3H-imidazol-4-yl]-methylamine |
| 33a | C-[5-(2,4-Dichloro-phenyl)-3-furan-2-ylmethyl-3H-imidazol-4-yl]-methylamine |
| 35a | C-[5-(2,4-Dichloro-phenyl)-3-(5-methyl-furan-2-ylmethyl)-3H-imidazol-4-yl]-methylamine |
| 72a | C-[5-(2,4-Difluoro-phenyl)-3-furan-2-ylmethyl-3H-imidazol-4-yl]-methylamine |
| 84a | C-[5-(2,4-Difluoro-phenyl)-3-(2-trifluoromethoxy-benzyl)-3H-imidazol-4-yl]-methylamine |

The following compounds of the invention were also prepared by preparative synthesis following essentially the route used for the parallel synthesis.

| Ex. No. | IUPAC Name |
|---|---|
| 11b | C-[5-(2,4-dichloro-phenyl)-3-(2,2-dimethyl-propyl)-3H-imidazol-4-yl]-methylamine |
| 17b | C-[5-(2,4-dichloro-phenyl)-3-(tetrahydro-furan-2-ylmethyl)-3H-imidazol-4-yl]-methylamine |
| 21b | C-[3-[2-(2-chloro-phenyl)-ethyl]-5-(2,4-dichloro-phenyl)-3H-imidazol-4-yl]-methylamine |
| 23b | C-[5-(2,4-dichloro-phenyl)-3-(3,3-dimethyl-butyl)-3H-imidazol-4-yl]-methylamine |
| 24b | C-[3-Benzyl-5-(2,4-dichloro-phenyl)-3H-imidazol-4-yl]-methylamine |
| 28b | C-[5-(2,4-dichloro-phenyl)-3-(3-fluoro-benzyl)-3H-imidazol-4-yl]-methylamine |
| 32b | C-{5-(2,4-dichloro-phenyl)-3-[2-(2,4-dichloro-phenyl)-ethyl]-3H-imidazol-4-yl}-methylamine |
| 33b | C-[5-(2,4-dichloro-phenyl)-3-(2-methyl-benzyl)-3H-imidazol-4-yl]-methylamine |
| 38b | 5-[5-aminomethyl-4-(2,4-dichloro-phenyl)-imidazol-1-yl]-pentan-1-ol |
| 39b | C-[5-(2,4-dichloro-phenyl)-3-pyridin-2-ylmethyl-3H-imidazol-4-yl]-methylamine |
| 54b | C-[5-(2,4-dichloro-phenyl)-3-(2,4-difluoro-benzyl)-3H-imidazol-4-yl]-methylamine |

-continued

| Ex. No. | IUPAC Name |
|---|---|
| 59b | C-[5-(2,4-dichloro-phenyl)-3-(3-methoxy-benzyl)-3H-imidazol-4-yl]-methylamine |
| 81b | C-[3-(2-chloro-benzyl)-5-(2,4-dichloro-phenyl)-3H-imidazol-4-yl]-methylamine |
| 92b | C-[5-(2,4-dichloro-phenyl)-3-(3,4-difluoro-benzyl)-3H-imidazol-4-yl]-methylamine |
| 104b | C-[5-(2,4-dichloro-phenyl)-3-(3-imidazol-1-yl-propyl)-3H-imidazol-4-yl]-methylamine |
| 112b | C-[5-(2,4-dichloro-phenyl)-3-(2-fluoro-benzyl)-3H-imidazol-4-yl]-methylamine |
| 120b | C-[5-(2,4-dichloro-phenyl)-3-(2-methoxy-benzyl)-3H-imidazol-4-yl]-methylamine |
| 121b | C-[5-(2,4-dichloro-phenyl)-3-pyridin-3-ylmethyl-3H-imidazol-4-yl]-methylamine |
| 125b | C-[3-benzo[1,3]dioxol-5-ylmethyl-5-(2,4-dichloro-phenyl)-3H-imidazol-4-yl]-methylamine |
| 126b | 2-[5-aminomethyl-4-(2,4-dichloro-phenyl)-imidazol-1-yl]-2-phenyl-ethanol |
| 127b | C-{5-(2,4-dichloro-phenyl)-3-[2-(6-methyl-1H-indol-3-yl)-ethyl]-3H-imidazol-4-yl}-methylamine |
| 128b | C-[5-(2,4-dichloro-phenyl)-3-(2-ethoxy-benzyl)-3H-imidazol-4-yl]-methylamine |
| 129b | C-[5-(2,4-dichloro-phenyl)-3-(2-trifluoromethoxy-benzyl)-3H-imidazol-4-yl]-methylamine |
| 130b | C-[5-(2,4-dichloro-phenyl)-3-thiophen-3-ylmethyl-3H-imidazol-4-yl]-methylamine |
| 131b | C-[5-(2,4-dichloro-phenyl)-3-(1-methyl-1H-pyrazol-4-ylmethyl)-3H-imidazol-4-yl]-methylamine |

General Workup

The appropriate amine (V) (4 mmol) and aldehyde (IV) (1 mmol) were combined in methanol (5 ml, dry). After 30 min the isocyanide (II) (1 mmol) was added. The reaction was heated to 40° C. and stirred for 24 h. After evaporation of the solvent the residue was purified with chromatographic methods.

The subsequent cleavage of the Boc-protecting group was done with the addition of 4M HCl in dioxan (3 ml) and water (320 µl). After 2-3 h the solvent was evaporated. The crude reaction product could then be purified via semi-preparative LC-MS.

The purity of the compounds was determined by HPLC-MS. The $IC_{50}$ value against DP IV was measured using the fluorescent assay.

Purification and Characterisation

The resulting crude reaction products were purified in an automatic process using a semi-preparative HPLC-MS with mass-triggered sampling of the desired peak:

Purification via semi-preparative HPLC-MS
Instrumentation:
2× Varian PrepStar SD-1
1× Dionex P580 Pump 1 Channel(MakeUP I)
1× Dionex AXP-MS (MakeUP II)
1× Dionex MSQ
1× Dionex UVD 340V—Prep Flow Cell
Gilson 215 Liquid Handler
Column:
SunFire Prep C18 OBD 5 µm 19×50 mm
Method:
Column Flow: 30 ml/min
Solvent A: methanol, 0.3% acetic acid
Solvent B: water, 0.3% acetic acid
Time table for gradient:

| Time (min) | Solvent A | Solvent B |
|---|---|---|
| 0.0 | 30.00 | 70.00 |
| 10.0 | 100.00 | 0.00 |
| 14.0 | 100.00 | 0.00 |
| 14.4 | 30.00 | 70.00 |
| 16.4 | 30.00 | 70.00 |

Detection:

UV 254 nm, Mass Spectrometer Detector (API-ES, positive)

Compound Verfication

The compound verification via analytical HPLC-MS was done after purification using the following instrumentation, column and method:

Analytical method for compound purity
Instrumentation:
Agilent MSD 1100
Column:
YMC ODS-A 2.1×50, 3 um
Method:
Column Flow: 0.600 ml/min
Solvent A: acetonitrile, 0.5% acetic acid
Solvent B: 90% water, 10% acetonitrile, 0.5% acetic acid
Time table for gradient:

| Time (min) | Solvent A | Solvent B |
|---|---|---|
| 0.0 | 0.00 | 100.00 |
| 2.5 | 90.00 | 10.00 |
| 4.0 | 90.00 | 10.00 |
| 4.5 | 0.00 | 100.00 |
| 6.0 | 0.00 | 100.00 |

Detection:

UV 254 nm, Mass Spectrometer Detector (API-ES, positive)

Compound 11a: C-[5-(2-Chloro-4-fluoro-phenyl)-3-thiophen-3-ylmethyl-3H-imidazol-4-yl]-methylamine

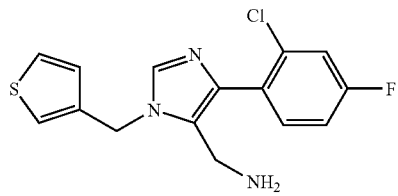

4 mmol C-Thiophen-3-yl-methylamine and 1 mmol (2-Oxo-ethyl)-carbamic acid tert-butyl ester were added in 5 ml MeOH (dry). After 30 min the 1 mmol 2-Chloro-4-fluoro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent Cleavage of the Boc-Protectiongroup was done with the addition of 3 ml of 4M HCl in Dioxan and 320 µl H$_2$O. After 2-3 h the solvent is evaporated. The crude reaction product can be purified now via semi-prep. LC-MS

| molecular weight (g/mol): | 441.91 |
|---|---|
| RT-UV254 nm (min): | 2.39 |
| IC$_{50}$ DP4 (nM): | 120.5 |

Compound 18a: C-[5-(2-Chloro-4-fluoro-phenyl)-3-(2-ethoxy-benzyl)-3H-imidazol-4-yl]-methylamine

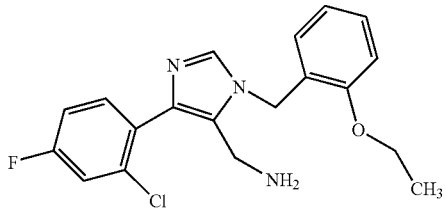

4 mmol 2-Ethoxy-benzylamine and 1 mmol (2-Oxo-ethyl)-carbamic acid tert-butyl ester were added in 5 ml MeOH (dry). After 30 min the 1 mmol 2-Chloro-4-fluoro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent Cleavage of the Boc-Protectiongroup was done with the addition of 3 ml of 4M HCl in Dioxan and 320 µl H$_2$O. After 2-3 h the solvent is evaporated. The crude reaction product can be purified now via semi-prep. LC-MS

| molecular weight (g/mol): | 479.94 |
|---|---|
| RT-UV254 nm (min): | 2.67 |
| IC$_{50}$ DP4 (nM): | 141.2 |

Compound 33a: C-[5-(2,4-Dichloro-phenyl)-3-furan-2-ylmethyl-3H-imidazol-4-yl]-methylamine

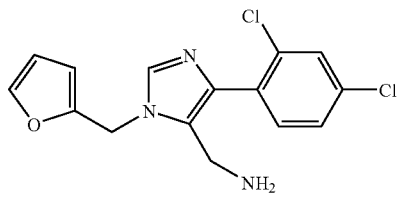

4 mmol C-Furan-2-yl-methylamine and 1 mmol (2-Oxo-ethyl)-carbamic acid tert-butyl ester were added in 5 ml MeOH (dry). After 30 min the 1 mmol 2,4-dichloro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent Cleavage of the Boc-Protectiongroup was done with the addition of 3 ml of 4M HCl in Dioxan and 320 µl H$_2$O. After 2-3 h the solvent is evaporated. The crude reaction product can be purified now via semi-prep. LC-MS

| molecular weight (g/mol): | 442.30 |
|---|---|
| RT-UV254 nm (min): | 2.53 |
| IC$_{50}$ DP4 (nM): | 93.3 |

Compound 35a: C-[5-(2,4-Dichloro-phenyl)-3-(5-methyl-furan-2-ylmethyl)-3H-imidazol-4-yl]-methylamine

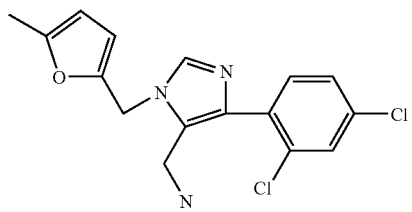

4 mmol C-(5-Methyl-furan-2-yl)-methylamine and 1 mmol (2-Oxo-ethyl)-carbamic acid tert-butyl ester were added in 5 ml MeOH (dry). After 30 min the 1 mmol 2,4-dichloro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent Cleavage of the Boc-Protectiongroup was done with the addition of 3 ml of 4M HCl in Dioxan and 320 µl H$_2$O. After 2-3 h the solvent is evaporated. The crude reaction product can be purified now via semi-prep. LC-MS

| molecular weight (g/mol): | 456.33 |
|---|---|
| RT-UV254 nm (min): | 2.69 |
| IC$_{50}$ DP4 (nM): | 98.9 |

Compound 72a: C-[5-(2,4-Difluoro-phenyl)-3-furan-2-ylmethyl-3H-imidazol-4-yl]-methylamine

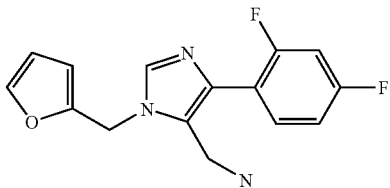

4 mmol C-Furan-2-yl-methylamine and 1 mmol (2-Oxo-ethyl)-carbamic acid tert-butyl ester were added in 5 ml MeOH (dry). After 30 min the 1 mmol 2,4-difluoro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent Cleavage of the Boc-Protectiongroup was done with the addition of 3 ml of 4 M HCl in Dioxan and 320 µl H$_2$O. After 2-3 h the solvent is evaporated. The crude reaction product can be purified now via semi-prep. LC-MS

| | |
|---|---|
| molecular weight (g/mol): | 409.39 |
| RT-UV254 nm (min): | 1.26 |
| IC$_{50}$ DP4 (nM): | 3828.2 |

Compound 84a: C-[5-(2,4-Difluoro-phenyl)-3-(2-trifluoromethoxy-benzyl)-3H-imidazol-4-yl]-methylamine

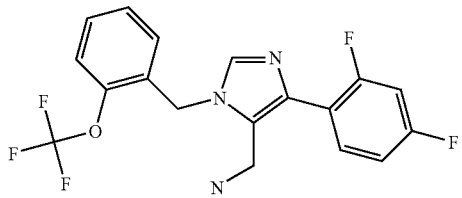

4 mmol 2-Trifluoromethoxy-benzylamine and 1 mmol (2-Oxo-ethyl)-carbamic acid tert-butyl ester were added in 5 ml MeOH (dry). After 30 min the 1 mmol 2,4-difluoro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent Cleavage of the Boc-Protectiongroup was done with the addition of 3 ml of 4M HCl in Dioxan and 320 µl H$_2$O. After 2-3 h the solvent is evaporated. The crude reaction product can be purified now via semi-prep. LC-MS

| | |
|---|---|
| molecular weight (g/mol): | 503.43 |
| RT - UV254nm (min): | 2.83 |
| IC$_{50}$ DP4 (nM): | 1017.5 |

Compound 11b: C-[5-(2,4-dichloro-phenyl)-3-(2,2-dimethyl-propyl)-3H-imidazol-4-yl]-methylamine

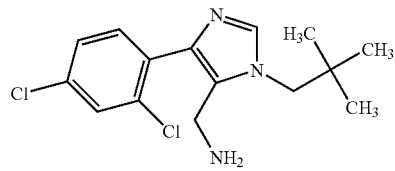

2,2-dimethyl-propylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 312.24 |
| RT - UV254nm (min): | 2.69 |
| IC$_{50}$ DP IV fluorescent (nM): | 2584 |

Compound 17b: C-[5-(2,4-dichloro-phenyl)-3-(tetrahydro-furan-2-ylmethyl)-3H-imidazol-4-yl]-methylamine

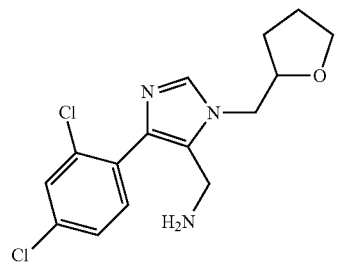

C-(Tetrahydro-furan-2-yl)-methylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 326.23 |
| RT - UV254nm (min): | 1.79 |
| IC$_{50}$ DP IV fluorescent (nM): | 410 |

Compound 21b: C-[3-[2-(2-chloro-phenyl)-ethyl]-5-(2,4-dichloro-phenyl)-3H-imidazol-4-yl]-methylamine

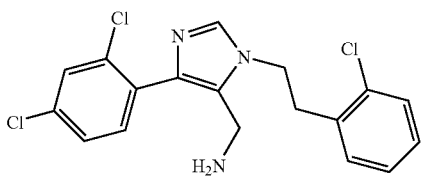

2-(2-chloro-phenyl)-ethylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 380.71 |
| RT - UV254nm (min): | 2.78 |
| IC$_{50}$ DP IV fluorescent (nM): | 514 |

Compound 24b: (1-benzyl-4-(2,4-dichlorophenyl)-1H-imidazol-5-yl)methanamine

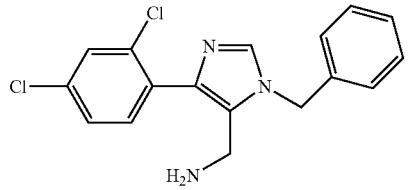

Benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 332.24 |
| RT - UV254nm (min): | 2.65 |
| IC$_{50}$ DP IV fluorescent (nM): | 123 |

Compound 23b: C-[5-(2,4-dichloro-phenyl)-3-(3,3-dimethyl-butyl)-3H-imidazol-4-yl]-methylamine

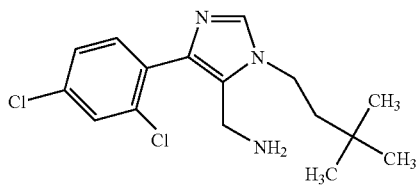

3,3-dimethyl-butylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 362.26 |
| RT - UV254nm (min): | 2.77 |
| IC$_{50}$ DP IV fluorescent (nM): | 903 |

Compound 28b: C-[5-(2,4-dichloro-phenyl)-3-(3-fluoro-benzyl)-3H-imidazol-4-yl]-methylamine

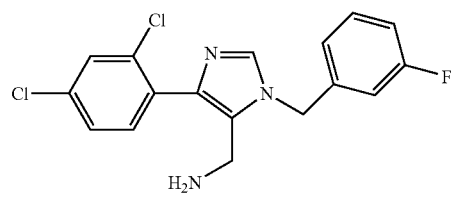

3-Fluoro-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 350.23 |
| RT - UV254nm (min): | 2.80 |
| IC$_{50}$ DP IV fluorescent (nM): | 158 |

Compound 32b: C-{5-(2,4-dichloro-phenyl)-3-[2-(2,4-dichloro-phenyl)-ethyl]-3H-imidazol-4-yl}-methylamine

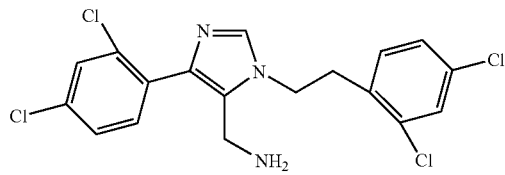

2-(2,4-dichloro-phenyl)-ethylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

PREPARATIVE EXAMPLE NO.: 3

| molecular weight (g/mol): | 415.15 |
|---|---|
| RT - UV254nm (min): | 3.00 |
| $IC_{50}$ DP IV fluorescent (nM): | 139 |

Compound 33b: C-[5-(2,4-dichloro-phenyl)-3-(2-methyl-benzyl)-3H-imidazol-4-yl]-methylamine

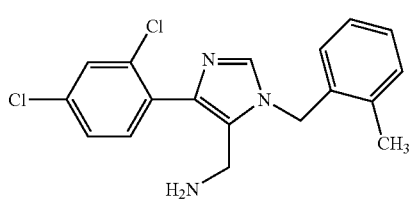

2-methyl-bentylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 346.26 |
|---|---|
| RT - UV254nm (min): | 2.84 |
| $IC_{50}$ DP IV fluorescent (nM): | 167 |

Compound 38b: 5-[5-aminomethyl-4-(2,4-dichloro-phenyl)-imidazol-1-yl]-pentan-1-ol

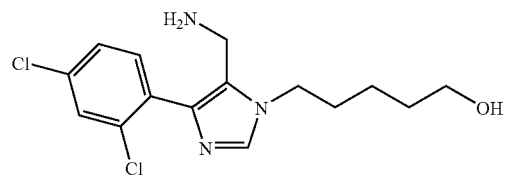

5-Amino-pentan-1-ol (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 328.24 |
|---|---|
| RT - UV254nm (min): | 0.99 |
| $IC_{50}$ DP IV fluorescent (nM): | 848 |

Compound 39b: 4-(2,4-dichlorophenyl)-1-((pyridin-2-yl)methyl)-1H-imidazol-5-yl)methanamine

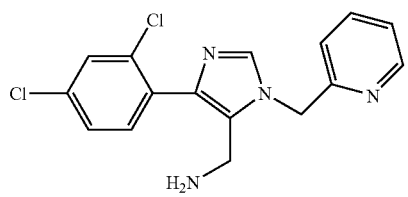

C-pyridin-2-yl-methylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 333.22 |
|---|---|
| RT - UV254nm (min): | 2.05 |
| $IC_{50}$ DP IV fluorescent (nM): | 59 |

Compound 54b: C-[5-(2,4-dichloro-phenyl)-3-(2,4-difluoro-benzyl)-3H-imidazol-4-yl]-methylamine

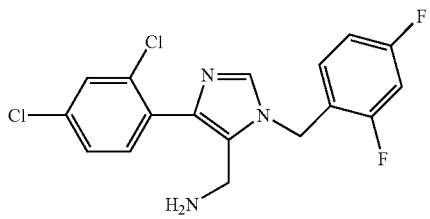

2,4-Difluoro-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 μl). After 2-3 h the solvent was evaporated. The crude reaction product was purified via semi-preparative chromatography.

| molecular weight (g/mol): | 368.22 |
|---|---|
| RT - UV254nm (min): | 2.83 |
| IC$_{50}$ DP IV fluorescent (nM): | 270 |

Compound 59b: C-[5-(2,4-dichloro-phenyl)-3-(3-methoxy-benzyl)-3H-imidazol-4-yl]-methylamine

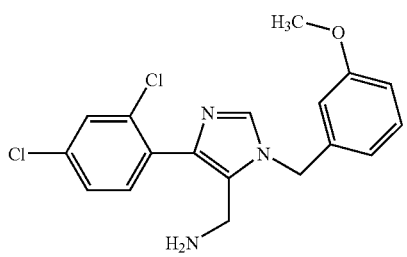

3-methoxy-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 μl). After 2-3 h the solvent was evaporated. The crude reaction product was purified via semi-preparative chromatography.

| molecular weight (g/mol): | 362.26 |
|---|---|
| RT - UV254nm (min): | 2.75 |
| IC$_{50}$ DP IV fluorescent (nM): | 221 |

Compound 81b: C-[3-(2-chloro-benzyl)-5-(2,4-dichloro-phenyl)-3H-imidazol-4-yl]-methylamine

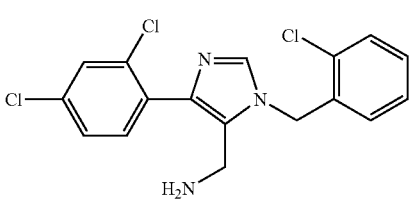

2-chloro-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 μl). After 2-3 h the solvent was evaporated. The crude reaction product was purified via semi-preparative chromatography.

| molecular weight (g/mol): | 366.68 |
|---|---|
| RT - UV254nm (min): | 2.79 |
| IC$_{50}$ DP IV fluorescent (nM): | 139 |

Compound 92b: C-[5-(2,4-dichloro-phenyl)-3-(3,4-difluoro-benzyl)-3H-imidazol-4-yl]-methylamine

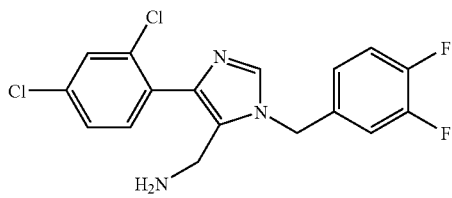

3,4-difluoro-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 μl). After 2-3 h the solvent was evaporated. The crude reaction product was purified via semi-preparative chromatography.

| molecular weight (g/mol): | 368.23 |
|---|---|
| RT - UV254nm (min): | 2.88 |
| IC$_{50}$ DP IV fluorescent (nM): | 242 |

Compound 104b: C-[5-(2,4-dichloro-phenyl)-3-(3-imidazol-1-yl-propyl)-3H-imidazol-4-yl]-methylamine

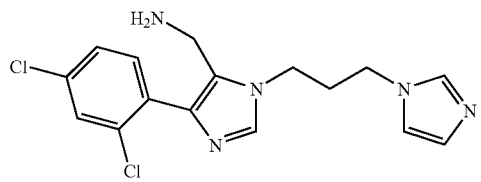

3-imidazol-1-yl-propylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 350.25 |
| RT - UV254nm (min): | 0.43 |
| $IC_{50}$ DP IV fluorescent (nM): | 408 |

Compound 112b: C-[5-(2,4-dichloro-phenyl)-3-(2-fluoro-benzyl)-3H-imidazol-4-yl]-methylamine

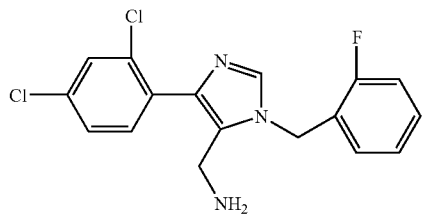

2-fluoro-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 350.23 |
| RT - UV254nm (min): | 2.72 |
| $IC_{50}$ DP IV fluorescent (nM): | 195 |

Compound 120b: C-[5-(2,4-dichloro-phenyl)-3-(2-methoxy-benzyl)-3H-imidazol-4-yl]-methylamine

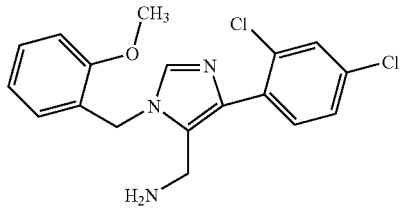

2-methoxy-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 362.26 |
| RT - UV254nm (min): | 2.68 |
| $IC_{50}$ DP IV fluorescent (nM): | 261 |

Compound 121b: (4-(2,4-dichlorophenyl)-1-((pyridin-3-yl)methyl)-1H-imidazol-5-yl)methanamine

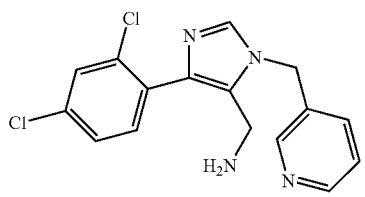

C-pyridin-3-yl-methylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| molecular weight (g/mol): | 333.22 |
| RT - UV254nm (min): | 1.36 |
| $IC_{50}$ DP IV fluorescent (nM): | 83 |

Compound 125b: C-[3-benzo[1,3]dioxol-5-ylmethyl-5-(2,4-dichloro-phenyl)-3H-imidazol-4-yl]-methylamine

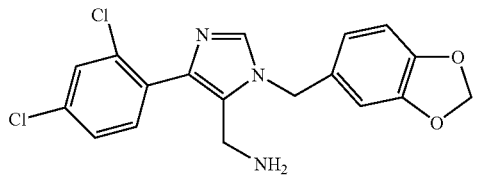

C-Benzo[1,3]dioxol-5-yl-methylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 376.24 |
| RT - UV254nm (min): | 2.61 |
| IC$_{50}$ DP IV fluorescent (nM): | 371 |

Compound 126b: 2-[5-aminomethyl-4-(2,4-dichlorophenyl)-imidazol-1-yl]-2-phenyl-ethanol

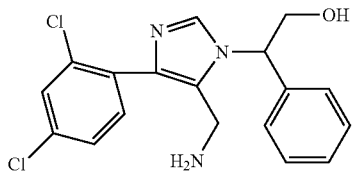

2-amino-2-phenyl-ethanol (4 mmol) and (2-oxo-ethyl)-carbamic acid tert-butyl ester (1 mmol) were added to methanol (5 ml, dry). After 30 min the 1 mmol 2,4-dichloro-1-[isocyano-(toluene-4-sulfonyl)-methyl]-benzene was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 362.26 |
| RT - UV254nm (min): | 2.64 |
| IC$_{50}$ DP IV fluorescent (nM): | 145 |

Compound 127b: C-{5-(2,4-dichloro-phenyl)-3-[2-(6-methyl-1H-indol-3-yl)-ethyl]-3H-imidazol-4-yl}-methylamine

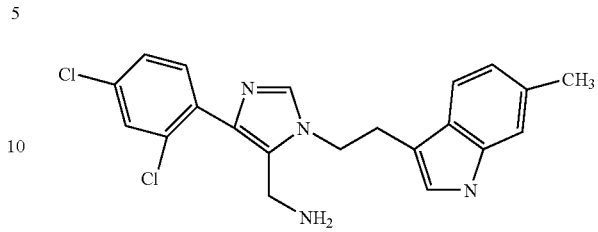

2-(6-Methyl-1H-indol-3-yl)-ethylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 399.32 |
| RT - UV254nm (min): | 2.97 |
| IC$_{50}$ DP IV fluorescent (nM): | 387 |

Compound 128b: (1-(2-ethoxybenzyl)-4-(2,4-dichlorophenyl)-1H-imidazol-5-yl)methanamine

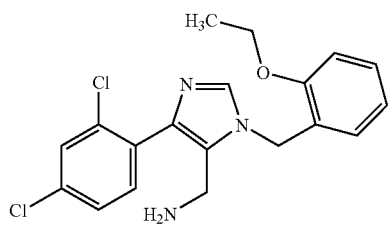

2-Ethoxy-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 376.29 |
| RT - UV254nm (min): | 2.08 |
| IC$_{50}$ DP IV fluorescent (nM): | 54 |

Compound 129b: C-[5-(2,4-dichloro-phenyl)-3-(2-trifluoromethoxy-benzyl)-3H-imidazol-4-yl]-methylamine

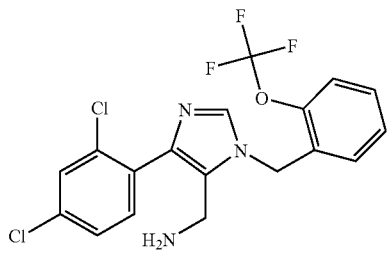

2-trifluoromethoxy-benzylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 416.23 |
| RT - UV254nm (min): | 2.95 |
| $IC_{50}$ DP IV fluorescent (nM): | 70 |

Compound 130b: (4-(2,4-dichlorophenyl)-1-((thiophen-3-yl)methyl)-1H-imidazol-5-yl)methanamine

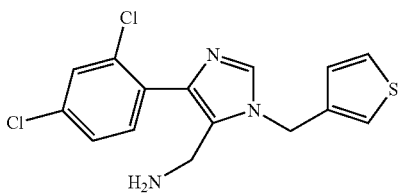

C-thiophen-3-yl-methylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 338.26 |
| RT - UV254nm (min): | 2.66 |
| $IC_{50}$ DP IV fluorescent (nM): | 62 |

Compound 131b: C-[5-(2,4-dichloro-phenyl)-3-(1-methyl-1H-pyrazol-4-ylmethyl)-3H-imidazol-4-yl]-methylamine

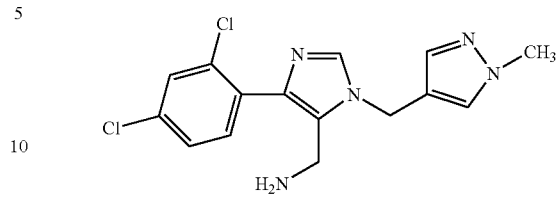

C-(1-methyl-1H-pyrazol-4-yl)-methylamine (4 mmol) and (2-oxo-ethyl)-carbamic acid tert-butyl ester (1 mmol) were added to methanol (5 ml, dry). After 30 min 2,4-dichloro-1-[isocyano-(toluene-4-sulfonyl)-methyl]-benzene (1 mmol) was added. The reaction was heated to 40° C. and stirred for 24 h. After evaporation of the solvent the residue was purified with chromatographic methods.

The subsequent cleavage of the carbamic acid tert-butyl ester was done with the addition of 4 molar hydrochloric acid in dioxan (3 ml) and water (320 µl). After 2-3 h the solvent was evaporated. The crude reaction product was purified via semi-preparative chromatography.

| | |
|---|---|
| molecular weight (g/mol): | 336.23 |
| RT - UV254nm (min): | 1.26 |
| $IC_{50}$ DP IV fluorescent (nM): | 335 |

Biological Testing

Compounds may be tested for biological activity in a number of assays:

BIOLOGICAL EXAMPLE 1

Determination of $IC_{50}$ Against DP IV

Substances are screened for inhibition of dipeptidyl peptidase (DP IV) by their ability to inhibit the hydrolysis of the DP IV specific substrate Glycyl-Prolyl-4-Nitroanilide (Gly-Pro-pNA). All compounds are diluted in DMSO and $IC_{50}$ will be determined with 11 serial dilutions (1:2) starting with an final concentration of 100 µM. The final DMSO concentration in the assay is 5% (v/v). The method was automated using a Tecan Genesis Freedom liquid handler and a Genius Pro (Tecan) microplate reader.

Stock Solutions

HEPES Buffer

A stock solution of 0.102 M HEPES is prepared. Ionic strength (I=0.32) is adjusted by KCl and pH (pH 7.6) by KOH.

Substrate 2.16 mM solution of Gly-Pro-pNA in deionized water is prepared.

Samples

All samples are dissolved in DMSO preparing a 10 mM stock solution.

DP IV

DP IV from porcine kidney (pDP IV) or recombinant human DP IV (rhDP IV) is diluted in HEPES buffer to a final activity of approximately 40-50 $\mu U*ml^{-1}$. The DP IV is stored in a cooling rack (4° C.) on the liquid handler.

Assay Method

The assay may becarried out at room temperature using Freedom liquid handler connected with a Genios Pro microplate reader. Each sample is measured in duplicate. Each sample stock solution is prediluted with DMSO in a ratio of 1:5 in a polypropylen 96-well plate. From this predilution 10 serial (1:2) dilutions in DMSO are prepared. 13.5 µl of the 11 DMSO dilutions and DMSO alone are transferred to the measurement microplate (duplicates) and 86.5 µl water, 100 µl HEPES buffer and 50 µl substrate solution are added to each well. The enzymatic reaction is started by addition of 20 µl enzyme solution to each well, and then the microplate is immediately transferred to the microplate reader.

After short mixing (20 s) the release of 4-Nitroanilin (pNA) is monitored at 405 nm for 30 cycles (approx. 18 min).

Post assay calculations are done by the Magellan (Tecan) and Graphit Software. The linear slopes are calculated for each well and averaged for the duplicates. The residue activities are calculated in relation to a sample containing only solvent instead of inhibitor and expressed in %. Residue activities are plotted against the log of inhibitor concentrations and $IC_{50}$ is calculated by an 4-parameter fitting ranging from 0 to 100%.

Ki and Inhibition Type

Measurement of DP IV activities for $K_i$ determination is carried out as described for $IC_{50}$. For $K_i$ determination samples were analysed in triplicates. 7 serial dilutions of the inhibitor (range calculated from the $IC_{50}$ determination) in water are analyzed with 4 serial dilutions of the substrate.

Data are analysed by non-linear regression to the inhibitor equations using Graphit software. $K_i$-value and inhibition type are determined using the inhibitor equation (competitive, partiell competitive, non-competitive) which gives the best fitting results.

DP9 and DPII Assay

Determination of $IC_{50}$ values for DPII and DP9 are done similarly as described for DP IV.

For DP9 Gly Pro-AMC is used as substrate in a final concentration of 0.25 mM.

For DPII instead of the HEPES buffer a 0.2 M sodium acetate buffer pH 5.5 is used. As substrate Gly-Pro-AMC is used in a final concentration of 1 mM.

The results of testing certain example compounds (in each case obtained by preparative synthesis) were as follows:

BIOLOGICAL EXAMPLE 2

Cytotoxicity Screening and LD50 Determination

Cytotoxicity of the compounds may be screened using the liver cell carcinoma cell line Hep-G2.

After 24 h of cultivation in a 96 well plate (50 000 cells/well) compounds (dissolved in DMSO) are added and cytotoxicity and vitality of the cells are analysed after another 24 h of cultivation using the CytoTox-One Homogenoeous membrane toxicity assay (Promega).

Three concentrations (100 µM, 2 µM, 40 nM) of each compound are analysed in triplicates. The final DMSO concentration was 1%.

For cytotoxicity the LDH activity in the cell culture media after 24 h of incubation are analysed. The untreated control is set to 0% cytotoxicity. For the 100% value LDH activity of lysed untreated cells are analysed.

For viability cell culture media are removed from the cells and all cells are lysed using the lysis buffer. LDH activity is determined and untreated control is set to 100% viability.

For determination of LD50 the liver carcinoma cell line HEP-G2 and the neuroblastoma cell line SY5Y may be used. The effect of 8 serial dilutions of the compounds (highest concentration 1 mM) is investigated as described above.

Results

The cytotoxicity of certain example compounds (in each case prepared by preparative synthesis) was screened using Hep-G2 cells. Compounds were tested in concentrations of 100 µM, 2 µM and 40 nM.

No cytotoxicity was observed with the low concentrations (2 µM and 40 nM) of the tested examples. The data on the 100 µM concentration of example compounds are summarized in table 3.

No cytotoxic effects were observed with examples 2b, 8b, 11b, 12b, 14b and 15b. Strong cytotoxic effects were observed with examples 1b, and 7b. The strongest cytotoxicity was found for example 7b which is the compound with the highest efficacy for DPII and DP9 inhibition (i.e. the lowest selectivity for DP IV).

All other tested compounds showed marginal to low cytotoxicity.

TABLE 2

Kinetic constants of compounds of formula 1 for DP IV, DPII and DP9

| Ex. No. | $IC_{50}$ DPII (M)* | $K_i$ DPII (M) | $IC_{50}$ DP9 (M) | $K_i$ DP9 (M) | $IC_{50}$ DP IV (M)* | $K_i$ DP IV (M) | Selectivity DPII($IC_{50}$)/ DPIV($K_i$) | Selectivity DP9($IC_{50}$)/ DPIV($K_i$) |
|---|---|---|---|---|---|---|---|---|
| 11b | $8.38 * 10^{-5}$ | | n.d. | | $2.58 * 10^{-6}$ | $5.75 * 10^{-8}$ | 1,457 | |
| 21b | $4.62 * 10^{-6}$ | $3,18 * 10^{-6}$ | $1.28 * 10^{-6}$ | $9.25 * 10^{-7}$ | $5.14 * 10^{-7}$ | $2.94 * 10^{-8}$ | 157 | 44 |
| 23b | n.d. | | $5.61 * 10^{-5}$ | | $9.03 * 10^{-7}$ | $2.36 * 10^{-8}$ | | 2,377 |
| 24b | $3.00 * 10^{-5}$ | | $1.21 * 10^{-4}$ | | $1.23 * 10^{-7}$ | $4.74 * 10^{-9}$ | 6,329 | 25,527 |
| 38b | $6.06 * 10^{-5}$ | | $4.65 * 10^{-5}$ | | $8.48 * 10^{-7}$ | $4.11 * 10^{-8}$ | 1,474 | 1,131 |
| 39b | n.d., $>1 * 10^{-4}$ | | $1.19 * 10^{-4}$ | | $5.9 * 10^{-8}$ | $5.68 * 10^{-9}$ | >176,056 | 20,951 |
| 59b | $3.89 * 10^{-5}$ | | $1.22 * 10^{-4}$ | | $2.21 * 10^{-7}$ | $1.53 * 10^{-8}$ | 2,542 | 7,974 |
| 81b | $7.46 * 10^{-6}$ | $2.18 * 10^{-6}$ | $3.83 * 10^{-5}$ | $7.65 * 10^{-6}$ | $1.39 * 10^{-7}$ | $1.95 * 10^{-8}$ | 383 | 1,964 |
| 104b | $2.77 * 10^{-4}$ | | $1.75 * 10^{-5}$ | | $4.08 * 10^{-7}$ | $3.02 * 10^{-8}$ | 9,172 | 579 |
| 112b | $3.69 * 10^{-5}$ | | $1.02 * 10^{-4}$ | | $1.95 * 10^{-7}$ | $1.05 * 10^{-8}$ | 3,514 | 9,714 |
| 120b | $1.86 * 10^{-5}$ | | $5.97 * 10^{-5}$ | | $2.61 * 10^{-7}$ | $1.58 * 10^{-8}$ | 1,177 | 3,778 |
| 121b | $1.22 * 10^{-4}$ | | $1.03 * 10^{-4}$ | | $8.3 * 10^{-8}$ | $2.96 * 10^{-9}$ | 41,216 | 34,797 |
| 125b | $1.79 * 10^{-5}$ | | $7.47 * 10^{-5}$ | | $3.71 * 10^{-7}$ | $3.80 * 10^{-8}$ | 471 | 1,966 |
| 126b | $2.00 * 10^{-5}$ | | $7.07 * 10^{-5}$ | | $1.45 * 10^{-7}$ | $1.06 * 10^{-8}$ | 1,887 | 6,670 |
| 128b | $3.42 * 10^{-6}$ | $1.57 * 10^{-6}$ | $3.43 * 10^{-5}$ | | $5.4 * 10^{-8}$ | $6.33 * 10^{-9}$ | 540 | 5,419 |
| 129b | $1.55 * 10^{-6}$ | $4.42 * 10^{-6}$ | $5.32 * 10^{-5}$ | | $7.0 * 10^{-8}$ | $6.54 * 10^{-9}$ | 237 | 8,135 |
| 130b | $1.43 * 10^{-6}$ | $3.84 * 10^{-6}$ | $9.73 * 10^{-5}$ | $2.15 * 10^{-5}$ | $6.2 * 10^{-8}$ | $7.69 * 10^{-9}$ | 186 | 12,653 |

* values >1e−4 are extrapolated values
n.d.—not determined

TABLE 3

Summary of compound cytotoxicity on Hep-G2 or SY5Y cells

| Ex. No. | Cytotox 100 μM (%) HEPG2 | Viability 100 μM (%) HEP-G2 | Observed cytotox | LD50 cytotox HEP-G2 (mM) | LD50 Viability HEP-G2 (mM) | LD50 cytotox SY5Y (mM) | LD50 Viability SY5Y (mM) |
|---|---|---|---|---|---|---|---|
| 11b | 4.6 | 113.1 | | | | | |
| 21b | 97.1 | 9.8 | 100% lysis | | | | |
| 23b | 56.8 | 98.6 | 50% lysis, 100% spheric cells | | | | |
| 24b | 5.9 | 119.2 | 10% spheric cells | 0.18 | 0.20 | 0.19 | 0.11 |
| 38b | 0 | 106.7 | | | | | |
| 39b | 3.9 | 115.7 | 20% spheric cells | 0.74 | 0.80 | 0.60 | 0.29 |
| 59b | 1.2 | 116.3 | 10% spheric cells | | | | |
| 81b | n.d. | n.d. | | 0.12 | 0.14 | 0.16 | 0.07 |
| 104b | 2.9 | 104.1 | | | | | |
| 112b | 3.0 | 111.4 | | | | | |
| 120b | 11.6 | 108.9 | 50% spheric cells | 0.17 | 0.21 | 0.16 | 0.10 |
| 121b | 0 | 104.0 | | 0.92 | 1.05 | 0.68 | 0.46 |
| 125b | 10.6 | 88.9 | | | | | |
| 126b | 5.8 | 118.8 | 10% spheric cells | | | | |
| 128b | n.d. | n.d. | | 0.14 | 0.15 | 0.15 | 0.07 |
| 129b | n.d. | n.d. | | 0.16 | 0.15 | 0.21 | 0.13 |
| 130b | n.d. | n.d. | | 0.21 | 0.24 | 0.28 | 0.17 | n.d. not determined

BIOLOGICAL EXAMPLE 3

Caco-2 Transport Assay

Determination of Inhibitor Concentration in Caco Experiments

The concentration of compounds in the Caco experiments may be determined from their potency to inhibit recombinant human DP IV.

100 μl sample, 100 μl HEPES buffer and 50 μl substrate (Gly Pro-pNA, 0.15 mM final concentration, corresponding to 1.5 Km) are mixed. Reaction is started by addition of 20 μl rhDP IV and release of pNA was monitored at 405 nm. Samples are analyzed in several dilutions (undiluted, 1:10, 1:100, 1:000). Dilutions are done in the Caco assay buffer. Activity measured with Caco-assay buffer alone is set to 100% and inhibitor concentration is calculated from the dilutions resulting in 20 to 80% inhibition according to the equation for competitive inhibition.

$$I = \left(\frac{v_0}{v_i} - 1\right) * 2.5 K_i * 2.7 * DF$$

I=inhibitor concentration
$v_0$=velocity of the reaction without inhibitor (Caco assay buffer alone)
$v_i$=velocity of the reaction with inhibitor sample
$K_i$=$K_i$-value of the compound
DF=dilution factor of the sample Transport Assay The human colon adenocarcinome cell line Caco-2 are grown in 6- or 24-transwell microplates (Costar) for 21 days with MEM-alpha containing 10% FBS and 0.5% Gentamycin (Invitrogen). After 21 days of cultivation integrity of the cell layer are assessed by measurement of the transepitelial electrical resistance.

Transport measurements are carried out in triplicates at a pH of 7.5. For each compound and direction (apical to basal (a-b), basal to apical (b-a)) two separate experiments are done. Samples are collected from the donor and acceptor compartments at the beginning of the experiment and after 60 min (for 6-well plates, Donor at 0 and 120 min, Acceptor at 15, 30, 60 and 120 min).

Samples are analyzed in several dilutions for their ability to inhibit human recombinant DP IV and compound concentrations may be calculated using the prior determined $K_i$-value (see above).

The permeability coefficient $P_{app}$ is calculated according to the following equation:

$$P_{app} = \frac{V_A}{A * t} * \frac{c_{At}}{c_{D0}}$$

$V_A$=Volume of the acceptor compartment
A=Area of the transwell membrane
t=sampling time
$c_{At}$=concentration in the acceptor compartment at sampling time
$C_{DO}$=concentration in the donor compartment at t=0

$P_{app}$-values>1e-5 cm/s are assessed as good permeable, value<1e-6 cm/s as not permeable. $P_{app}$-values in between as medium permeable. Compounds where no significant difference were found between a-b and b-a transport are assessed to be passive transported.

Results

Certain compounds with the best $K_i$ values concerning DP IV and low cytotoxicity were analyzed for their ability to penetrate through a Caco-2 monolayer. Transport data are summarized in Table 4.

$P_{app}$-values above 1e-5 cm/s for all compounds indicate a good transport through the cell layer. These determined transport rates are in the same range as the predicted transport rates. Comparable transport rates from apical to basal and from basal to apical indicate that there is a pure passive transport and the compounds are not substrates of P-Glycoprotein (PgP).

TABLE 4

Transport of compounds across the Caco-2 monolayer

| Ex. No. | Caco apical to basal Papp (cm/s) | Caco basal to apical Papp (cm/s) | Transport | predicted Caco-2 Permeability (cm/s) |
|---|---|---|---|---|
| 24b | $3.75 * 10^{-5}$ | $4.17 * 10^{-5}$ | good, passive | $4.83 * 10^{-5}$ |
| 39b | $4.06 * 10^{-5}$ | $4.25 * 10^{-5}$ | good, passive | $3.40 * 10^{-5}$ |
| 59b | $4.97 * 10^{-5}$ | $3.83 * 10^{-5}$ | good, passive | $4.97 * 10^{-5}$ |
| 81b | $4.19 * 10^{-5}$ | $1.60 * 10^{-5}$ | good, active in | $5.49 * 10^{-5}$ |
| 112b | $4.48 * 10^{-5}$ | $4.21 * 10^{-5}$ | good, passive | $4.68 * 10^{-5}$ |
| 120b | $5.12 * 10^{-5}$ | $5.28 * 10^{-5}$ | good, passive | $7.50 * 10^{-5}$ |
| 121b | $3.64 * 10^{-5}$ | $4.04 * 10^{-5}$ | good, passive | $2.49 * 10^{-5}$ |
| 126b | $2.25 * 10^{-5}$ | $1.65 * 10^{-5}$ | good | $2.45 * 10^{-5}$ |
| 128b | $4.51 * 10^{-5}$ | $1.50 * 10^{-5}$ | good, active in | $8.87 * 10^{-5}$ |
| 129b | | | n.d. | $8.12 * 10^{-5}$ |
| 130b | $4.00 * 10^{-5}$ | $3.12 * 10^{-5}$ | good, passive | $6.01 * 10^{-5}$ | n.d. not determined

BIOLOGICAL EXAMPLE 4

Anti-anxiety Testing in vivo

The compounds of the invention may be expected to be of use for the prevention or treatment of anxiety or depression. The efficacy of the compounds of the invention can be tested in the following in vivo models:
(i) the elevated plus maze test, the protocol of which is described in example 2, pp. 19-21 of WO 02/34243, and which is incorporated herein by reference in its entirety.
(ii) the social interaction test, the protocol of which is described in example 3, pp. 21-23 of WO 02/34243, and which is incorporated herein by reference in its entirety.

BIOLOGICAL EXAMPLE 5

Tetradic Encounter Test and Circadian Courses of Activity, Feeding and Drinking Behaviour Compounds Test Compound C: Example 130b as Hydrochloride Salt For Aacute Administration (via Gavage):

| Vehicle: | 0.5% Natrosol |
|---|---|
| Storage of the solution: | dark at −20° C. |

Example 130b was dissolved in 0.5% Natrosol and administered acutely p.o. (gavage) 40 minutes before behavioural testing. Example 130b was administered in doses of 0.3, 1.0 and 3.0 mg/kg in a volume of 5 ml/kg, each.

For Chronic Administration (p.o. via Drinking Fluid):

| Vehicle: | Tap water |
|---|---|
| Storage of the solution: | room temperature |

Example 130b as hydrochloride salt was dissolved in tap water in concentrations of 0.03, 0.1 and 0.3 mg/ml. Assuming a daily fluid intake of approx. 30 ml per animal (animal's weight: approx. 300 g), these concentrations should result in doses of approx. 3, 10 and 30 mg/kg/day. The solutions were prepared freshly every day. During chronic administration, solution offer was limited to 40 ml per day for each animal.

Reference Compounds

Reference compound A: Chlordiazepoxide (CDZ)

| Batch No.: | 94H1023 |
|---|---|
| CAS No.: | 438-41-5 |
| Supplier: | Sigma-Aldrich Chemie GmbH |

For Acute Administration (i.p.):

| Vehicle: | 0.9% NaCl (Saline) |
|---|---|

Chlordiazepoxide was dissolved in 0.9% NaCl and administered acutely i.p. 30 minutes before behavioural testing with a dose of 3 mg/kg in a volume of 1 ml/kg (test group TG 2, see below). The solution was prepared freshly every day.

Reference Compound B: Imipramine Hydrochloride

| Batch No.: | 014K0800 |
|---|---|
| Supplier: | Sigma Aldrich |
| Description: | Powder |
| Vehicle: | 0.9% NaCl (Saline) |

For Chronic Administration (i.p. Once per Day):

| Vehicle: | 0.9% NaCl (Saline) |
|---|---|

Imipramine was dissolved 0.5% Natrosol and administered once daily i.p. for 8 days (test group TG 11, see below) with a dose of 15 mg/kg/day in a volume of 1 ml/kg.

Vehicle

Vehicle for All Test Compounds (Acute Administration): 0.5% Natrosol (Hydroxyethylcellulose)

| Supplier: | Boehringer Ingelheim Pharma GmbH & Co KG |
|---|---|
| Batch No.: | 302121 |

In the control group (test group TG 1, see below) 0.5% Natrosol was administered acutely p.o. (gavage) 40 minutes before behavioural testing in a volume of 5 ml/kg.

Vehicle for Chlordiazepoxide and Imipramine (Acute Administration): 0.9% NaCl(Saline)

| Supplier: | Braun Melsungen AG |
|---|---|
| Batch No.: | 5441A162 |
| Description: | 0.9% solution |

Vehicle for All Test Compounds (Chronic Administration):

During chronic administration, the control group (test group TG 10, see below) received 40 ml tap water per day as drinking fluid.

Materials

Test system 216 male Sprague Dawley rats. The animals were 6 weeks old at the start of the study. They were housed in groups of 4 animals ("acute animals") or in single cages ("chronic animals") at 12 h/12 h light/dark (start of the light phase at 2 a.m.), 20° C., 60% rH. Animals were provided by Elevage Janvier, France.

Housing

Depending on the test group ("acute animals" or "chronic animals"), animals were housed in groups of four animals per cage in Makrolon type IV group housing cages ("acute animals") or in single cages Makrolon type III ("chronic animals"), each with heightened lids (5 cm). During the whole phase, standard diet (Altromin 1324) and tap water were provided ad libitum, except for the period of food restriction prior to the H maze test and for the phase of chronic compound administration (see below). Animals' cages were changed twice weekly. At this time, the animals' weight was recorded on protocol sheets.

Test Groups

The animals were assigned to the following test groups (TG) by chance.

TABLE 5

Test groups

| | Tetradic encounter (compound acute) | Circadian activity (compound chronic) | No. of animals |
|---|---|---|---|
| TG1 | Vehicle (Natrosol) | | 12 |
| TG2 | CDZ 3 mg/kg | | 12 |
| TG7 | Example 130b 0.3 mg/kg | | 12 |
| TG8 | Example 130b 1.0 mg/kg | | 12 |
| TG9 | Example 130b 3.0 mg/kg | | 12 |
| TG10 | | Vehicle (Water) | 12 |
| TG11 | | Imipramine 15 mg/kg/day | 12 |
| TG16 | | Example 130b 3 mg/kg/day | 12 |
| TG17 | | Example 130b 10 mg/kg/day | 12 |
| TG18 | | Example 130b 30 mg/kg/day | 12 |
| | Total number of animals | | 120 |

Materials and Instruments

Open field (100×100×50 $cm^3$ black wooden arena) for the tetradic encounter test Video Equipment PB3002 scales, Mettler-Toledo Altromin diet 1324, Altromin GmbH, Lage Infrared activity monitoring cages, TSE Scientific Equipment GmbH, Bad Homburg. Cages are 46×46×26 $cm^3$. Each cage is equipped with 2 infrared frames in 4.5 and 13.5 cm height respectively. 16 beams per axis allow a spatial resolution of 1.4 cm and a temporal resolution of 20 ms Methods Planning of the Tests The study was conducted with 9 series with an inter-series interval of 1-3 days. Test groups were unevenly distributed across the series. Within each series, the behavioural tests were conducted as described below:

Two sets of animals were used:
1. "Acute animals" received compounds acutely in TE test
   TE test was conducted at one day during the dark phase. Each animal was tested once after acute administration of vehicle, test compound or reference compound. Prior to TE test, 3 training sessions took place.
2. "Chronic animals" received compounds chronically, they were tested in CIRC test.
   Measurement of circadian activity was conducted at two consecutive days. Two days prior to the test, the animals were habituated to the chronic test compound administration (1 day).

Tetradic Encounter Test (TE)

Animals were kept in group cages until compound administration. Each two animals derived from the same home cage and were treated the same way. During the time from compound administration to the beginning of the test, animals were kept in single cages for 40 minutes.

Circadian Courses of Activity Feeding and Drinking Behaviour (CIRC)

During the 7 days lasting period of chronic compound administration, animals were kept singly. On the first day they were kept in single Macrolon home cages. On the next day they were transferred to activity monitoring cages and kept there for 3 days. For the following 3 days they returned to their home cages (single housing).

Tetradic Encounter Test

The tetradic encounter test was conducted according to the protocol of Wolffgramm (1990). Four rats were placed for 15 minutes in an open field arena of 1 m×1 m; all four animals of an encounter group were treated in the same way, they received either test compound, reference compound, or vehicle. Each two animals were from the same home cage. The open field was illuminated by dim red light (3-4 Lux). Rats were familiar with the open field and their encounter partners by means of three prior training sessions (no compound administration). Testing (compound administration) started at 2:20 p.m. (dark phase). All animals were marked individually by means of black symbols on their back. Behaviour was recorded on videotapes. Each animal was tested once.

Circadian Courses of Activity, Feeding and Drinking Behaviour

Animals received the test compound chronically via the drinking fluid. The reference compound Imipramine was given i.p. (one administration per day, one hour before the respective tests). Fluid supply was restricted to 40 ml per day for all test groups. On the first day of chronic test compound exposure, animals were kept singly in standard single home cages to enable an individual assessment of test compound intake. On the second day, animals were transferred to infrared monitoring cages for 3 days. Food and fluid offer were the same as in the home cage. Measuring rearing activity near fluid bottles and food grid enabled an assessment of the time structure of food and water (compound) consumption. Behavioural observation started one hour before the beginning of the dark phase (2 p.m.). After 22 hours, body weight, food and fluid consumption were measured. 2 hours later, the next recording started.

Data Analysis

Tetradic Encounter Test

Spatial Behaviour

Raw data were provided as videotapes and protocol sheets of application and test time. From the videotapes the trajectory of the animal's movement was tracked and coordinates and time stamps were continually noted in a data file. The resulting file was transferred to a computer program for further analysis.

The following parameters were calculated for the whole test phase (15 minutes):
- Total distance travelled (m)
- Use of available space (%)
- Portion of time spent in the centre (%)
- Portion of time spent in the corners (%)
- Mean distance to the encounter mates (cm)
- Distribution of spatial distance to the encounter mates
- Dynamics of spatial distance to the encounter mates (cross-distance course)

Social Behaviour

Raw data were provided as videotapes and protocol sheets of application and test time. From the videotapes the social behaviour of each rat was rated by an experienced ethologist using a list of predefined behavioural patterns. The observer was blind to the animal's treatment. The resulting file containing the time series of behavioural patterns was transferred to a computer program for further analysis.

Reliability of rating was examined by comparing the results of repeated rating of the same recordings. Spearman's rank correlation coefficients were calculated for each class of behavioural patterns (duration of patterns per trial): aggressive behaviour, defensive behaviour, non-agonistic social behaviour, non-social behaviour. To assess temporal accuracy, cross-coincidence coefficients were calculated. Cross-coincidence coefficients near 0 indicate concomitant occurrence by chance; cross-coincidence coefficients near 1 mean complete temporal simultaneity. According to internal standards, sufficient reliability can be stated if Spearman's rank correlation coefficient for the accuracy of rating is sr>+0.75 and the cross-coincidence coefficient indicating temporal accuracy is cc>0.50. The reliability check performed for the present data revealed a high degree of reliability: Mean value sr=+0.99. Temporal accuracy revealed also a high degree of reliability (cc=+0.73).

The following parameters were calculated for the whole test phase (15 minutes):
- Number of non-agonistic social acts (N)
- Number of aggressive acts (N)
- Number of defensive acts (N)
- Time spent with non-agonistic social acts (%)
- Time spent with aggressive acts (%)
- Time spent with defensive acts (%)
- Behavioural synchrony To quantify inter-individual synchrony, coefficients of synchrony were calculated that base on rank correlation coefficients. For this purpose, the time series of behavioural patterns was subdivided into equidistant interval sections (here: 1 s intervals). To calculate synchrony coefficients, the user must define "pattern sets of interest". Each set contained one or more behavioural patterns that were taken together for the analysis (e.g. "friendly contact" or "all kinds of social interaction").

A computerized program that is part of the program system first calculated the relative portion of time for each interval and each set of patterns, then the data was submitted to a Spearman rank transformation (portion parameters are converted to ranks within each time series). The rank numbers were subsequently correlated with each other among the participants of an encounter. If, for instance, the encounter mates were well synchronized according to non-agonistic ("friendly") contacts, there were high contacting ranks concomitantly for all rats in the same intervals and correspondingly, low ranks coincided in the time periods with a low frequency of contacting. A Spearman rank correlation coefficient was calculated for each animal versus the three other ones.

Synchrony may be extended over more than a single time interval. To assess the temporal structure of behavioural synchrony, cross-correlation calculations were used. For this purpose, the two time series of the encounter mates (each one containing the rank numbers) were shifted against each other. The temporal dislocation was done stepwise: 1 interval, 2 intervals and so on. In the present study, all participants of an encounter had received the same acute treatment. Therefore, the cross-correlation curves were necessarily symmetric and it was sufficient to shift them only into one direction.

In the present study, cross-synchrony coefficients were calculated for different sets of behavioural parameters:

All types: Non-social, friendly, aggressive and defensive behaviour

Friendly (non-agonistic) behaviour: Attaching the encounter mate with snout or forepaw, snout contact to anal and/or genital region of encounter mate, pursuit of the encounter mate Aggressive behaviour: Pinning, mounting, fighting, offensive manipulation of the partner with snout or paw, boxing Defensive behaviour: Active rejection of body contact from the partner, withdrawal from the partner, which tries to contact, flight Circadian Courses of Activity, Feeding and Drinking Behaviour Raw data were provided as computer files accompanied by written protocol sheets. As the animals were still adapting to the environment and administration the time courses of the following parameters were calculated only for the last day of registration:
- Food and fluid intake (time %)
- Number of feeding and eating bouts
- Meal pattern parameters reflecting e.g. the duration and recurrence of feeding and drinking bouts
- Total distance travelled (cm/min)
- Small movements (cm/min)
- Distance travelled with rapid locomotion (cm/min)
- Distance travelled with slow locomotion (cm/min)
- Immobility (time %)
- Use of available space (%)
- Locomotor stereotypies (score, first hour of the dark phase only)
- Rearing (time %)
- Number of rearing acts (N)

Feeding and Drinking Bouts and Bout-Related Analysis:

On the basis of high-resolution infrared beam recordings, feeding and drinking is identified by means of beam interruption in the upper frame near to the positions of food or water. Feeding or drinking acts are then defined as temporally contingent behavioural pattern separated from each other by intervals not longer than 0.5 seconds. Normally, several acts form a feeding or drinking bout. The intervals within a bout are definitely shorter than between subsequent bouts. A threshold interval can be set to distinguish between intra-bout and inter-bout intervals.

To fix this threshold interval, the accumulation of several acts to a bout must be analysed by means of a stochastic mathematical model. For this purpose, the log-survivor procedure has been established. The basic idea is to calculate a "survivor curve". We consider the entirety of intervals between two subsequent feeding acts and proceed with time after the onset of the intervals. A very short time after the onset, all intervals are still surviving, i.e. they have not been ended. The probability of surviving is 1.0. Some time later, 20% of the intervals have been finished because a new eating act has started; the probability of surviving is 0.8. The probability is monotonously decreasing with time. According to the laws of probability the curve is exponential provided that the end of an interval (the start of the next feeding act) is occurring by chance. If the probability of surviving is shown in a diagram against time and the y-axis (probability) is logarithmic, the curve will be linear. This log survivor plot enables a good assessment whether intervals are really distributed by chance or whether there exist accumulations of short intervals indicating bouts.

Figure 7:
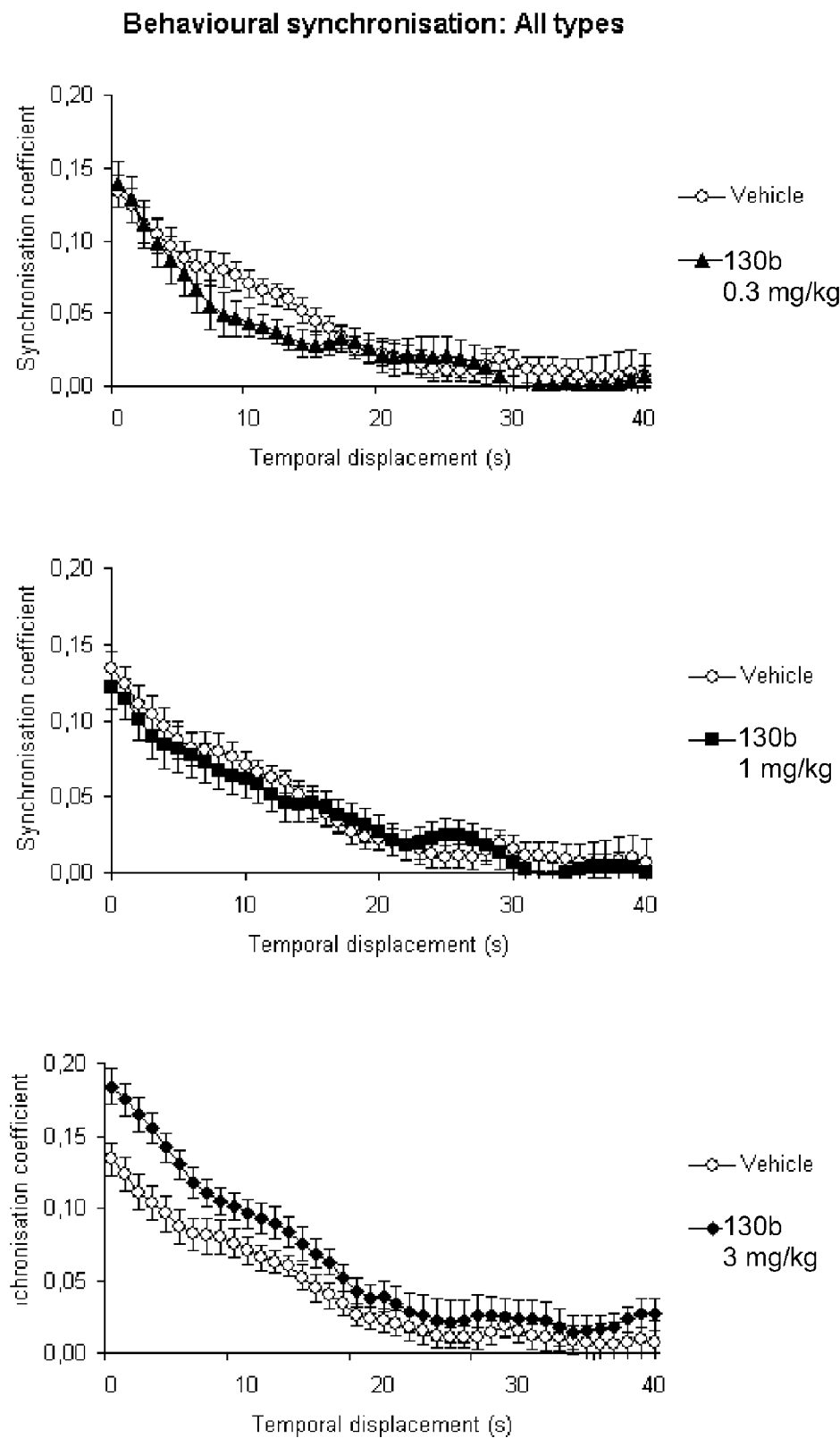
FIG. 7 Tetradic encounter test: Behavioural synchronisation of animals treated with vehicle and with the different doses of Example 130b. Synchronisation was tested according to the four patterns non-social activity, friendly contact, aggression, defense. Mean values±SEM.
Figure 8:
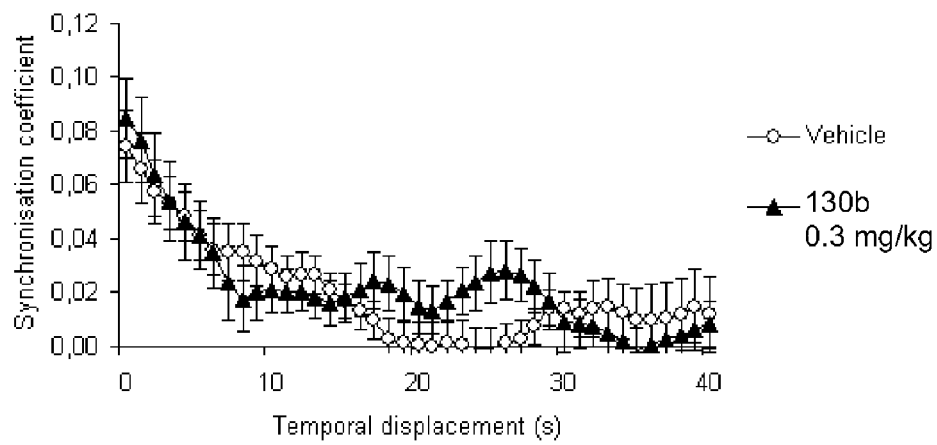
FIG. 8 Tetradic encounter test: Behavioural synchronisation of animals treated with vehicle and with the different doses of Example 130b. Synchronisation was tested according to the three patterns concerning social behaviour friendly contact, aggression, defense. Mean values±SEM.
Figure 8:
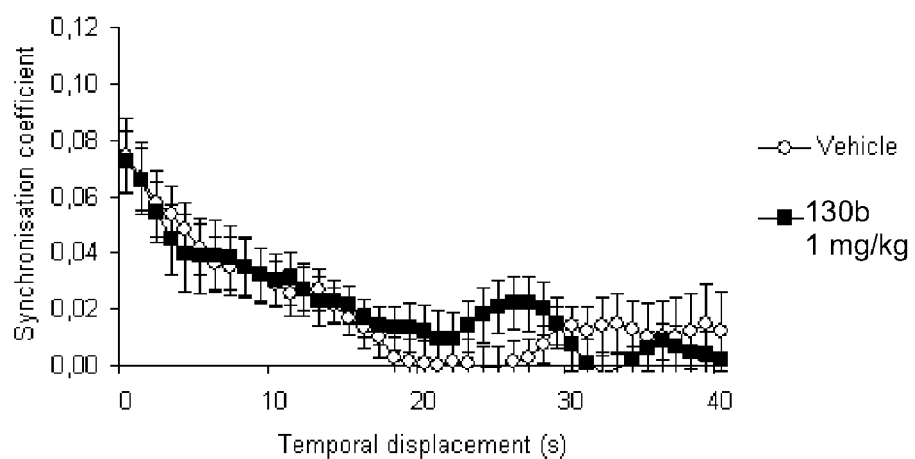
Figure 8:
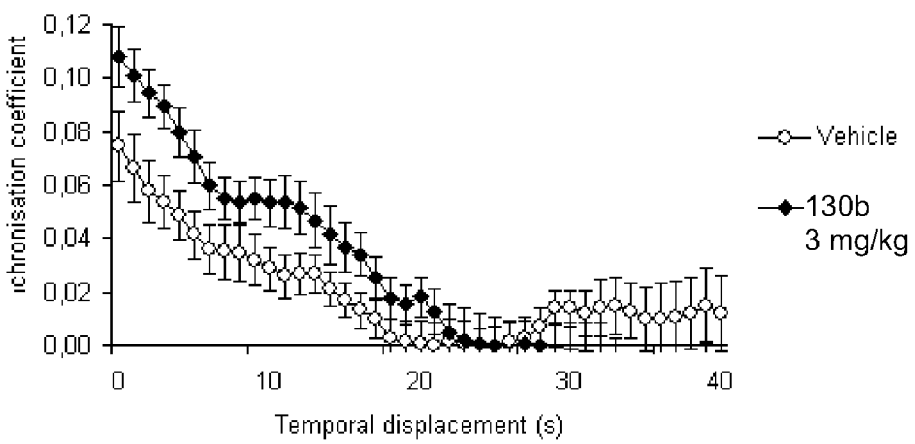
Figure 9:
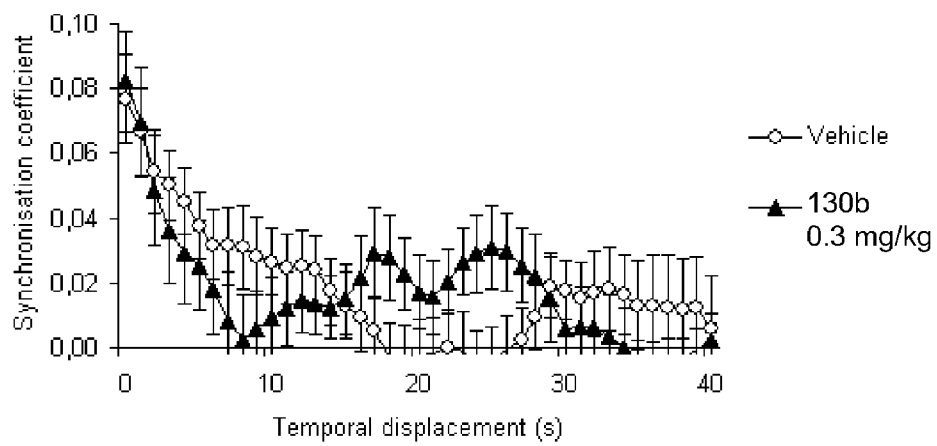
FIG. 9 Tetradic encounter test: Behavioural synchronisation of animals treated with vehicle and with the different doses of Example 130b. Synchronisation was tested according to friendly contact. Mean values±SEM.
Figure 9:
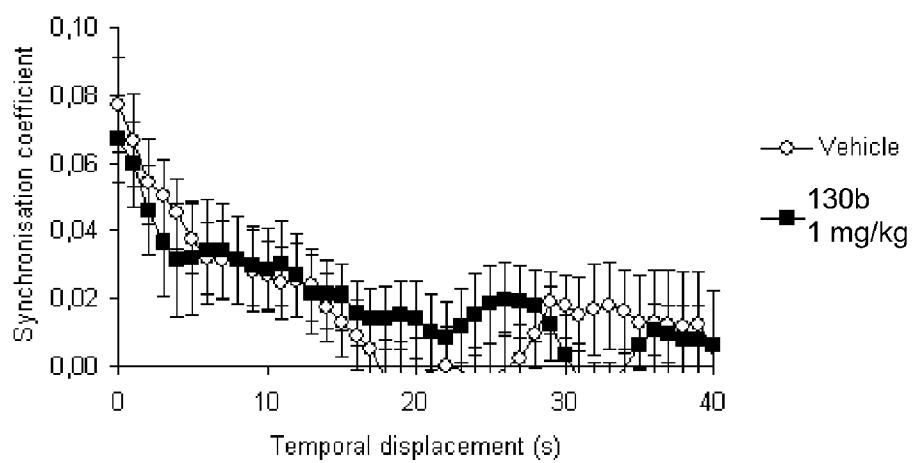
Figure 9:
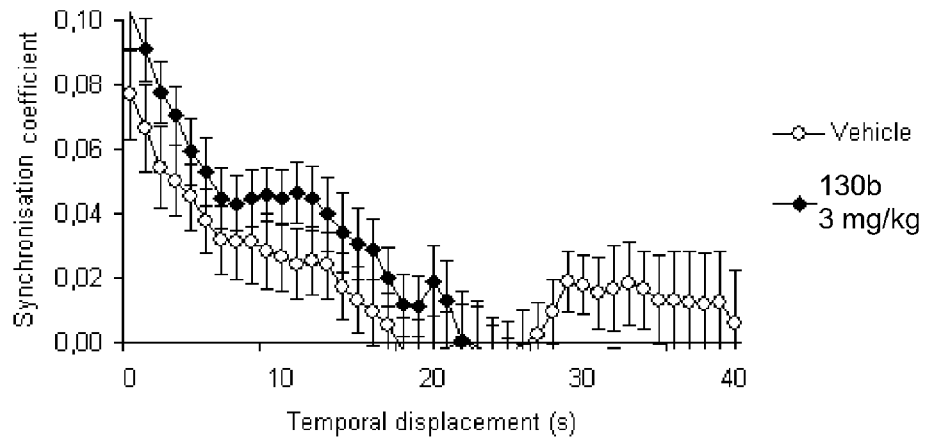
Figure 10:
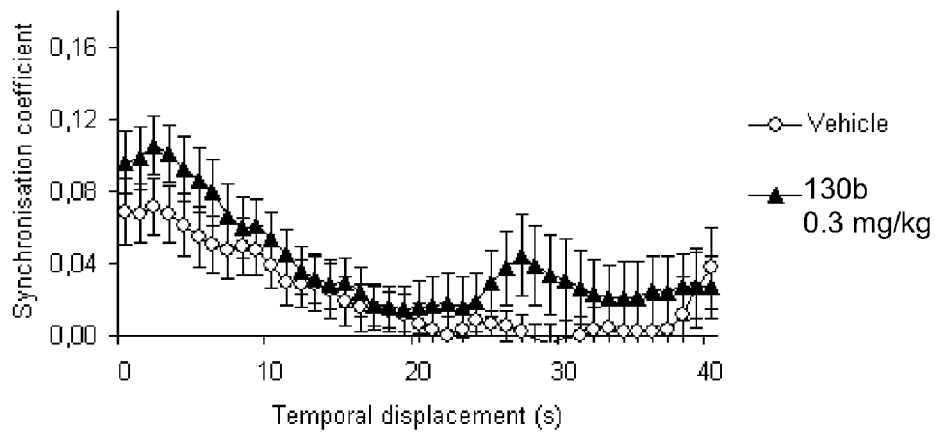
FIG. 10 Tetradic encounter test: Behavioural synchronisation of animals treated with vehicle and with the different doses of Example 130b. Synchronisation was tested according to aggression. Mean values±SEM.
Figure 10:
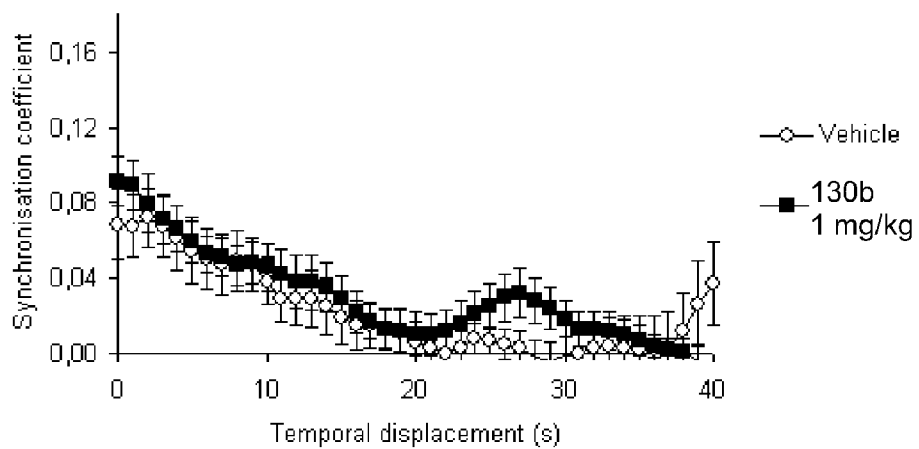
Figure 10:
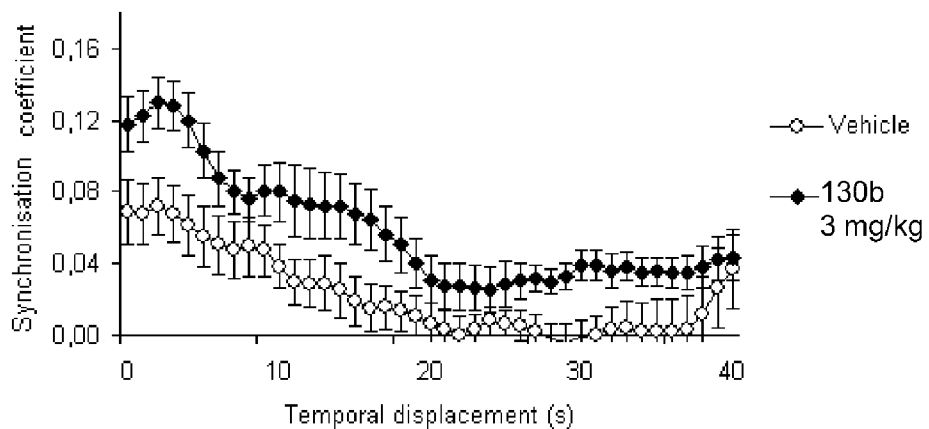

When short intervals are more frequent than expected by chance, the log survivor curve drops rapidly in the beginning and the returns to a flat slope of decline (see FIG. 7). The flection of the early part of a log survivor curve (in mathematical terms: the second derivative of the curve) indicates intra-bout intervals. When inter-bout intervals occur randomly, the flection returns to zero. We can therefore consider the second derivative of the log survivor curve as a "bout score" curve that enables the discrimination between intra-bout and inter-bout intervals. The investigator has analysed great amounts of data material from meal pattern recordings and has found a threshold interval of 120 seconds. The present data have also been analysed using the above-described procedures (log-survivor curve and bout-score flection analysis). The results for vehicle treated animals shown in FIGS. 7 and 8 are in good accordance to investigator's former analysis. Thus, the threshold interval of 120 seconds was confirmed and taken for bout characterisation.

The following bout-related parameters were measured:
Cumulative number of feeding and drinking bouts over the course of recording Stereotyped locomotion was assessed by means of statistical comparisons between the observed locomotor sequences (as described by the movement from one of the 4×4 sub-squares to another) and a "random walk". The comparison is performed at 5 different levels:

Level 0: Number of stays in each subsquare (S);
Level 1: Number of transitions from one subsquare to a specified other one (first order: S1 → S2)
Level 2: Number of 2nd order transitions (second order: S1 → S2 → S3)
Level 3: Number of 3rd order transitions (third order: S1 → S2 → S3 → S4)
Level 4: Number of 4th order transitions (fourth order: S1 → S2 → S3 → S4 → S5)

The coefficient of locomotor stereotypies (SC, in %) at each level has a value of SC=0 when there are no regularities within the movement pattern (random walk). The maximum value of SC=100% indicates that the animal always uses the same pathway.

Body Weight, Food and Fluid Consumption During Chronic Compound Administration

Raw data of body weight, fluid intake and food consumption were provided as protocol sheets. All protocol sheets were entered into a computer program. In case of missing or obviously wrong measurements (e.g. empty drinking bottles due to activities of the rat) missing values were introduced (less than 0.1% of the data). Missing values were interpolated by the program. After verification of the data, relevant parameters were calculated. The resulting time courses were the basis for subsequent statistical analysis.

Time courses of the following parameters were calculated:
Body weight (g)
Total food consumption (g/day)
Total fluid intake (ml/day)
Dose of Test compound (mg/kg/day)

Statistical Analysis

For all statistical tests a result of $p<0.05$ (two-tailed testing) was considered as significant.

Tetradic Encounter Test

All statistical testing was done for each animal of the tetradic encounters. For all statistical tests a result of $p<0.05$ (two-tailed testing) was considered as significant.

Statistical analysis was performed by GLM (general linear model) analysis for each parameter in four steps. First, a GLM analysis was performed including the reference compound group and the vehicle group with one factor of reference compound treatment. By means of this analysis, effects of reference compound treatment were tested against vehicle treatment. Effects of Example 130b were assessed by means of two additional GLM analyses including all dose groups of the respective test compound and the vehicle group. As most of the effects did not show a linear dose-response, all analyses were performed with vehicle and the three respective doses of a test compound as categorical factors.

For cross-distance and synchrony calculations, a GLM analysis with one categorial factor of treatment and one repeated factor of displacement was performed separately for vehicle versus reference compound, and vehicle versus Example 130b. A uniform effect of a treatment on these parameters (general increase or decrease) should result in a statistically significant effect of treatment whereas an effect that was only present at certain temporal displacements should result in an interaction effect (displacement×treatment).

Circadian Courses of Activity, Feeding and Drinking Behaviour

Statistical analysis for stereotypies during the first hour of the dark phase was performed by GLM (general linear model) analysis in four steps. First, a GLM analysis was performed including the reference compound group and the vehicle group with one factor of reference compound treatment. By means of this analysis, effects of reference compound treatment were tested against vehicle treatment.

For comparing circadian courses, a GLM analysis with one categorial factor of treatment and one repeated factor of time was performed separately for vehicle versus reference compound and vehicle versus Example 130b. A uniform effect of a treatment on these parameters should result in a statistically significant effect of treatment while an effect that was only present at certain times should result in an interaction effect (time×treatment).

Body Weight, Food and Fluid Consumption During Chronic Compound Administration

For comparing courses of body weight, food and fluid consumption, a GLM analysis with one categorial factor of treatment and one repeated factor of time was performed separately for vehicle versus reference compound and vehicle versus Example 130b. A uniform effect of a treatment on these parameters should result in a statistically significant effect of treatment whereas an effect that was only present at certain temporal displacements should result in an interaction effect (time×treatment)

For body weight, food and fluid consumption at the last day of circadian registration, additionally a GLM (general linear model) analysis was performed in four steps. First, a GLM analysis was performed including the reference compound group and the vehicle group with one factor of reference compound treatment. By means of this analysis, effects of reference compound treatment were tested against vehicle treatment.

Results

Effects of Acute Administration of Chlordiazepoxide

Tetradic Encounter Test

Chlordiazepoxide led to a statistically significant decrease in the number of defensive acts and an increase in the time spent with friendly (non-agonistic) social behaviour compared with vehicle-treated animals. All other behavioural types were unaffected. There were no significant effects of Chlordiazepoxide on the distance to encounter mates. Chlordiazepoxide-treated animals showed a decrease of time spent with a distance of 25-50 cm and an increase of time spent with a distance of 75-100 cm to encounter mates. Furthermore, there was a significant interaction between treatment and displacement in the cross-distance analysis due to a slightly higher distance at a displacement of 0 seconds, shifting towards a slightly lower distance at a displacement of about 15-20 seconds. Such shift indicates asymmetric social interactions (pursuit of an encounter mate)

Chlordiazepoxide affected inter-individual synchrony of behaviour. In all analyses, a statistically significant interaction of treatment and displacement appeared compared with vehicle-treated animals. Chlordiazepoxide tended to reduce immediate inter-individual synchrony of behaviour, especially concerning aggressive behaviour, whereas it also prolonged synchrony.

Effects of Chronic Administration of Imipramine

Body Weight, Food and Fluid Consumption

Imipramine significantly reduced body weight gain, food and fluid intake during the period of administration.

Circadian Courses of Activity, Feeding and Drinking Behaviour

Imipramine significantly affected almost every parameter measured. Imipramine-treated animals tended to weigh less and consumed significantly less food and water than vehicle-treated animals. They travelled less distance with both fast and slow locomotion, showed less small movements, spent more time immobile and spent a lower amount of time accessing food and water. The effects were strongest during the first and the last three hours of the dark phase. During the first hour of the dark phase Imipramine led to a reduction of level 2, 3 and 4 stereotypies, i.e. locomotion was less predictable.

Effects of Acute Administration of Example 130b

Tetradic Encounter Test

The low and high dose of Example 130b led to a statistically significant increase of the number of defensive acts and of the distance travelled during the first five minutes of the test compared with vehicle-treated animals. The high dose of Example 130b significantly increased the time spent in the centre of the open field and the usage of available space (FIG. 1 to 4). The medium dose tended to increase the time spent with friendly (non-agonistic) social behaviour.

Figure 5:
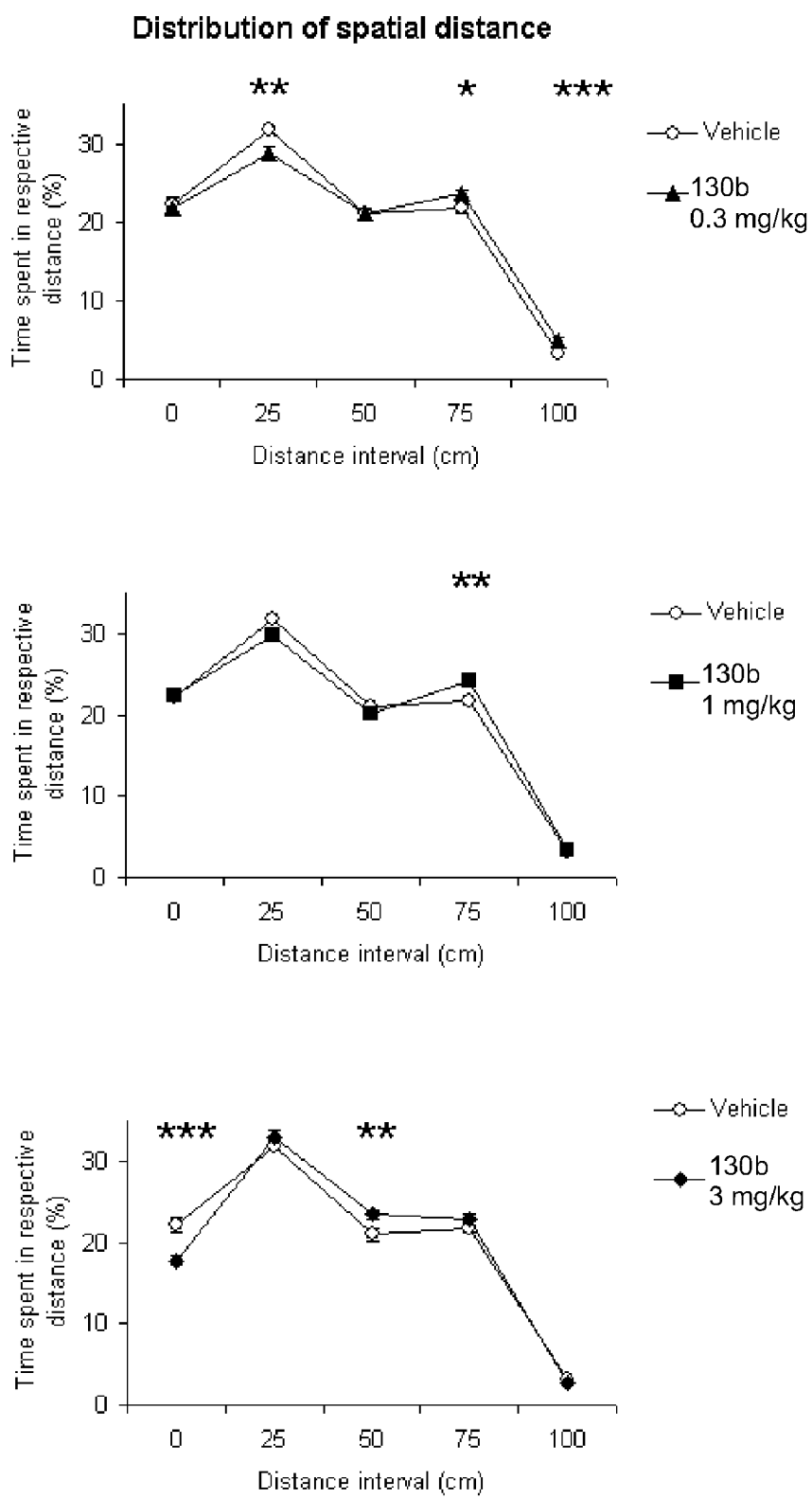
FIG. 5 Tetradic encounter test: Distribution of spatial distance to the encounter mate for animals treated with vehicle and with the different doses of Example 130b. Mean values±SEM, Single comparisons vs. vehicle: * $p<0.05$,  $p<0.01$, * $p<0.001$.
Figure 6:
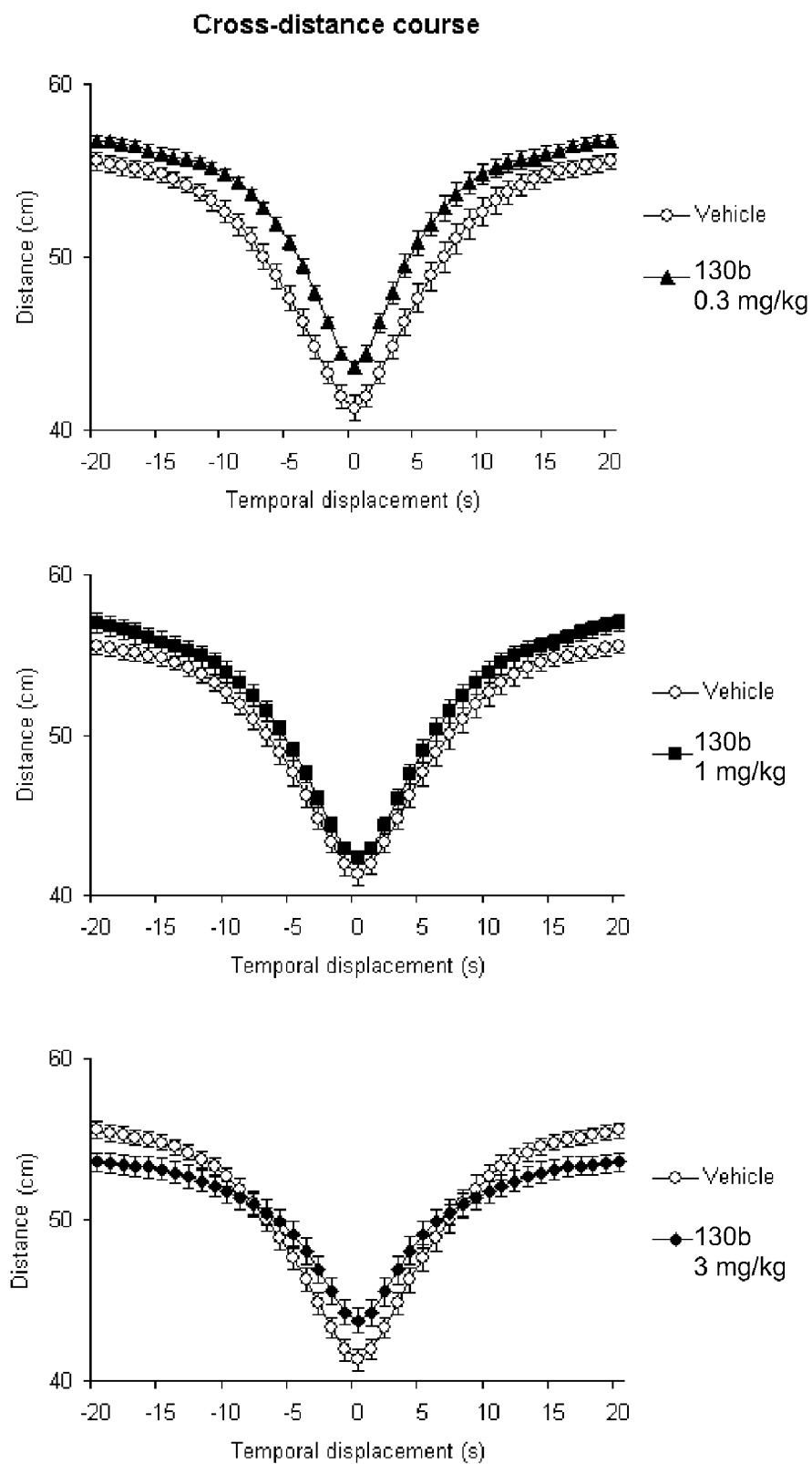
FIG. 6 Tetradic encounter test: Dynamics of spatial distance (cross-distance course) for animals treated with vehicle and with the different doses of Example 130b. Mean values±SEM.

The low and the high dose of Example 130b led to a significantly higher distance to the encounter mates compared with vehicle treatment. This effect was also seen in the distribution of spatial distances to the encounter mates, resulting in a significantly lower amount of time spent in a distance of less than 25 cm (high dose) and a distance of 25-50 cm (low dose) and a higher amount in a distance of 50-75 cm (high dose), 75-100 cm (low and medium dose) and more than 100 cm (low dose, FIG. 5). The effect was also seen in the cross-distance analyses (FIG. 6).

Example 130b revealed strong effects on the inter-individual synchrony of behaviour. Statistical analysis yielded a significant interaction between treatment and displacement in the synchrony analyses including all behavioural types, social behaviour, and friendly (non-agonistic) social behaviour and an effect of treatment on the synchrony of aggressive behaviour. Especially the high dose of Example 130b increased synchrony, with the strongest effect on aggressive behaviour (FIG. 7 to 10).

Effects of Chronic Administration of Example 130b

Body Weight, Food and Fluid Consumption

Example 130b led to a statistically significant effect of treatment and an interaction between time and treatment on fluid intake compared with vehicle controls whereas body weight and food intake were not affected.

Figure 11:
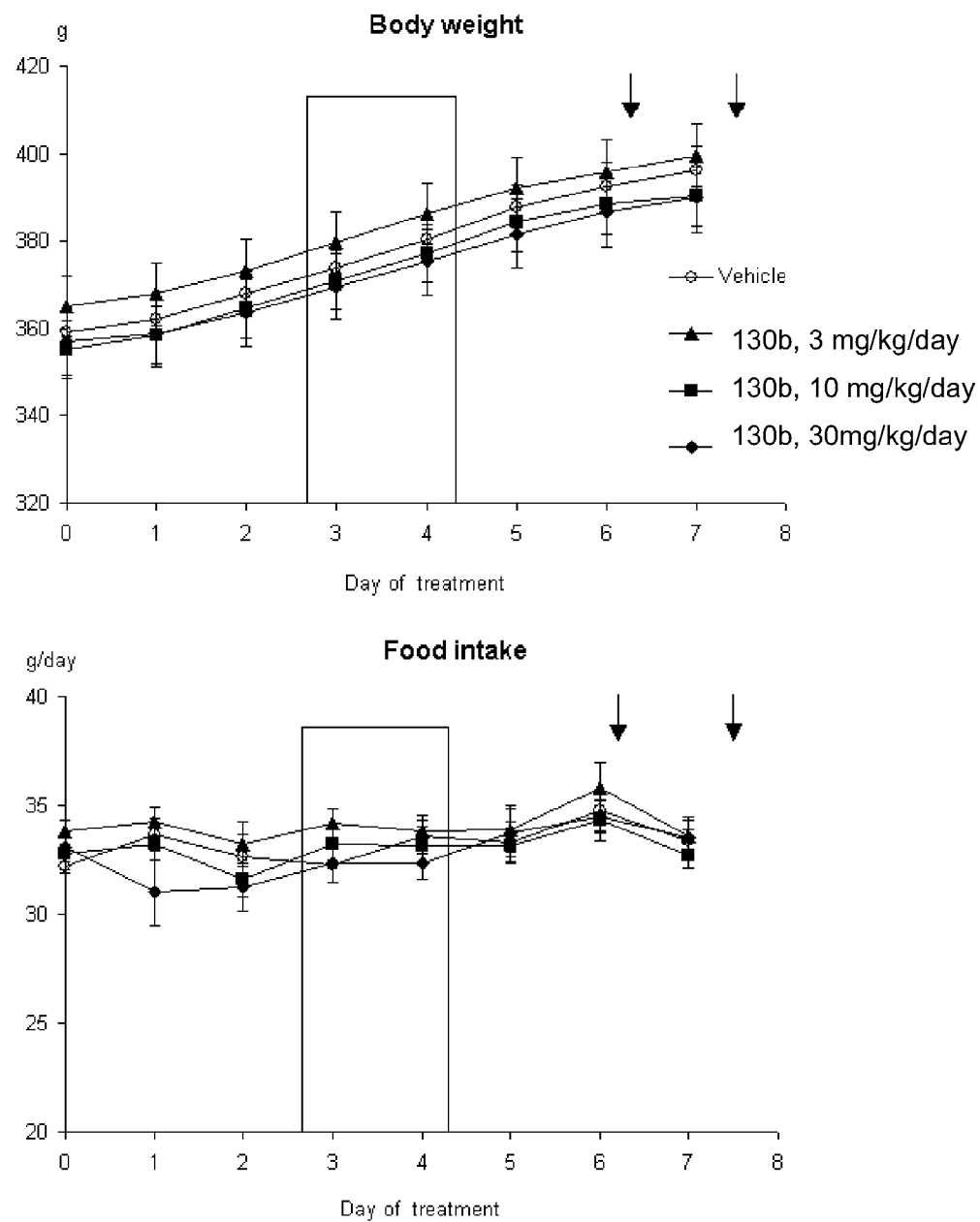
FIG. 11 Development of body weight and food intake for animals treated with vehicle and with the different doses of Example 130b. Days of circadian measurement are indicated by a square, time points of forced swimming are indicated by arrows. Mean values±SEM.
Figure 12:
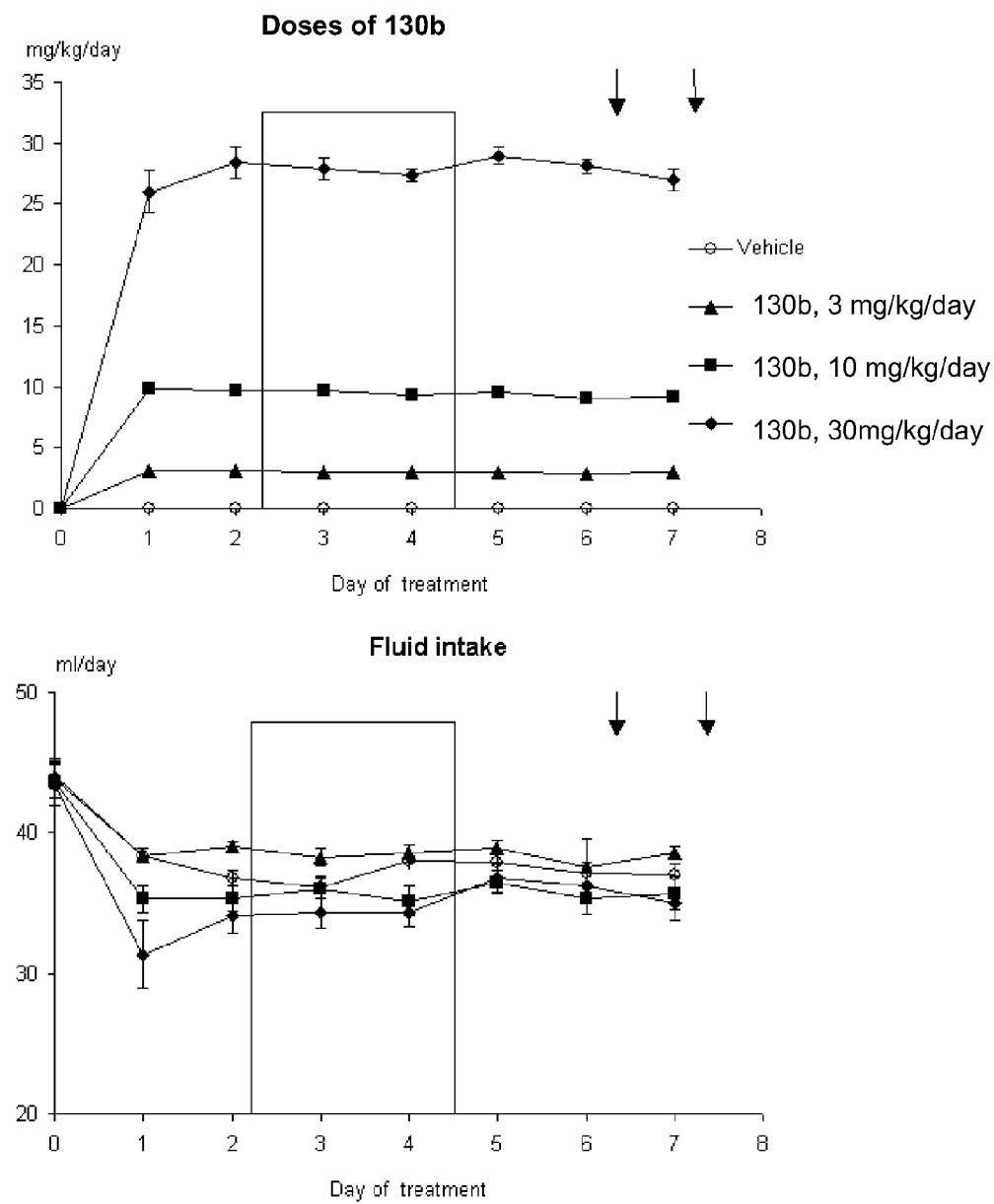
FIG. 12 Development of fluid intake and Example 130b doses for animals treated with vehicle and with the different doses of Example 130b. Days of circadian measurement are indicated by a square, time points of forced swimming are indicated by arrows. Mean values±SEM.
Figure 13:
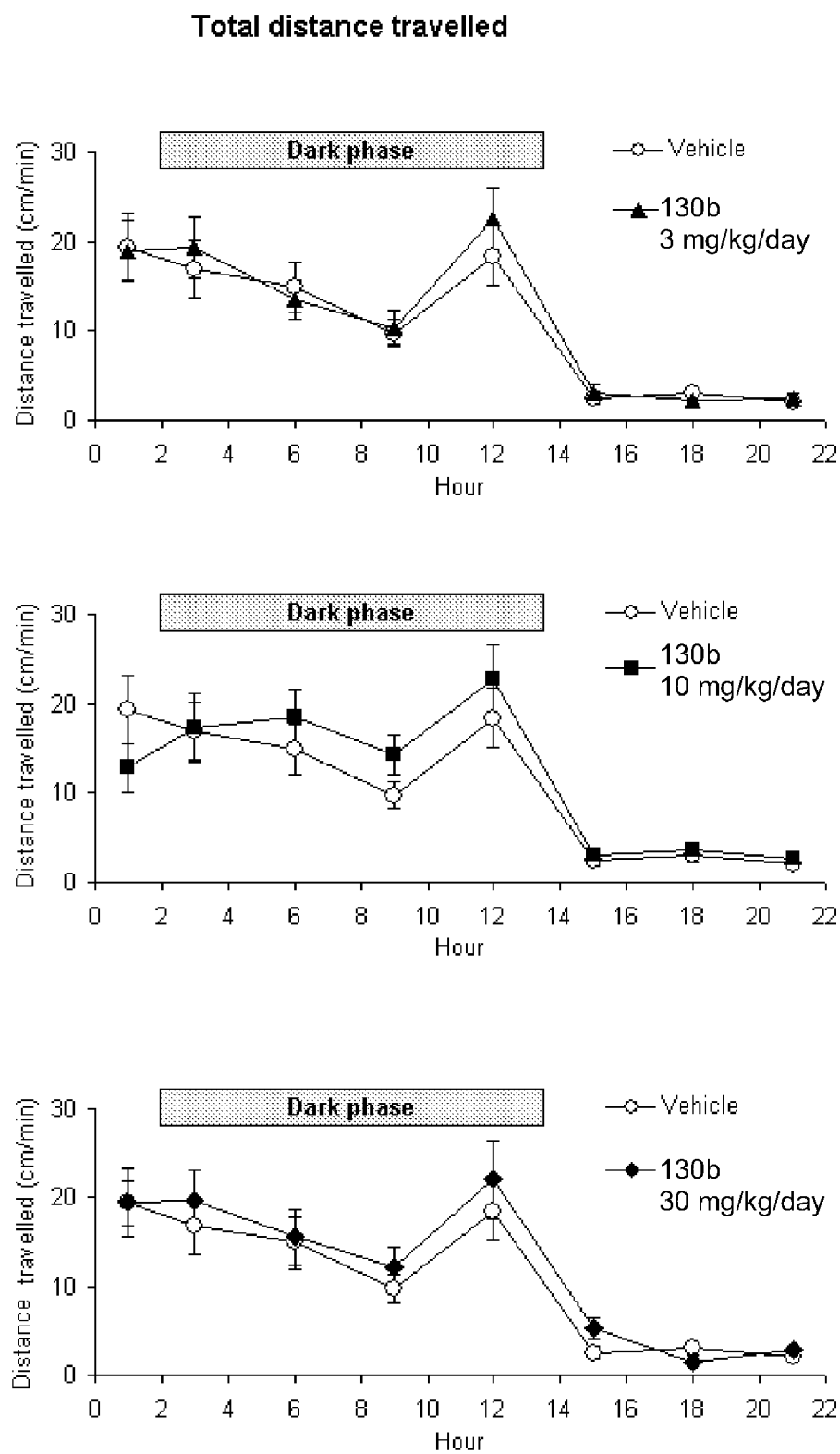
FIG. 13 Total distance travelled during day 2 of circadian measurement for animals treated with vehicle and with the different doses of Example 130b. Mean values±SEM. The dark phase is indicated by a square.
Figure 14:
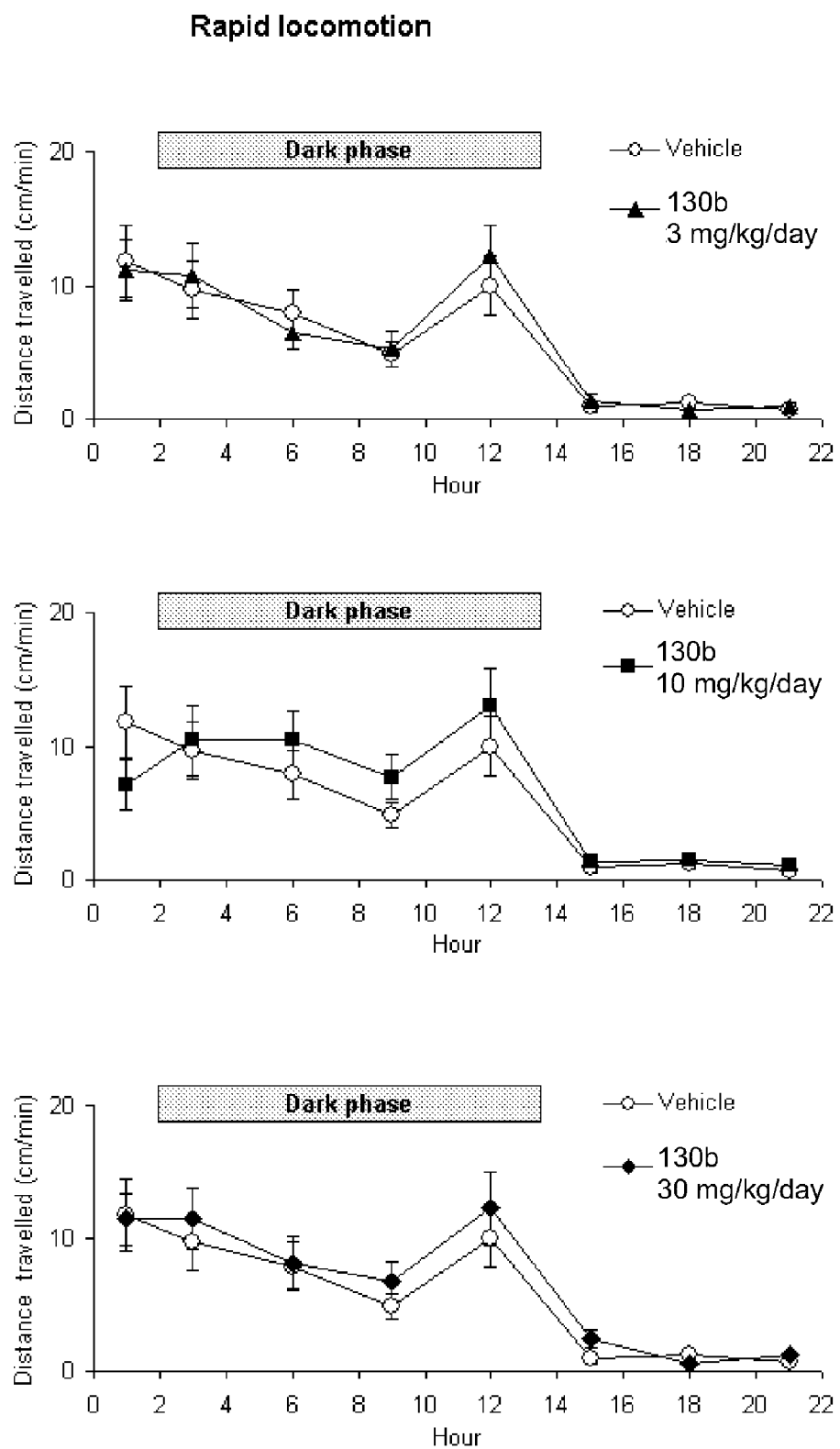
FIG. 14 Rapid locomotion during day 2 of circadian measurement for animals treated with vehicle and with the different doses of Example 130b. Mean values±SEM.
Figure 15:
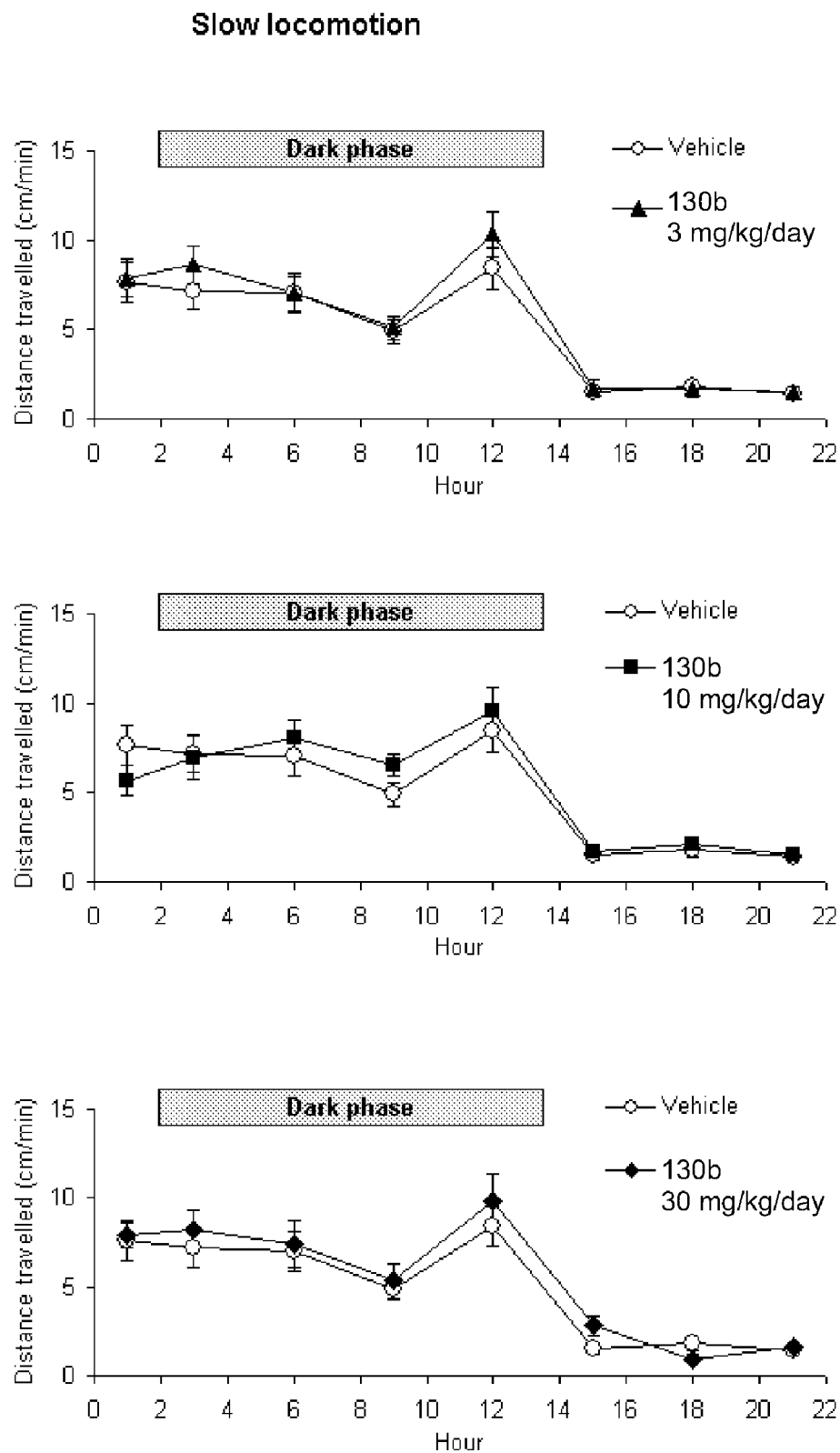
FIG. 15 Slow locomotion during day 2 of circadian measurement for animals treated with vehicle and with the different doses of Example 130b. Mean values±SEM.
Figure 16:
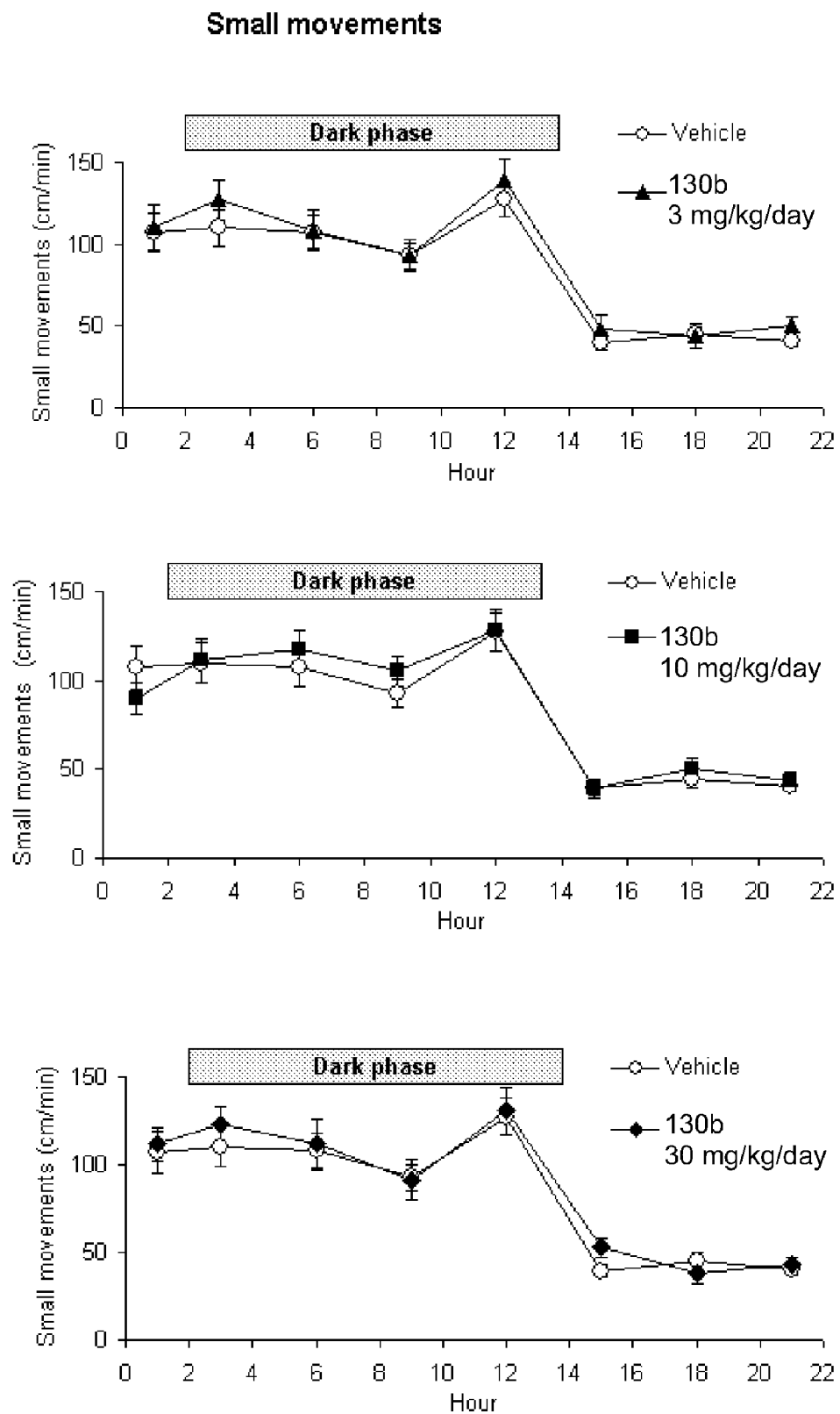
FIG. 16 Small movements during day 2 of circadian measurement for animals treated with vehicle and with the different doses of Example 130b. Mean values±SEM.
Figure 17:
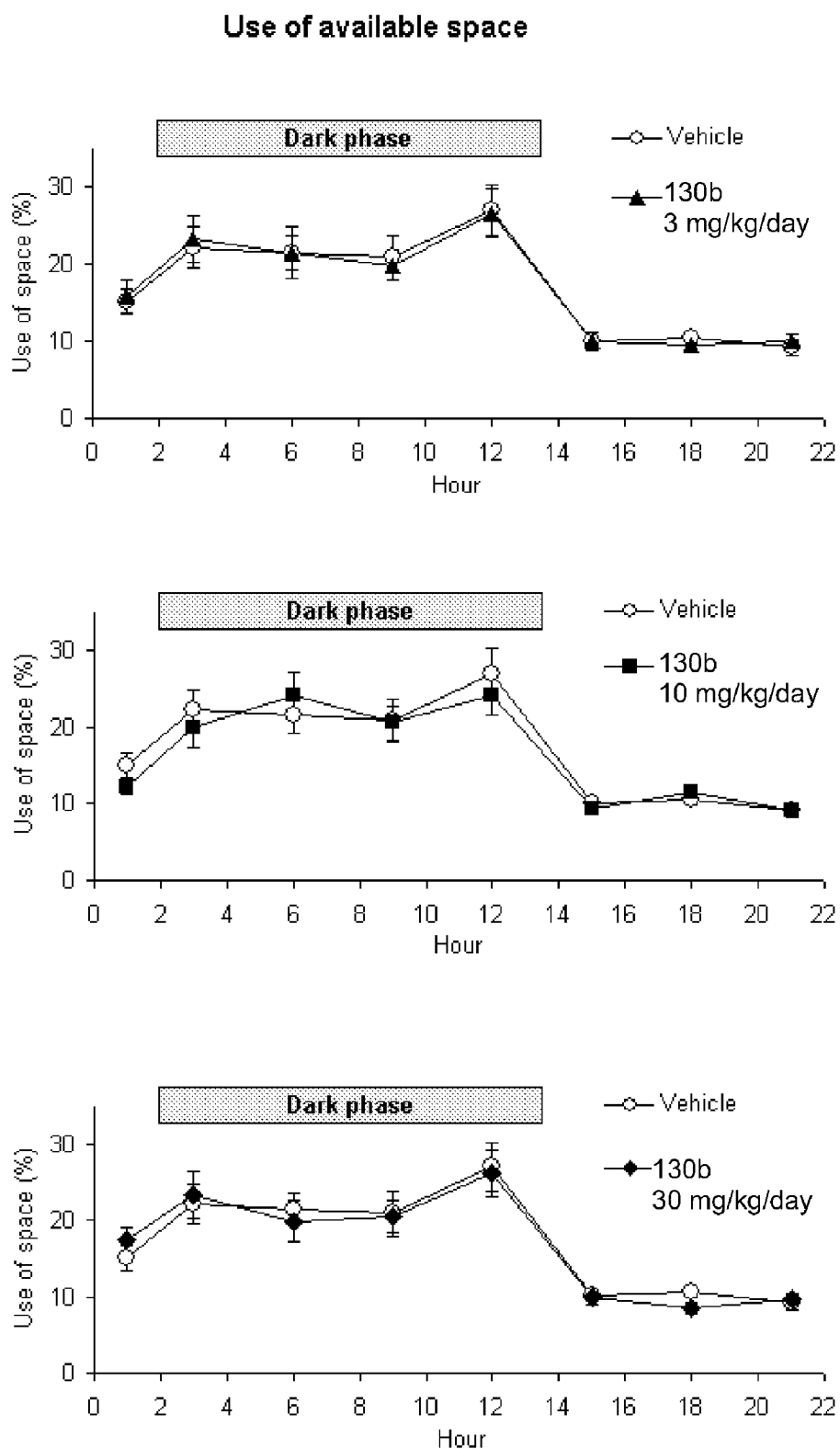
FIG. 17 Use of available space during day 2 of circadian measurement for animals treated with vehicle and with the different doses of Example 130b. Mean values±SEM.
Figure 18:
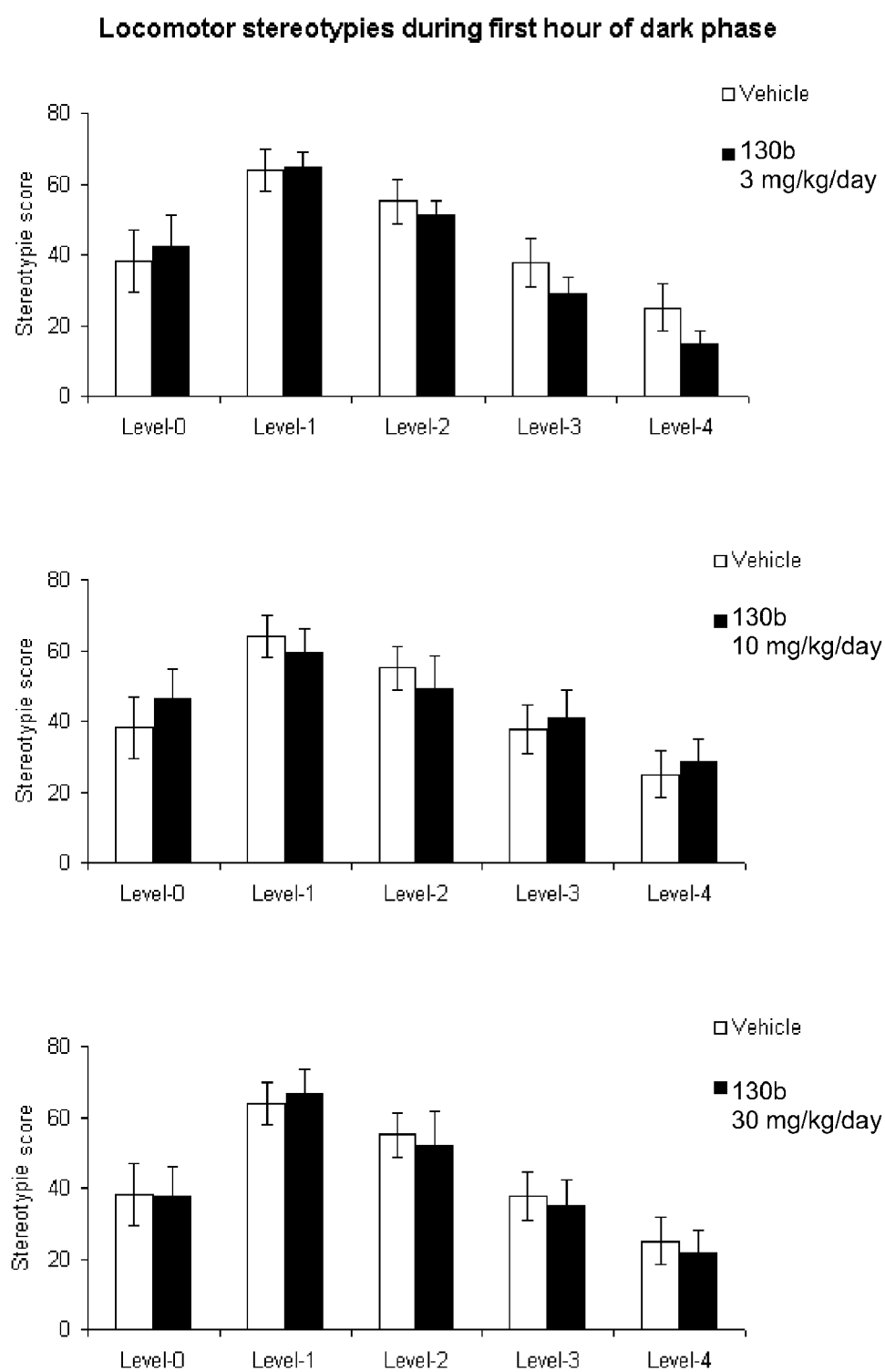
FIG. 18 Locomotor stereotypies during first hour of dark phase (day 2 of circadian measurement) for animals treated with vehicle and with the different doses of Example 130b. Mean values±SEM.
Figure 19:
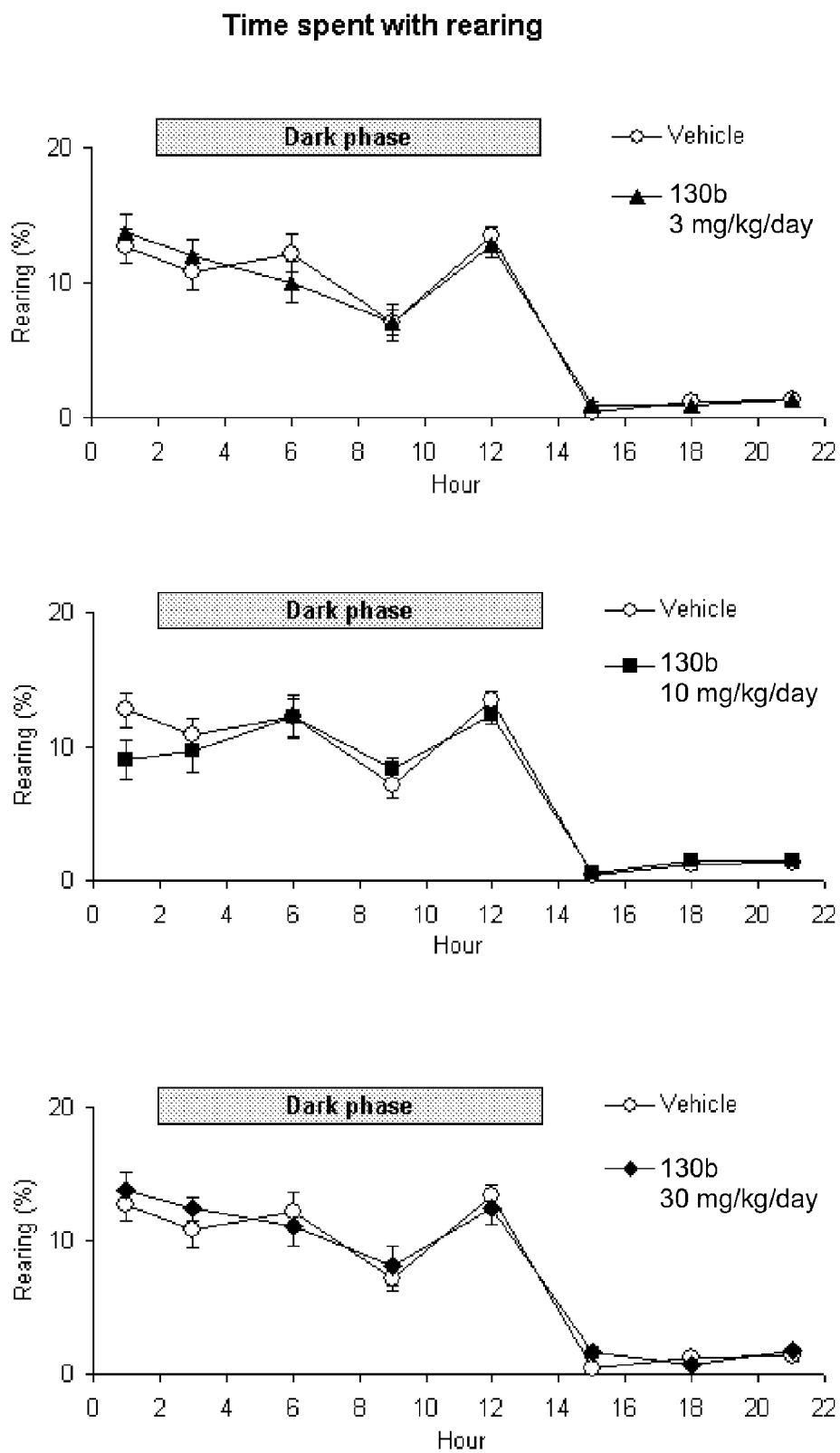
FIG. 19 Portion of time spent with rearing during day 2 of circadian measurement for animals treated with vehicle and with the different doses of Example 130b. Mean values±SEM.
Figure 20:
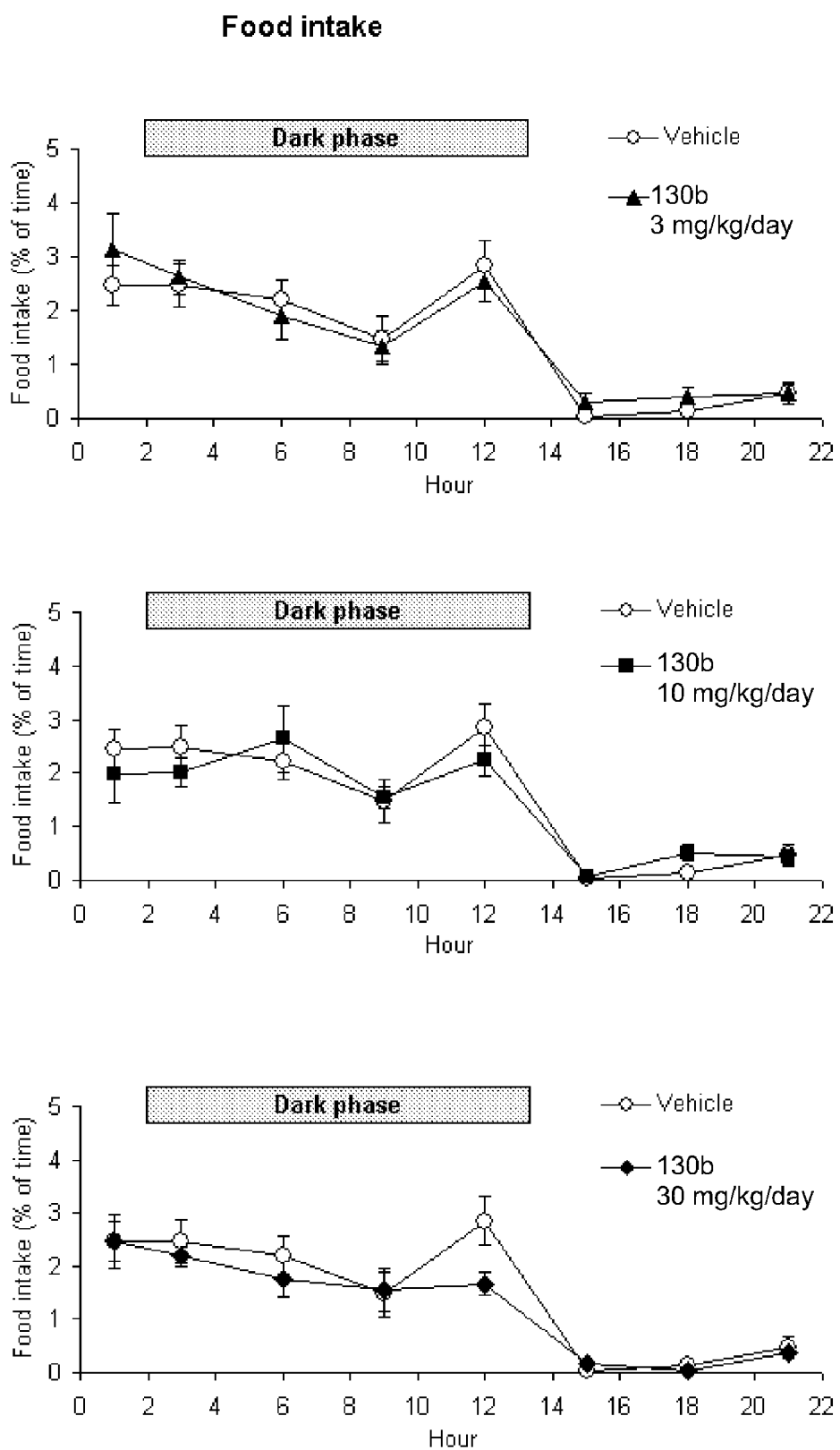
FIG. 20 Portion of time spent with rearing at food place during day 2 of circadian measurement for animals treated with vehicle and with the different doses of Example 130b. Mean values±SEM.
Figure 21:
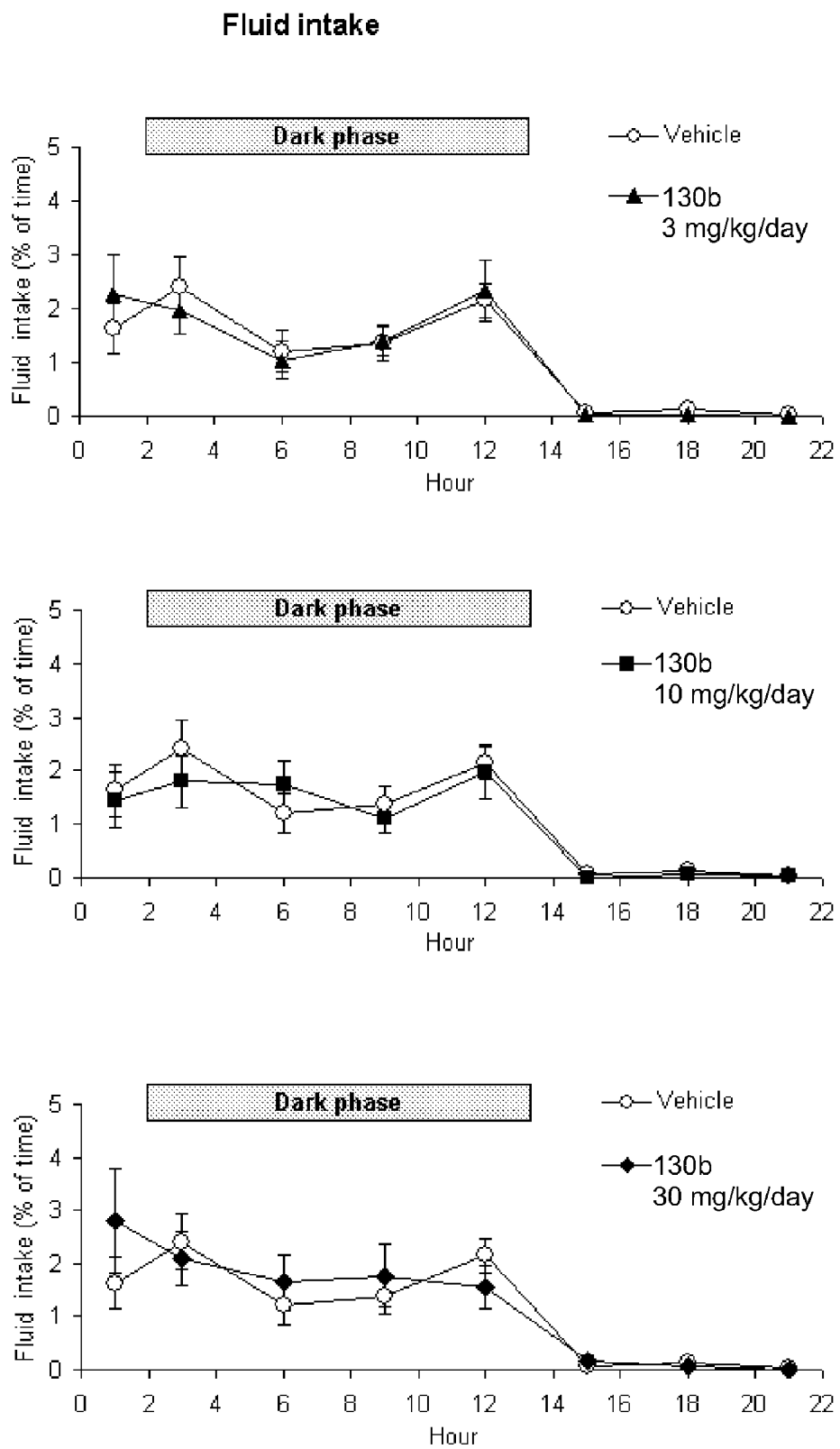
FIG. 21 Portion of time spent with rearing at fluid place during day 2 of circadian measurement for animals treated with vehicle and with the different doses of Example 130b. Mean values±SEM.
Figure 22:
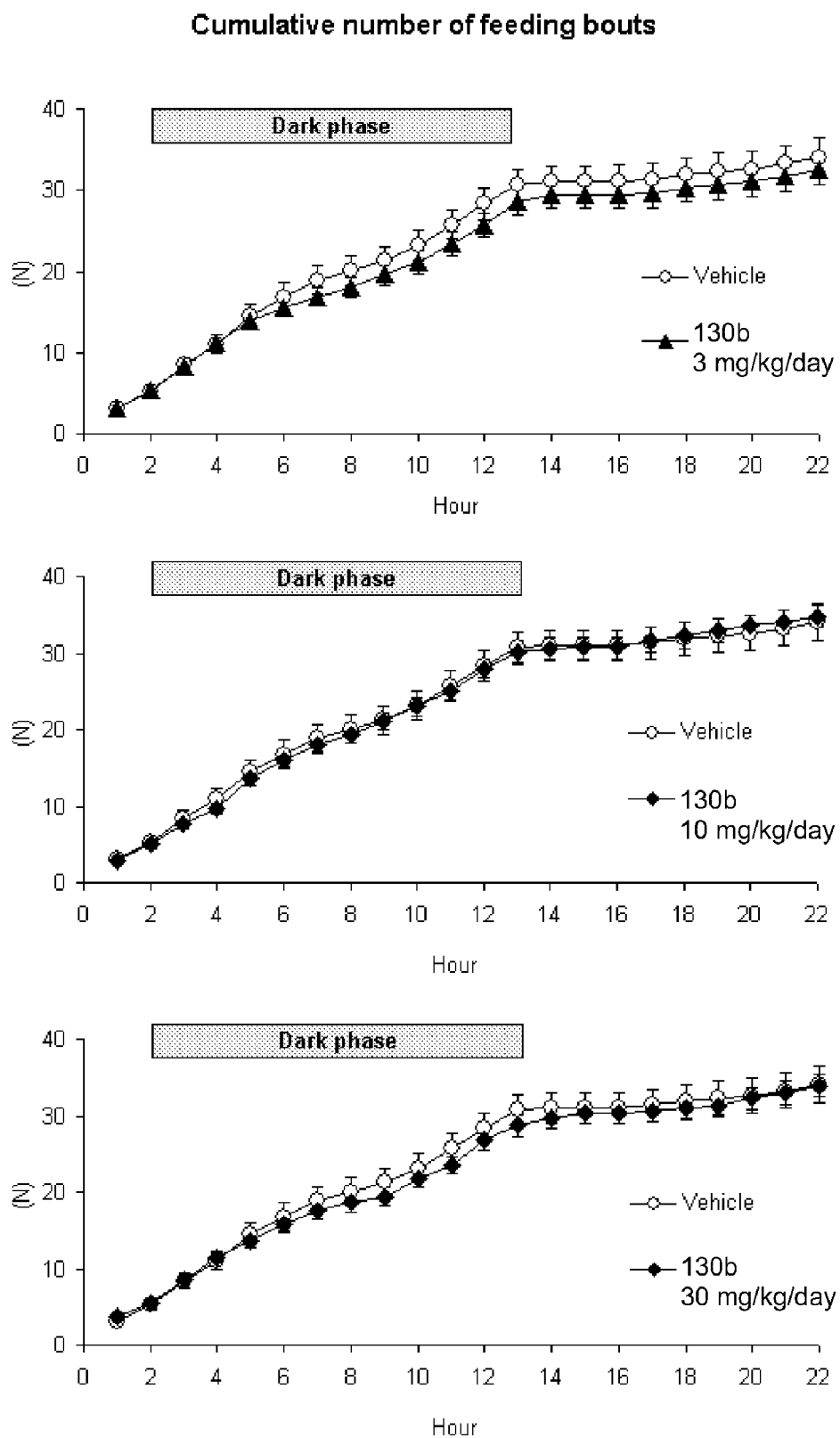
FIG. 22 Cumulated number of drinking bouts on day 2 of circadian measurement for animals treated with vehicle and with the different doses of Example 130b. Mean values±SEM. The dark phase is indicated by a square.
Figure 23:
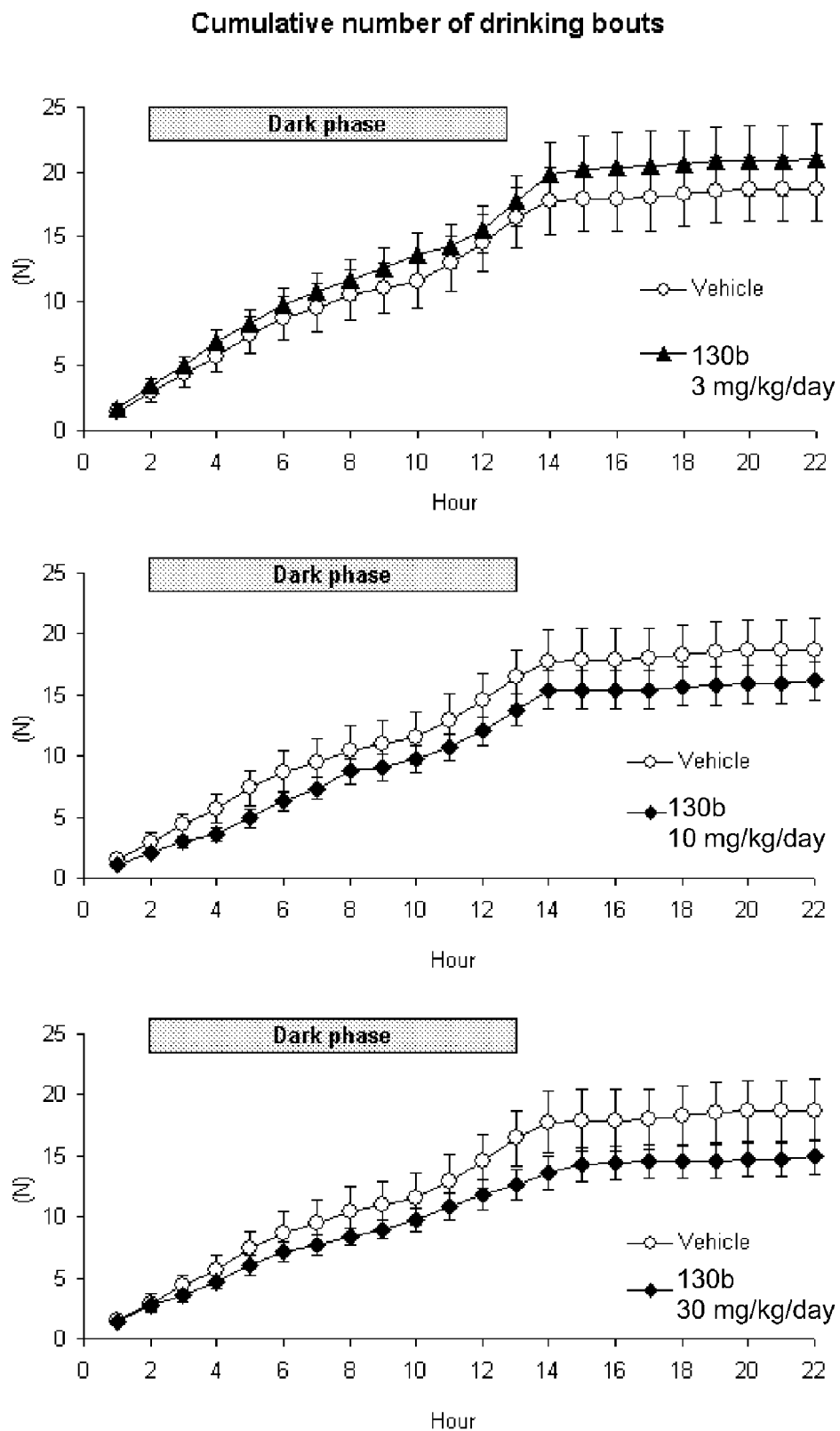
FIG. 23 Cumulated number of feeding bouts on day 2 of circadian measurement for animals treated with vehicle and with the different doses of Example 130b. Mean values±SEM. The dark phase is indicated by a square.

The effect was strongest during the first days of administration when Example 130b dose-dependently led to a reduction of fluid intake with the highest dose having the strongest effect. Fluid intake remained slightly lower during ongoing treatment (FIGS. 11, 12). Example 130b dose ranged between 2.8-3.1 mg/kg/day (low dose), 9.1-9.9 mg/kg/day (medium dose) and 26.0-29.0 mg/kg/day (high dose, FIG. 12).

Circadian Courses of Activity, Feeding and Drinking Behaviour

Example 130b led to a significantly slight decrease of fluid intake, measured during the last day of circadian recording compared with vehicle-treated animals. Body weight and food intake were not affected.

There were no statistically significant effects of Example 130b on horizontal or vertical locomotor activity compared with vehicle-treated animals. There were no statistically significant effects of Example 130b on usage of available space or stereotypy index. Access times to food and fluid did not differ from vehicle-treated animals whereas there was a statistically significant time×treatment interaction effect on the cumulated number of drinking bouts compared with vehicle treated animals. Example 130b-treated animals dose-dependently reached a lower total number of drinking bouts during the 22 hours of measurement (FIG. 13 to 23).

Discussion and Conclusions

Tetradic Encounter Test

Chlordiazepoxide had no effects on locomotor activity and led to weak effects on behavioural patterns. It decreased defensive and increased non-agonistic social behaviour. There were indications of a weakly increasing effect on the distance between the encounter mates. Chlordiazepoxide had clear effects on inter-individual synchrony of behaviour in reducing immediate and prolonging synchronisation especially for aggressive behaviour. This course indicates a unidirectional way of interaction (no mutual stimulation).

Example 130b altered locomotor activity. The low and high dose increased the activity at the beginning of the tests. Only the high dose increased the time spent in the centre of the open field and the use of available space. Low and high dose increased the distance to encounter mates. Example 130b had strong effects on inter-individual synchrony of behaviour. Effects were strongest for the high dose and to a lower degree visible for the low dose. Example 130b increased immediate synchrony in all cases. The effects were strongest for aggressive behaviour indicating bidirectional (mutual) inter-individual interactions.

Body Weight, Food and Fluid Consumption During Chronic Compound Administration

Imipramine reduced body weight gain, food and fluid consumption throughout the time of administration compared with vehicle-treated animals.

Example 130b dose-dependently led to a reduction in fluid intake especially during the first days of administration compared with vehicle-treated animals. The effect remained visible for the whole period of treatment. It was most probably due to the fact that the animals had to adapt to the changed taste of their drinking solution, resulting in a strong reduction of fluid intake at the first day of administration that did not completely recover. Food intake and body weight were not affected.

Circadian courses of Activity, Feeding and Drinking Behaviour

Imipramine had strong effects on almost all parameters of the circadian registration compared with vehicle-treated animals. It clearly reduced horizontal and vertical activity, feeding and drinking especially during the first and the last three hours of the dark phase. It also reduced total food and fluid intake.

Example 130b had no effects on time courses of activity and feeding compared with vehicle-treated animals. While the reduction of fluid intake did not lead to differences in time course of fluid access, it could be seen in a dose dependent reduction of cumulated drinking bouts.

BIOLOGICAL EXAMPLE 6

Bioavailability Studies

Material and Methods

Animals

Male Wistar rats (N=25; Crl:WI) with a body weight ranging between 300 and 350 g were purchased from Harlan Winkelmann GmbH (Borchen, Germany).

Animals were single-housed under conventional conditions with controlled temperature ($22\pm2°$ C.) on a 12/12 hours light/dark cycle (light on at 06:00 AM). Standard pelleted chow (ssniff® Soest, Germany) and tap water acidified with HCl were allowed ad libitum.

Study Compounds
Example 24b, C-[3-Benzyl-5-(2,4-dichloro-phenyl)-3H-imidazol-4-yl]-methylamine
Example 39b, C-[5-(2,4-dichloro-phenyl)-3-pyridin-2-ylmethyl-3H-imidazol-4-yl]-methylamine
Example 121b, C-[5-(2,4-dichloro-phenyl)-3-pyridin-3-ylmethyl-3H-imidazol-4-yl]-methylamine
Example 128b, C-[5-(2,4-dichloro-phenyl)-3-(2-ethoxy-benzyl)-3H-imidazol-4-yl]-methylamine
Example 130b C-[5-(2,4-dichloro-phenyl)-3-thiophen-3-ylmethyl-3H-imidazol-4-yl]-methylamine All studycompounds were used in the form of the hydrochloride salt.

Experimental Procedure

Implantation of Catheter:

One week after adaptation to the housing conditions, catheters were implanted into the carotid artery of the rats under general anaesthesia (i.p. injection of 0.25 mL/kg b.w. Rompun® [2%], BayerVital, Germany and 0.5 mL/kg b.w. Ketamin 10, Atarost GmbH & Co., Twistringen, Germany). The animals were allowed to recover for one week. The catheters were flushed with heparin-saline (100 IU/mL) three times per week.

In case of dysfunction of the catheter, a second catheter was implanted into the contra-lateral carotid artery.

Treatment:

After overnight fast, the inhibitors were administered the oral route via a feeding tube (15 g, 75 mm; Fine Science Tools, Heidelberg, Germany) and the intraarterial route via the arterial catheter. In case of intraarterial administration, the catheter was immediately flushed with 30 µL saline.

The animals were treated by a single oral dose of 3 mg/kg (5 mL/kg b.w.; treatment A) followed by a wash-out period of at least 3 days before intraarterial administration of 3 mg/kg (2 mL/kg b.w.; treatment B). The compounds were dissolved in saline to a final concentration adequate for an application of 3 mg/kg b.w. As an exception, MB56232 was adminisistered with a dose of 0.19052 mg/kg b.w. due to its low solubility.

Treatment Groups:

Three groups with N=5 animals were formed for testing 3 compounds (inhibitor 1-3).

| Group 1 (Example 24b): | A) 3 mg/kg oral |
| | B) 3 mg/kg intraarterial |
| Group 2 (Example 39b): | A) 3 mg/kg oral |
| | B) 3 mg/kg intraarterial |
| Group 3 (Example 121b): | A) 3 mg/kg oral |
| | B) 3 mg/kg intraarterial |

After completion of this testing and a wash out of ≧4 days, the catheterised rats were taken for testing in groups 4 to 6.

| Group 4 (Example 128b): | A) 0.19052 mg/kg oral |
| | B) 0.19052 mg/kg intraarterial |
| Group 5 (Example 130b): | A) 3 mg/kg oral |
| | B) 3 mg/kg intraarterial |

Blood Sampling:

Heparinized blood samples of 170 µL were collected in ice cooled sample tubes at −5, 0 (before medication) and at 5, 15, 30, 45, 60, 120, 240, 360 and 480 min. Blood samples in sample tubes were put shortly on ice and centrifuged thereafter (12,000 rpm for 2 min).

Plasma Preparation, Storage and Delivery:

Plasma samples of at least 80 µL were shock frozen in liquid nitrogen and stored at −70° C. until measurement. Plasma samples were sent to Probiodrug on dry ice.

Determination of Inhibitor Plasma Concentration:

Plasma levels of the DP IV inhibitors were determined by measurement of plasma DP IV activity under standardized conditions using Gly-Pro-pNA as substrate. Plasma levels were calculated from the degree of inhibition using the known inhibition constants and the equation for competitive inhibition.

For determination of plasma DP IV activity, 50 µL sample in an appropriate dilution were incubated with 100 µL Hepes buffer (0.102 M, pH 7.6, I=0.319 M by KCl) and 50 µL water in a 96 well plate. Reaction was started by addition of 50 µL of a 2 mM Gly-Pro-pNA solution. Release of pNA was monitored for 20 min at 30° C. and 405 nm using a GeniousPro plate reader (Tecan). DP IV activity (deltaAbsorbtion/min) was calculated by linear regression of the time response curve. From this activity the concentration of the inhibitor was calculated using the following equation derived from the inhibitor equation for competitive inhibition.

$$I = \left(\frac{v_0}{v_i} - 1\right) \cdot \left(\frac{S}{K_M} + 1\right) \cdot K_I \cdot DF \quad \text{Equation 1}$$

were

I=concentration of inhibitor $v_0$=plasma DP IV activity without inhibitor, determined before application of inhibitor $v_i$=plasma DP IV activity with inhibitor S=concentration of substrate $K_M$=Michaelis-Menten constant of the substrate $K_I$=inhibition constant of the inhibitor DF=dilution factor Knowing the $K_M$-value (0.1 µM) and the concentration (0.4 µM) of the substrate, the equation simplifies to:

$$I = \left(\frac{v_0}{v_i} - 1\right) \cdot 5K_I \cdot /DF \quad \text{Equation 2}$$

For calculation of $v_0$ the mean of the two values before compound application (−5 and 0 min) was used. The $K_i$-values used for calculation are determined with the purified human recombinant enzyme.

Pharmacokinetic Analysis:

Pharmacokinetic analyses (parameters of the individual PK profiles) and descriptive statistics were carried out using WinNonlin (Version 4.0.1, Professional). Based on plasma concentration data of inhibitors, the following model-independent pharmacokinetic variables were determined:

$AUC_{(0-inf)}$, $AUC_{(0-t)}$, Cmax, tmax, terminal half-life ($t_{1/2}$) and bioavailability (F).

F (in %) was calculated from the ratio of observed AUC upon oral route of administration to the AUC upon intraarterial administration.

Individual concentration-time curves were plotted in linear-linear and log-linear forms. Mean concentration-time curves (means±SD) were plotted as log-linear plots. Descriptive statistics was calculated and tabulated per scheduled sampling time.

For the determination of pharmacokinetic parameters of MB101 only post-dose concentrations above LOQ were used. For determination of plasma concentrations of DP IV Inhibitors calculated from enzyme activity data, only those results, where enzyme activity was between 10% to 90% of the activity observed without inhibitor ($v_0$), were considered for pharmacokinetic evaluation.

Results

Plasma Concentrations

Figure 24:
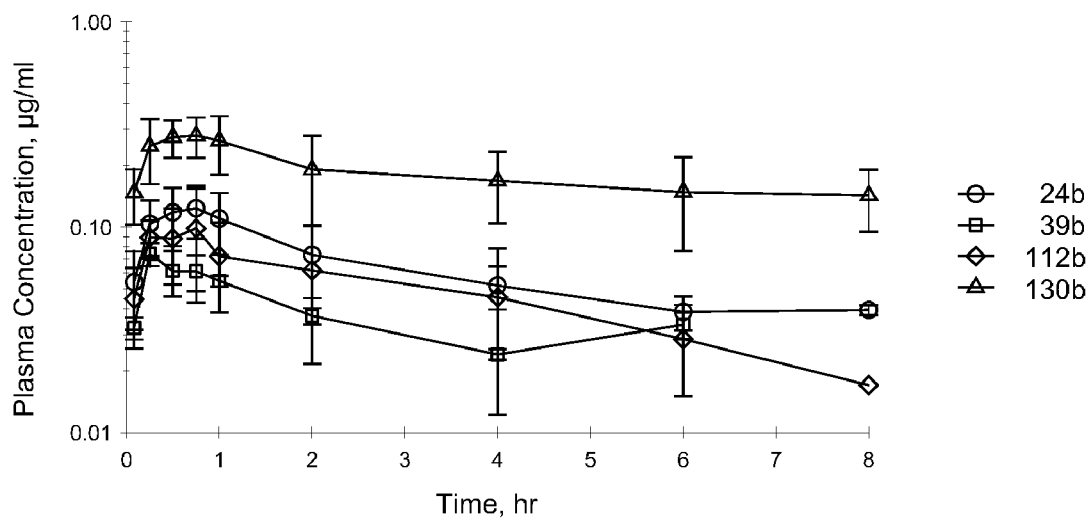
FIG. 24 Mean plasma concentrations (µg/ml) of DP IV inhibitors after oral administration of to male Wistar rats (n=4-6; mean±sd).
Figure 25:
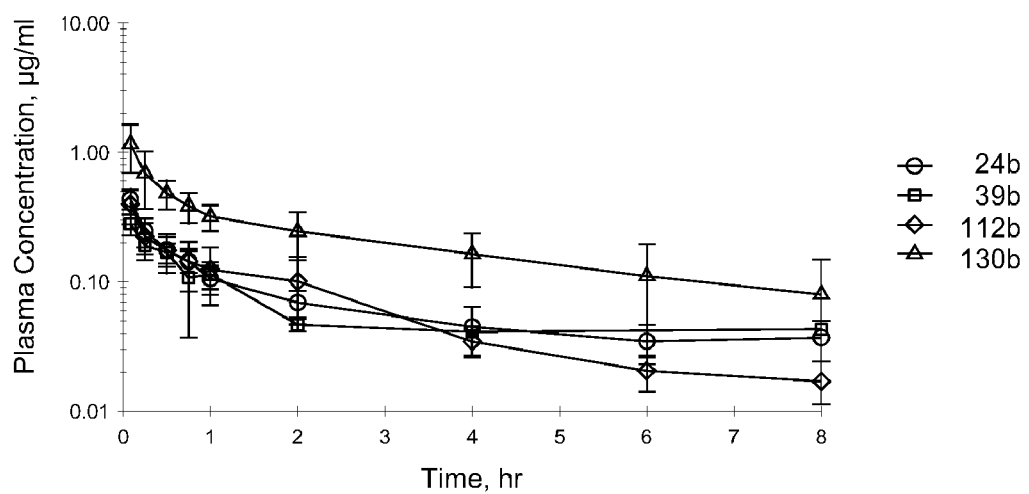
FIG. 25 Mean plasma concentrations (µg/ml) of DP IV inhibitors after intraarterial administration to male Wistar rats (n=4-6; mean±sd).

Mean plasma concentrations after oral and intraarterial administration of DP IV inhibitors are shown in FIGS. 24 and 25.

Pharmacokinetic Parameter of DP IV Inhibitors

Pharmacokinetic parameters for intraarterial route of administration of DP IV Inhibitors are summarized in Table 6, and for the oral route of administration in Table 7.

TABLE 6

Summary of Pharmacokinetic Parameters of DP IV Inhibitors after Intraarterial Administration in Male Wistar Rats (Mean ± SD; N = 4-6)

| Parameter | Example 24b | Example 39b | Example 121b | Example 130b |
|---|---|---|---|---|
| Half-life (h) | 2.94 ± 1.388 | 1.57 ± 1.138 | 1.98 ± 0.994 | 4.00 ± 2.308 |
| Cmax (µg/mL) | 0.44 ± 0.073 | 0.28 ± 0.051 | 0.40 ± 0.120 | 1.16 ± 0.470 |
| AUC(0-inf) (h * µg/mL) | 0.64 ± 0.205 | 0.41 ± 0.191 | 0.63 ± 0.350 | 2.47 ± 1.440 |
| AUC(0-t) (h * µg/mL) | 0.51 ± 0.151 | 0.33 ± 0.148 | 0.44 ± 0.215 | 1.68 ± 0.516 |
| AUC/Dose (h * kg * µg/mL/mg) | 0.18 ± 0.093 | 0.14 ± 0.064 | 0.21 ± 0.115 | 0.82 ± 0.480 |

TABLE 7

Summary of Pharmacokinetic Parameters of DP IV Inhibitors after Oral Administration in Male Wistar Rats (Mean ± SD; N = 5)

| Parameter | Example 24b | Example 39b | Example 121b | Example 130b |
|---|---|---|---|---|
| Half-life (h) | 4.83 ± 4.076 | 3.18 ± 2.129 | 3.26 ± 3.867 | 5.49 ± 1.518 |
| tmax (h) | 0.75 ± 0.177 | 0.40 ± 0.224 | 0.45 ± 0.274 | 0.55 ± 0.326 |
| Cmax (µg/mL) | 0.13 ± 0.036 | 0.08 ± 0.009 | 0.11 ± 0.051 | 0.30 ± 0.064 |
| AUC(0-inf) (h * µg/mL) | 0.65 ± 0.314 | 0.29 ± 0.141 | 0.35 ± 0.207 | 2.33 ± 1.183 |
| AUC(0-t) (h * µg/mL) | 0.39 ± 0.149 | 0.14 ± 0.075 | 0.23 ± 0.206 | 1.27 ± 0.618 |
| AUC/Dose (h * kg * µg/mL/mg) | 0.22 ± 0.105 | 0.10 ± 0.047 | 0.12 ± 0.069 | 0.78 ± 0.394 |

All tested compounds revealed similar pharmacokinetics with no principal differences. The terminal half-life after intraarterial administration was calculated with 1.6 (Example 39b) and 5.5 hours (Example 130b). The highest dose-normalized AUC after intraarterial administration was found with compound Example 130b, the lowest with Example 39b. After oral administration of DP IV inhibitors the values for Cmax were estimated to be between 0.08 µg/mL (Example 39b) and 0.3 µg/mL (Example 130b). Maximal plasma concentrations were observed approximately between 0.4 and 0.75 hours.

The calculated bioavailability data of DP IV inhibitors from the valid study in a cross-over design are shown in Table 8.

TABLE 8

Bioavailability of DP IV Inhibitors calculated from Mean AUC

| | Mean AUC p.o. (h * µg/mL) | Mean AUC i.a. (h * µg/mL) | F (%) |
|---|---|---|---|
| Example 24b | 0.39 (N = 5) | 0.51 (N = 5) | 76 |
| Example 39b | 0.14 (N = 5) | 0.33 (N = 5) | 43 |
| Example 121b | 0.23 (N = 5) | 0.44 (N = 4) | 53 |
| Example 130b | 1.27 (N = 5) | 1.68 (N = 6) | 76 |

BIOLOGICAL EXAMPLE 7

Blood-Brain Distribution/LogBB of Example Compounds

Materials and Methods

Animals

Male Wistar rats (N=20, 5 per Group; Crl:WI) with a body weight ranging between 300 and 350 g were purchased from Charles River Laboratories (Sulzfeld, Germany).

Animals were single-housed under conventional conditions with controlled temperature (22±2° C.) on a 12/12 hours light/dark cycle (light on at 06:00 AM). Standard pelleted chow (ssniff® Soest, Germany) and tap water acidified with HCl were allowed ad libitum.

Study Compounds

Example 24b, Example 39b, Example 121b, Example 130b

Doses of Study Compounds

TABLE 9

Doses of bolus and continuous intravenous infusions

| Compound | Bolus i.a. dose (mg/kg b.w.) | Infusion Dose (mg/kg b.w.) |
| --- | --- | --- |
| Example 24b | 3 | 3 |
| Example 39b | 3 | 3 |
| Example 121b | 3 | 3 |
| Example 130b | 1 | 1 |

Animal Preparation for in vivo Testing

Implantation of Catheter

One week after adaptation to the housing conditions, catheters were implanted into the carotid artery and jugular vein of the rats under general anaesthesia (i.p. injection of 0.25 ml/kg b.w. Rompun® [2%], BayerVital, Germany and 0.5 ml/kg b.w. Ketamin 10, Atarost GmbH & Co., Twistringen, Germany). The animals were allowed to recover for one week. The catheters were flushed with heparin-saline (100 IU/ml) three times per week. In case of dysfunction of the catheter, a new animal were recruited to implant catheters into the carotid artery and jugular vein of this new rat under general anaesthesia. No anaesthetics were administered during infusion for compound transfer.

Bolus and Continuous Infusion

Doses for bolus and continuous infusion by the intravenous route are shown in Table 9. The bolus dose of compounds were dissolved in 10 µl DMSO and than diluted to 1 ml with saline (0.154 mol/l) and were injected via the venous catheter (n=5 rats). Thereafter, a continuous i.v. infusion of the compound solved in 10 µl DMSO and diluted to 5 ml with saline (infusion rate 0.083 ml/min; Perfusor$^R$ fm, B. Braun, Melsungen AG, Germany) were commenced for 60 min. 150 µl arterial blood samples were taken at 0, 20, 40, 50 and 60 min and stored on ice until centrifugation (12000 rpm for 2 min). Separated plasma were frozen in liquid nitrogen for further analysis.

Brain Preparation and Conservation

After 60 min primed-continuous infusion the N=5 rats were heparinized with 50 IU per 100 g b.w. heparin 5 min before the end of protease inhibitor infusion. The rats were quickly anaesthetized with i.a. ketamin® injection and bled to death from the abdominal vessels. The aorta supplying the upper part of the body were separated and canulated. The upper part of the body (including the brain) were perfused with 20 ml ice cold saline to flush the vessels free within the brain. The brains were taken out of the skull, rinsed briefly in ice cold saline and placed on filter paper.

Preparation: The brains were divided into their hemispheres, which were weighed and frozen in liquid nitrogen for further analysis.

Estimation of Concentration in Plasma and Brain Tissue

In plasma samples and brain tissues concentrations of compounds were measured using the aforementioned LC-MS methods.

Results

The logBB values calculated from the measured plasma and brain concentrations of the DPIV inhibitors are shown in Table 10.

TABLE 10

LogBB values of examples

| Animal No. | Example 24b | Example 39b | Example 121b | Example 130b |
| --- | --- | --- | --- | --- |
| 1 | −0.36 | −0.56 | −0.57 | −0.65 |
| 2 | −0.33 | −0.43 | −0.50 | −0.63 |
| 3 | −0.26 | −0.53 | −0.70 | −1.03 |
| 4 | −0.34 | −0.38 | −0.91 | −0.12 |
| 5 | −0.29 | −0.39 | | −0.76 |
| Mean | −0.3160 | −0.4580 | −0.6700 | −0.6380 |
| Std. Deviation | 0.04037 | 0.08228 | 0.1802 | 0.3306 |
| Brain/Plasma ratio | 0.483 | 0.275 | 0.214 | 0.230 |
| % in brain | 48.3 | 27.5 | 21.4 | 23.0 |

The tested example compounds penetrate the blood-brain-barrier very well and are thus very suitable for use in the treatment of diseases of the CNS.

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

Abbreviations

5-HT1A Human serotonin receptor
Boc t-butyloxycarbonyl
CDZ chlordiazepoxide
CNS Central nervous system
CoA Coenzyme A
CRH Corticotropin-Releasing-Hormone
Da Dalton
DMSO Dimethylsulfoxide
Ex. Example GABA Gamma-aminobutyric acid
GAD Generalized anxiety disorder
GM-CSF Anti-granulocyte-macrophage colony-stimulating factor
HEPES 4-(2-Hydroxyethyl)piperazine-1-ethanesulfonic acid
HMG-CoA DL-3-Hydroxy-3-methylglutaryl coenzyme A
IFG Impaired fasting glucose
IGM Impaired glucose metabolism
IGT Impaired glucose tolerance
LDH L-Lactic Dehydrogenase
MAO Monoamine oxidase inhibitors
NIDDM Non-insulin-dependent diabetes mellitus
NPY Neuropeptide Y
NRI's Norepinephrine reuptake inhibitors
OCD Obsessive-compulsive disorder
PD Panic disorder
PIMT Protein-L-isoaspartyl methyltransferase
PPARδ Peroxisome proliferator-activated receptor delta
PPARα Peroxisome proliferator-activated receptor alpha
PPARγ Peroxisome proliferator-activated receptor gamma
PTSD Posttraumatic stress disorder
RT Retention time
SAD Social anxiety disorder
SNRI's Serotonin-norepinephrine reuptake inhibitors
SSRI's Selective serotonin reuptake inhibitors

The invention claimed is:
1. A compound of formula (I)

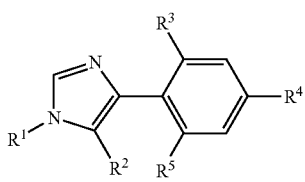

(I)

wherein
R$^1$ represents a group selected from the list consisting of:
C$_{1-12}$alkyl; —C$_{1-6}$alkylOC$_{1-6}$alkyl; C$_{2-12}$alkenyl; C$_{2-12}$alkynyl; C$_{1-12}$alkylamino; aryl, -aryl-aryl; —C$_{1-6}$alkylaryl; —C$_{1-6}$alkylaryl-aryl; —C$_{1-6}$alkylaryl-heteroaryl; —C$_{1-6}$alkylheteroaryl-aryl; —C$_{1-6}$alkylheteroaryl-heteroaryl; —C$_{1-6}$alkyl(aryl)$_2$; —C$_{1-6}$alkyl(heteroaryl)$_2$; —C$_{1-6}$alkyl (heteroaryl)(aryl); —C$_{1-6}$alkylOaryl; —C$_{1-6}$alkylNR$^9$aryl; —C$_{2-6}$alkenylaryl; —C$_{2-6}$alkynylaryl; heteroaryl; —C$_{1-6}$alkylheteroaryl; —C$_{1-6}$alkylOheteroaryl; —C$_{1-6}$alkylNR$^9$heteroaryl; —C$_{2-6}$alkenylheteroaryl; —C$_{2-6}$alkynylheteroaryl; —C$_{3-12}$carbocycle; —C$_{1-6}$alkylC$_{3-12}$carbocycle; —C$_{1-6}$alkylOC$_{3-12}$carbocycle; —C$_{1-6}$alkylNR$^9$C$_{3-12}$carbocycle; —C$_{2-6}$alkenylC$_{3-12}$carbocycle; —C$_{2-6}$alkynylC$_{3-12}$carbocycle; —C$_{3-12}$heterocycle; —C$_{1-6}$alkylC$_{3-1-2}$heterocycle; —C$_{2-6}$alkenylC$_{3-12}$heterocycle; and —C$_{2-6}$alkynylC$_{3-12}$heterocycle;
any of which alkyl, alkenyl or alkynyl groups may optionally be substituted by one or more halogen and/or hydroxyl groups; and
any of which carbocycle and heterocycle may optionally be substituted by one or more methyl groups
R$^2$ represents a group selected for the list consisting of —C$_{1-6}$alkylNR$^{10}$R$^{11}$ and —C$_{3-6}$cycloalkylimine optionally N substituted by R$^{12}$;

and R$^9$, R$^{10}$, R$^{11}$ and R$^{12}$ independently represents hydrogen or lower alkyl;
R$^3$ represents H; halogen; C$_{1-4}$alkyl; C$_{1-4}$haloalkyl; C$_{1-4}$alkoxy or C$_{1-4}$haloalkoxy;
R$^4$ represents H; halogen; C$_{1-4}$alkyl; C$_{1-4}$haloalkyl; C$_{1-4}$alkoxy or C$_{1-4}$haloalkoxy;
R$^5$ represents H; halogen; C$_{1-4}$alkyl; C$_{1-4}$haloalkyl; C$_{1-4}$alkoxy or C$_{1-4}$haloalkoxy;
and wherein any of the aforesaid carbocycle and heterocycle groups may optionally be substituted by one or more groups selected from the list consisting of:
(i) C$_{1-6}$alkyl, C$_{1-6}$alkenyl, C$_{1-6}$alkynyl;
(ii) C$_{1-6}$haloalkyl;
(iii) halogen;
(iv) oxo;
(v) —S—C$_{1-6}$alkyl (e.g. methylthio), —S(O)—C$_{1-6}$alkyl and —S(O)$_2$—C$_{1-6}$alkyl;
(vi) cyano;
(vii) nitro;
(viii) amino;
(ix) —OR$^{13}$; wherein R$^{13}$ may represent hydrogen, C$_{1-6}$alkyl, C$_{2-6}$alkenyl, C$_{2-6}$alkynyl or C$_{1-6}$haloalkyl;
(x) —C(O)OR$^{13}$; wherein R$^{13}$ is as defined above;
(xi) —S(O)$_2$—C$_{3-12}$cycloalkyl;
(xii) —S(O)$_2$—C$_{1-6}$alkyl;
(xiii) —S(O)$_2$-amino;
(xiv) —C(O)-amino;
(xv) C$_{1-6}$alkanoyl; and
(xvi) C$_{1-6}$alkoxyC$_{1-6}$alkanoyl;
wherein any of the aforesaid aryl and heteroaryl groups may optionally be substituted by one or more groups selected from the list consisting of:
(i) C$_{1-6}$alkyl, C$_{2-6}$alkenyl, C$_{2-6}$alkynyl;
(ii) C$_{1-6}$haloalkyl;
(iii) halogen;
(iv) —S—C$_{1-6}$alkyl (e.g. methylthio), —S(O)—C$_{1-6}$alkyl and —S(O)$_2$—C$_{1-6}$alkyl;
(v) cyano;
(vi) nitro;
(viii) —OR$^{13}$; wherein R$^{13}$ may represent hydrogen, C$_{1-6}$alkyl, C$_{2-6}$alkenyl, C$_{2-6}$alkynyl or C$_{1-6}$haloalkyl;
(ix) —C(O)OR$^{13}$; wherein R$^{13}$ is as defined above;
(x) —S(O)$_2$—C$_{3-12}$cycloalkyl;
(xi) —S(O)$_2$—C$_{1-6}$alkyl;
(xii) —S(O)$_2$-amino;
(xiii) —C(O)-amino;
(xiv) C$_{1-6}$alkanoyl;
(xv) C$_{1-6}$alkoxyC$_{1-6}$alkanoyl;
(xvi) —C$_{2-6}$alkenyloxy-;
(xvii) C$_{2-6}$alkynyloxy-;
(xviii) C$_{1-6}$alkoxyC$_{1-6}$alkyl-;
(xix) —C(O)N(C$_{1-6}$alkyl)$_2$, —C(O)NH$_2$ and —C(O)NH(C$_{1-6}$alkyl); and
(xx) C$_{3-12}$cycloalkyl;
and wherein amino is a primary amine, secondary amine, or tertiary amine or represented by the formula —NR$^a$R$^b$, and R$^a$ and R$^b$ are selected from hydrogen and alkyl or R$^a$ and R$^b$ are joined to form a 4-7 membered ring optionally containing a N or O atom;
or a pharmaceutically acceptable salt thereof, including all tautomers and stereoisomers thereof.
2. A compound of formula (I) according to claim 1 wherein R$^1$ represents C$_{1-12}$alkyl; C$_{2-12}$alkenyl, wherein the double bond is not at the C-1 position; C$_{2-12}$alkynyl, wherein the triple bond is not at the C-1 position; C$_{3-12}$carbocycle; which may optionally be substituted by one or more methyl groups; C$_{1-6}$-alkyl-C$_{3-12}$carbocycle, in which the carbocycle ring may optionally be substituted by one or more methyl groups; $C_{1-6}$haloalkyl; —$C_{1-6}$alkyl-aryl; —$C_{1-6}$alkyl-$C_{3-12}$heterocycle in which the heterocycle ring may optionally be substituted by one or more methyl groups; or —$C_{1-6}$alkyl-heteroaryl;

$R^2$ represents —$C_{1-4}$alkyl-$NH_2$; azetidin-2-yl; azetidin-3-yl; pyrrolidin-2-yl or pyrrolidin-3-yl;

$R^3$ represents H; halogen; $C_{1-4}$alkyl; $C_{1-4}$haloalkyl; $C_{1-4}$alkoxy or $C_{1-4}$haloalkoxy;

$R^4$ represents H; halogen; $C_{1-4}$alkyl; $C_{1-4}$haloalkyl; $C_{1-4}$alkoxy or $C_{1-4}$haloalkoxy;

$R^5$ represents H; halogen; $C_{1-4}$alkyl; $C_{1-4}$haloalkyl; $C_{1-4}$alkoxy or $C_{1-4}$haloalkoxy;

wherein any of the forementioned aryl and heteroaryl groups may optionally be substituted by one or more substituent groups selected from $C_{1-6}$ alkyl, $C_{2-6}$ alkenyl, $C_{2-6}$alkynyl, $C_{1-6}$haloalkyl, -thio$C_{1-6}$alkyl, —$SO_2C_{1-6}$alkyl, $C_{1-6}$alkoxy, $C_{3-12}$cycloalkyl, —$SO_2C_{3-12}$cycloalkyl, $C_{2-6}$alkenyloxy-, $C_{2-6}$alkynyloxy-, —C(O)-$C_{1-6}$alkyl, $C_{1-6}$alkoxy $C_{1-6}$alkyl-, nitro, halogen, cyano, hydroxyl, —C(O)OH, —C(O)O$C_{1-6}$alkyl, —C(O)N($C_{1-6}$alkyl)$_2$, —C(O)$NH_2$ and —C(O)NH($C_{1-6}$alkyl);

or a pharmaceutically acceptable salt thereof, including all tautomers and stereoisomers thereof.

3. A compound according to claim 1 wherein $R^1$ represents —$C_{1-6}$alkyl-aryl which aryl may optionally be substituted.

4. A compound according to claim 3 wherein $R^1$ represents —$CH_2$-aryl which aryl may optionally be substituted.

5. A compound according to claim 1 wherein $R^1$ represents —$C_{1-6}$alkyl-heteroaryl which heteroaryl may optionally be substituted.

6. A compound according to claim 5 wherein $R^1$ represents —$CH_2$-heteroaryl which heteroaryl may optionally be substituted.

7. A compound according to claim 1 wherein $R^1$ represents —$C_{1-6}$alkyl.

8. A compound according to claim 1 wherein $R^2$ represents -azetidin-3-yl.

9. A compound according to claim 1 wherein $R^2$ represents —$C_{1-4}$alkyl-$NH_2$.

10. A compound according to claim 9 wherein $R^2$ represents -methyl-$NH_2$.

11. A compound according to claim 1 wherein $R^3$ represents F.

12. A compound according to claim 1 wherein $R^3$ represents Cl.

13. A compound according to claim 1 wherein $R^3$ represents methyl.

14. A compound according to claim 1 wherein $R^4$ represents Cl.

15. A compound according to claim 1 wherein $R^4$ represents F.

16. A compound according to claim 1 wherein $R^4$ represents methyl.

17. A compound according to claim 1 wherein $R^4$ represents methoxy.

18. A compound according to claim 1 wherein $R^5$ represents H.

19. A compound according to claim 1 wherein
$R^1$ represents a group selected from the list consisting of:
$C_{1-12}$alkyl; —$C_{1-6}$alkylO$C_{1-6}$alkyl; —$C_{2-12}$alkenyl; —$C_{2-12}$alkynyl; —$C_{1-12}$alkylamino; aryl; -aryl-aryl; —$C_{1-6}$alkylaryl; —$C_{1-6}$alkylaryl-aryl; —$C_{1-6}$alkylaryl-heteroaryl; —$C_{1-6}$alkylheteroaryl-aryl; —$C_{1-6}$alkylheteroaryl-heteroaryl; —$C_{1-6}$alkyl(aryl)$_2$; —$C_{1-6}$alkyl(heteroaryl)$_2$; —$C_{1-6}$alkyl(heteroaryl)(aryl); —$C_{1-6}$alkylOaryl; —$C_{1-6}$alkylNR$^9$aryl; —$C_{2-6}$alkenylaryl; —$C_{2-6}$alkynylaryl; heteroaryl; —$C_{1-6}$alkylheteroaryl; —$C_{1-6}$alkylOheteroaryl; —$C_{1-6}$alkylNR$^9$heteroaryl; —$C_{2-6}$alkenylheteroaryl; —$C_{2-6}$alkynylheteroaryl; $C_{3-12}$carbocycle; —$C_{1-6}$alkyl$C_{3-12}$carbocycle; —$C_{1-6}$alkylO$C_{3-12}$carbocycle; —$C_{1-6}$alkylNR$^9C_{3-12}$carbocycle; —$C_{2-6}$alkenyl-$C_{3-12}$carbocycle; —$C_{2-6}$alkynyl$C_{3-12}$carbocycle; —$C_{3-12}$heterocycle; —$C_{1-6}$alkyl$C_{3-12}$heterocycle; —$C_{2-6}$alkenyl$C_{3-12}$heterocycle; and —$C_{2-6}$alkynyl$C_{3-12}$heterocycle;

any of which alkyl, alkenyl or alkynyl groups may optionally be substituted by one or more halogen and/or hydroxyl groups;

$R^2$ represents a group selected from the list consisting of: $C_{1-6}$alkylNR$^{10}$R$^{11}$ and $C_{3-6}$cycloalkylimine optionally N substituted by $R^{12}$; and $R^9$, $R^{10}$, $R^{11}$ and $R^{12}$ independently represents hydrogen or $C_{1-4}$alkyl.

$R^3$ represents Cl;

$R^4$ represents Cl and $R^5$ represents H;

wherein any of the aforementioned carbocycle and heterocycle groups may optionally be substituted by one or more groups selected from the list consisting of:
(i) $C_{1-6}$alkyl, $C_{2-6}$alkenyl, $C_{2-6}$alkynyl;
(ii) $C_{1-6}$haloalkyl;
(iii) halogen;
(iv) oxo
(v) —S—$C_{1-6}$alkyl, —S(O)—$C_{1-6}$alkyl and —S(O)$_2$—$C_{1-6}$alkyl;
(vi) cyano;
(vii) nitro;
(viii) amino;
(ix) —OR$^{13}$; wherein $R^{13}$ may represent hydrogen, $C_{1-6}$alkyl, $C_{2-6}$alkenyl, $C_{2-6}$alkynyl or $C_{1-6}$haloalkyl;
(x) —C(O)OR$^{13}$; wherein $R^{13}$ is as defined above;
(xi) —S(O)$_2$—$C_{3-12}$cycloalkyl
(xii) —S(O)$_2$—$C_{1-6}$alkyl
(xiii) —S(O)$_2$-amino;
(xiv) —C(O)-amino;
(xv) $C_{1-6}$alkanoyl; and
(xvi) $C_{1-6}$alkoxy$C_{1-6}$alkanoyl;

and wherein any of the aforesaid aryl and heteroaryl groups may optionally be substituted by one or more groups selected from the list consisting of:
(i) $C_{1-6}$alkyl, $C_{2-6}$alkenyl, $C_{2-6}$alkynyl;
(ii) $C_{1-6}$haloalkyl;
(iii) halogen;
(iv) —S—$C_{1-6}$alkyl, —S(O)—$C_{1-6}$alkyl and —S(O)$_2$—$C_{1-6}$alkyl;
(v) cyano;
(vi) nitro;
(viii) —OR$^{13}$; wherein $R^{13}$ may represent hydrogen, $C_{1-6}$alkyl, $C_{2-6}$alkenyl, $C_{2-6}$alkynyl or $C_{1-6}$haloalkyl;
(ix) —C(O)OR$^{13}$; wherein $R^{13}$ is as defined above;
(xi) —S(O)$_2$—$C_{3-12}$cycloalkyl;
(xii) —S(O)$_2$—$C_{1-6}$alkyl;
(xiii) —S(O)$_2$-amino;
(xiv) —C(O)-amino;
(xv) $C_{1-6}$alkanoyl;
(xvi) $C_{1-6}$alkoxy$C_{1-6}$alkanoyl;

or a pharmaceutically acceptable salt, including all tautomers and stereoisomers thereof.

20. A compound according to claim 1, wherein $R^2$ represents $C_{1-6}$alkylNR$^{10}$R$^{11}$.

21. A compound according to claim 20, wherein $R^2$ represents 1-ethylamine.

22. A compound according to claim 20, wherein $R^2$ represents 2-ethylamine.

23. A compound according to claim 20, wherein $R^2$ represents 3-propylamine.

24. A compound according to claim 1, wherein $R^2$ represents $C_{3-6}$cycloalkylimine optionally N substituted by $R^{12}$.

25. A compound according to claim 1, wherein $R^1$ represents $C_{1-12}$alkyl, which may be optionally substituted.

26. A compound according to claim 1, wherein $R^1$ represents $C_{2-12}$alkenyl, which may be optionally substituted.

27. A compound according to claim 1, wherein $R^1$ represents $C_{2-12}$alkynyl, which may be optionally substituted.

28. A compound according to claim 1, wherein $R^1$ represents aryl, which may optionally be substituted.

29. A compound according to claim 1, wherein $R^1$ represents heteroaryl, which may optionally be substituted.

30. A compound according to claim 1, wherein $R^1$ represents $C_{1-6}$alkyl$OC_{1-6}$alkyl, which alkyl groups may be optionally substituted.

31. A compound according to claim 1, wherein $R^1$ represents $C_{1-12}$alkylamino, which alkyl group may be optionally substituted.

32. A compound according to claim 1, wherein $R^1$ represents -aryl-aryl, which aryl groups may optionally be substituted.

33. A compound according to claim 1, wherein $R^1$ represents $C_{1-6}$alkylaryl, which alkyl and aryl groups may be optionally substituted.

34. A compound according to claim 1, wherein $R^1$ represents —$C_{1-6}$alkylaryl aryl, which alkyl and aryl groups may be optionally substituted.

35. A compound according to claim 1, wherein $R^1$ represents $C_{1-6}$alkyl(aryl)$_2$, which alkyl and aryl groups may be optionally substituted.

36. A compound according to claim 1, wherein $R^1$ represents $C_{1-6}$alkyl(heteroaryl)$_2$, which alkyl and heteroaryl groups may be optionally substituted.

37. A compound according to claim 1, wherein $R^1$ represents $C_{2-6}$alkenylaryl, which alkenyl and aryl groups may be optionally substituted.

38. A compound according to claim 1, wherein $R^1$ represents $C_{2-6}$alkynylaryl, which alkynyl and aryl groups may be optionally substituted.

39. A compound according to claim 1, wherein $R^1$ represents $C_{1-6}$alkylaryl-heteroaryl, which alkyl, aryl and heteroaryl groups may be optionally substituted.

40. A compound according to claim 1, wherein $R^1$ represents $C_{1-6}$alkylheteroaryl-aryl, which alkyl, aryl and heteroaryl groups may be optionally substituted.

41. A compound according to claim 1, wherein $R^1$ represents $C_{1-6}$alkylheteroaryl-heteroaryl, which alkyl and heteroaryl groups may be optionally substituted.

42. A compound according to claim 1, wherein $R^1$ represents $C_{1-6}$alkyl(heteroaryl)(aryl) which alkyl, aryl and heteroaryl groups may be optionally substituted.

43. A compound according to claim 1, wherein $R^1$ represents $C_{1-6}$alkylheteroaryl, which alkyl and heteroaryl groups may be optionally substituted.

44. A compound according to claim 1, wherein $R^1$ represents $C_{2-6}$alkenylheteroaryl, which alkenyl and heteroaryl groups may be optionally substituted.

45. A compound according to claim 1, wherein $R^1$ represents $C_{2-6}$alkynylheteroaryl, which alkynyl and heteroaryl groups may be optionally substituted.

46. A compound according to claim 1, wherein $R^1$ represents $C_{3-12}$carbocycle, which carbocycle may optionally be substituted.

47. A compound according to claim 1, wherein $R^1$ represents $C_{3-12}$heterocycle, which heterocycle may optionally be substituted.

48. A compound according to claim 1, wherein $R^1$ represents $C_{1-6}$alkyl$C_{3-12}$carbocycle, which alkyl and carbocycle groups may be optionally substituted.

49. A compound according to claim 1, wherein $R^1$ represents $C_{2-6}$alkenyl$C_{3-12}$carbocycle, which alkenyl and carbocycle groups may be optionally substituted.

50. A compound according to claim 1, wherein $R^1$ represents $C_{2-6}$alkynyl$C_{3-12}$carbocycle, which alkynyl and carbocycle groups may be optionally substituted.

51. A compound according to claim 1, wherein $R^1$ represents $C_{1-6}$alkyl$NR^9$aryl, which alkyl and aryl groups may be optionally substituted.

52. A compound according to claim 1, wherein $R^1$ represents $C_{1-6}$alkyl$NR^9$heteroaryl, which alkyl and heteroaryl groups may be optionally substituted.

53. A compound according to claims 1, wherein $R^1$ represents $C_{1-6}$alkyl$OC_{3-12}$carbocycle, which alkyl and carbocycle groups may be optionally substituted.

54. A compound according to claim 1, wherein $R^1$ represents $C_{1-6}$alkyl$NR^9C_{3-12}$carbocycle, which alkyl and carbocycle groups may be optionally substituted.

55. A compound according to claim 1, wherein $R^1$ represents $C_{1-6}$alkylOaryl, which alkyl and aryl groups may be optionally substituted.

56. A compound according to claim 1, wherein $R^1$ represents $C_{1-6}$alkylOheteroaryl, which alkyl and heteroaryl groups may be optionally substituted.

57. A compound according to claim 1, wherein $R^1$ represents $C_{1-6}$alkyl$C_{3-12}$heterocycle, which alkyl and heterocycle groups may be optionally substituted.

58. A compound according to claim 1, wherein $R^1$ represents $C_{2-6}$alkenyl$C_{3-12}$heterocycle, which alkenyl group and heterocycle groups may be optionally substituted.

59. A compound according to claim 1, wherein $R^1$ represents $C_{2-6}$alkynyl$C_{3-12}$heterocycle, which alkynyl and heterocycle groups may be optionally substituted.

60. A compound selected from the group consisting of:
- C-[5-(2-Chloro-4-fluoro-phenyl)-3-thiophen-2-ylmethyl-3H-imidazol-4-yl]-methylamine;
- C-[5-(2-Chloro-4-fluoro-phenyl)-3-furan-2-ylmethyl-3H-imidazol-4-yl]-methylamine;
- C-[3-(2-Chloro-benzyl)-5-(2-chloro-4-fluoro-phenyl)-3H-imidazol-4-yl]-methylamine;
- C-[5-(2-Chloro-4-fluoro-phenyl)-3-(5-methyl-furan-2-ylmethyl)-3H-imidazol-4-yl]-methylamine;
- C-[5-(2-Chloro-4-fluoro-phenyl)-3-(4-fluoro-benzyl)-3H-imidazol-4-yl]-methylamine;
- C-[5-(2-Chloro-4-fluoro-phenyl)-3-(3-trifluoromethyl-benzyl)-3H-imidazol-4-yl]-methylamine;
- C-[5-(2-Chloro-4-fluoro-phenyl)-3-(2,4-difluoro-benzyl)-3H-imidazol-4-yl]-methylamine;
- C-[5-(2-Chloro-4-fluoro-phenyl)-3-propyl-3H-imidazol-4-yl]-methylamine;
- C-[5-(2-Chloro-4-fluoro-phenyl)-3-(3-methoxy-benzyl)-3H-imidazol-4-yl]-methylamine;
- C-[5-(2-Chloro-4-fluoro-phenyl)-3-(3-fluoro-benzyl)-3H-imidazol-4-yl]-methylamine;
- C-[5-(2-Chloro-4-fluoro-phenyl)-3-thiophen-3-ylmethyl-3H-imidazol-4-yl]-methylamine;
- C-[3-(5-Bromo-2-fluoro-benzyl)-5-(2-chloro-4-fluoro-phenyl)-3H-imidazol-4-yl]-methylamine;
- C-[3-(2-Chloro-6-fluoro-benzyl)-5-(2-chloro-4-fluoro-phenyl)-3H-imidazol-4-yl]-methylamine;

C-[5-(2-Chloro-4-fluoro-phenyl)-3-(2-methyl-benzyl)-3H-imidazol-4-yl]-methylamine;
C-[3-Benzyl-5-(2-chloro-4-fluoro-phenyl)-3H-imidazol-4-yl]-methylamine;
C-[3-Benzo[1,3]dioxol-5-ylmethyl-5-(2-chloro-4-fluoro-phenyl)-3H-imidazol-4-yl]-methylamine;
C-[5-(2-Chloro-4-fluoro-phenyl)-3-(3,4-difluoro-benzyl)-3H-imidazol-4-yl]-methylamine;
C-[5-(2-Chloro-4-fluoro-phenyl)-3-(2-ethoxy-benzyl)-3H-imidazol-4-yl]-methylamine;
C-[5-(2-Chloro-4-fluoro-phenyl)-3-(2-trifluoromethyl-benzyl)-3H-imidazol-4-yl]-methylamine;
C-[5-(2-Chloro-4-fluoro-phenyl)-3-(2,3-dichloro-benzyl)-3H-imidazol-4-yl]-methylamine;
C-[5-(2-Chloro-4-fluoro-phenyl)-3-(2,2-dimethyl-propyl)-3H-imidazol-4-yl]-methylamine;
C-[3-(4-Chloro-benzyl)-5-(2-chloro-4-fluoro-phenyl)-3H-imidazol-4-yl]-methylamine;
C-[5-(2-Chloro-4-fluoro-phenyl)-3-(2-trifluoromethoxy-benzyl)-3H-imidazol-4-yl]-methylamine;
C-[5-(2-Chloro-4-fluoro-phenyl)-3-(4-methyl-benzyl)-3H-imidazol-4-yl]-methylamine;
C-[5-(2-Chloro-4-fluoro-phenyl)-3-(3,4-dichloro-benzyl)-3H-imidazol-4-yl]-methylamine;
C-[5-(2-Chloro-4-fluoro-phenyl)-3-(2,6-dichloro-benzyl)-3H-imidazol-4-yl]-methylamine;
C-[5-(2-Chloro-4-fluoro-phenyl)-3-(2,5-difluoro-benzyl)-3H-imidazol-4-yl]-methylamine;
C-[5-(2-Chloro-4-fluoro-phenyl)-3-(2-fluoro-benzyl)-3H-imidazol-4-yl]-methylamine;
C-[3-(2-Chloro-4-fluoro-benzyl)-5-(2-chloro-4-fluoro-phenyl)-3H-imidazol-4-yl]-methylamine;
C-[5-(2-Chloro-4-fluoro-phenyl)-3-pyridin-2-ylmethyl-3H-imidazol-4-yl]-methylamine;
C-[5-(2-Chloro-4-fluoro-phenyl)-3-pyridin-3-ylmethyl-3H-imidazol-4-yl]-methylamine;
C-[5-(2,4-Dichloro-phenyl)-3-thiophen-2-ylmethyl-3H-imidazol-4-yl]-methylamine;
C-[5-(2,4-Dichloro-phenyl)-3-furan-2-ylmethyl-3H-imidazol-4-yl]-methylamine;
C-[3-(2-Chloro-benzyl)-5-(2,4-dichloro-phenyl)-3H-imidazol-4-yl]-methylamine;
C-[5-(2,4-Dichloro-phenyl)-3-(5-methyl-furan-2-ylmethyl)-3H-imidazol-4-yl]-methylamine;
C-[5-(2,4-Dichloro-phenyl)-3-(4-fluoro-benzyl)-3H-imidazol-4-yl]-methylamine;
C-[5-(2,4-Dichloro-phenyl)-3-(2,6-difluoro-benzyl)-3H-imidazol-4-yl]-methylamine;
C-[5-(2,4-Dichloro-phenyl)-3-(3-trifluoromethyl-benzyl)-3H-imidazol-4-yl]-methylamine;
C-[5-(2,4-Dichloro-phenyl)-3-(2,4-difluoro-benzyl)-3H-imidazol-4-yl]-methylamine;
C-[5-(2,4-Dichloro-phenyl)-3-propyl-3H-imidazol-4-yl]-methylamine;
C-[5-(2,4-Dichloro-phenyl)-3-(3-methoxy-benzyl)-3H-imidazol-4-yl]-methylamine;
C-[5-(2,4-Dichloro-phenyl)-3-(3-fluoro-benzyl)-3H-imidazol-4-yl]-methylamine;
C-[5-(2,4-Dichloro-phenyl)-3-thiophen-3-ylmethyl-3H-imidazol-4-yl]-methylamine;
C-[3-(5-Bromo-2-fluoro-benzyl)-5-(2,4-dichloro-phenyl)-3H-imidazol-4-yl]-methylamine;
C-[3-(2-Chloro-6-fluoro-benzyl)-5-(2,4-dichloro-phenyl)-3H-imidazol-4-yl]-methylamine;
C-[5-(2,4-Dichloro-phenyl)-3-(2-methyl-benzyl)-3H-imidazol-4-yl]-methylamine;
C-[3-Benzyl-5-(2,4-dichloro-phenyl)-3H-imidazol-4-yl]-methylamine;
C-[3-Benzo[1,3]dioxol-5-ylmethyl-5-(2,4-dichloro-phenyl)-3H-imidazol-4-yl]-methylamine;
C-[5-(2,4-Dichloro-phenyl)-3-(3,4-difluoro-benzyl)-3H-imidazol-4-yl]-methylamine;
C-[5-(2,4-Dichloro-phenyl)-3-(2-ethoxy-benzyl)-3H-imidazol-4-yl]-methylamine;
C-[5-(2,4-Dichloro-phenyl)-3-(2-trifluoromethyl-benzyl)-3H-imidazol-4-yl]-methylamine;
C-[3-(2,3-Dichloro-benzyl)-5-(2,4-dichloro-phenyl)-3H-imidazol-4-yl]-methylamine;
C-[5-(2,4-Dichloro-phenyl)-3-(2,2-dimethyl-propyl)-3H-imidazol-4-yl]-methylamine;
C-[3-(4-Chloro-benzyl)-5-(2,4-dichloro-phenyl)-3H-imidazol-4-yl]-methylamine;
C-[5-(2,4-Dichloro-phenyl)-3-(2-trifluoromethoxy-benzyl)-3H-imidazol-4-yl]-methylamine;
C-[5-(2,4-Dichloro-phenyl)-3-(4-methyl-benzyl)-3H-imidazol-4-yl]-methylamine;
C-[3-(2,4-Dichloro-benzyl)-5-(2,4-dichloro-phenyl)-3H-imidazol-4-yl]-methylamine;
C-[3-(3,4-Dichloro-benzyl)-5-(2,4-dichloro-phenyl)-3H-imidazol-4-yl]-methylamine;
C-[5-(2,4-Dichloro-phenyl)-3-ethyl-3H-imidazol-4-yl]-methylamine;
C-[3-(2,6-Dichloro-benzyl)-5-(2,4-dichloro-phenyl)-3H-imidazol-4-yl]-methylamine;
C-[5-(2,4-Dichloro-phenyl)-3-(2,5-difluoro-benzyl)-3H-imidazol-4-yl]-methylamine;
C-[5-(2,4-Dichloro-phenyl)-3-(2-fluoro-benzyl)-3H-imidazol-4-yl]-methylamine;
C-[3-(2-Chloro-4-fluoro-benzyl)-5-(2,4-dichloro-phenyl)-3H-imidazol-4-yl]-methylamine;
C-[5-(2,4-Dichloro-phenyl)-3-(1-methyl-1H-pyrrol-2-ylmethyl)-3H-imidazol-4-yl]-methylamine;
C-[5-(2,4-Dichloro-phenyl)-3-pyridin-2-ylmethyl-3H-imidazol-4-yl]-methylamine;
C-[5-(2,4-Dichloro-phenyl)-3-pyrid in-3-ylmethyl-3H-imidazol-4-yl]-methylamine;
C-[5-(2,4-Dimethyl-phenyl)-3-thiophen-3-ylmethyl-3H-imidazol-4-yl]-methylamine;
C-[3-(5-Bromo-2-fluoro-benzyl)-5-(2,4-dimethyl-phenyl)-3H-imidazol-4-yl]-methylamine;
C-[3-Benzyl-5-(2,4-dimethyl-phenyl)-3H-imidazol-4-yl]-methylamine;
C-[5-(2,4-Dimethyl-phenyl)-3-(2-ethoxy-benzyl)-3H-imidazol-4-yl]-methylamine;
C-[3-(5-Bromo-2-fluoro-benzyl)-5-(4-methoxy-2-methyl-phenyl)-3H-imidazol-4-yl]-methylamine;
C-[5-(2,4-Difluoro-phenyl)-3-furan-2-ylmethyl-3H-imidazol-4-yl]-methylamine;
C-[3-(2-Chloro-benzyl)-5-(2,4-difluoro-phenyl)-3H-imidazol-4-yl]-methylamine;
C-[5-(2,4-Difluoro-phenyl)-3-(4-fluoro-benzyl)-3H-imidazol-4-yl]-methylamine;
C-[5-(2,4-Difluoro-phenyl)-3-(3-trifluoromethyl-benzyl)-3H-imidazol-4-yl]-methylamine;
C-[3-(2,4-Difluoro-benzyl)-5-(2,4-difluoro-phenyl)-3H-imidazol-4-yl]-methylamine;
C-[5-(2,4-Difluoro-phenyl)-3-(3-methoxy-benzyl)-3H-imidazol-4-yl]-methylamine;
C-[5-(2,4-Difluoro-phenyl)-3-(3-fluoro-benzyl)-3H-imidazol-4-yl]-methylamine;
C-[3-(5-Bromo-2-fluoro-benzyl)-5-(2,4-difluoro-phenyl)-3H-imidazol-4-yl]-methylamine;

C-[3-Benzyl-5-(2,4-difluoro-phenyl)-3H-imidazol-4-yl]-methylamine;
C-[3-Benzo[1,3]dioxol-5-ylmethyl-5-(2,4-difluoro-phenyl)-3H-imidazol-4-yl]-methylamine;
C-[5-(2,4-Difluoro-phenyl)-3-(2-ethoxy-benzyl)-3H-imidazol-4-yl]-methylamine;
C-[5-(2,4-Difluoro-phenyl)-3-(2,2-dimethyl-propyl)-3H-imidazol-4-yl]-methylamine;
C-[5-(2,4-Difluoro-phenyl)-3-(2-trifluoromethoxy-benzyl)-3H-imidazol-4-yl]-methylamine;
C-[3-(2,5-Difluoro-benzyl)-5-(2,4-difluoro-phenyl)-3H-imidazol-4-yl]-methylamine;
C-[5-(2,4-Difluoro-phenyl)-3-(2-fluoro-benzyl)-3H-imidazol-4-yl]-methylamine;
C-[3-(2-Chloro-4-fluoro-benzyl)-5-(2,4-difluoro-phenyl)-3H-imidazol-4-yl]-methylamine;
C-[5-(2,4-Difluoro-phenyl)-3-pyridin-2-ylmethyl-3H-imidazol-4-yl]-methylamine; and
C-[5-(2,4-Difluoro-phenyl)-3-pyridin-3-ylmethyl-3H-imidazol-4-yl]-methylamine;
or a pharmaceutically acceptable salt of any one thereof.

61. A compound selected from the group consisting of:
C-[3-(2-Chloro-benzyl)-5-(2,4-dichloro-phenyl)-3H-imidazol-4-yl]-methylamine;
C-[5-(2,4-Dichloro-phenyl)-3-(4-fluoro-benzyl)-3H-imidazol-4-yl]-methylamine;
C-[5-(2,4-Dichloro-phenyl)-3-(3-trifluoromethyl-benzyl)-3H-imidazol-4-yl]-methylamine;
C-[5-(2,4-Dichloro-phenyl)-3-(2,4-difluoro-benzyl)-3H-imidazol-4-yl]-methylamine;
C-[5-(2,4-Dichloro-phenyl)-3-(3-methoxy-benzyl)-3H-imidazol-4-yl]-methylamine;
C-[5-(2,4-Dichloro-phenyl)-3-(3-fluoro-benzyl)-3H-imidazol-4-yl]-methylamine;
C-[5-(2,4-Dichloro-phenyl)-3-(2-methyl-benzyl)-3H-imidazol-4-yl]-methylamine;
C-[3-Benzyl-5-(2,4-dichloro-phenyl)-3H-imidazol-4-yl]-methylamine;
C-[5-(2,4-Dichloro-phenyl)-3-(3,4-difluoro-benzyl)-3H-imidazol-4-yl]-methylamine;
C-[5-(2,4-Dichloro-phenyl)-3-(2-ethoxy-benzyl)-3H-imidazol-4-yl]-methylamine;
C-[5-(2,4-Dichloro-phenyl)-3-(2-trifluoromethoxy-benzyl)-3H-imidazol-4-yl]-methylamine; and
C-[5-(2,4-Dichloro-phenyl)-3-(2-fluoro-benzyl)-3H-imidazol-4-yl]-methylamine;
or a pharmaceutically acceptable salt of any one thereof.

62. A compound selected from the group consisting of:
C-[5-(2,4-Dichloro-phenyl)-3-(2,6-difluoro-benzyl)-3H-imidazol-4-yl]-methylamine;
C-[3-(2-Chloro-6-fluoro-benzyl)-5-(2,4-dichloro-phenyl)-3H-imidazol-4-yl]-methylamine;
C-[5-(2,4-Dichloro-phenyl)-3-(2-trifluoromethyl-benzyl)-3H-imidazol-4-yl]-methylamine;
C-[3-(2,3-Dichloro-benzyl)-5-(2,4-dichloro-phenyl)-3H-imidazol-4-yl]-methylamine;
C-[3-(4-Chloro-benzyl)-5-(2,4-dichloro-phenyl)-3H-imidazol-4-yl]-methylamine;
C-[5-(2,4-Dichloro-phenyl)-3-(4-methyl-benzyl)-3H-imidazol-4-yl]-methylamine;
C-[3-(3,4-Dichloro-benzyl)-5-(2,4-dichloro-phenyl)-3H-imidazol-4-yl]-methylamine;
C-[3-(2,6-Dichloro-benzyl)-5-(2,4-dichloro-phenyl)-3H-imidazol-4-yl]-methylamine;
C-[5-(2,4-Dichloro-phenyl)-3-(2,5-difluoro-benzyl)-3H-imidazol-4-yl]-methylamine; and
C-[3-(2-Chloro-4-fluoro-benzyl)-5-(2,4-dichloro-phenyl)-3H-imidazol-4-yl]-methylamine;
or a pharmaceutically acceptable salt of any one thereof.

63. A compound selected from the group consisting of:
C-{5-(2,4-Dichloro-phenyl)-3-[2-(1H-indol-3-yl)-ethyl]-3H-imidazol-4-yl}-methylamine;
1-[5-(2,4-Dichloro-phenyl)-3-phenethyl-3H-imidazol-4-yl]-ethylamine;
C-[5-(2,4-Dichloro-phenyl)-3-(3-fluoro-5-trifluoromethyl-benzyl)-3H-imidazol-4-yl]-methylamine;
{2-[5-Aminomethyl-4-(2,4-dichloro-phenyl)-imidazol-1-yl]-ethyl}-cyclohexyl-amine;
C-[5-(2,4-Dichloro-phenyl)-3-(3,4-dimethoxy-benzyl)-3H-imidazol-4-yl]-methylamine;
{2-[5-Aminomethyl-4-(2,4-dichloro-phenyl)-imidazol-1-yl]-ethyl}-diisopropyl-amine;
C-[5-(2,4-Dichloro-phenyl)-3-(3-methyl-butyl)-3H-imidazol-4-yl]-methylamine;
C-[5-(2,4-Dichloro-phenyl)-3-(2,4-dimethoxy-benzyl)-3H-imidazol-4-yl]-methylamine;
C-[5-(2,4-Dichloro-phenyl)-3-(2-pyridin-3-yl-ethyl)-3H-imidazol-4-yl]-methylamine;
C-[5-(2,4-Dichloro-phenyl)-3-(2-morpholin-4-yl-ethyl)-3H-imidazol-4-yl]-methylamine;
C-[5-(2,4-Dichloro-phenyl)-3-(2,2-dimethyl-propyl)-3H-imidazol-4-yl]-methylamine;
C-[5-(2,4-Dichloro-phenyl)-3-pentyl-3H-imidazol-4-yl]-methylamine;
C-[5-(2,4-Dichloro-phenyl)-3-(5-methyl-isoxazol-3-ylmethyl)-3H-imidazol-4-yl]-methylamine;
C-[3-Adamantan-1-ylmethyl-5-(2,4-dichloro-phenyl)-3H-imidazol-4-yl]-methylamine;
1-[5-(2,4-Dichloro-phenyl)-3-(2-methyl-benzyl)-3H-imidazol-4-yl]-ethylamine;
6-[5-Aminomethyl-4-(2,4-dichloro-phenyl)-imidazol-1-yl]-hexan-1-ol
C-[5-(2,4-Dichloro-phenyl)-3-(tetrahydro-furan-2-ylmethyl)-3H-imidazol-4-yl]-methylamine;
2-{2-[5-Aminomethyl-4-(2,4-dichloro-phenyl)-imidazol-1-yl]-ethoxy}-ethanol
{3-[5-Aminomethyl-4-(2,4-dichloro-phenyl)-imidazol-1-yl]-propyl}-cyclohexyl-amine;
{2-[5-Aminomethyl-4-(2,4-dichloro-phenyl)-imidazol-1-yl]-ethyl}-(5-nitro-pyridin-2-yl)-amine;
C-[3-[2-(2-Chloro-phenyl)-ethyl]-5-(2,4-dichloro-phenyl)-3H-imidazol-4-yl]-methylamine;
1-{3-[5-(1-Amino-ethyl)-4-(2,4-dichloro-phenyl)-imidazol-1-yl]-propyl}-pyrrolidin-2-one;
C-[5-(2,4-Dichloro-phenyl)-3-(3,3-dimethyl-butyl)-3H-imidazol-4-yl]-methylamine;
C-[3-Benzyl-5-(2,4-dichloro-phenyl)-3H-imidazol-4-yl]-methylamine;
C-[3-(4-Bromo-benzyl)-5-(2,4-dichloro-phenyl)-3H-imidazol-4-yl]-methylamine;
C-[5-(2,4-Dichloro-phenyl)-3-(2-pyrrolidin-1-yl-ethyl)-3H-imidazol-4-yl]-methylamine;
C-[5-(2,4-Dichloro-phenyl)-3-(5-methyl-pyrazin-2-ylmethyl)-3H-imidazol-4-yl]-methylamine;
C-[5-(2,4-Dichloro-phenyl)-3-(3-fluoro-benzyl)-3H-imidazol-4-yl]-methylamine;
1-{3-[5-Aminomethyl-4-(2,4-dichloro-phenyl)-imidazol-1-yl]-propyl}-pyrrolidin-2-one
3-[3-(5-Bromo-2-fluoro-benzyl)-5-(2,4-dichloro-phenyl)-3H-imidazol-4-yl]-propylamine;
C-[5-(2,4-Dichloro-phenyl)-3-(2,2-diphenyl-ethyl)-3H-imidazol-4-yl]-methylamine;

C-{5-(2,4-Dichloro-phenyl)-3-[2-(2,4-dichloro-phenyl)-ethyl]-3H-imidazol-4-yl}-methylamine;
C-[5-(2,4-Dichloro-phenyl)-3-(2-methyl-benzyl)-3H-imidazol-4-yl]-methylamine;
6-[5-(1-Amino-ethyl)-4-(2,4-dichloro-phenyl)-imidazol-1-yl]-hexan-1-ol;
C-[5-(2,4-Dichloro-phenyl)-3-(4-methoxy-benzyl)-3H-imidazol-4-yl]-methylamine;
1-[5-(2,4-Dichloro-phenyl)-3-(2,5-difluoro-benzyl)-3H-imidazol-4-yl]-ethylamine;
2-[3-[2-(3-Chloro-phenyl)-ethyl]-5-(2,4-dichloro-phenyl)-3H-imidazol-4-yl]-ethylamine;
5-[5-Aminomethyl-4-(2,4-dichloro-phenyl)-imidazol-1-yl]-pentan-1-ol;
C-[5-(2,4-Dichloro-phenyl)-3-pyridin-2-ylmethyl-3H-imidazol-4-yl]-methylamine;
C-[5-(2,4-Dichloro-phenyl)-3-(2,6-difluoro-benzyl)-3H-imidazol-4-yl]-methylamine;
{2-[5-Aminomethyl-4-(2,4-dichloro-phenyl)-imidazol-1-yl]-ethyl}-phenyl-amine;
C-[5-(2,4-Dichloro-phenyl)-3-(4-phenyl-butyl)-3H-imidazol-4-yl]-methylamine;
1-[5-(2,4-Dichloro-phenyl)-3-(4-methoxy-benzyl)-3H-imidazol-4-yl]-ethylamine;
1-[5-(2,4-Dichloro-phenyl)-3-(3-methyl-butyl)-3H-imidazol-4-yl]-ethylamine;
C-{5-(2,4-Dichloro-phenyl)-3-[2-(4-methoxy-phenyl)-ethyl]-3H-imidazol-4-yl}-methylamine;
C-[3-(2,3-Dichloro-benzyl)-5-(2,4-dichloro-phenyl)-3H-imidazol-4-yl]-methylamine;
3-[5-Aminomethyl-4-(2,4-dichloro-phenyl)-imidazol-1-yl]-propan-1-ol;
C-[5-(2,4-Dichloro-phenyl)-3-(5-methyl-furan-2-ylmethyl)-3H-imidazol-4-yl]-methylamine;
C-[3-[2-(4-Bromo-phenyl)-ethyl]-5-(2,4-dichloro-phenyl)-3H-imidazol-4-yl]-methylamine;
C-[5-(2,4-Dichloro-phenyl)-3-(2-fluoro-3-trifluoromethyl-benzyl)-3H-imidazol-4-yl]-methylamine;
1-[5-(2,4-Dichloro-phenyl)-3-(7-methyl-octyl)-3H-imidazol-4-yl]-ethylamine;
C-[3-[2-(3-Chloro-phenyl)-ethyl]-5-(2,4-dichloro-phenyl)-3H-imidazol-4-yl]-methylamine;
C-[5-(2,4-Dichloro-phenyl)-3-(3,3-diphenyl-propyl)-3H-imidazol-4-yl]-methylamine;
C-[5-(2,4-Dichloro-phenyl)-3-(2,4-difluoro-benzyl)-3H-imidazol-4-yl]-methylamine;
C-{5-(2,4-Dichloro-phenyl)-3-[2-(4-fluoro-phenyl)-ethyl]-3H-imidazol-4-yl}-methylamine;
2-[5-Aminomethyl-4-(2,4-dichloro-phenyl)-imidazol-1-yl]-ethanol;
C-[5-(2,4-Dichloro-phenyl)-3-phenethyl-3H-imidazol-4-yl]-methylamine;
C-[5-(2,4-Dichloro-phenyl)-3-(2-piperidin-1-yl-ethyl)-3H-imidazol-4-yl]-methylamine;
C-[5-(2,4-Dichloro-phenyl)-3-(3-methoxy-benzyl)-3H-imidazol-4-yl]-methylamine;
C-[5-(2,4-Dichloro-phenyl)-3-(2-methoxy-ethyl)-3H-imidazol-4-yl]-methylamine;
1-[5-(2,4-Dichloro-phenyl)-3-hexyl-3H-imidazol-4-yl]-ethylamine;
(S)-1-[5-(2,4-Dichloro-phenyl)-3-(2,4-dimethoxy-benzyl)-3H-imidazol-4-yl]-ethylamine;
1-[3-[2-(2-Chloro-phenyl)-ethyl]-5-(2,4-dichloro-phenyl)-3H-imidazol-4-yl]-ethylamine;
1-[3-[2-(3-Chloro-phenyl)-ethyl]-5-(2,4-dichloro-phenyl)-3H-imidazol-4-yl]-ethylamine;
C-[3-(2-Cyclohex-1-enyl-ethyl)-5-(2,4-dichloro-phenyl)-3H-imidazol-4-yl]-methylamine;
C-[5-(2,4-Dichloro-phenyl)-3-(4-methyl-benzyl)-3H-imidazol-4-yl]-methylamine;
1-[3-(2-Chloro-benzyl)-5-(2,4-dichloro-phenyl)-3H-imidazol-4-yl]-ethylamine;
1-[5-(2,4-Dichloro-phenyl)-3-(3,4-difluoro-benzyl)-3H-imidazol-4-yl]-ethylamine;
{2-[5-Aminomethyl-4-(2,4-dichloro-phenyl)-imidazol-1-yl]-ethyl}-ethyl-amine;
1-[5-(2,4-Dichloro-phenyl)-3-(3-phenyl-propyl)-3H-imidazol-4-yl]-ethylamine;
1-[3-(2-Cyclohex-1-enyl-ethyl)-5-(2,4-dichloro-phenyl)-3H-imidazol-4-yl]-ethylamine;
1-[5-Aminomethyl-4-(2,4-dichloro-phenyl)-imidazol-1-yl]-propan-2-ol;
1-[5-(2,4-Dichloro-phenyl)-3-(2-pyridin-2-yl-ethyl)-3H-imidazol-4-yl]-ethylamine;
{2-[5-(3-Amino-propyl)-4-(2,4-dichloro-phenyl)-imidazol-1-yl]-ethyl}-(5-nitro-pyridin-2-yl)-amine;
C-[3-Biphenyl-4-ylmethyl-5-(2,4-dichloro-phenyl)-3H-imidazol-4-yl]-methylamine;
1-[5-(2,4-Dichloro-phenyl)-3-(3-methoxy-benzyl)-3H-imidazol-4-yl]-ethylamine;
C-[3-(3,4-Dichloro-benzyl)-5-(2,4-dichloro-phenyl)-3H-imidazol-4-yl]-methylamine;
1-[5-(2,4-Dichloro-phenyl)-3-pyridin-3-ylmethyl-3H-imidazol-4-yl]-ethylamine;
{2-[5-(2-Amino-ethyl)-4-(2,4-dichloro-phenyl)-imidazol-1-yl]-ethyl}-(5-nitro-pyridin-2-yl)-amine;
1-[5-(2,4-Dichloro-phenyl)-3-(2-methoxy-benzyl)-3H-imidazol-4-yl]-ethylamine;
C-[3-(2-Chloro-benzyl)-5-(2,4-dichloro-phenyl)-3H-imidazol-4-yl]-methylamine;
C-[3-(4-Chloro-benzyl)-5-(2,4-dichloro-phenyl)-3H-imidazol-4-yl]-methylamine;
C-{5-(2,4-Dichloro-phenyl)-3-[2-(2-fluoro-phenyl)-ethyl]-3H-imidazol-4-yl}-methylamine;
C-[5-(2,4-Dichloro-phenyl)-3-hexyl-3H-imidazol-4-yl]-methylamine;
C-[5-(2,4-Dichloro-phenyl)-3-(2-pyridin-2-yl-ethyl)-3H-imidazol-4-yl]-methylamine;
C-[5-(2,4-Dichloro-phenyl)-3-propyl-3H-imidazol-4-yl]-methylamine;
C-{5-(2,4-Dichloro-phenyl)-3-[3-(5-methyl-1H-pyrazol-4-yl)-propyl]-3H-imidazol-4-yl}-methylamine;
(S)-1-[5-(2,4-Dichloro-phenyl)-3-(3,3-diphenyl-propyl)-3H-imidazol-4-yl]-ethylamine;
C-[5-(2,4-Dichloro-phenyl)-3-(3-trifluoromethyl-benzyl)-3H-imidazol-4-yl]-methylamine;
3-[3-[2-(2-Chloro-phenyl)-ethyl]-5-(2,4-dichloro-phenyl)-3H-imidazol-4-yl]-propylamine;
C-[5-(2,4-Dichloro-phenyl)-3-(3-phenyl-propyl)-3H-imidazol-4-yl]-methylamine;
C-[5-(2,4-Dichloro-phenyl)-3-(3,4-difluoro-benzyl)-3H-imidazol-4-yl]-methylamine;
C-[3-(2,4-Dichloro-benzyl)-5-(2,4-dichloro-phenyl)-3H-imidazol-4-yl]-methylamine;
C-[5-(2,4-Dichloro-phenyl)-3-pyridin-4-ylmethyl-3H-imidazol-4-yl]-methylamine;
1-[5-(2,4-Dichloro-phenyl)-3-(3,4-dimethoxy-benzyl)-3H-imidazol-4-yl]-ethylamine;
1-[5-(2,4-Dichloro-phenyl)-3-pyridin-2-ylmethyl-3H-imidazol-4-yl]-ethylamine;
C-[5-(2,4-Dichloro-phenyl)-3-(4-trifluoromethoxy-benzyl)-3H-imidazol-4-yl]-methylamine;

C-[5-(2,4-Dichloro-phenyl)-3-(4-trifluoromethyl-benzyl)-3H-imidazol-4-yl]-methylamine;
C-[5-(2,4-Dichloro-phenyl)-3-(7-methyl-octyl)-3H-imidazol-4-yl]-methylamine;
C-[5-(2,4-Dichloro-phenyl)-3-(2-phenoxy-ethyl)-3H-imidazol-4-yl]-methylamine;
(S)-1-[3-[2-(6-Chloro-1H-indol-3-yl)-ethyl]-5-(2,4-dichloro-phenyl)-3H-imidazol-4-yl]-ethylamine;
C-[3-[2-(4-Chloro-phenyl)-ethyl]-5-(2,4-dichloro-phenyl)-3H-imidazol-4-yl]-methylamine;
(S)-1-{5-(2,4-Dichloro-phenyl)-3-[2-(1H-indol-3-yl)-ethyl]-3H-imidazol-4-yl}-ethylamine;
C-[5-(2,4-Dichloro-phenyl)-3-(3-imidazol-1-yl-propyl)-3H-imidazol-4-yl]-methylamine;
3-[3-[2-(6-Chloro-1H-indol-3-yl)-ethyl]-5-(2,4-dichloro-phenyl)-3H-imidazol-4-yl]-propylamine;
1-[5-(2,4-Dichloro-phenyl)-3-(4-phenyl-butyl)-3H-imidazol-4-yl]-ethylamine;
3-[3-[2-(3-Chloro-phenyl)-ethyl]-5-(2,4-dichloro-phenyl)-3H-imidazol-4-yl]-propylamine;
C-[5-(2,4-Dichloro-phenyl)-3-(2-trifluoromethyl-benzyl)-3H-imidazol-4-yl]-methylamine;
1-[3-Benzyl-5-(2,4-dichloro-phenyl)-3H-imidazol-4-yl]-ethylamine;
(S)-1-{5-(2,4-Dichloro-phenyl)-3-[2-(6-fluoro-1H-indol-3-yl)-ethyl]-3H-imidazol-4-yl}-ethylamine;
{2-[5-((S)-1-Amino-ethyl)-4-(2,4-dichloro-phenyl)-imidazol-1-yl]-ethyl}-(5-nitro-pyridin-2-yl)-amine;
C-[5-(2,4-Dichloro-phenyl)-3-(2-fluoro-benzyl)-3H-imidazol-4-yl]-methylamine;
4-{2-[5-Aminomethyl-4-(2,4-dichloro-phenyl)-imidazol-1-yl]-ethyl}-phenol;
C-{5-(2,4-Dichloro-phenyl)-3-[2-(6-fluoro-1H-indol-3-yl)-ethyl]-3H-imidazol-4-yl}-methylamine;
1-[5-(2,4-Dichloro-phenyl)-3-pentyl-3H-imidazol-4-yl]-ethylamine;
1-[5-(2,4-Dichloro-phenyl)-3-(4-methyl-benzyl)-3H-imidazol-4-yl]-ethylamine;
5-Azetidin-3-yl-1-[2-(2-chloro-phenyl)-ethyl]-4-(2,4-dichloro-phenyl)-1H-imidazole 1-[5-(2,4-Dichloro-phenyl)-3-(2-morpholin-4-yl-ethyl)-3H-imidazol-4-yl]-ethylamine;
C-[5-(2,4-Dichloro-phenyl)-3-(2,5-difluoro-benzyl)-3H-imidazol-4-yl]-methylamine;
C-[5-(2,4-Dichloro-phenyl)-3-(2-methoxy-benzyl)-3H-imidazol-4-yl]-methylamine;
C-[5-(2,4-Dichloro-phenyl)-3-pyridin-3-ylmethyl-3H-imidazol-4-yl]-methylamine;
C-[5-(2,4-Dichloro-phenyl)-3-ethyl-3H-imidazol-4-yl]-methylamine;
C-[3-(2-Chloro-6-fluoro-benzyl)-5-(2,4-dichloro-phenyl)-3H-imidazol-4-yl]-methylamine;
C-[3-(5-Bromo-2-fluoro-benzyl)-5-(2,4-dichloro-phenyl)-3H-imidazol-4-yl]-methylamine;
C-[3-benzo[1,3]dioxol-5-ylmethyl-5-(2,4-dichloro-phenyl)-3H-imidazol-4-yl]-methylamine;
2-[5-aminomethyl-4-(2,4-dichloro-phenyl)-imidazol-1-yl]-2-phenyl-ethanol;
C-{5-(2,4-dichloro-phenyl)-3-[2-(6-methyl-1H-indol-3-yl)-ethyl]-3H-imidazol-4-yl}-methylamine;
C-[5-(2,4-dichloro-phenyl)-3-(2-ethoxy-benzyl)-3H-imidazol-4-yl]-methylamine;
C-[5-(2,4-dichloro-phenyl)-3-(2-trifluoromethoxy-benzyl)-3H-imidazol-4-yl]-methylamine;
C-[5-(2,4-dichloro-phenyl)-3-thiophen-3-ylmethyl-3H-imidazol-4-yl]-methylamine; and
C-[5-(2,4-dichloro-phenyl)-3-(1-methyl-1H-pyrazol-4-ylmethyl)-3H-imidazol-4-yl]-methylamine;

or a pharmaceutically acceptable salt of any one thereof.

64. A pharmaceutical composition comprising a compound according to claim 1 optionally in combination with one or more therapeutically acceptable diluents or carriers.

65. A process for preparation of a compound of formula (I) according to claim 1, wherein $R^1$, $R^2$, $R^3$, $R^4$ and $R^5$ are as defined in claim 1, which comprises reaction of a compound of formula (II)

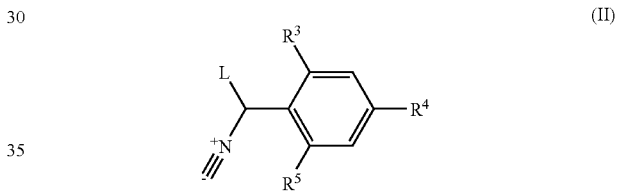

wherein L represents an anion-stabilising leaving group;
with a compound of formula (III)

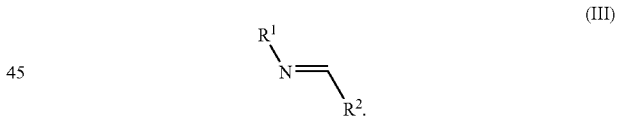

* * * * *